(12) United States Patent
Palani et al.

(10) Patent No.: US 7,763,623 B2
(45) Date of Patent: Jul. 27, 2010

(54) HETEROCYCLES AS NICOTINIC ACID RECEPTOR AGONISTS FOR THE TREATMENT OF DYSLIPIDEMIA

(75) Inventors: Anandan Palani, Bridgewater, NJ (US);
Jun Qin, Edison, NJ (US); Dong Xiao, Warren, NJ (US); Ying R. Huang, Berkeley Heights, NJ (US); Xiao Chen, Edison, NJ (US); Zhidan Liu, Edison, NJ (US); Sylvia J. Degrado, Scotch Plains, NJ (US); Robert G. Aslanian, Rockaway, NJ (US); Xianhai Huang, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 30 days.

(21) Appl. No.: 11/654,137

(22) Filed: Jan. 17, 2007

(65) Prior Publication Data

US 2007/0173495 A1    Jul. 26, 2007

Related U.S. Application Data

(60) Provisional application No. 60/760,555, filed on Jan. 20, 2006.

(51) Int. Cl.
| | | |
|---|---|---|
| C07D 491/052 | (2006.01) | |
| A61K 31/519 | (2006.01) | |
| A61P 9/00 | (2006.01) | |
| A61P 25/00 | (2006.01) | |
| A61P 7/00 | (2006.01) | |
| A61P 35/00 | (2006.01) | |
| A61P 29/00 | (2006.01) | |
| A61P 11/00 | (2006.01) | |
| A61P 1/00 | (2006.01) | |
| A61P 3/10 | (2006.01) | |

(52) U.S. Cl. .................................. 514/260.1; 544/278
(58) Field of Classification Search ............... 514/260.1; 544/278
See application file for complete search history.

(56) References Cited

U.S. PATENT DOCUMENTS

| | | | |
|---|---|---|---|
| 2,826,580 | A | 3/1958 | Fischer et al. |
| 6,399,653 | B1 | 6/2002 | Henke |
| 2003/0199526 | A1 | 10/2003 | Choquette et al. |
| 2004/0122033 | A1 | 6/2004 | Nargund et al. |
| 2004/0142377 | A1 | 7/2004 | Unett et al. |
| 2004/0229844 | A1 | 11/2004 | Cheng et al. |
| 2005/0251869 | A1 | 11/2005 | Cai et al. |
| 2006/0264489 | A1 | 11/2006 | Palani et al. |
| 2007/0065917 | A1 | 3/2007 | Chen et al. |
| 2007/0066630 | A1 | 3/2007 | Palani et al. |
| 2007/0167469 | A1 | 7/2007 | Bourrie et al. |
| 2007/0173495 | A1 | 7/2007 | Palani et al. |
| 2008/0019978 | A1 | 1/2008 | Palani et al. |

FOREIGN PATENT DOCUMENTS

| | | | |
|---|---|---|---|
| DE | 263 891 | A3 | 12/1986 |
| DE | 265 760 | A3 | 5/1987 |
| WO | WO 00/69829 | A1 | 11/2000 |
| WO | WO 02/084298 | A2 | 10/2002 |
| WO | WO 2004/037159 | A2 | 5/2004 |
| WO | WO 2004/047755 | A2 | 6/2004 |
| WO | WO 2004/083388 | A2 | 9/2004 |
| WO | WO 2004/110368 | A2 | 12/2004 |
| WO | WO 2004/110375 | A2 | 12/2004 |
| WO | WO 2005/000217 | A2 | 1/2005 |
| WO | WO 2005/077950 | A2 | 8/2005 |
| WO | WO 2005/105097 | A2 | 11/2005 |
| WO | WO 2006/045564 | A1 | 5/2006 |
| WO | WO 2006/045565 | A1 | 5/2006 |
| WO | WO 2006/078834 | A1 | 7/2006 |
| WO | WO 2006/089009 | A2 | 8/2006 |
| WO | WO 2006/092430 | A1 | 9/2006 |
| WO | WO 2006124490 | * | 11/2006 |
| WO | WO 2007/021744 | A1 | 2/2007 |
| WO | WO 2007/027661 | A2 | 3/2007 |
| WO | WO 2008/127591 | A2 | 10/2008 |

OTHER PUBLICATIONS

Chemical Abstract No. 45:8600 for Ridi, Mario et al., "Barbituric acid and its derivatives. VII. Some reactions with ethyl acetate", *Gazzetta Chimica Italiana* 80:121-128, (1950) (which is attached to said abstract).

Chemical Abstract No. 48:3424 for Ridi, Mario et al., "Barbituric acid and its derivatives. XI. Some reactions with esters of ketonic acids", *Gazzetta Chimica Italiana* 82:23-30, (1952) (which is attached to said abstract).

(Continued)

*Primary Examiner*—James O Wilson
*Assistant Examiner*—Cecilia M Jaisle
(74) *Attorney, Agent, or Firm*—Jeffrey P. Bergman; Palaiyur S. Kalyanaraman

(57) ABSTRACT

A compound having the general structure of Formula (I):

(I)

or a pharmaceutically acceptable salt, solvate, ester, or tautomer thereof, are useful in treating diseases, disorders, or conditions such as metabolic syndrome and dyslipidemia.

39 Claims, No Drawings

OTHER PUBLICATIONS

Paterson et al., "Specific Enzyme Inhibitors in Vitamin Biosynthesis. Part I. The Synthesis of 8-Substituted Pyrido [2,3-d] Pyrimidines", *J. Chem. Soc.*, Perkin Trans. I, 8:1041-1050 (1972).

Rao, et al., "Synthesis of Heterocycles: Part II—Pyrano[2,3-d]pyrimidines", *Indian Journal of Chemistry*, 12:1028-1030 (1974).

Skof et al. "A One-Step Transformation of (S)-1-Benzoyl-3-[(E)-Dimethylaminomethylidene]-5- Methoxycarbonyl-Pyrrolidin-2-One Into quinolizinyl-AND 2H-2-Pyranonyl-Substituted Alanine Derivatives", *Heterocycles*, 51(5):1051-1058 (1999).

Toplak et al. "The Synthesis of Methyl-2-(Benzyloxycarbonyl)amino-3-dimethylaminopropenoate. The Synthesis of Trisubstituted Pyrroles, 3-Amino-2H-pyran-2-ones, Fused 2H-Pyran-2-ones and 4H Pyridin-4-ones", *J. Heterocyclic Chem.*, 36:225-235 (1999).

PCT International Search Report for corresponding PCT Application No. PCT/US2007/001178 dated Jul. 13, 2007.

Ahluwalia et al., "Base Catalysed Condensation of Acetone with Uracil Derivatives: One Step Synthesis of Pyranopyrimidines", *Synthetic Communications*, 17(12):1435-1440 (1987).

Kvita et al., "158. Reaktionen des Cumalinsaure-methylesters and Cumalinaidehyds mit ambidenten Nucleophilen", *Helv. Chim. Acta.*, 71:1467-1473 (1988).

Selles et al., "Expedient Synthesis of Highly Substituted Fused Heterocoumarins", *Organic Letters*, 6( 2):277-279 (1997).

Tietze et al., "Multicomponent Domino Reactions for the Synthesis of Biologically Active Natural Products and Drugs", *Medicinal Research Reviews*, 20:304-322 (2000).

Zooroob et al., 1,3-Dimethylpyrimidoheterozyklen als antibakterielle Substanzen, *Arzneimittel-Forschung*, 47:958-962 (1997).

Database Beilstein, Beilstein Institute for Organic Chemistry, Frankfurt-Main, DE; XP002482949 retrieved from CrossFire Database accession Nos. 5954253, 595391 and 5975043 Abstract.

Database Beilstein, Beilstein Institute for Organic Chemistry, Frankfurt-Main, DE; XP002482950 retrieved from CrossFire Database accession No. 233231 Abstract.

Database Beilstein, Beilstein Institute for Organic Chemistry, Frankfurt-Main, DE; XP002482951 retrieved from CrossFire Database accession Nos. 5935847, 5942970, 5959486 Abstract.

Database Beilstein, Beilstein Institute for Organic Chemistry, Frankfurt-Main, DE; XP002482952 retrieved from CrossFire Database accession No. 191230 Abstract.

Database Beilstein, Beilstein Institute for Organic Chemistry, Frankfurt-Main, DE; XP002482953 retrieved from CrossFire Database accession No. 1037486 Abstract.

Database Beilstein, Beilstein Institute for Organic Chemistry, Frankfurt-Main, DE; XP002482954 retrieved from CrossFire Database accession No. 617130 Abstract.

Database Beilstein, Beilstein Institute for Organic Chemistry, Frankfurt-Main, DE; XP002482955 retrieved from CrossFire Database accession No. 1018983 Abstract.

Database Beilstein, Beilstein Institute for Organic Chemistry, Frankfurt-Main, DE; XP002482956 retrieved from CrossFire Database accession No. 1128908 Abstract.

Office Action mailed Oct. 26, 2007 in connection with U.S. Appl. No. 11/432,133 (10 Pages).

Office Action mailed Feb. 29, 2008 in connection with U.S. Appl. No. 11/432,133 (16 Pages).

Office Action mailed Oct. 3, 2008 in connection with U.S. Appl. No. 11/432,133 (15 Pages).

Office Action mailed Oct. 26, 2007 in connection with U.S. Appl. No. 11/600,216 (10 Pages).

Office Action mailed Jan. 8, 2008 in connection with U.S. Appl. No. 11/600,216 (15 Pages).

Office Action mailed Sep. 19, 2008 in connection with U.S. Appl. No. 11/600,216 (6 Pages).

Office Action mailed Aug. 1, 2008 in connection with U.S. Appl. No. 11/771,538 (63 Pages).

\* cited by examiner

HETEROCYCLES AS NICOTINIC ACID RECEPTOR AGONISTS FOR THE TREATMENT OF DYSLIPIDEMIA

PRIORITY INFORMATION

This application claims the benefit of U.S. Provisional Application No. 60/760,555, filed Jan. 20, 2006, which is incorporated herein by reference in its entirety.

FIELD OF THE INVENTION

The present invention relates to nicotinic acid receptor agonist compounds useful for treating metabolic syndrome, dyslipidemia, cardiovascular diseases, disorders of the peripheral and central nervous system, hematological diseases, cancer, inflammation, respiratory diseases, gastroenterological diseases, diabetes, and non-alcoholic fatty liver disease; pharmaceutical compositions comprising such compounds; pharmaceutical compositions comprising nicotinic acid receptor agonist compounds in combination with other therapeutic agents; and methods of treatment using the compounds and compositions to treat conditions such as metabolic syndrome, dyslipidemia, cardiovascular diseases, disorders of the peripheral and central nervous system, hematological diseases, cancer, inflammation, respiratory diseases, gastroenterological diseases, diabetes, hepatic steatosis and non-alcoholic fatty liver disease.

BACKGROUND OF THE INVENTION

Nicotinic acid has been used to treat metabolic syndrome and dyslipidemia. However, nicotinic acid has undesirable side effects such as flushing and diarrhea. It is therefore desirable to provide improved nicotinic acid receptor agonists with improved efficacy at treating metabolic syndrome and dyslipidemia, yet without the undesirable side effects. The compounds of the present invention provide such improved nicotinic acid receptor agonists.

M. Ridi, Gazzetta Chim. Ital. (1950) vol. 80, p. 121 and M. Ridi, Gazzetta Chim. Ital. (1952) vol. 82, p. 23 disclose syntheses of barbituric acid derivatives. FR 2563223 discloses nucleoside analogs. T. Paterson et al., J. Chem. Soc., Perkins Trans. 1 (1972), vol. 8, pp. 1041-1050 discloses the synthesis of 8-substituted pyrido[2,3-d]pyrimidines. S. Rao, Indian J. Chem. (1974), 12(10), pp. 1028-1030 discloses the synthesis of pyrano[2,3-d]pyrimidines. M. Skof, Heterocycles, (1999), 51(5), pp. 1051-1058 discloses one step transformations of (S)-1-benzoyl-3-[(E)-dimethylaminomethylidene]-5-methoxycarbonyl-pyrrolidin-2-one into quinolizinyl- and 2H-2-pyranonyl-substituted alanine derivatives. R. Toplak J. Heterocyclic Chem. (1999), 36(1), pp. 225-235 discloses the synthesis of pyran-2-ones. However, the compounds of the above references differ from those of the present invention. WO 2004/110368 describes combination therapies for the treatment of hypertension comprising the combination of an anti-obesity agent and an anti-hypertensive agent. However, WO 2004/110368 fails to describe nicotinic acid receptor agonists, or combinations of one or more nicotinic acid receptor agonists with a second therapeutic agent. WO 2005/000217 describes combination therapies for the treatment of dyslipidemia comprising the administration of a combination of an anti-obesity agent and an anti-dyslipidemic agent. However, WO 2005/000217 fails to describe nicotinic acid receptor agonists, or combinations of one or more nicotinic acid receptor agonists with a second therapeutic agent.

WO 2004/110375 describes combination therapies for the treatment of diabetes comprising the administration of a combination of an anti-obesity agent and an anti-diabetic agent. However, WO 2004/110375 fails to describe nicotinic acid receptor agonists, or combinations of one or more nicotinic acid receptor agonists with a second therapeutic agent.

US 2004/0122033 describes combination therapies for the treatment of obesity comprising the administration of a combination of an appetite suppressant and/or metabolic rate enhancers and/or nutrient absorption inhibitors. However, US 2004/0122033 fails to describe nicotinic acid receptor agonists, or combinations of one or more nicotinic acid receptor agonists with a second therapeutic agent. US 2004/0229844 describes combination therapies for treating atherosclerosis comprising the administration of a combination of nicotinic acid or another nicotinic acid receptor agonist and a DP receptor antagonist. However, the nicotinic acid agonists of US 2004/0229844 are quite different from those of the present invention.

WO2005/077950 describes xanthine derivatives which are agonists of the nicotinic acid receptor HM74A. However, the xanthine derivatives of WO2005/077950 are quite different from the compounds of the present invention.

SUMMARY OF THE INVENTION

In one embodiment, the invention provides compounds of Formula (I):

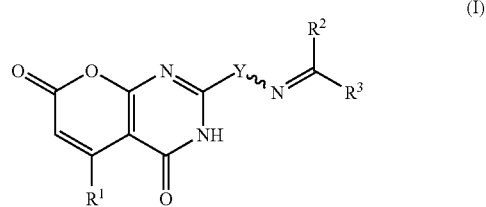

and pharmaceutically acceptable salts, solvates, esters, and tautomers thereof, wherein $R^1$ is selected from the group consisting of H, $R^4$, haloalkyl, -alkylene-$R^4$, -alkylene-$R^5$, -alkylene-$R^6$, alkenyl, alkynyl, and -alkylene-O-alkyl;

$R^2$ is selected from the group consisting of $R^7$, alkyl, haloalkyl, -alkylene-$R^5$, $R^4$, $R^5$, $R^6$, $R^7$ and -alkylene-O—$R^8$;

$R^3$ is selected from the group consisting of alkyl, haloalkyl, -alkylene-$R^5$, $R^4$, $R^5$, $R^6$, and $R^7$; or $R^2$ and $R^3$ together with the carbon atom to which they are both attached form a cycloalkyl or heterocycloalkyl ring, wherein said cycloalkyl or heterocycloalkyl ring is unsubstituted or independently substituted with one or more $X^5$ groups, or wherein said cycloalkyl ring can form a spirocyclic compound with a second cycloalkyl ring or with a heterocycloalkyl ring, wherein the second cycloalkyl ring or the heterocycloalkyl ring is unsubstituted or independently substituted with one or more $X^5$ groups;

$R^4$ is unsubstituted cycloalkyl or cycloalkyl substituted with one or more $X^1$ groups;

$R^5$ is unsubstituted aryl and aryl substituted with one or more $X^2$ groups;

$R^6$ is selected from the group consisting of unsubstituted heteroaryl and heteroaryl substituted with one or more $X^3$ groups;

$R^7$ is unsubstituted heterocycloalkyl and heterocycloalkyl substituted with one or more $X^4$ groups;

$R^8$ is selected from the group consisting of H, alkyl, $R^4$, $R^5$, $R^6$, $R^7$, —C(O)-alkyl, —C(O)—$R^5$ each $R^9$ is independently selected from the group consisting of H, alkyl, $R^4$, $R^5$, $R^6$, and $R^7$;

$R^{10}$ is selected from the group consisting of $R^9$, —C(O)-alkyl, and —C(O)—$R^5$;

each $R^{11}$ is independently alkyl or phenyl;

Y is —O— or —N($R^{10}$)—;

each $X^1$ is independently selected from the group consisting of halogen, alkyl, —O-alkyl, —OH, haloalkyl, aryl, and alkyne;

each $X^2$ is independently selected from the group consisting of halogen, alkyl, —O-alkyl, —OH, haloalkyl, aryl, and alkyne;

each $X^3$ is independently selected from the group consisting of halogen, alkyl, and N-oxide;

each $X^4$ is independently selected form the group consisting of alkyl, $R^5$, —C(O)-alkyl, —C(O)—$R^5$, —C(O)—O-alkyl, -alkylene-$R^5$, $R^4$, and —S(O$_2$)-alkyl; and each $X^5$ is independently selected from the group consisting of alkyl, -aryl, —CN, halo, haloalkyl, —O-alkyl, -alkylene-$R^5$, —O—Si($R^{11}$)$_3$, a fused aryl ring, —C(O)-alkyl, a fused heteroaryl ring, —C(O)—O-alkyl, —C(O)—$R^5$, —S(O$_2$)-alkyl, —C(O)—N($R^9$)$_2$, $R^5$, $R^6$, —C(O)—$R^4$, —C(O)—O—$R^4$, —S(O$_2$)—$R^4$, —S(O$_2$)-alkylene-$R^4$, —S(O$_2$)-alkylene-$R^5$, —N($R^9$)—C(O)—O-alkyl, —N($R^9$)—C(O)—O—$R^4$, —N($R^9$)—C(O)—N($R^9$)$_2$ and —N($R^9$)$_2$;

wherein said fused aryl ring of $X^5$ is unsubstituted or independently substituted with one or more substitutent selected from -alkylene-$R^7$ or $X^2$, and said fused heteroaryl ring of $X^5$ is unsubstituted or substituted with one or more $X^3$ groups.

In another embodiment, the present invention is directed to a pharmaceutical composition comprising a therapeutically effective amount of at least one compound of Formula (I), or a pharmaceutically acceptable salt, solvate, ester, or tautomer thereof, and at least one pharmaceutically acceptable carrier.

In another embodiment, the present invention is directed to a method of treating a disease or disorder in a patient, such as metabolic syndrome, dyslipidemia, cardiovascular diseases, disorders of the peripheral and central nervous system, hematological diseases, cancer, inflammation, respiratory diseases, gastroenterological diseases, diabetes, and non-alcoholic fatty liver disease. The method comprises administering to the patient an effective amount of at least one compound of Formula (I), or a pharmaceutically acceptable salt, solvate, ester, or tautomer thereof.

In another embodiment, the present invention is directed to a method of treating a disease or disorder in a patient, such as metabolic syndrome, dyslipidemia, cardiovascular diseases, disorders of the peripheral and central nervous system, hematological diseases, cancer, inflammation, respiratory diseases, gastroenterological diseases, diabetes, hepatic steatosis, and non-alcoholic fatty liver disease. The method comprises administering to the patient an effective amount of at least one compound of Formula (I), or a pharmaceutically acceptable salt, solvate, ester, or tautomer thereof, in combination with at least one additional active ingredient selected from the group consisting of hydroxy-substituted azetidinone compounds, substituted β-lactam compounds, HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, inorganic cholesterol sequestrants, AcylCoA:Cholesterol O-acyltransferase inhibitors, cholesteryl ester transfer protein inhibitors, fish oils containing Omega 3 fatty acids, natural water soluble fibers, plant stanols and/or fatty acid esters of plant stanols, low-density lipoprotein receptor activators, anti-oxidants, PPAR α agonists, PPAR γ-agonists, FXR receptor modulators, LXR receptor agonists, lipoprotein synthesis inhibitors, renin angiotensin inhibitors, microsomal triglyceride transport protein inhibitors, bile acid reabsorption inhibitors, PPAR δ agonists, triglyceride synthesis inhibitors, squalene epoxidase inhibitors, low density lipoprotein receptor inducers, platelet aggregation inhibitors, 5-LO or FLAP inhibitors, PPAR δ partial agonists, niacin or niacin receptor agonists, 5HT transporter inhibitors, NE transporter inhibitors, CB1 antagonists/inverse agonists, ghrelin antagonists, H3 antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, leptin derivatives, opioid antagonists, orexin receptor antagonists, BRS3 agonists, CCK-A agonists, CNTF, CNTF derivatives, CNTF agonists/modulators, 5HT2c agonists, Mc4r agonists, monoamine reuptake inhibitors, serotonin reuptake inhibitors, GLP-1 agonists, phentermine, topiramate, phytopharm compound 57, ghrelin antibodies, Mc3r agonists, ACC2 inhibitors, β3 agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanocyte-stimulating hormone receptor analogs, melanin concentrating hormone antagonists, leptons, galanin receptor antagonists, bombesin agonists, neuropeptide-Y antagonists, thyromimetic agents, dehydroepiandrosterone, analogs of dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, MSH-receptor analogs, α-glucosidase inhibitors, apo A1 milano reverse cholesterol transport inhibitors, fatty acid binding protein inhibitors (FABP), and fatty acid transporter protein inhibitors (FATP).

DETAILED DESCRIPTION OF THE INVENTION

The nicotinic acid receptor agonist compounds of the present invention are useful for treating conditions such as metabolic syndrome, dyslipidemia, cardiovascular diseases, disorders of the peripheral and central nervous system, hematological diseases, cancer, inflammation, respiratory diseases, gastroenterological diseases, diabetes, hepatic steatosis, and non-alcoholic fatty liver disease. One or more compounds of the present invention can be administered alone or in combination with one or more other therapeutic agents as described herein.

In a first embodiment, the present invention is directed to a compound of Formula (I), or a pharmaceutically acceptable salt, solvate, ester, or tautomer thereof, as described herein.

In another embodiment of the compounds of Formula (I), or a pharmaceutically acceptable salt, solvate, ester, or tautomer thereof, $R^1$ is selected from the group consisting of H, $R^4$, $(C_1-C_6)$haloalkyl, —$(C_1-C_6)$alkylene-$R^4$, —$(C_1-C_6)$alkylene-$R^5$, —$(C_1-C_6)$alkylene-$R^6$, $(C_1-C_6)$alkenyl, $(C_1-C_6)$alkynyl, and —$(C_1-C_6)$alkylene-O—$(C_1-C_6)$alkyl;

$R^2$ is selected from the group consisting of $R^7$, $(C_1-C_6)$alkyl, $(C_1-C_6)$haloalkyl, —$(C_1-C_6-)$alkylene-$R^5$, $R^4$, $R^5$, $R^6$, $R^7$ and —$(C_1-C_6)$alkylene-O—$R^8$;

$R^3$ is selected from the group consisting of $(C_1-C_6)$alkyl, $(C_1-C_6)$haloalkyl, —$(C_1-C_6-)$alkylene-$R^5$, $R^4$, $R^5$, $R^6$, and $R^7$; or $R^2$ and $R^3$ together with the carbon atom to which they are both attached form a $(C_3-C_{10})$cycloalkyl or $(C_2-C_{10})$heterocycloalkyl ring, wherein said $(C_3-C_{10})$cycloalkyl or $(C_2-C_{10})$heterocycloalkyl ring is unsubstituted or substituted with one or more $X^5$ groups.

$R^4$ is unsubstituted $(C_3-C_{10})$cycloalkyl or $(C_3-C_{10})$cycloalkyl substituted with one or more $X^1$ groups;

$R^5$ is unsubstituted $(C_6-C_{14})$aryl and $(C_6-C_{14})$aryl substituted with one or more $X^2$ groups;

$R^6$ is selected from the group consisting of unsubstituted $(C_2-C_{10})$heteroaryl and $(C_2-C_{10})$heteroaryl substituted with one or more $X^3$ groups;

$R^7$ is unsubstituted $(C_2-C_{10})$heterocycloalkyl and $(C_2-C_{10})$heterocycloalkyl substituted with one or more $X^4$ groups;

$R^8$ is selected from the group consisting of H, $(C_1-C_6)$alkyl, $R^4$, $R^5$, $R^6$, $R^7$, —C(O)—$(C_1-C_6)$ alkyl, —C(O)—$R^5$ each $R^9$ is independently selected from the group consisting of H, $(C_1-C_6)$alkyl, $R^4$, $R^5$, $R^6$, and $R^7$;

$R^{10}$ is selected from the group consisting of $R^9$, —C(O)—$(C_1-C_6)$alkyl, and —C(O)—$R^5$;

Y is —O— or —N($R^{10}$)—;

each $X^1$ is independently selected from the group consisting of halogen, $(C_1-C_6)$alkyl, —O—$(C_1-C_6)$alkyl, —OH, $(C_1-C_6)$haloalkyl, $(C_6-C_{14})$aryl, and $(C_1-C_6)$alkyne;

each $X^2$ is independently selected from the group consisting of halogen, $(C_1-C_6)$alkyl, —O—$(C_1-C_6)$alkyl, —OH, $(C_1-C_6)$haloalkyl, $(C_6-C_{14})$aryl, and $(C_1-C_6)$alkyne;

each $X^3$ is independently selected from the group consisting of halogen, $(C_1-C_6)$alkyl, and N-oxide;

each $X^4$ is independently selected form the group consisting of $(C_1-C_6)$alkyl, $R^5$, —C(O)—$(C_1-C_6)$alkyl, —C(O)—$R^5$, —C(O)—O—$(C_1-C_6)$alkyl, —$(C_1-C_6-)$alkylene-$R^5$, $R^4$, and —S(O$_2$)—$(C_1-C_6)$alkyl; and each $X^5$ is independently selected from the group consisting of $(C_1-C_6)$alkyl, a fused $(C_6-C_{14})$aryl ring, —C(O)—$(C_1-C_6)$alkyl, a fused $(C_2-C_{10})$heteroaryl ring, —C(O)—O—$(C_1-C_6)$alkyl, —C(O)—$R^5$, —S(O$_2$)—$(C_1-C_6)$alkyl, —C(O)—N($R^9$)$_2$, $R^5$, $R^6$, —C(O)—$R^4$, —C(O)—O—$R^4$, —S(O$_2$)—$R^4$, —S(O$_2$)—$(C_1-C_6)$alkylene-$R^4$, —S(O$_2$)—$(C_1-C_6-)$alkylene-$R^5$, —N($R^9$)—C(O)—O—$(C_1-C_6)$alkyl, —N($R^9$)—C(O)—O—$R^4$, —N($R^9$)—C(O)—N($R^9$)$_2$ and —N($R^9$)$_2$;

wherein said fused $(C_6-C_{14})$aryl ring of $X^5$ is unsubstituted or independently substituted with one or more substitutent selected from —$(C_1-C_6)$alkylene-$R^7$ or $X^2$, and said fused $(C_2-C_{10})$heteroaryl ring of $X^5$ is unsubstituted or substituted with one or more $X^3$ groups.

In one embodiment, $R^1$ is alkyl.

In another embodiment, $R^1$ is -alkylene-cycloalkyl.

In another embodiment, $R^1$ is haloalkyl.

In still another embodiment, $R^1$ is -alkylene-O-alkyl.

In yet another embodiment, $R^1$ is —(CH$_2$)$_3$CF$_3$.

In another embodiment, $R^1$ is n-butyl, n-pentyl, n-hexyl, isopentyl, isohexyl or neoheptyl.

In a further embodiment, $R^1$ is —(CH$_2$)$_2$-cyclopropyl, —(CH$_2$)$_3$-cyclopropyl, —(CH$_2$)$_4$-cyclopropyl, —(CH$_2$)$_2$-cyclobutyl, —(CH$_2$)$_2$-cyclopentyl, —CH$_2$-cyclohexyl, —(CH$_2$)$_2$-cyclohexyl or

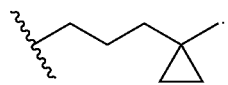

In another embodiment, $R^1$ is —(CH$_2$)$_3$—O—(CH$_2$)$_2$CH$_3$.

In one embodiment, $R^2$, $R^3$ and the carbon atom to which they are both attached, combined to form a monocyclic cycloalkyl group.

In another embodiment, $R^2$, $R^3$ and the carbon atom to which they are both attached, combined to form a bicyclic cycloalkyl group.

In another embodiment, $R^2$, $R^3$ and the carbon atom to which they are both attached, combined to form a monocyclic hetercycloalkyl group.

In still another embodiment, $R^2$, $R^3$ and the carbon atom to which they are both attached, combined to form a bicyclic hetercycloalkyl group.

In yet another embodiment, $R^2$, $R^3$ and the carbon atom to which they are both attached, combined to form a cyclopentyl or cyclohexyl group.

In another embodiment, $R^2$, $R^3$ and the carbon atom to which they are both attached, combined to form a decahydronaphtyl, 1,2,3,4-tetrahydronaphthyl, bicyclo[2.2.2]octyl or spiro[2.5]octyl group.

In a further embodiment, $R^2$, $R^3$ and the carbon atom to which they are both attached, combined to form a piperidinyl, tetrahydropyranyl, tetrahydrothiopyranyl or tetrahydrothiopyranyl-1,1,-dioxide group In another embodiment, $R^2$, $R^3$ and the carbon atom to which they are both attached, combined to form a 8-aza-bicyclo[3.2.1]octyl, 1,4-dioxa-spiro[4.5]decanyl, 4,5,6,7-tetrahydro-benzo[b]thiophenyl, 5,6,7,8-tetrahydroquinolinyl or 1,3-diaza-spiro[4.5]decanyl-2,4,-dione group.

In one embodiment, $R^1$ is alkyl, and $R^2$, $R^3$ and the carbon atom to which they are both attached, combined to form a monocyclic cycloalkyl group.

In another embodiment, $R^1$ is alkyl, and $R^2$, $R^3$ and the carbon atom to which they are both attached, combined to form a bicyclic cycloalkyl group.

In another embodiment, $R^1$ is alkyl, and $R^2$, $R^3$ and the carbon atom to which they are both attached, combined to form a monocyclic heterocycloalkyl group.

In still another embodiment, $R^1$ is alkyl, and $R^2$, $R^3$ and the carbon atom to which they are both attached, combined to form a bicyclic heterocycloalkyl group.

In one embodiment, $R^1$ is haloalkyl, and $R^2$, $R^3$ and the carbon atom to which they are both attached, combined to form a monocyclic cycloalkyl group.

In another embodiment, $R^1$ is haloalkyl, and $R^2$, $R^3$ and the carbon atom to which they are both attached, combined to form a bicyclic cycloalkyl group.

In another embodiment, $R^1$ is haloalkyl, and $R^2$, $R^3$ and the carbon atom to which they are both attached, combined to form a monocyclic heterocycloalkyl group.

In still another embodiment, $R^1$ is haloalkyl, and $R^2$, $R^3$ and the carbon atom to which they are both attached, combined to form a bicyclic heterocycloalkyl group.

In one embodiment, $R^1$ is -alkylene-cycloalkyl, and $R^2$, $R^3$ and the carbon atom to which they are both attached, combined to form a monocyclic cycloalkyl group.

In another embodiment, $R^1$ is -alkylene-cycloalkyl, and $R^2$, $R^3$ and the carbon atom to which they are both attached, combined to form a bicyclic cycloalkyl group.

In another embodiment, $R^1$ is -alkylene-cycloalkyl, and $R^2$, $R^3$ and the carbon atom to which they are both attached, combined to form a monocyclic heterocycloalkyl group.

In still another embodiment, $R^1$ is -alkylene-cycloalkyl, and $R^2$, $R^3$ and the carbon atom to which they are both attached, combined to form a bicyclic heterocycloalkyl group.

In one embodiment, $R^1$ is -alkylene-O-alkyl, and $R^2$, $R^3$ and the carbon atom to which they are both attached, combined to form a monocyclic cycloalkyl group.

In another embodiment, $R^1$ is -alkylene-O-alkyl, and $R^2$, $R^3$ and the carbon atom to which they are both attached, combined to form a bicyclic cycloalkyl group.

In another embodiment, $R^1$ is -alkylene-O-alkyl, and $R^2$, $R^3$ and the carbon atom to which they are both attached, combined to form a monocyclic heterocycloalkyl group.

In still another embodiment, $R^1$ is -alkylene-O-alkyl, and $R^2$, $R^3$ and the carbon atom to which they are both attached, combined to form a bicyclic heterocycloalkyl group.

In another embodiment of the compounds of Formula (I), or a pharmaceutically acceptable salt, solvate, ester, or tautomer thereof, $R^1$ is alkyl and Y is —O—.

In another embodiment of the compounds of Formula (I), or a pharmaceutically acceptable salt, solvate, ester, or tautomer thereof, $R^1$ is alkyl and Y is —N($R^{10}$)—.

In another embodiment of the compounds of Formula (I), or a pharmaceutically acceptable salt, solvate, ester, or tautomer thereof, $R^1$ is -alkylene-$R^4$.

In another embodiment of the compounds of Formula (I), or a pharmaceutically acceptable salt, solvate, ester, or tautomer thereof, $R^1$ is -alkylene-$R^4$ and Y is —O—.

In another embodiment of the compounds of Formula (I), or a pharmaceutically acceptable salt, solvate, ester, or tautomer thereof, $R^1$ is -alkylene-$R^4$ and Y is —N($R^{10}$)—.

In another embodiment of the compounds of Formula (I), or a pharmaceutically acceptable salt, solvate, ester, or tautomer thereof, $R^1$ is -alkylene-$R^5$.

In another embodiment of the compounds of Formula (I), or a pharmaceutically acceptable salt, solvate, ester, or tautomer thereof, $R^1$ is -alkylene-$R^5$ and Y is —O—.

In another embodiment of the compounds of Formula (I), or a pharmaceutically acceptable salt, solvate, ester, or tautomer thereof, $R^1$ is -alkylene-$R^5$ and Y is —N($R^{10}$)—.

In another embodiment of the compounds of Formula (I), or a pharmaceutically acceptable salt, solvate, ester, or tautomer thereof, $R^1$ is -alkylene-$R^6$.

In another embodiment of the compounds of Formula (I), or a pharmaceutically acceptable salt, solvate, ester, or tautomer thereof, $R^1$ is -alkylene-$R^6$ and Y is —O—.

In another embodiment of the compounds of Formula (I), or a pharmaceutically acceptable salt, solvate, ester, or tautomer thereof, $R^1$ is -alkylene-$R^6$ and Y is —N($R^{10}$)—.

In another embodiment of the compounds of Formula (I), or a pharmaceutically acceptable salt, solvate, ester, or tautomer thereof, $R^1$ is $R^1$ is alkyl; $R^2$ and $R^3$ are each independently selected from the group consisting of alkyl, haloalkyl, -alkylene-$R^5$, $R^4$, $R^5$, $R^6$, and $R^7$.

In another embodiment of the compounds of Formula (I), or a pharmaceutically acceptable salt, solvate, ester, or tautomer thereof, $R^1$ is $R^1$ is alkyl; $R^2$ and $R^3$ are each independently selected from the group consisting of alkyl, haloalkyl, -alkylene-$R^5$, $R^4$, $R^5$, $R^6$, and $R^7$; and Y is —O—.

In another embodiment of the compounds of Formula (I), or a pharmaceutically acceptable salt, solvate, ester, or tautomer thereof, $R^1$ is alkyl; $R^2$ and $R^3$ are each independently selected from the group consisting of alkyl, haloalkyl, -alkylene-$R^5$, $R^4$, $R^5$, $R^6$, and $R^7$; and Y is —N($R^{10}$)—.

In another embodiment of the compounds of Formula (I), or a pharmaceutically acceptable salt, solvate, ester, or tautomer thereof, $R^1$ is haloalkyl; and $R^2$ and $R^3$ are each independently selected from the group consisting of alkyl, haloalkyl, -alkylene-$R^5$, $R^4$, $R^5$, $R^6$, and $R^7$.

In another embodiment of the compounds of Formula (I), or a pharmaceutically acceptable salt, solvate, ester, or tautomer thereof, $R^1$ is haloalkyl; $R^2$ and $R^3$ are each independently selected from the group consisting of alkyl, haloalkyl, -alkylene-$R^5$, $R^4$, $R^5$, $R^6$, and $R^7$; and Y is —O—.

In another embodiment of the compounds of Formula (I), or a pharmaceutically acceptable salt, solvate, ester, or tautomer thereof, $R^1$ is haloalkyl; $R^2$ and $R^3$ are each independently selected from the group consisting of alkyl, haloalkyl, -alkylene-$R^5$, $R^4$, $R^5$, $R^6$, and $R^7$; and Y is —N($R^{10}$)—.

In another embodiment of the compounds of Formula (I), or a pharmaceutically acceptable salt, solvate, ester, or tautomer thereof, $R^1$ is -alkylene-$R^4$; and $R^2$ and $R^3$ are each independently selected from the group consisting of alkyl, haloalkyl, -alkylene-$R^5$, $R^4$, $R^5$, $R^6$, and $R^7$.

In another embodiment of the compounds of Formula (I), or a pharmaceutically acceptable salt, solvate, ester, or tautomer thereof, $R^1$ is -alkylene-$R^4$; $R^2$ and $R^3$ are each independently selected from the group consisting of alkyl, haloalkyl, -alkylene-$R^5$, $R^4$, $R^5$, $R^6$, and $R^7$; and Y is —O—.

In another embodiment of the compounds of Formula (I), or a pharmaceutically acceptable salt, solvate, ester, or tautomer thereof, $R^1$ is -alkylene-$R^4$; $R^2$ and $R^3$ are each independently selected from the group consisting of alkyl, haloalkyl, -alkylene-$R^5$, $R^4$, $R^5$, $R^6$, and $R^7$; and Y is —N($R^{10}$)—.

In another embodiment of the compounds of Formula (I), or a pharmaceutically acceptable salt, solvate, ester, or tautomer thereof, $R^1$ is -alkylene-$R^5$; and $R^2$ and $R^3$ are each independently selected from the group consisting of alkyl, haloalkyl, -alkylene-$R^5$, $R^4$, $R^5$, $R^6$, and $R^7$.

In another embodiment of the compounds of Formula (I), or a pharmaceutically acceptable salt, solvate, ester, or tautomer thereof, $R^1$ is -alkylene-$R^5$; $R^2$ and $R^3$ are each independently selected from the group consisting of alkyl, haloalkyl, -alkylene-$R^5$, $R^4$, $R^5$, $R^6$, and $R^7$; and Y is —O—.

In another embodiment of the compounds of Formula (I), or a pharmaceutically acceptable salt, solvate, ester, or tautomer thereof, $R^1$ is -alkylene-$R^5$; $R^2$ and $R^3$ are each independently selected from the group consisting of alkyl, haloalkyl, -alkylene-$R^5$, $R^4$, $R^5$, $R^6$, and $R^7$; and Y is —N($R^{10}$)—.

In another embodiment of the compounds of Formula (I), or a pharmaceutically acceptable salt, solvate, ester, or tautomer thereof, $R^1$ is -alkylene-$R^6$; and $R^2$ and $R^3$ are each independently selected from the group consisting of alkyl, haloalkyl, -alkylene-$R^5$, $R^4$, $R^5$, $R^6$, and $R^7$.

In another embodiment of the compounds of Formula (I), or a pharmaceutically acceptable salt, solvate, ester, or tautomer thereof, $R^1$ is -alkylene-$R^6$; $R^2$ and $R^3$ are each independently selected from the group consisting of alkyl, haloalkyl, -alkylene-$R^5$, $R^4$, $R^5$, $R^6$, and $R^7$; and Y is —O—.

In another embodiment of the compounds of Formula (I), or a pharmaceutically acceptable salt, solvate, ester, or tautomer thereof, $R^1$ is -alkylene-$R^6$; $R^2$ and $R^3$ are each independently selected from the group consisting of alkyl, haloalkyl, -alkylene-$R^5$, $R^4$, $R^5$, $R^6$, and $R^7$; and Y is —N($R^{10}$)—.

In another embodiment of the compounds of Formula (I), or a pharmaceutically acceptable salt, solvate, ester, or tautomer thereof, $R^1$ is alkyl; and $R^2$ and $R^3$ together with the carbon atom to which they are both attached form a cycloalkyl ring, wherein said cycloalkyl ring is unsubstituted or substituted with one or more $X^1$ groups.

In another embodiment of the compounds of Formula (I), or a pharmaceutically acceptable salt, solvate, ester, or tautomer thereof, $R^1$ is alkyl; $R^2$ and $R^3$ together with the carbon atom to which they are both attached form a cycloalkyl ring, wherein said cycloalkyl ring is unsubstituted or substituted with one or more $X^1$ groups; and Y is —O—.

In another embodiment of the compounds of Formula (I), or a pharmaceutically acceptable salt, solvate, ester, or tautomer thereof, $R^1$ is alkyl; $R^2$ and $R^3$ together with the carbon atom to which they are both attached form a cycloalkyl ring, wherein said cycloalkyl ring is unsubstituted or substituted with one or more $X^1$ groups; and Y is —N($R^{10}$)—.

In another embodiment of the compounds of Formula (I), or a pharmaceutically acceptable salt, solvate, ester, or tautomer thereof, $R^1$ is alkyl; and $R^2$ and $R^3$ together with the carbon atom to which they are both attached form a heterocycloalkyl ring, wherein said heterocycloalkyl ring is unsubstituted or substituted with one or more $X^4$ groups.

In another embodiment of the compounds of Formula (I), or a pharmaceutically acceptable salt, solvate, ester, or tautomer thereof, $R^1$ is alkyl; $R^2$ and $R^3$ together with the carbon atom to which they are both attached form a heterocycloalkyl ring, wherein said heterocycloalkyl ring is unsubstituted or substituted with one or more $X^4$ groups; and Y is —O—.

In another embodiment of the compounds of Formula (I), or a pharmaceutically acceptable salt, solvate, ester, or tautomer thereof, $R^1$ is alkyl; $R^2$ and $R^3$ together with the carbon atom to which they are both attached form a heterocycloalkyl ring, wherein said heterocycloalkyl ring is unsubstituted or substituted with one or more $X^4$ groups; and Y is —N($R^{10}$)—.

In another embodiment of the compounds of Formula (I), or a pharmaceutically acceptable salt, solvate, ester, or tautomer thereof, $R^1$ is —$CH_2CH_3$, —$CH_2CH_2CH_2CH_3$, —$CH_2CH_2CH_2CH_2CH_3$, —$CH_2CH_2CH(CH_3)_2$, or —$CH_2CH_2CH_2$-cyclopropyl; $R^2$ and $R^3$ are each independently selected from the group consisting of —$CH_3$, —$CH_2CH_3$, —$CH_2CH_2CH_3$, —$CH_2CH_2CH_2CH_3$, —$CH_2C(CH_3)_3$, —$CH_2CH_2CF_3$, —$CH_2CH_2$—$R^5$, cyclopropyl, piperazinyl, piperidinyl, morpholinyl, phenyl, thiophenyl, pyridyl, and thiazolyl; and $R^5$ is phenyl.

In another embodiment of the compounds of Formula (I), or a pharmaceutically acceptable salt, solvate, ester, or tautomer thereof, $R^1$ is —$CH_2CH_3$, —$CH_2CH_2CH_2CH_3$, —$CH_2CH_2CH_2CH_2CH_3$, —$CH_2CH_2CH(CH_3)_2$, or —$CH_2CH_2CH_2$-cyclopropyl; $R^2$ and $R^3$ are each independently selected from the group consisting of —$CH_3$, —$CH_2CH_3$, —$CH_2CH_2CH_3$, —$CH_2CH_2CH_2CH_3$, —$CH_2C(CH_3)_3$, —$CH_2CH_2CF_3$, —$CH_2CH_2$—$R^5$, cyclopropyl, piperazinyl, piperidinyl, morpholinyl, phenyl, thiophenyl, pyridyl, and thiazolyl; and $R^5$ is phenyl; and Y is —O—.

In another embodiment of the compounds of Formula (I), or a pharmaceutically acceptable salt, solvate, ester, or tautomer thereof, $R^1$ is —$CH_2CH_3$, —$CH_2CH_2CH_2CH_3$, —$CH_2CH_2CH_2CH_2CH_3$, —$CH_2CH_2CH(CH_3)_2$, or —$CH_2CH_2CH_2$-cyclopropyl; $R^2$ and $R^3$ are each independently selected from the group consisting of —$CH_3$, —$CH_2CH_3$, —$CH_2CH_2CH_3$, —$CH_2CH_2CH_2CH_3$, —$CH_2C(CH_3)_3$, —$CH_2CH_2CF_3$, —$CH_2CH_2$—$R^5$, cyclopropyl, piperazinyl, piperidinyl, morpholinyl, phenyl, thiophenyl, pyridyl, and thiazolyl; and $R^5$ is phenyl; and Y is —N($R^{10}$)—.

In another embodiment of the compounds of Formula (I), or a pharmaceutically acceptable salt, solvate, ester, or tautomer thereof, $R^1$ is —$CH_2CH_3$, —$CH_2CH_2CH_2CH_3$, —$CH_2CH_2CH_2CH_2CH_3$, or —$CH_2CH_2CH(CH_3)_2$; $R^2$ and $R^3$ together with the carbon atom to which they are both attached form a cycloalkyl or heterocycloalkyl group selected from:

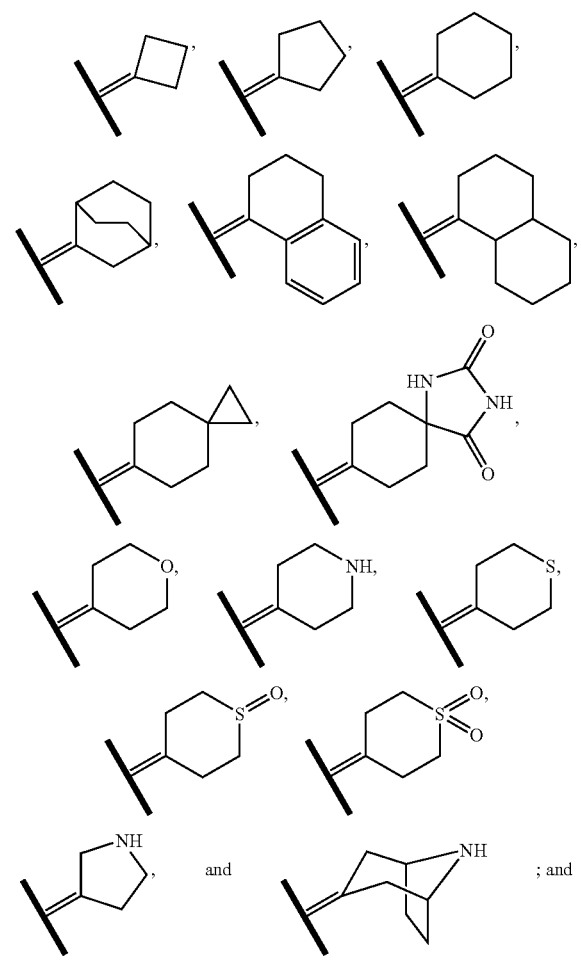

each of said cycloalkyl or heterocycloalkyl rings is unsubstituted or substituted with one or more $X^4$ groups.

In another embodiment of the compounds of Formula (I), or a pharmaceutically acceptable salt, solvate, ester, or tautomer thereof, $R^1$ is —$CH_2CH_3$, —$CH_2CH_2CH_2CH_3$, —$CH_2CH_2CH_2CH_2CH_3$, or —$CH_2CH_2CH(CH_3)_2$; $R^2$ and $R^3$ together with the carbon atom to which they are both attached form a cycloalkyl or heterocycloalkyl group selected from:

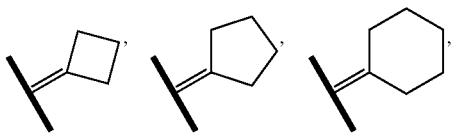

-continued

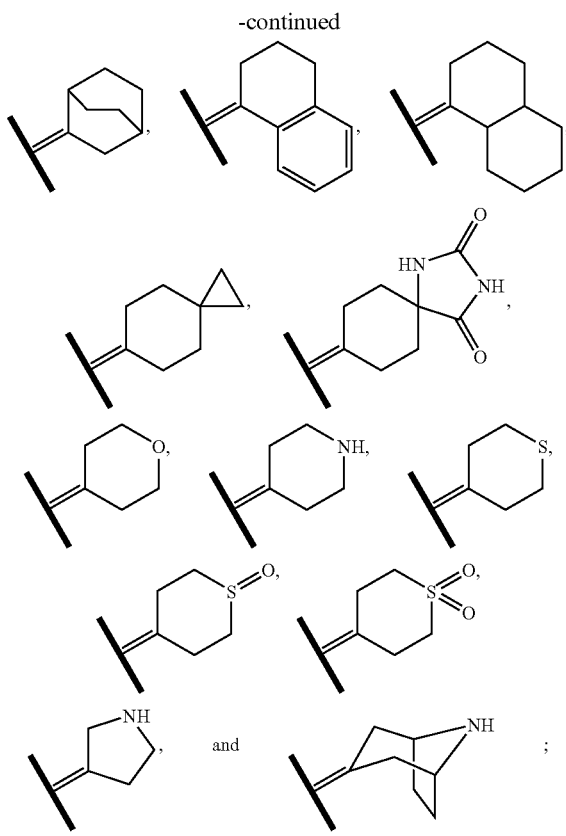

each of said cycloalkyl or heterocycloalkyl rings is unsubstituted or substituted with one or more $X^4$ groups; and Y is —O—.

In another embodiment of the compounds of Formula (I), or a pharmaceutically acceptable salt, solvate, ester, or tautomer thereof, $R^1$ is —$CH_2CH_3$, —$CH_2CH_2CH_2CH_3$, —$CH_2CH_2CH_2CH_2CH_3$, or —$CH_2CH_2CH(CH_3)_2$; $R^2$ and $R^3$ together with the carbon atom to which they are both attached form a cycloalkyl or heterocycloalkyl selected from the group consisting of:

each of said cycloalkyl or heterocycloalkyl rings is unsubstituted or substituted with one or more $X^4$ groups; and Y is —$N(R^{10})$—.

In another embodiment of the compounds of Formula (I), or a pharmaceutically acceptable salt, solvate, ester, or tautomer thereof, $R^1$ is $R^1$ is —$CH_2CH_2CH_2CF_3$, —$CH_2CH_2$—$R^4$, —$CH_2CH_2CH_2$—$R^4$, —$CH_2$—$R^5$, or —$CH_2$—$R^6$.

In another embodiment of the compounds of Formula (I), or a pharmaceutically acceptable salt, solvate, ester, or tautomer thereof, $R^1$ is $R^1$ is —$CH_2CH_2CH_2CF_3$, —$CH_2CH_2$—$R^4$, —$CH_2CH_2CH_2$—$R^4$, —$CH_2$—$R^5$, or —$CH_2$—$R^6$; and Y is —O—.

In another embodiment of the compounds of Formula (I), or a pharmaceutically acceptable salt, solvate, ester, or tautomer thereof, $R^1$ is —$CH_2CH_2CH_2CF_3$, —$CH_2CH_2$—$R^4$, —$CH_2CH_2CH_2$—$R^4$, —$CH_2$—$R^5$, or —$CH_2$—$R^6$; and Y is —$N(R^{10})$—.

In another embodiment of the compounds of Formula (I), or a pharmaceutically acceptable salt, solvate, ester, or tautomer thereof, $R^1$ is —$CH_2CH_2CH_2CF_3$, —$CH_2CH_2$—$R^4$, —$CH_2CH_2CH_2$—$R^4$, —$CH_2$—$R^5$, or —$CH_2$—$R^6$; $R^2$ and $R^3$ together with the carbon atom to which they are both attached form a cycloalkyl or heterocycloalkyl group selected from:

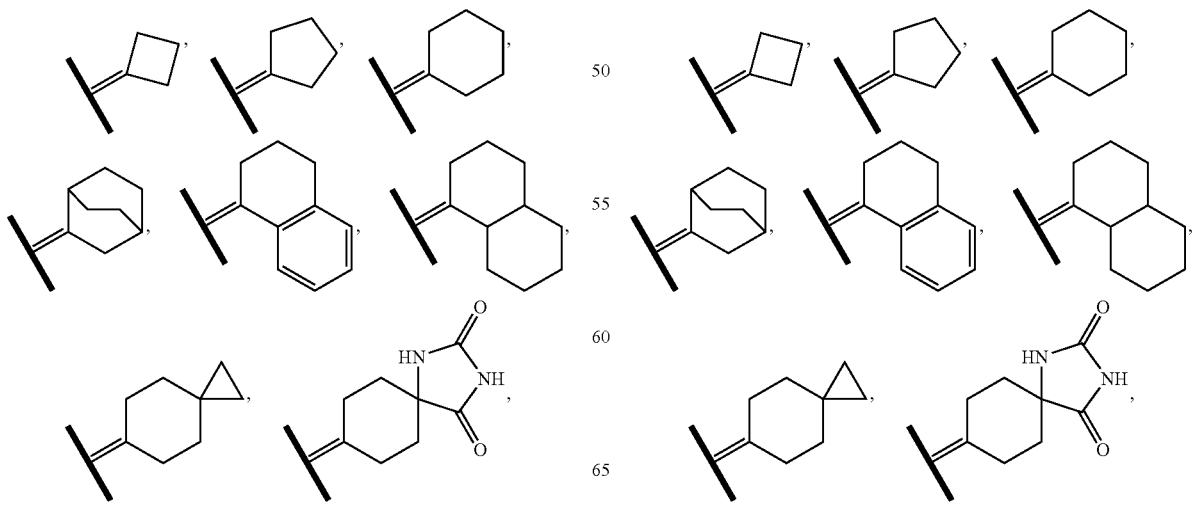

-continued

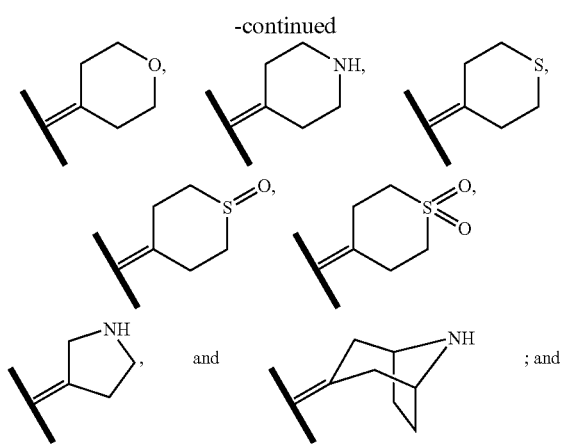

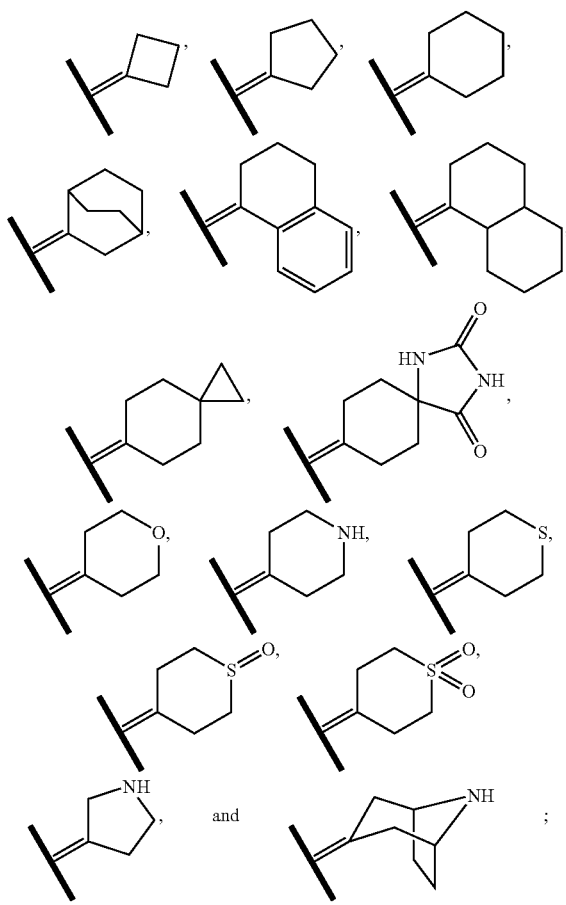

each of said cycloalkyl or heterocycloalkyl rings is unsubstituted or substituted with one or more $X^4$ groups.

In another embodiment of the compounds of Formula (I), or a pharmaceutically acceptable salt, solvate, ester, or tautomer thereof, $R^1$ is —$CH_2CH_2CH_2CF_3$, —$CH_2CH_2$—$R^4$, —$CH_2CH_2CH_2$—$R^4$, —$CH_2$—$R^5$, or —$CH_2$—$R^6$; $R^2$ and $R^3$ together with the carbon atom to which they are both attached form a cycloalkyl or heterocycloalkyl group selected from:

each of said cycloalkyl or heterocycloalkyl rings is unsubstituted or substituted with one or more $X^4$ groups; and Y is —O—.

In another embodiment of the compounds of Formula (I), or a pharmaceutically acceptable salt, solvate, ester, or tautomer thereof, $R^1$ is —$CH_2CH_2CH_2CF_3$, —$CH_2CH_2$—$R^4$, —$CH_2CH_2CH_2$—$R^4$, —$CH_2$—$R^5$, or —$CH_2$—$R^6$; $R^2$ and $R^3$ together with the carbon atom to which they are both attached form a cycloalkyl or heterocycloalkyl group selected from:

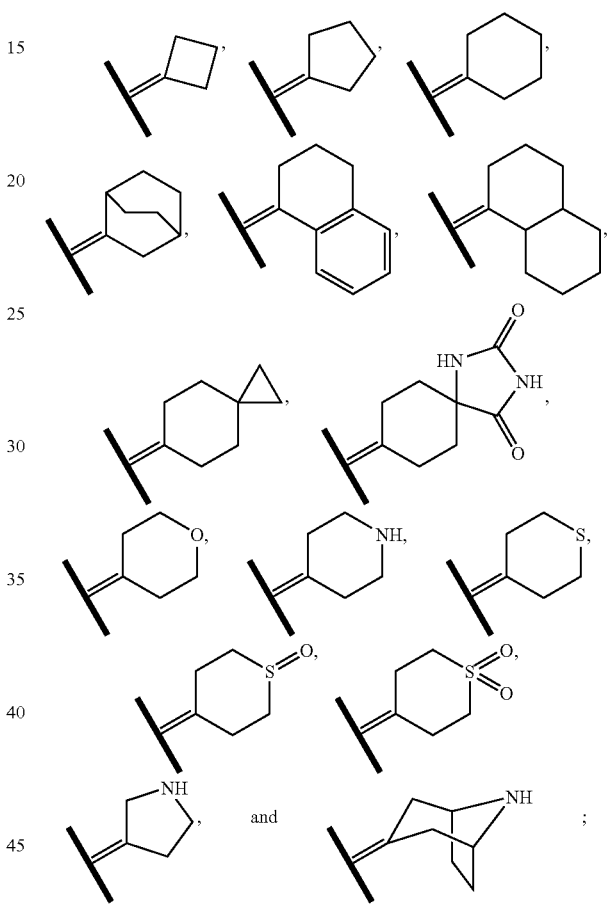

each of said cycloalkyl or heterocycloalkyl rings is unsubstituted or substituted with one or more $X^4$ groups; and Y is —$N(R^{10})$—.

In another embodiment of the compounds of Formula (I), or a pharmaceutically acceptable salt, solvate, ester, or tautomer thereof, $R^1$ is —$CH_2CH_2CH_2CF_3$ or —$CH_2CH_2$—$R^4$; and $R^2$ and $R^3$ are each independently selected from the group consisting of —$CH_3$, —$CH_2CH_3$, —$CH_2CH_2CH_3$, —$CH_2CH_2CH_2CH_3$, —$CH_2C(CH_3)_3$, —$CH_2CH_2CF_3$, —$CH_2CH_2$—$R^5$, cyclopropyl, piperazinyl, piperidinyl, morpholinyl, phenyl, thiophenyl, pyridyl, and thiazolyl.

In another embodiment of the compounds of Formula (I), or a pharmaceutically acceptable salt, solvate, ester, or tautomer thereof, $R^1$ is —$CH_2CH_2CH_2CF_3$ or —$CH_2CH_2$—$R^4$; $R^2$ and $R^3$ are each independently selected from the group consisting of —$CH_3$, —$CH_2CH_3$, —$CH_2CH_2CH_3$, —$CH_2CH_2CH_2CH_3$, —$CH_2C(CH_3)_3$, —$CH_2CH_2CF_3$, —$CH_2CH_2$—$R^5$, cyclopropyl, piperazinyl, piperidinyl, morpholinyl, phenyl, thiophenyl, pyridyl, and thiazolyl; and Y is —O—.

In another embodiment of the compounds of Formula (I), or a pharmaceutically acceptable salt, solvate, ester, or tautomer thereof, $R^1$ is —$CH_2CH_2CH_2CF_3$ or —$CH_2CH_2$—$R^4$; $R^2$ and $R^3$ are each independently selected from the group consisting of —$CH_3$, —$CH_2CH_3$, —$CH_2CH_2CH_3$, —$CH_2CH_2CH_2CH_3$, —$CH_2C(CH_3)_3$, —$CH_2CH_2CF_3$, —$CH_2CH_2$—$R^5$, cyclopropyl, piperazinyl, piperidinyl, morpholinyl, phenyl, thiophenyl, pyridyl, and thiazolyl; and Y is —$N(R^{10})$—.

In yet another embodiment, the present invention is directed to a composition comprising compound of Formula (I), or a pharmaceutically acceptable salt, solvate, ester, or tautomer thereof, in combination with at least one additional therapeutic agent selected from the group consisting of hydroxy-substituted azetidinone compounds, substituted β-lactam compounds, HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, inorganic cholesterol sequestrants, AcylCoA:Cholesterol O-acyltransferaseinhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, leptin derivatives, opioid antagonists, orexin receptor antagonists, BRS3 agonists, CCK-A agonists, CNTF, CNTF derivatives, CNTF agonists/modulators, 5HT2c agonists, Mc4r agonists, monoamine reuptake inhibitors, serotonin reuptake inhibitors, GLP-1 agonists, phentermine, topiramate, phytopharm compound 57, ghrelin antibodies, Mc3r agonists, ACC inhibitors, β3 agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanocyte-stimulating hormone receptor analogs, melanin concentrating hormone antagonists, leptons, galanin receptor antagonists, bombesin agonists, neuropeptide-Y antagonists, thyromimetic agents, dehydroepiandrosterone, analogs of dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, MSH-receptor analogs, α-glucosidase inhibitors, apo A1 milano reverse cholesterol transport inhibitors, fatty acid binding protein inhibitors (FABP), and fatty acid transporter protein inhibitors (FATP).

In yet another embodiment, the present invention is directed to a composition comprising compound of Formula (I), or a pharmaceutically acceptable salt, solvate, ester, or tautomer thereof, in combination with a HMG CoA synthetase inhibitor selected from the group consisting of lovastatin, simvastatin, pravastatin, atorvastatin, fluvastatin, cerivastatin, rivastatin, rosuvastatin calcium, and pitavastatin.

In yet another embodiment, the present invention is directed to a composition comprising compound of Formula (I), or a pharmaceutically acceptable salt, solvate, ester, or tautomer thereof, in combination with simvastatin.

In yet another embodiment, the present invention is directed to a composition comprising compound of Formula (I), or a pharmaceutically acceptable salt, solvate, ester, or tautomer thereof, in combination with a cholesteryl ester transfer protein inhibitor.

In yet another embodiment, the present invention is directed to a composition comprising compound of Formula (I), or a pharmaceutically acceptable salt, solvate, ester, or tautomer thereof, in combination with torcetrapib.

In still another embodiment, the present invention is directed to a method of treating a disease, disorder, or condition with a compound of Formula (I), or a composition comprising a compound of Formula (I) together with at least one addition therapeutic agent, for example one of the therapeutic agents, or classes of therapeutic agents described herein. The diseases, disorders, or conditions which may be treated with the compound or compositions of the present invention include metabolic syndrome, dyslipidemia, cardiovascular diseases, disorders of the peripheral and central nervous system, hematological diseases, cancer, inflammation, respiratory diseases, gastroenterological diseases, diabetes, and non-alcoholic fatty liver disease.

$R^1$ is selected from the group consisting of H, $R^4$, haloalkyl, -alkylene-$R^4$, -alkylene-$R^5$, -alkylene-$R^6$, alkenyl, alkynyl, and -alkylene-O-alkyl. When $R^1$ is $R^4$, non-limiting examples of $R^4$ groups can include, for example, any of the $R^4$ groups described below. Likewise, when $R^1$ is -alkylene-$R^4$, -alkylene-$R^5$, or -alkylene-$R^6$, non-limiting examples of the $R^4$, $R^5$, or $R^6$ portion thereof can include, for example, any of the $R^4$, $R^5$, or $R^6$ groups described below. In addition, non-limiting examples of the "alkylene" portion thereof can include, for example, —$CH_2$—, —$CH_2CH_2$—, —$CH(CH_3)$—, —$CH_2CH_2CH_2$—, —$CH(CH_3)CH_2$—, —$CH_2CH(CH_3)$—, —$CH_2CH_2CH_2CH_2$—, etc. When $R^1$ is haloalkyl, non-limiting examples of suitable haloalkyl groups include —$CF_3$, —$CH_2CF_3$, —$CH_2F$, —$CF_2H$, etc. When $R^1$ is alkenyl, non-limiting examples of suitable alkenyl groups include —$CH_2CH=CH_2$, —$CH_2CH_2CH=CH_2$, —$CH_2CH=CH(CH_3)$, —$CH_2CH=C(CH_3)_2$, etc. When $R^1$ is alkynyl, non-limiting examples of suitable alkynyl groups include —$CH_2CH_2C\equiv CH$, —$CH_2CH_2CH_2C\equiv CH$, —$CH_2CH_2C\equiv C$—$CH_3$, etc. When $R^1$ is -alkylene-O-alkyl, the alkyl and alkylene portions thereof can include, for example, any of the alkyl and alkylene groups described above, in any combination.

$R^2$ is selected from the group consisting of $R^7$, alkyl, haloalkyl, -alkylene-$R^5$, $R^4$, $R^5$, $R^6$, and -alkylene-O—$R^8$. When $R^2$ is $R^4$, $R^5$, $R^6$, or $R^7$, non-limiting examples of suitable $R^4$, $R^5$, $R^6$, or $R^7$ groups include those described below. When $R^2$ is alkyl, suitable alkyl groups include methyl, ethyl, n-propyl, 1-propyl, n-butyl, sec-butyl, t-butyl, 1-butyl, n-pentyl, neo-pentyl, iso-pentyl, etc. When $R^2$ is -alkylene-$R^5$, non-limiting examples of -alkylene-$R^5$ include those described above for $R^1$. Likewise, when $R^2$ is haloalkyl, non-limiting examples of suitable haloalkyl groups include those described above for $R^1$. When $R^2$ is -alkylene-O—$R^8$, non-limiting examples of the alkylene portion thereof include those alkylene groups described above, and non-limiting examples of the $R^8$ portion thereof includes those described below.

$R^3$ is selected from the group consisting of alkyl, haloalkyl, -alkylene-$R^5$, $R^4$, $R^5$, $R^6$, and $R^7$. When $R^3$ is $R^4$, $R^5$, $R^6$, or $R^7$, non-limiting examples of suitable $R^4$, $R^5$, $R^6$, or $R^7$ groups include those described below. When $R^3$ is -alkylene-$R^5$, non-limiting examples of -alkylene-$R^5$ include those described above for $R^1$.

$R^2$ and $R^3$ together with the carbon atom to which they are both attached form a cycloalkyl or heterocycloalkyl ring, wherein said cycloalkyl or heterocycloalkyl ring is unsubstituted or substituted with one or more $X^5$ groups. Non-limiting examples of these cycloalkyl or heterocycloalkyl groups include cyclopropyl, cyclobutyl, cyclopentyl, cyclohexyl, cycloheptyl, cyclooctyl, cyclononyl, pyrrolyl, morpholinyl, piperidinyl, piperazinyl, tetrahydrofuranyl, tetrahydropyranyl, tetrahydrothiofuranyl, tetrahydrothiopyranyl, etc.

$R^4$ is unsubstituted cycloalkyl or cycloalkyl substituted with one or more $X^1$ groups. Non-limiting examples of suitable cycloalkyl groups include those described above.

$R^5$ is unsubstituted aryl and aryl substituted with one or more $X^2$ groups. Non-limiting examples of suitable aryl groups include phenyl, naphthyl, biphenyl, etc.

$R^6$ is selected from the group consisting of unsubstituted heteroaryl and heteroaryl substituted with one or more $X^3$ groups. Non-limiting examples of suitable heteroaryl groups include, for example, pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidinyl, pyrrolopyridyl, imidazopyridyl, isoquinolinyl, benzoazaindolyl, 1,2,4-triazinyl, benzothiazolyl, etc.

$R^7$ is unsubstituted heterocycloalkyl and heterocycloalkyl substituted with one or more $X^4$ groups. Non-limiting examples of suitable heterocycloalkyl groups include piperidyl, pyrrolidinyl, piperazinyl, morpholinyl, thiomorpholinyl, thiazolidinyl, 1,4-dioxanyl, tetrahydrofuranyl, tetrahydrothiophenyl.

$R^8$ is selected from the group consisting of H, alkyl, $R^4$, $R^5$, $R^6$, $R^7$, —C(O)-alkyl, —C(O)—$R^5$. When $R^8$ is alkyl, non-limiting examples of suitable alkyl groups can include those described above for $R^2$. When $R^8$ is $R^4$, $R^5$, $R^6$, or $R^7$, non-limiting examples of suitable $R^4$, $R^5$, $R^6$, or $R^7$ groups include those described above. When $R^8$ is —C(O)-alkyl, non-limiting examples of the alkyl portion thereof include the alkyl groups described for $R^2$. When $R^8$ is —C(O)—$R^5$, non-limiting examples of $R^5$ include those described above.

Each $R^9$ is independently selected from the group consisting of H, alkyl, $R^4$, $R^5$, $R^6$, and $R^7$. Non-limiting examples of suitable alkyl groups include those described above for $R^2$. Non-limiting examples of $R^4$, $R^5$, $R^6$, or $R^7$ include any of the groups described above for $R^4$, $R^5$, $R^6$, and $R^7$.

$R^{10}$ is selected from the group consisting of $R^9$, —C(O)-alkyl, and —C(O)—$R^5$. When $R^{10}$ is $R^9$, non-limiting examples of suitable $R^9$ groups include those described above. When $R^{10}$ is —C(O)-alkyl, non-limiting examples of the alkyl portion thereof include the alkyl groups described for $R^2$. When $R^{10}$ is —C(O)—$R^5$, non-limiting examples of $R^5$ include those described above.

Y is —O— or —N($R^{10}$)—. When Y is —N($R^{10}$)—, non-limiting examples of the $R^{10}$ portion thereof include those described above.

Each $X^1$ and $X^2$ is independently selected from the group consisting of halogen, alkyl, —O-alkyl, —OH, haloalkyl, aryl, and alkyne. When $X^1$ or $X^2$ are halogen, suitable examples of halogen include F, Cl, Br, and I. When $X^1$ or $X^2$ are alkyl, non-limiting examples of suitable alkyl groups include those describe above for $R^2$. When $X^1$ or $X^2$ are —O-alkyl, non-limiting examples of the alkyl portion thereof include those described above for $R^2$. When $X^1$ or $X^2$ are haloalkyl, non-limiting examples of suitable haloalkyl groups include those described above for $R^1$. When $X^1$ or $X^2$ are aryl, non-limiting examples of suitable aryl groups include those described above for $R^5$. When $X^1$ or $X^2$ are alkyne, non-limiting examples of suitable alkynes include ethynyl, 2-propynyl, 1-propynyl, 1-butynyl, 2-butynyl, 3-butynyl, etc.

Each $X^3$ is independently selected from the group consisting of halogen, alkyl, and N-oxide. When $X^3$ is halogen, suitable examples of halogen include F, Cl, Br, and I. When $X^3$ is alkyl, non-limiting examples of suitable alkyl groups include those describe above for $R^2$.

Each $X^4$ is independently selected form the group consisting of alkyl, $R^5$, —C(O)-alkyl, —C(O)—$R^5$, —C(O)—O-alkyl, -alkylene-$R^5$, $R^4$, and —S(O$_2$)-alkyl. When $X^4$ is alkyl, non-limiting examples of suitable alkyl groups include those described above for $R^2$. When $X^4$ is $R^4$ or $R^5$, non-limiting examples of suitable $R^4$ or $R^5$ groups include those described above. When $X^4$ is —S(O$_2$)-alkyl, —C(O)-alkyl, or —C(O)—O-alkyl, non-limiting examples of the alkyl portion thereof include those described above for $R^2$. When $X^4$ is -alkylene-$R^5$, non-limiting examples of the alkylene portion thereof includes those described above for $R^1$, and the $R^5$ portion thereof includes $R^5$ groups described above.

Each $X^5$ is independently selected from the group consisting of alkyl, a fused aryl ring, —C(O)-alkyl, a fused heteroaryl ring, —C(O)—O-alkyl, —C(O)—$R^5$, —S(O$_2$)-alkyl, —C(O)—N($R^9$)$_2$, $R^5$, $R^6$, —C(O)—$R^4$, —C(O)—O—$R^4$, —S(O$_2$)—$R^4$, —S(O$_2$)-alkylene-$R^4$, —S(O$_2$)-alkylene-$R^5$, —N($R^9$)—C(O)—O-alkyl, —N($R^9$)—C(O)—O—$R^4$, —N($R^9$)—C(O)—N($R^9$)$_2$ and —N($R^9$)$_2$; wherein said fused aryl ring of $X^5$ is unsubstituted or independently substituted with one or more substitutent selected from -alkylene-$R^7$ or $X^2$, and said fused heteroaryl ring of $X^5$ is unsubstituted or substituted with one or more $X^3$ groups. When $X^5$ is alkyl, non-limiting examples of suitable alkyl groups include those described above for $R^2$. When $X^5$ is —C(O)-alkyl, —C(O)—O-alkyl, —C(O)—$R^5$, —S(O$_2$)-alkyl, —C(O)—N($R^9$)$_2$, —C(O)—$R^4$, —C(O)—O—$R^4$, —S(O$_2$)—$R^4$, —S(O$_2$)-alkylene-$R^4$, —S(O$_2$)-alkylene-$R^5$, —N($R^9$)—C(O)—O-alkyl, —N($R^9$)—C(O)—O—$R^4$, —N($R^9$)—C(O)—N($R^9$)$_2$ and —N($R^9$)$_2$, non-limiting examples of the alkyl, alkylene, $R^4$, $R^5$, and $R^9$ portions thereof include those described above.

When $X^5$ is a fused heteroaryl ring or fused aryl ring, two adjacent ring atoms of the fused heteroaryl ring or fused aryl ring are part of the cycloalkyl or heterocycloalkyl ring to which they are fused. Examples of an aryl ring fused to a cycloalkyl ring include a phenyl ring fused to a cyclopentyl ring (i.e., indanyl).

In one embodiment, the compounds of formula (I) have the formula (II):

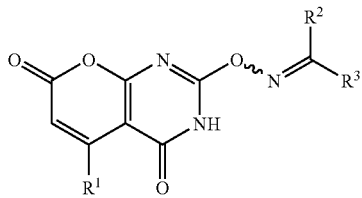

(II)

wherein
$R^1$ is alkyl, -alkylene-cycloalkyl, haloalkyl or -alkylene-O-alkyl;
$R^2$ and $R^3$ together with the carbon atom to which they are both attached, combine to form a monocyclic cycloalkyl, bicyclic cycloalkyl or monocyclic heterocycloalkyl, wherein a monocyclic cycloalkyl, bicyclic cycloalkyl or monocyclic heterocycloalkyl group is unsubstituted or optionally and independently substituted with one or more $X^5$ groups, and wherein a monocyclic cycloalkyl group may be fused to a benzene ring, an aromatic heterocycle or a non-aromatic heterocycle, and wherein the monocyclic cycloalkyl ring can form a spirocyclic compound with a second cycloalkyl ring or with a heterocycloalkyl ring, wherein the second cycloalkyl ring or the heterocycloalkyl ring is unsubstituted or independently substituted with one or more $X^5$ groups;
each occurrence of $X^5$ is independently alkyl, —O-alkyl, -alkylene-aryl, halo, —O—Si$(R^{11})_3$, haloalkyl, —CN, —C(O)—$R^4$, —C(O)—O—$R^4$, —NHC(O)—O—$R^4$, —S$(O_2)$—$R^4$, or phenyl;
$R^4$ is alkyl or cycloalkyl, wherein the cycloalkyl group can be optionally and independently substituted with one or more $X^1$ groups, and wherein the alkyl group can be optionally substituted with a cycloalkyl group;
each $R^{11}$ is independently alkyl or phenyl; and
each occurrence of $X^1$ is independently halogen, alkyl, —O-alkyl, —OH, haloalkyl, aryl or alkynyl.

The following embodiments refer to the compounds of formula (II):

In one embodiment, $R^1$ is alkyl.
In another embodiment, $R^1$ is -alkylene-cycloalkyl.
In another embodiment, $R^1$ is haloalkyl.
In still another embodiment, $R^1$ is -alkylene-O-alkyl.
In yet another embodiment, $R^1$ is —$(CH_2)_3CF_3$.
In another embodiment, $R^1$ is n-butyl, n-pentyl, n-hexyl, isopentyl, isohexyl or neoheptyl.
In a further embodiment, $R^1$ is —$(CH_2)_2$-cyclopropyl, —$(CH_2)_3$-cyclopropyl, —$(CH_2)_4$-cyclopropyl, —$(CH_2)_2$-cyclobutyl, —$(CH_2)_2$-cyclopentyl, —$CH_2$-cyclohexyl, —$(CH_2)_2$-cyclohexyl or

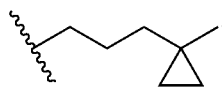

In another embodiment, $R^1$ is —$(CH_2)_3$—O—$(CH_2)_2CH_3$.
In one embodiment, $R^2$, $R^3$ and the carbon atom to which they are both attached, combined to form a monocyclic cycloalkyl group.

In another embodiment, $R^2$, $R^3$ and the carbon atom to which they are both attached, combined to form a bicyclic cycloalkyl group.
In another embodiment, $R^2$, $R^3$ and the carbon atom to which they are both attached, combined to form a monocyclic hetercycloalkyl group.
In still another embodiment, $R^2$, $R^3$ and the carbon atom to which they are both attached, combined to form a bicyclic hetercycloalkyl group.
In yet another embodiment, $R^2$, $R^3$ and the carbon atom to which they are both attached, combined to form a cyclopentyl or cyclohexyl group.
In another embodiment, $R^2$, $R^3$ and the carbon atom to which they are both attached, combined to form a decahydronaphtyl, 1,2,3,4-tetrahydronaphthyl, bicyclo[2.2.2]octyl or spiro[2.5]octyl group.
In a further embodiment, $R^2$, $R^3$ and the carbon atom to which they are both attached, combined to form a piperidinyl, tetrahydropyranyl, tetrahydrothiopyranyl or tetrahydrothiopyranyl-1,1,-dioxide group
In another embodiment, $R^2$, $R^3$ and the carbon atom to which they are both attached, combined to form a 8-azabicyclo[3.2.1]octyl, 1,4-dioxa-spiro[4.5]decanyl, 4,5,6,7-tetrahydro-benzo[b]thiophenyl, 5,6,7,8-tetrahydroquinolinyl or 1,3-diaza-spiro[4.5]decanyl-2,4,-dione group.
In one embodiment, $R^1$ is alkyl, and $R^2$, $R^3$ and the carbon atom to which they are both attached, combined to form a monocyclic cycloalkyl group.
In another embodiment, $R^1$ is alkyl, and $R^2$, $R^3$ and the carbon atom to which they are both attached, combined to form a bicyclic cycloalkyl group.
In another embodiment, $R^1$ is alkyl, and $R^2$, $R^3$ and the carbon atom to which they are both attached, combined to form a monocyclic heterocycloalkyl group.
In still another embodiment, $R^1$ is alkyl, and $R^2$, $R^3$ and the carbon atom to which they are both attached, combined to form a bicyclic heterocycloalkyl group.
In one embodiment, $R^1$ is haloalkyl, and $R^2$, $R^3$ and the carbon atom to which they are both attached, combined to form a monocyclic cycloalkyl group.
In another embodiment, $R^1$ is haloalkyl, and $R^2$, $R^3$ and the carbon atom to which they are both attached, combined to form a bicyclic cycloalkyl group.
In another embodiment, $R^1$ is haloalkyl, and $R^2$, $R^3$ and the carbon atom to which they are both attached, combined to form a monocyclic heterocycloalkyl group.
In still another embodiment, $R^1$ is haloalkyl, and $R^2$, $R^3$ and the carbon atom to which they are both attached, combined to form a bicyclic heterocycloalkyl group.
In one embodiment, $R^1$ is -alkylene-cycloalkyl, and $R^2$, $R^3$ and the carbon atom to which they are both attached, combined to form a monocyclic cycloalkyl group.
In another embodiment, $R^1$ is -alkylene-cycloalkyl, and $R^2$, $R^3$ and the carbon atom to which they are both attached, combined to form a bicyclic cycloalkyl group.
In another embodiment, $R^1$ is -alkylene-cycloalkyl, and $R^2$, $R^3$ and the carbon atom to which they are both attached, combined to form a monocyclic heterocycloalkyl group.
In still another embodiment, $R^1$ is -alkylene-cycloalkyl, and $R^2$, $R^3$ and the carbon atom to which they are both attached, combined to form a bicyclic heterocycloalkyl group.
In one embodiment, $R^1$ is -alkylene-O-alkyl, and $R^2$, $R^3$ and the carbon atom to which they are both attached, combined to form a monocyclic cycloalkyl group.

In another embodiment, $R^1$ is -alkylene-O-alkyl, and $R^2$, $R^3$ and the carbon atom to which they are both attached, combined to form a bicyclic cycloalkyl group.

In another embodiment, $R^1$ is -alkylene-O-alkyl, and $R^2$, $R^3$ and the carbon atom to which they are both attached, combined to form a monocyclic heterocycloalkyl group.

In still another embodiment, $R^1$ is -alkylene-O-alkyl, and $R^2$, $R^3$ and the carbon atom to which they are both attached, combined to form a bicyclic heterocycloalkyl group.

Non-limiting Illustrative examples of the compounds of formula (I), include compounds 1-285, and pharmaceutically acceptable salts, solvates, esters, and tautomers thereof, as depicted in the Examples section below.

The present invention encompasses all metabolites of the compounds of formula (I). Such metabolites may be formed in vitro or alternatively, may be formed in vivo when a compound of formula (I) is administered to a patient.

The compounds of Formula (I) can be purified to a degree suitable for use as a pharmaceutically active substance. That is, the compounds of Formula (I) can have a purity of 95 wt % or more (excluding adjuvants such as pharmaceutically acceptable carriers, solvents, etc., which are used in formulating the compound of Formula (I) into a conventional form, such as a pill, capsule, IV solution, etc. suitable for administration into a patient). The purity can be 97 wt % or more, or, 99 wt % or more. A purified compound of Formula (I) includes a single isomer having a purity, as discussed above, of 95 wt % or more, 97 wt % or more, or 99 wt % or more, as discussed above.

Alternatively, the purified compound of Formula (I) can include a mixture of isomers, each having a structure according to Formula (I), where the amount of impurity (i.e., compounds or other contaminants, exclusive of adjuvants as discussed above) is 5 wt % or less, 3 wt % or less, or 1 wt % or less. For example, the purified compound of Formula (I) can be an isomeric mixture of compounds of Structure (I), where the ratio of the amounts of the two isomers is approximately 1:1, and the combined amount of the two isomers is 95 wt % or more, 97 wt % or more, or 99 wt % or more.

Compounds of Formula (I), and salts, solvates, esters and prodrugs thereof, may exist in their tautomeric form (for example, as an amide or imino ether). All such tautomeric forms are contemplated herein as part of the present invention. Such tautomeric forms are considered equivalent.

As used above, and throughout this disclosure, the following terms, unless otherwise indicated, shall be understood to have the following meanings:

"Ac" means acetyl.
"Boc" means t-butyloxycarbonyl (—C(O)—O—C(CH$_3$)$_3$.
"Bu" means butyl.
"DCM" means dichloromethane (CH$_2$Cl$_2$).
"DMF" means dimethylformamide.
"CDI" means 1,1'-carbonyl diimdazole
"Et" means ethyl.
"EtO$_2$" or "ether" means diethyl ether.
"EtOAc" means ethylacetate.
"EtOH" means ethanol.
"HOAc" means acetic acid.
"LCMS" means liquid chromatography mass spectroscopy.
"m-CPBA" means m-chloroperoxybenzoic acid.
"Me" means methyl.
"MeOH" means methanol.
"MS" means mass spectroscopy.
"NCS" means N-chlorosuccimimide.
"NEt$_3$" or "Et$_3$N" mean triethylamine.
"satd." means saturated.

"TFA" means trifluoroacetic acid.
"THF" means tetrahydrofuran.

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"Alkyl" means an aliphatic hydrocarbon group which may be straight or branched and comprising about 1 to about 20 carbon atoms in the chain. The alkyl groups can contain about 1 to about 12 carbon atoms in the chain, and in another embodiment, the alkyl groups can contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkylene" means a difunctional group obtained by removal of a hydrogen atom from an alkyl group that is defined above. Non-limiting examples of alkylene include methylene (i.e., —CH$_2$—), ethylene (i.e., —CH$_2$CH$_2$— or —CH(CH$_3$)—), propylene (i.e., —CH$_2$CH$_2$CH$_2$—, —CH$_2$CH(CH$_3$)—, —CH(CH$_3$)CH$_2$—, or —CH(CH$_2$CH$_3$)—), butylene (i.e., —CH$_2$CH$_2$CH$_2$CH$_2$—, —CH$_2$CH$_2$CH(CH$_3$)—, —CH$_2$CH(CH$_3$)CH$_2$—, —CH(CH$_2$CH$_2$CH$_3$)—, etc.). "Lower alkylene" means a group having about 1 to about 6 carbon atoms in the chain which may be straight or branched.

"Alkenyl" means a hydrocarbon group containing at least one carbon-carbon double bond and which may be straight or branched and comprising about 2 to about 15 carbon atoms in the chain. Alkenyl groups can have about 2 to about 12 carbon atoms in the chain; and in another embodiment, about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy, and —S(alkyl). Non-limiting examples of suitable alkenyl groups include ethenyl, propenyl (i.e., allyl), n-butenyl, 3-methylbut-2-enyl, n-pentenyl, octenyl and decenyl.

"Alkynyl" means a hydrocarbon group containing at least one carbon-carbon triple bond and which may be straight or branched and comprising about 2 to about 15 carbon atoms in the chain. Alkynyl groups can have about 2 to about 12 carbon atoms in the chain, and in another embodiment, about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, an in another embodiment, about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, and in another embodiment, about 5 to about 10 ring atoms, in which one or more of the ring atoms is an element other than carbon, for example nitrogen, oxygen or sulfur, alone or in combination. Heteroaryls can contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidinyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl, indazolyl, and the like, in which there is at least one aromatic ring.

"Alkylene-aryl" (or aryl-alkylene-) means a group in which the aryl and alkylene are as previously described. The bond to the parent moiety is through the alkylene. The alkylene moiety can be bonded to one or more aryl moieties. Alkylene-aryls can comprise a lower alkylene group. Non-limiting examples of suitable alkylene-aryl groups include benzyl, 2-phenethyl, 2,2-diphenylethylene and naphthalenylmethyl.

"Alkylaryl" means an alkyl-aryl- group in which the alkyl and aryl are as previously described. Alkylaryls can comprise a lower alkyl group. Non-limiting examples of suitable alkylaryl groups include tolyl and xylyl. The bond to the parent moiety is through the aryl.

"Alkylheteroaryl" means an alkyl-heteroaryl- group in which the alkyl and heteroaryl are as previously described. Alkylheteroaryls can comprise a lower alkyl group. A non-limiting example of a suitable alkylheteroaryl group includes 2-methylpyridine. The bond to the parent moiety is through the heteroaryl.

"Cycloalkyl" means a non-aromatic mono- or multicyclic ring system comprising about 3 to about 10 carbon atoms. In one embodiment, a cycloalkyl has from about 5 to about 10 ring carbon atoms. In another embodiment, a cycloalkyl has from about 3 to about 7 ring carbon atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. In one embodiment, a cycloalkyl is a monocyclic cycloalkyl. In another embodiment, a cycloalkyl is a bicyclic cycloalkyl. In another embodiment, a cycloalkyl is a monocyclic cycloalkyl fused to a benzene ring. In still another embodiment, a cycloalkyl is a monocyclic cycloalkyl fused to an aromatic heterocycle, including, but not limited to pyridine. In a further embodiment, a monocyclic cycloalkyl group can form a spirocycle with a second cycloalkyl group or with a heterocycloalkyl group. Illustrative examples of such spirocycles include, but are not limited to:

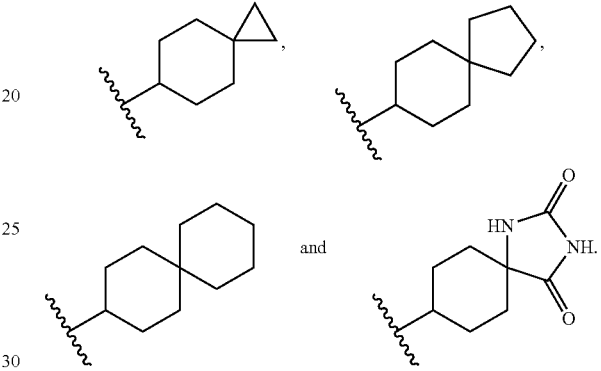

"Cycloalkenyl" means an unsaturated, non-aromatic mono- or multicyclic ring system having at least 1 carbon-carbon double bond. In one embodiment, a cycloalkenyl has from about 5 to about 10 ring carbon atoms. In another embodiment, a cycloalkenyl has from about 3 to about 7 ring carbon atoms. The cycloalkenyl can be optionally substituted with one or more "ring system substituents" which may be the same or different, and are as defined above. Non-limiting examples of suitable monocyclic cycloalkenyls include cyclopropenyl, cyclopentenyl, cyclohexenyl, cycloheptenyl and the like. Non-limiting examples of suitable multicyclic cycloalkyls include norbornenyl, adamantenyl and the like.

"Cycloalkylene" means a difunctional group obtained by removal of a hydrogen atom from a cycloalkyl group that is defined above. Non-limiting examples of cycloalkylene include

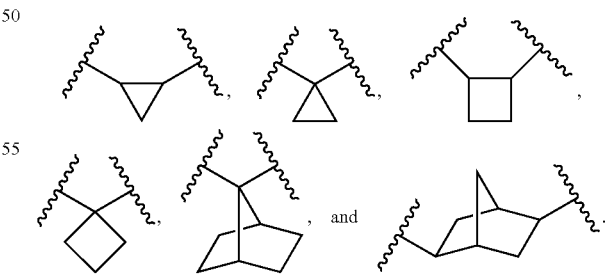

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, alkylene-aryl, alkylaryl, alkylene-heteroaryl, heteroaryl-alkenylene-, heteroaryl-alkynylene-, alkylheteroaryl, hydroxy, hydroxyalkyl, alkoxy, aryloxy, aryl-alkoxy-, acyl, aroyl, halo, nitro, cyano, carboxy, alkoxycarbonyl, aryloxycarbonyl, aryl-alkoxycarbonyl, alkylsulfonyl, arylsulfonyl, heteroarylsulfonyl, alkylthio, arylthio, heteroarylthio, aryl-alkylthio, heteroaryl-alkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aryl-alkylene-. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

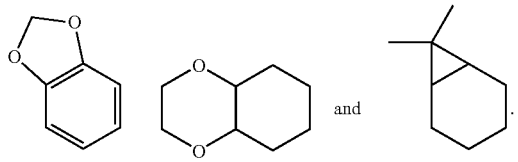

"Heterocyclyl" or "heterocyclic" means a monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Heterocyclyls have at least 2 ring carbon atoms, and preferably up to about 10 ring carbon atoms. There are no adjacent oxygen and/or sulfur atoms present in the ring system. Heterocyclyls may be completely saturated, partially unsaturated, or aromatic. Aromatic heterocyclyls are termed "heteroaryl", as defined above. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBn), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include saturated heterocyclyls, for example piperidyl, pyrrolidinyl, piperazinyl, morpholinyl, thiomorpholinyl, thiazolidinyl, 1,4-dioxanyl, tetrahydrofuranyl, tetrahydrothiophenyl, lactams, lactones, and the like. Non-limiting examples of partially unsaturated monocyclic heterocyclyl rings include, for example, thiazolinyl, and the like.

"Heterocycloalkyl" means a monocyclic or multicyclic, saturated heterocyclyl as defined above. In one embodiment, a heterocycloalkyl is a monocyclic heterocycloalkyl. In another embodiment, a heterocycloalkyl is a bicyclic heterocycloalkyl. In another embodiment, a heterocycloalkyl is a monocyclic heterocycloalkyl fused to a benzene. In one embodiment, a monocyclic heterocycloalkyl has 5 or 6 ring atoms.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

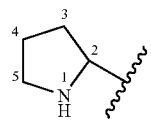

there is no —OH attached directly to carbons marked 2 and 5.

"Alkynylalkyl" means an alkynyl-alkyl- group in which the alkynyl and alkyl are as previously described. Alkynylalkyls can contain a lower alkynyl and a lower alkyl group. The bond to the parent moiety is through the alkyl. Non-limiting examples of suitable alkynylalkyl groups include propargylmethyl.

"Heteroarylalkyl" means a heteroaryl-alkyl- group in which the heteroaryl and alkyl are as previously described. Heteroaralkyls can contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Hydroxyalkyls can contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Acyls can contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryl-alkyloxy" (or arylalkoxy) means an aryl-alkyl-O— group in which the aryl-alkyl group is as previously described. Non-limiting examples of suitable aryl-alkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aryl-alkylthio" (or arylalkylthio) means an aryl-alkyl-S— group in which the aryl-alkyl group is as previously described. Non-limiting example of a suitable aryl-alkylthio group is benzylthio. The bond to the parent moiety is through the sulfur.

"Alkoxycarbonyl" means an alkyl-O—C(O)— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylalkoxycarbonyl" means an aryl-alkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties. An optionally substituted moiety may be unsubstituted or substituted with one or more substituents.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York.

When any variable (e.g., aryl, heterocycle, $R^1$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino ($C_1$-$C_4$)alkyl or mono-N— or di-N,N-($C_1$-$C_6$)alkylaminoalkyl, —C($Y^4$)$Y^5$ wherein $Y^4$ is H or methyl and $Y^5$ is mono-N— or di-N,N-($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, MPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the diseases or conditions noted below, and thus producing the desired therapeutic, ameliorative, inhibitory or preventative effect.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $(C_1-C_4)$alkyl, or $(C_1-C_4)$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $(C_1-C_{20})$ alcohol or reactive derivative thereof, or by a 2,3-di-$(C_6-C_{24})$acyl glycerol.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, (and including those of the salts, solvates, esters and prodrugs of the compounds as well as the salts, solvates and esters of the prodrugs) form part of the present invention. In addition, the present invention embraces all geometric and positional isomers, as well as enantiomeric forms (which may exist even in the absence of asymmetric carbons), rotameric forms, atropisomers (e.g., substituted biaryls), and diastereomeric forms. For example, if a compound of Formula (I) incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically labeled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of Formula (I) can generally be prepared by following procedures analogous to those disclosed in the Schemes and/or in the Examples hereinbelow, by substituting an appropriate isotopically labeled reagent for a non-isotopically labeled reagent.

Polymorphic forms of the compounds of Formula (I), and of the salts, solvates, esters and prodrugs of the compounds of Formula (I), are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds of Formula (I), or pharmaceutically acceptable salts, solvates, or esters thereof according to the invention have pharmacological properties; in particular, the compounds of Formula (I) can be nicotinic acid receptor agonists.

The compounds of Formula (I) of the present invention, or pharmaceutically acceptable salts, solvates, or esters thereof are useful in treating diseases or conditions including dyslipidemia and metabolic syndrome.

The compounds of Formula (I), or pharmaceutically acceptable salts, solvates, or esters thereof, can be administered in any suitable form, e.g., alone, or in combination with a pharmaceutically acceptable carrier, excipient or diluent in a pharmaceutical composition, according to standard pharmaceutical practice. The compounds of Formula (I), or pharmaceutically acceptable salts, solvates, or esters thereof, can be administered orally or parenterally, including intravenous, intramuscular, interperitoneal, subcutaneous, rectal, or topical routes of administration.

Pharmaceutical compositions comprising at least one compound of Formula (I), or a pharmaceutically acceptable salt, solvate, ester, or tautomer thereof can be in a form suitable for oral administration, e.g., as tablets, troches, capsules, lozenges, aqueous or oily suspensions, dispersible powders or granules, emulsions, syrups, or elixirs. Oral compositions may be prepared by any conventional pharmaceutical method, and may also contain sweetening agents, flavoring agents, coloring agents, and preserving agents.

The amount of compound of Formula (I), or a pharmaceutically acceptable salt, solvate, ester, or tautomer thereof, administered to a patient can be determined by a physician based on the age, weight, and response of the patient, as well as by the severity of the condition treated. For example, the amount of compound of Formula I, or a pharmaceutically acceptable salt, solvate, ester, or tautomer thereof, administered to the patient can range from about 0.1 mg/kg body weight per day to about 60 mg/kg/d, preferably about 0.5 mg/kg/d to about 40 mg/kg/d.

The compounds of Formula (I), or pharmaceutically acceptable salts, solvates, or esters thereof, can also be administered in combination with other therapeutic agents. For example one or more compounds of Formula (I) or pharmaceutically acceptable salts, solvates, or esters thereof, can be administered with one or more additional active ingredients selected from the group consisting of hydroxy-substituted azetidinone compounds, substituted β-lactam compounds, HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, inorganic cholesterol sequestrants, AcylCoA:Cholesterol O-acyltransferase inhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport protein inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, leptin derivatives, opioid antagonists, orexin receptor antagonists, BRS3 agonists, CCK-A agonists, CNTF, CNTF derivatives, CNTF agonists/modulators, 5HT2c agonists, Mc4r agonists, monoamine reuptake inhibitors, serotonin reuptake inhibitors, GLP-1 agonists, phentermine, topiramate, phytopharm compound 57, ghrelin antibodies, Mc3r agonists, ACC inhibitors, β3 agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β

HSD-1 inhibitors, SCD-1 inhibitors, lipase inhibitors, fatty acid transporter inhibitors, dicarboxylate transporter inhibitors, glucose transporter inhibitors, phosphate transporter inhibitors, anti-diabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanocyte-stimulating hormone receptor analogs, melanin concentrating hormone antagonists, leptons, galanin receptor antagonists, bombesin agonists, neuropeptide-Y antagonists, thyromimetic agents, dehydroepiandrosterone, analogs of dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, MSH-receptor analogs, α-glucosidase inhibitors, apo A1 milano reverse cholesterol transport inhibitors, fatty acid binding protein inhibitors (FABP), and fatty acid transporter protein inhibitors (FATP).

Non-limiting examples of hydroxy-substituted azetidinone compounds and substituted β-lactam compounds useful in combination with the nicotinic acid receptor agonists of the present invention are those disclosed in U.S. Pat. Nos. 5,767,115, 5,624,920, 5,668,990, 5,656,624 and 5,688,787, 5,756,470, U.S. Patent Application Nos. 2002/0137690 and 2002/0137689 and PCT Patent Application No. WO 2002/066464, each of which is incorporated herein by reference in their entirety. A preferred azetidinone compound is ezetimibe (for example, ZETIA® which is available from Schering-Plough Corporation).

Non-limiting examples of HMG CoA reductase inhibitor compounds useful in combination with the nicotinic acid receptor agonists of the present invention are lovastatin (for example MEVACOR® which is available from Merck & Co.), simvastatin (for example ZOCOR® which is available from Merck & Co.), pravastatin (for example PRAVACHOL® which is available from Bristol Meyers Squibb), atorvastatin, fluvastatin, cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin calcium (CRESTOR® from AstraZeneca Pharmaceuticals), pitavastatin (such as NK-104 of Negma Kowa of Japan).

A non-limiting example of a HMG CoA synthetase inhibitor useful in combination with the nicotinic acid receptor agonists of the present invention is, for example, L-659,699 ((E,E)-1'-[3'R-(hydroxy-methyl)-4'-oxo-2'R-oxetanyl]-3,5,7R-trimethyl-2,4-undecadienoic acid).

A non-limiting example of a squalene synthesis inhibitor useful in combination with the nicotinic acid receptor agonists of the present invention is, for example, squalestatin 1.

A non-limiting example of a squalene epoxidase inhibitor useful in combination with the nicotinic acid receptor agonists of the present invention is, for example, NB-598 ((E)-N-ethyl-N-(6,6-dimethyl-2-hepten-4-ynyl)-3-[(3,3'-bithiophen-5-yl)methoxy]benzene-methanamine hydrochloride).

A non-limiting example of a sterol biosynthesis inhibitor useful in combination with the nicotinic acid receptor agonists of the present invention is, for example, DMP-565.

Non-limiting examples of nicotinic acid derivatives (e.g., compounds comprising a pyridine-3-carboxylate structure or a pyrazine-2-carboxylate structure, including acid forms, salts, esters, zwitterions and tautomers) useful in combination with the nicotinic acid receptor agonists of the present invention are niceritrol, nicofuranose and acipimox (5-methylpyrazine-2-carboxylic acid 4-oxide).

Non-limiting examples of bile acid sequestrants useful in combination with the nicotinic acid receptor agonists of the present invention are cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof.

Non-limiting examples of inorganic cholesterol sequestrants useful in combination with the nicotinic acid receptor agonists of the present invention are bismuth salicylate plus montmorillonite clay, aluminum hydroxide and calcium carbonate antacids.

Non-limiting examples of AcylCoA:Cholesterol O-acyltransferase ("ACAT") inhibitors useful in combination with the nicotinic acid receptor agonists of the present invention are avasimibe ([[2,4,6-tris(1-methylethyl)phenyl]acetyl]sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea), and the compounds described in P. Chang et al., "Current, New and Future Treatments in Dyslipidaemia and Atherosclerosis", Drugs 2000 July; 60(1); 55-93, which is incorporated by reference herein.

Non-limiting examples of cholesteryl ester transfer protein ("CETP") inhibitors useful in combination with the nicotinic acid receptor agonists of the present invention are those disclosed in PCT Patent Application No. WO 00/38721, U.S. Pat. Nos. 6,147,090, 6,958,346, 6,924,313 6,906,082, 6,861, 561, 6,803,388, 6,794,396, 6,787,570, 6,753,346, 6,723,752, 6,723,753, 6,710,089, 6,699,898, 6,696,472, 6,696,435, 6,683,113, 5,519,001, 5,512,548, 6,410,022, 6,426,365, 6,448,295, 6,387,929, 6,683,099, 6,677,382, 6,677,380, 6,677,379, 6,677,375, 6,677,353, 6,677,341, 6,605,624, 6,586,433, 6,451,830, 6,451,823, 6,462,092, 6,458,849, 6,458,803, 6,455,519, 6,583,183, 6,562,976, 6,555,113, 6,544,974, 6,521,607, 6,489,366, 6,482,862, 6,479,552, 6,476,075, 6,476,057, and 6,897,317, each of which are incorporated herein by reference; compounds described in Yan Xia et al., "Substituted 1,3,5-Triazines As Cholesteral Ester Transfer Protein Inhibitors", *Bioorganic & Medicinal Chemistry Letters*, vol. 6, No. 7, 1996, pp. 919-922, herein incorporated by reference; natural products described in S. Coval et al., "Wiedendiol-A and -B, Cholesteryl Ester Transfer Protein Inhibitors From The Marine Sponge Xestosponga Wiedenmayeri", *Bioorganic & Medicinal Chemistry Letter*, vol. 5, No. 6, pp. 605-610, 1995, herein incorporated by reference; the compounds described in Barrett et al. *J. Am. Chem. Soc.*, 188, 7863-63 (1996), herein incorporated by reference; the compounds described in Kuo et al. *J. Am. Chem. Soc.*, 117, 10629-34 (1995), herein incorporated by reference; the compounds described in Pietzonka et al. *Bioorg. Med. Chem. Lett.*, 6, 1951-54 (1996), herein incorporated by reference; the compounds described in Lee et al. *J. Antibiotics*, 49, 693-96 (1996), herein incorporated by reference; the compounds described by Busch et al. *Lipids*, 25, 216-220, (1990), herein incorporated by reference; the compounds described in Morton and Zilversmit *J. Lipid Res.*, 35, 836-47 (1982), herein incorporated by reference; the compounds described in Connolly et al. *Biochem. Biophys. Res. Comm.*, 223, 42-47 (1996), herein incorporated by reference; the compounds described in Bisgaier et al. *Lipids,* 29, 811-8 (1994), herein incorporated by reference; the compounds described in EP 818448, herein incorporated by reference; the compounds described in JP 10287662, herein incorporated by reference; the compounds described in PCT applications WO 98/35937, WO 9914174, WO 9839299, and WO 9914215, each of which is herein incorporated by reference; the compounds of EP applications EP 796846, EP 801060, 818448, and 818197, each of which is herein incorporated by reference; probucol or derivatives thereof, such as AGI-1067 and other derivatives disclosed in U.S. Pat. Nos. 6,121,319 and 6,147,250, herein incorporated by reference; low-density lipoprotein (LDL) receptor activators such as HOE-402, an imidazolidinyl-pyrimidine derivative that directly stimulates LDL receptor activity, described in M. Huettinger et al., "Hypolipidemic activity of HOE-402 is Mediated by Stimulation of the LDL Receptor Pathway", *Arterioscler. Thromb.* 1993; 13:1005-12, herein incorporated by reference; 4-carboxyamino-2-substituted-1,2,3,4-tetrahydroquinolines, e.g., torcetrapib, described in WO 00/017164, WO 00/017166, WO 00/140190, WO 00/213797, and WO 2005/033082 (each of which is herein incorporated by reference). Torcetrapib can be combined with HMG-CoA reductase inhibitors such as atorvastatin (WO 00/213797, WO 2004/056358, WO 2004/056359, and WO2005/011634).

A non-limiting example of a fish oil containing Omega 3 fatty acids useful in combination with the nicotinic acid receptor agonists of the present invention is 3-PUFA.

Non-limiting examples of natural water soluble fibers useful in combination with the nicotinic acid receptor agonists of the present invention are psyllium, guar, oat and pectin.

A non-limiting example of a plant stanol and/or fatty acid ester of plant stanols useful in combination with the nicotinic acid receptor agonists of the present invention is the sitostanol ester used in BENECOL® margarine.

A non-limiting example of an anti-oxidant useful in combination with the nicotinic acid receptor agonists of the present invention includes probucol.

Non-limiting examples of PPAR α agonists useful in combination with the nicotinic acid receptor agonists of the present invention include beclofibrate, benzafibrate, ciprofibrate, clofibrate, etofibrate, fenofibrate, and gemfibrozil.

Non-limiting examples of lipoprotein synthesis inhibitors useful in combination with the nicotinic acid receptor agonists of the present invention include niacin or nicotinic acid.

Non-limiting examples of 5HT (serotonin) transport inhibitors useful in combination with the nicotinic acid receptor agonists of the present invention include paroxetine, fluoxetine, fenfluramine, fluvoxamine, sertraline, and imipramine.

Non-limiting examples of NE (norepinephrine) transport inhibitors useful in combination with the nicotinic acid receptor agonists of the present invention include GW 320659, despiramine, talsupram, and nomifensine.

Non-limiting examples of $CB_1$ antagonists/inverse agonists useful in combination with the nicotinic acid receptor agonists of the present invention include rimonabant, SR-147778 (Sanofi Synthelabo), and the compounds described in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO 96/33159, WO 98/33765, WO 98/43636, WO 98/43635, WO 01/09120, WO 98/31227, WO 98/41519, WO 98/37061, WO 00/10967, WO 00/10968, WO 97/29079, WO 99/02499, WO 01/58869, WO 02/076949, and EP-658546 (each of the preceding references is herein incorporated by reference).

Non-limiting examples of ghrelin antagonists useful in combination with the nicotinic acid receptor agonists of the present invention include those described in WO 01/87335 and WO 02/08250 (each of the preceding references is herein incorporated by reference). Ghrelin antagonists are also known as GHS (growth hormone secretagogue receptor) antagonists. The pharmaceutical combinations and methods of the present invention therefore comprehend the use GHS antagonists in place of ghrelin antagonists (in combination with the nicotinic acid receptor agonists of the present invention).

Non-limiting examples of $H_3$ antagonists/inverse agonists useful in combination with the nicotinic acid receptor agonists of the present invention include thioperamide, 3-(1H-imidazol-4-yl)propyl N-(4-pentenyl)carbamate, clobenpropit, iodophenpropit, imoproxifan, and GT2394 (Gliatech), those described in WO 02/15905 (herein incorporated by reference); O-[3-(1H-imidazol-4-yl)propanol]carbamates described in Kiec-Kononowicz, K. et al., *Pharmazie,* 55:349-55 (2000) (herein incorporated by reference), piperidine-containing histamine $H_3$-receptor antagonists described in Lazewska, D. et al., *Pharmazie,* 56:927-32 (2001) (herein incorporated by reference), benzophenone derivatives and related compounds described in Sasse, A. et al., *Arch. Pharm. (Weinheim)* 334:45-52 (2001)(herein incorporated by reference), substituted N-phenylcarbamates described in Reidemeister, S. et al., *Pharmazie,* 55:83-6 (2000)(herein incorporated by reference), and proxifan derivatives described in Sasse, A. et al., *J. Med. Chem.* 43:3335-43 (2000)(each of the preceding references is herein incorporated by reference).

Non-limiting examples of MCH1R (melanin-concentrating hormone 1 receptor) antagonists and MCH2R (melanin-concentrating hormone 2 receptor) agonists/antagonists useful in combination with the nicotinic acid receptor agonists of the present invention include those described in WO 01/82925, WO 01/87834, WO 02/06245, WO 02/04433, WO 02/51809, and JP 13226269 (each of the preceding references is herein incorporated by reference), and T-226296 (Takeda).

Non-limiting examples of NPY1 antagonists useful in combination with the nicotinic acid receptor agonists of the present invention include those described in U.S. Pat. No. 6,001,836, WO 96/14307, WO 01/23387, WO 99/51600, WO 01/85690, WO 01/85098, WO 01/85173, and WO 01/89528 (each of the preceding references is herein incorporated by reference); and BIBP3226, J=115814, BIBO 3304, LY-357897, CP-671906, and GI-264879A.

Non-limiting examples of NPY5 antagonists useful in combination with the nicotinic acid receptor agonists of the present invention include those described in U.S. Pat. Nos. 6,140,354, 6,191,160, 6,258,837, 6,313,298, 6,337,332, 6,329,395, 6,340,683, 6,326,375, 6,335,345, EP-01010691, EP-01044970, WO 97/19682, WO 97/20820, WO 97/20821, WO 97/20822, WO 97/20823, WO 98/27063, WO 00/64880, WO 00/68197, WO 00/69849, WO 01/09120, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, WO 02/49648, WO 01/14376, WO 04/110375, WO 05/000217 and Norman et al., *J. Med. Chem.* 43:4288-4312 (2000) (each of the preceding references is herein incorporated by reference); and 152,804, GW-569180A, GW-594884A, GW-587081X, GW-548118X; FR226928, FR 240662, FR252384; 1229U91, GI-264879A, CGP71683A, LY-377897, PD-160170, SR-120562A, SR-120819A and JCF-104.

Non-limiting examples of NPY2 agonists useful in combination with the nicotinic acid receptor agonists of the present invention include PYY3-36 as described in Batterham, et al., *Nature.* 418:650-654 (2003), NPY3-36, and other Y2 agonists such as N acetyl [Leu(28,31)] NPY 24-36 (White-Smith and Potter, *Neuropeptides* 33:526-33 (1999)), TASP-V (Malis et al., Br. *J. Pharmacol.* 126:989-96 (1999)), cyclo-(28/32)-Ac-[Lys28-Glu32]-(25-36)-pNPY (Cabrele and Beck-Sickinger *J-Pept-Sci.* 6:97-122 (2000)) (each of the preceding references is herein incorporated by reference).

Non-limiting examples of NPY4 agonists useful in combination with the nicotinic acid receptor agonists of the present invention include pancreatic peptide (PP) as described in Batterham et al., *J. Clin. Endocrinol. Metab.* 88:3989-3992 (2003), and other Y4 agonists such as 1229U91 (Raposinho et al., *Neuroendocrinology.* 71:2-7 (2000) (both references are herein incorporated by reference).

Non-limiting examples of mGluR5 (Metabotropic glutamate subtype 5 receptor) antagonists useful in combination with the nicotinic acid receptor agonists of the present invention include 2-methyl-6-(phenylethynyl)-pyridine (MPEP) and (3-[(2-methyl-1,3-thiazol-4-yl)ethynyl]pyridine) (MTEP) and those compounds described in Anderson J. et al., *J, Eur J Pharmacol.* Jul. 18, 2003; 473(1):35-40; Cosford N. et al., *Bioorg Med Chem Lett.* Feb. 10, 2003; 13(3):351-4; and Anderson J. et al., *J Pharmacol Exp Ther.* December 2002:303(3):1044-51 (each of the preceding references is herein incorporated by reference).

Non-limiting examples of leptins, leptin derivatives, and leptin agonists/modulators useful in combination with the nicotinic acid receptor agonists of the present invention include recombinant human leptin (PEG-OB, Hoffman La Roche) and recombinant methionyl human leptin (Amgen). Leptin derivatives (e.g., truncated forms of leptin) useful in the present invention include those described in U.S. Pat. Nos. 5,552,524, 5,552,523, 5,552,522, 5,521,283, WO 96/23513, WO 96/23514, WO 96/23515, WO 96/23516, WO 96/23517, WO 96/23518, WO 96/23519, and WO 96/23520 (each of the preceding references is herein incorporated by reference).

Non-limiting examples of opioid antagonists useful in combination with the nicotinic acid receptor agonists of the present invention include nalmefene (Revex™), 3-methoxynaltrexone, naloxone, and naltrexone, as well as opioid antagonists described in WO 00/21509 (herein incorporated by reference).

Non-limiting examples of orexin receptor antagonists useful in combination with the nicotinic acid receptor agonists of the present invention include SB-334867-A, as well as those described in WO 01/96302, WO 01/68609, WO 02/51232, and WO 02/51838 (each of the preceding references is herein incorporated by reference).

Non-limiting examples of CNTF (specific ciliary neurotrophic factors) useful in combination with the nicotinic acid receptor agonists of the present invention include GI-181771 (Glaxo-SmithKline); SR146131 (Sanofi Synthelabo); butabindide; PD170,292, PD 149164 (Pfizer).

Non-limiting examples of CNTF derivatives and CNTF agonists/modulators useful in combination with the nicotinic acid receptor agonists of the present invention include axokine (Regeneron) and those described in WO 94/09134, WO 98/22128, and WO 99/43813 (each of which is herein incorporated by reference).

Non-limiting examples of 5HT2c agonists useful in combination with the nicotinic acid receptor agonists of the present invention include BVT933, DPCA37215, WAY161503, and R-1065, as well as those described in U.S. Pat. No. 3,914,250, WO 02/36596, WO 02/48124, WO 02/10169, WO 01/66548, WO 02/44152, WO 02/51844, WO 02/40456, and WO 02/40457 (each of which is herein incorporated by reference).

Non-limiting examples of Mc4r agonists useful in combination with the nicotinic acid receptor agonists of the present invention include CHIR86036 (Chiron); ME-10142, and ME-10145 (Melacure), as well as those described in WO 01/991752, WO 01/74844, WO 02/12166, WO 02/11715, and WO 02/12178 (each of which is herein incorporated by reference).

Non-limiting examples of monoamine reuptake inhibitors useful in combination with the nicotinic acid receptor agonists of the present invention include sibutramine (Meridia™/Reductil™), as well as those described in WO 01/27068, WO 01/62341, U.S. Pat. Nos. 4,746,680, 4,806,570, 5,436,272, and US 2002/0006964 (each of which is herein incorporated by reference).

Non-limiting examples of serotonin reuptake inhibitors useful in combination with the nicotinic acid receptor agonists of the present invention include dexfenfluramine, fluoxetine, and those described in U.S. Pat. No. 6,365,633, WO 01/27060, and WO 01/162341 (each of which is herein incorporated by reference).

Non-limiting examples of GLP-1 agonists useful in combination with the nicotinic acid receptor agonists of the present invention include exendin-3 and exendin-4.

A non-limiting example of an acyl-estrogen useful in combination with the nicotinic acid receptor agonists of the present invention includes oleoyl-estrone.

Non-limiting examples of 11β HSD-1 inhibitors useful in combination with the nicotinic acid receptor agonists of the present invention include those described in WO 03/065983 and WO 03/104207 (both of which are herein incorporated by reference).

A non-limiting example of a lipase inhibitor useful in combination with the nicotinic acid receptor agonists of the present invention include orlistat.

Anti-diabetic agents useful in combination with the nicotinic acid receptor agonists of the present invention include sulfonylureas, meglitinides, α-amylase inhibitors, α-glucoside hydrolase inhibitors, PPAR-γ agonists, PPARα/γ agonists, biguanides, PTP-1B inhibitors, DP-IV inhibitors, insulin secreatagogues, fatty acid oxidation inhibitors, A2 antagonists, c-jun amino-terminal kinase inhibitors, insulin, insulin mimetics, glycogen phosphorylase inhibitors, VPAC2 receptor agonists, glucokinase activators, and non-thiazolidinedione PPAR ligands. Non-limiting examples of sulfonylureas useful in combination with the nicotinic acid receptor agonists of the present invention include acetohexamide, chlorpropamide, diabinese, glibenclamide, glipizide, glyburide, glimepiride, gliclazide, glipentide, gliquidone, glisolamide, tolazamide, and tolbutamide.

Non-limiting examples of meglitinides useful in combination with the nicotinic acid receptor agonists of the present invention include repaglinide and nateglinide.

Non-limiting examples of α-amylase inhibitors useful in combination with the nicotinic acid receptor agonists of the present invention include tendamistat, trestatin, and AI-3688.

Non-limiting examples of α-glucoside hydrolase inhibitors useful in combination with the nicotinic acid receptor agonists of the present invention include acarbose, adipose, camiglibose, emiglitate, miglitol, voglibose, pradimicin-Q, salbostatin, CDK-711, MDL-25,637, MDL-73,945, and MOR 14.

Non-limiting examples of PPAR-γ agonists useful in combination with the nicotinic acid receptor agonists of the present invention include balaglitazone, ciglitazone, darglitazone, englitazone, isaglitazone (MCC-555), pioglitazone, rosiglitazone, troglitazone, tesaglitazar, netoglitazone, GW409544, GW-501516, CLX-0921, 5-BTZD, GW-0207, LG-100641, LY-300512, LY-519818, R483 (Roche), and T131 (Tularik).

Non-limiting examples of PPARα/γ agonists useful in combination with the nicotinic acid receptor agonists of the present invention include CLX-0940, GW-1536, GW-1929, GW-2433, KRP-297, L-796449, LR-90, MK-0767, and SB 219994.

Non-limiting examples of biguanides useful in combination with the nicotinic acid receptor agonists of the present invention include buformin, metformin, and phenformin.

Non-limiting examples of PTP-1B inhibitors (protein tyrosine phosphatase-1B inhibitors) useful in combination with the nicotinic acid receptor agonists of the present invention include A-401,674, KR 61639, OC-060062, OC-83839, OC-297962, MC52445, and MC52453.

Non-limiting examples of DP-IV inhibitors (dipeptidyl peptidase IVi inhibitors) useful in combination with the nicotinic acid receptor agonists of the present invention include isoleucine thiazolidide, NVP-DPP728, P32/98, LAF 237, TSL 225, valine pyrrolidide, TMC-2A/2B/2C, CD-26 inhibitors, and SDZ 274-444.

Non-limiting examples of insulin secreatagogues useful in combination with the nicotinic acid receptor agonists of the present invention include linogliride and A-4166.

Non-limiting examples of fatty acid oxidation inhibitors useful in combination with the nicotinic acid receptor agonists of the present invention include clomoxir and etomoxir.

Non-limiting examples of A2 antagonists useful in combination with the nicotinic acid receptor agonists of the present invention include midaglizole, isaglidole, deriglidole, idazoxan, earoxan, and fluparoxan.

Non-limiting examples of insulin mimetics useful in combination with the nicotinic acid receptor agonists of the present invention include biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-$NH_2$).

Non-limiting examples of glycogen phosphorylase inhibitors useful in combination with the nicotinic acid receptor agonists of the present invention include CP-368,296, CP-316,819, and BAYR3401.

Non-limiting examples of non-thiazolidinedione PPAR ligands useful in combination with the nicotinic acid receptor agonists of the present invention include JT-501 and farglitazar (GW-2570/GI-262579).

Anti-hypertensive agents useful in combination with the nicotinic acid receptor agonists of the present invention include diuretics, β-adrendergic blockers, α-adrenergic blockers, aldosterone inhibitors, alpha 1 blockers, calcium channel blockers, angiotensin converting enzyme inhibitors, neutral endopeptidase inhibitors, angiotensin 11 receptor antagonists, endothelin antagonists, vasodilators, alpha 2a agonists, and α/β adrenergic blockers.

Non-limiting examples of diuretics useful in combination with the nicotinic acid receptor agonists of the present invention include chlorthalidone, chlorthiazide, dichlorophenamide, hydroflumethiazide, indapamide, hydrochlorothiazide, bumetanide, ethacrynic acid, furosemide, torsemide, amiloride, triamterene, spironolactone, and epirenone.

Non-limiting examples of β-adrendergic blockers useful in combination with the nicotinic acid receptor agonists of the present invention include acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol.

Non-limiting examples of alpha 1 blockers useful in combination with the nicotinic acid receptor agonists of the present invention include terazosin, urapidil, prazosin, bunazosin, trimazosin, doxazosin, naftopidil, indoramin, WHIP 164, and XEN010.

Non-limiting examples of calcium channel blockers useful in combination with the nicotinic acid receptor agonists of the present invention include amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil.

Non-limiting examples of angiotensin converting enzyme inhibitors useful in combination with the nicotinic acid receptor agonists of the present invention include alacepril, benazepril, ceronapril, captopril, cilazapril, delapril, enalapril, fosinopril, imidapril, losinopril, moveltopril, moexipril, quinapril, quinaprilat, ramipril, perindopril, peridropril, quanipril, spirapril, temocapril, trandolapril, and zofenopril.

Non-limiting examples of neutral endopeptidase inhibitors useful in combination with the nicotinic acid receptor agonists of the present invention include omapatrilat, cadoxatril, ecadotril, fosidotril, sampatrilat, AVE7688, and ER4030.

Non-limiting examples of angiotensin 11 receptor antagonists useful in combination with the nicotinic acid receptor agonists of the present invention include candesartan, eprosartan, irbesartan, losartan, pratosartan, tasosartan, telisartan, valsartan, EXP-3137, F16828K, RNH6270, losartan monopotassium, and losartan potassium-hydrochlorothiazide.

Non-limiting examples of endothelin antagonists useful in combination with the nicotinic acid receptor agonists of the present invention include tezosentan, A308165, and YM62899.

Non-limiting examples of vasodilators useful in combination with the nicotinic acid receptor agonists of the present invention include hydralazine (apresoline), clonidine (catapres), minoxidil (loniten), and nicotinyl alcohol (roniacol).

Non-limiting examples of alpha 2a agonists useful in combination with the nicotinic acid receptor agonists of the present invention include lofexidine, tiamenidine, moxonidine, rilmenidine, and guanobenz.

Non-limiting examples of α/β adrenergic blockers useful in combination with the nicotinic acid receptor agonists of the present invention include nipradilol, arotinolol, and amosulalol.

DP receptor antagonists useful in combination with the nicotinic acid receptor agonists of the present invention include those described in US 2004/0229844 (herein incorporated by reference).

In addition, the nicotinic acid receptor agonists of the present invention can also be used in combination with two or more therapeutic agents. A non-limiting example of two or more therapeutic agents useful in combination with the nicotinic acid receptor agonists of the present invention is the combination of a compound of the present invention with VYTORIN® (a combination of simvastatin and ezetimibe).

EXAMPLES

General Procedure for Preparation of piperazine Oxime:

Example 1

Step A:

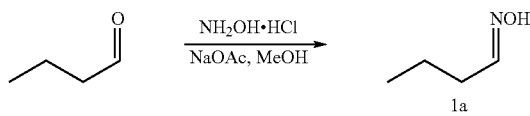

A solution of aldehyde (1 eq) in MeOH (ca. 1 M concentration) was added with NH₂OH.HCl (1.2 eq) and NaOAc (1.2 eq) and stirred at room temperature overnight. Then the resulting mixture was filtered, and the filtrate was concentrated, diluted with CH₂Cl₂, washed with water, dried over Na₂SO₄ and concentrated to give crude product 1a.

Step B:

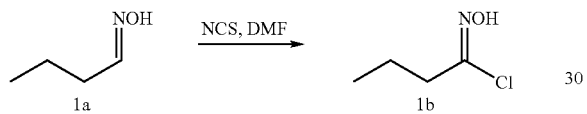

The crude product 1a was dissolved in DMF (ca. 2M concentration) and NCS (1.2 eq) was added portion-wise at 0° C. The resulting mixture was stirred at room temperature overnight and then diluted with water and extracted with ether. The ether layer was washed with brine, dried over Na₂SO₄ and concentrated to give crude oximinoyl chloride 1b.

Step C:

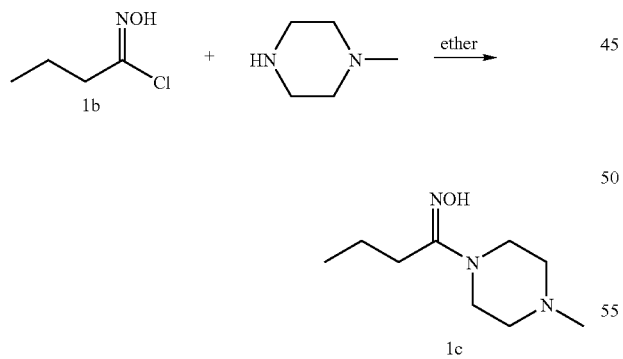

The crude oximinoyl chloride 1 b was dissolved in ether (ca. 1 M concentration) and N-methylpiperazine (1.2 eq) was added slowly. The resulting mixture was stirred at room temperature overnight and concentrated. The residue was dissolved in CH₂Cl₂ and washed with water and brine. The organic layer was dried over Na₂SO₄, concentrated and purified by silica gel chromatography (CH₂Cl₂:MeOH/10:1-5:1) to afford piperazine amidoxime 1c (geometry unassigned).

Step D:

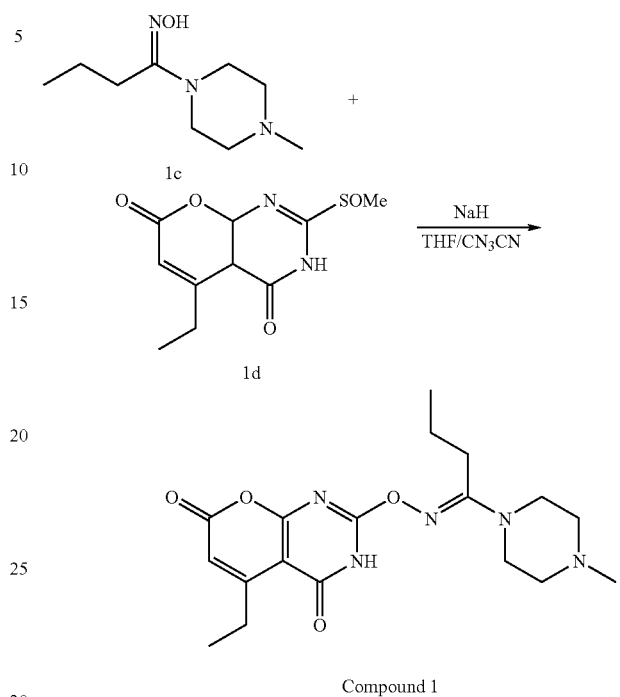

Compound 1

To a mixture of sulfoxide 1d (prepared as described below) (1 eq) and piperazine amidoxime 1c (1.5 eq) in THF/CH₃CH (1:1, ca. 0.1 M concentration) was added NaH (2.2 eq) and the resulting mixture was stirred at room temperature overnight. Then the reaction mixture was quenched with sat. aqueous NH₄Cl, extracted with CH₂Cl₂, dried over Na₂SO₄, concentrated and purified by silica gel chromatography (CH₂Cl₂: MeOH=12:1) to afford product (unassigned geometry). (The silica gel column was eluted with CH₂Cl₂:MeOH:Et₃N=20: 2:1 before the chromatographic separation).

Preparation of Sulfoxide

Step A:

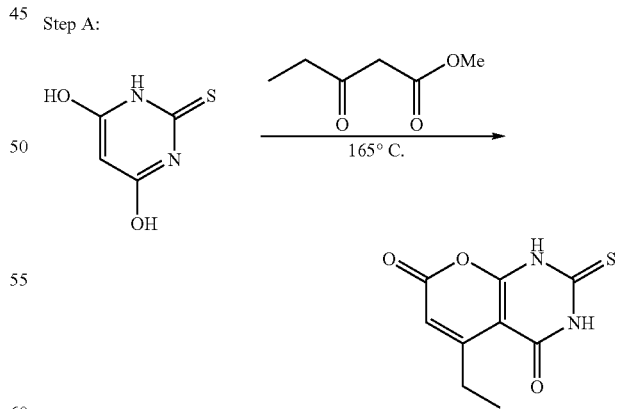

A mixture of 4,6-dihydroxy-2-mercapto-pyrimidine (20.0 g, 138.7 mmol) and methyl propionylacetate (21.8 mL, 173.4 mmol) was heated at 165° C. until the ester was completely reacted. The reaction mixture was cooled down and poured into water (75 mL) and then filtered through a sintered funnel. The solid residue was washed with water (2×20 mL) and dried under vacuum to yield 5-ethyl-2-thioxo-2,3-dihydro-1h-pyrano[2,3-d]pyrimidine-4,7-dione (11.6 g, 37%).

Step B:

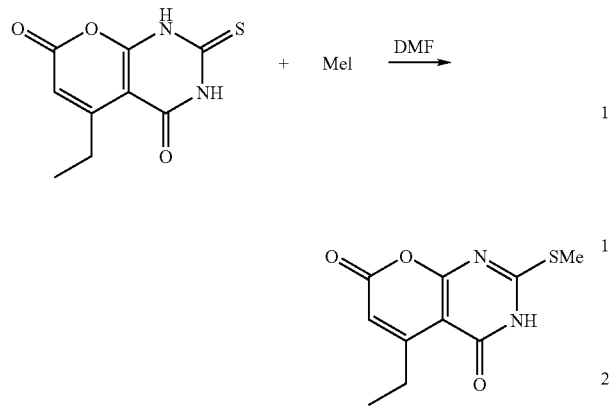

MeI (2.23 mL, 35.72 mmol) was added to a suspension of 5-ethyl-2-thioxo-2,3-dihydro-1h-pyrano[2,3-d]pyrimidine-4,7-dione (4.0 g, 17.86 mmol) in DMF (40 mL) at room temperature. The reaction mixture was stirred at room temperature overnight. The reaction mixture was then poured into water (250 mL) and filtered through a sintered funnel. The solid residue was washed with water (2×50 mL) and dried under vacuum to give 5-ethyl-2-methylsulfanyl-3H-pyrano[2,3-d]pyrimidine-4,7-dione (4.1 g, 96%).

Step C:

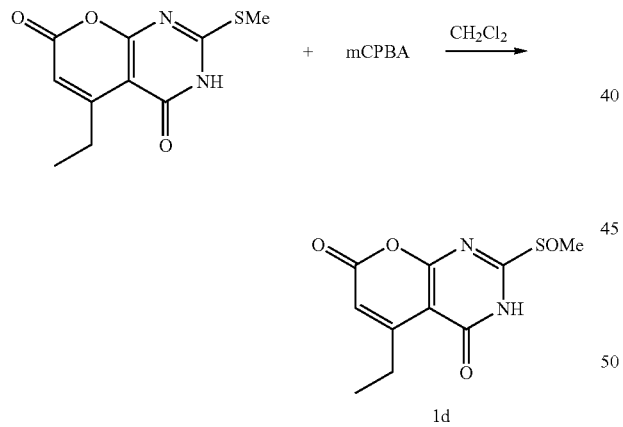

m-CPBA (3.1 g, 70%, 12.6 mmol) was added to a suspension of 5-ethyl-2-methylsulfanyl-3h-pyrano[2,3-d]pyrimidine-4,7-dione (2.0 g, 8.4 mmol) in $CH_2Cl_2$ (150 mL) at room temperature. The solvent was removed from the suspension after 3 hours and the crude product was purified using silica gel flash column chromatography, eluting first with hexane/EtOAc (v/v=1/1) then $CH_2Cl_2$/MeOH (v/v=2/1) to give 1d (2.0 g, 94%). Electrospray MS [M+1]$^+$255.1.

The following compounds were prepared following the general procedure of Example 1, steps A-D, using the appropriate starting materials (e.g., the appropriate aldehyde and/or heterocycloalkyl reagent):

Compound 1:

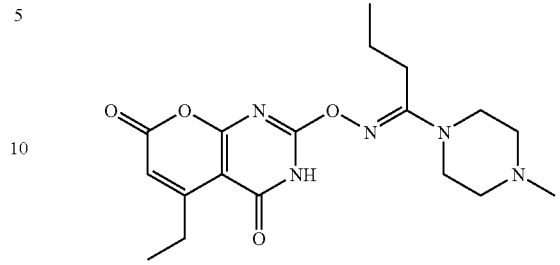

White powder (37% yield); $^1$H NMR (DMSO): δ 0.95 (t, 3 H, J=7.3 Hz), 1.14 (t, 3 H, J=7.6 Hz), 1.54-1.44 (m, 2 H), 2.25 (s, 3 H), 2.45-2.38 (m, 4 H), 2.56-2.50 (m, 2 H), 2.97-2.89 (m, 2 H), 3.42-3.36 (m, 4 H), 5.91 (s, 1 H); Mass for $C_{18}H_{26}N_5O_4$ (MH)$^+$: 376, Found: 376.

Compound 2:

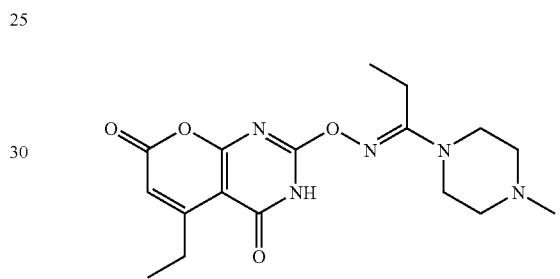

White powder (25% yield); $^1$H NMR (DMSO): δ 1.04 (t, 3 H, J=7.3 Hz), 1.11 (t, 3 H, J=7.3 Hz), 2.21 (s, 3 H), 2.42-2.34 (m, 4 H), 2.57-2.47 (m, 2 H), 2.95-2.85 (m, 2 H), 3.41-3.32 (m, 4 H), 5.87 (s, 1 H); Mass for $C_{17}H_{24}N_5O_4$ (MH)$^+$: 362, Found: 362.

Compound 3:

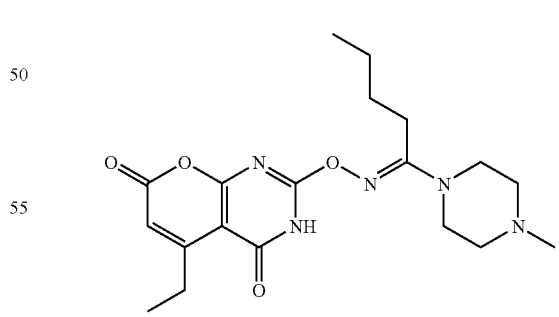

White powder (24% yield); $^1$H NMR (DMSO): δ 0.88 (t, 3 H, J=6.6 Hz), 1.11 (t, 3 H, J=6.7 Hz), 1.46-1.27 (m, 4 H), 2.21 (s, 3 H), 2.42-2.33 (m, 4 H), 2.55-2.46 (m, 2 H), 2.95-2.86 (m, 2 H), 3.40-3.30 (m, 4 H), 5.88 (s, 1 H); Mass for $C_{19}H_{28}N_5O_4$ (MH)$^+$: 390, Found: 390.

Compound 4:

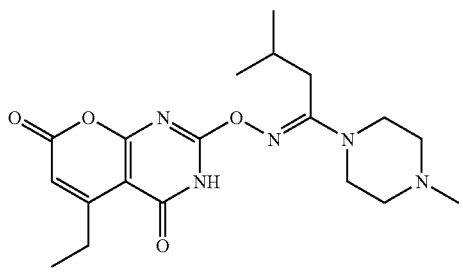

White powder (30% yield); $^1$H NMR (DMSO): δ 0.91 (d, 6 H, J=5.9 Hz), 1.11 (t, 3 H, J=8.4 Hz), 1.89-1.73 (m, 1 H), 2.22 (s, 3 H), 2.43-2.33 (m, 4 H), 2.53-2.43 (m, 2 H), 2.96-2.83 (m, 2 H), 3.44-3.33 (m, 4 H), 5.89 (s, 1 H); Mass for $C_{19}H_{28}N_5O_4$ (MH)$^+$: 390, Found: 390.

Compound 5:

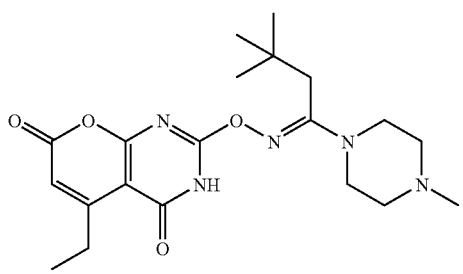

White powder (23% yield); $^1$H NMR (DMSO): δ 0.96 (s, 9 H), 1.11 (t, 3 H, J=7.3 Hz), 2.23 (s, 3 H), 2.44-2.37 (m, 4 H), 2.56 (s, 2 H), 2.95-2.85 (m, 2 H), 3.42-3.33 (m, 4 H), 5.89 (s, 1 H); Mass for $C_{20}H_{30}N_5O_4$ (MH)$^+$: 404, Found: 404.

Compound 6:

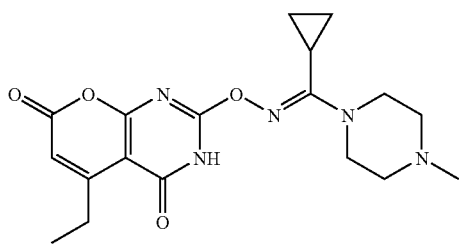

Off-white powder (38% yield); $^1$H NMR (CDCl$_3$): δ 0.88-0.81 (m, 2 H), 1.01 (t, 3 H, J=6.3 Hz), 1.28-1.21 (m, 2 H), 1.55-1.43 (m, 2 H), 1.70-1.57 (m, 3 H), 2.42 (s, 3 H), 2.59-2.52 (m, 4 H), 3.01 (t, 2 H, J=8.1 Hz), 3.41-3.61 (m, 4 H), 5.98 (s, 1 H); Mass for $C_{20}H_{27}N_5O_4$ (MH)$^+$: 402, Found: 402.

Compound 7:

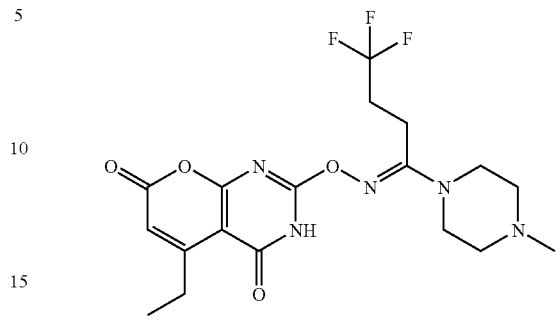

White powder (24% yield); $^1$H NMR (DMSO): δ 1.16 (t, 3 H, J=7.4 Hz), 2.47 (s, 3 H), 2.56-2.38 (m, 6 H), 2.83-2.73 (m, 2 H), 2.96-2.86 (m, 2 H), 3.42-3.32 (m, 4 H), 5.90 (s, 1 H); Mass for $C_{18}H_{23}F_3N_5O_4$ (MH)$^+$: 430, Found: 430.

Compound 8:

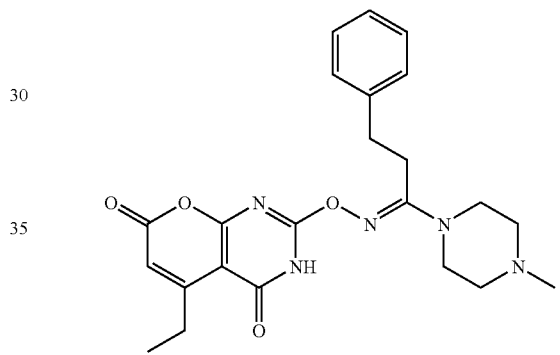

White powder (26% yield); $^1$H NMR (DMSO): δ 1.15 (t, 3 H, J=7.6 Hz), 2.24 (s, 3 H), 2.41-2.35 (m, 4 H), 2.88-2.74 (m, 4 H), 2.98-2.90 (m, 2 H), 3.40-3.30 (m, 4 H), 5.90 (s, 1 H), 7.30-7.10 (m, 5 H); Mass for $C_{23}H_{28}N_5O_4$ (MH)$^+$: 438, Found: 438.

Compound 9:

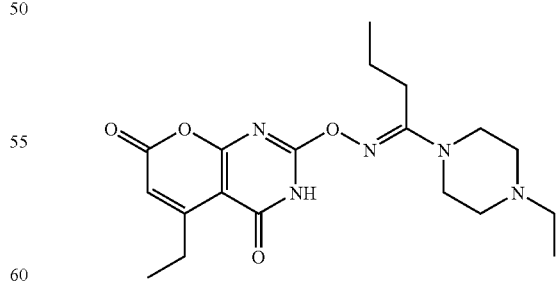

White powder (31% yield); $^1$H NMR (DMSO): δ 0.95 (t, 3 H, J=7.3 Hz), 1.04 (t, 3 H, J=6.9 Hz), 1.14 (t, 3 H, J=7.3 Hz), 1.55-1.43 (m, 2 H), 2.58-2.38 (m, 8 H), 2.98-2.88 (m, 2 H), 3.45-3.36 (m, 4 H), 5.92 (s, 1 H); Mass for $C_{19}H_{28}N_5O_4$ (MH)$^+$: 390, Found: 390.

Compound 10:

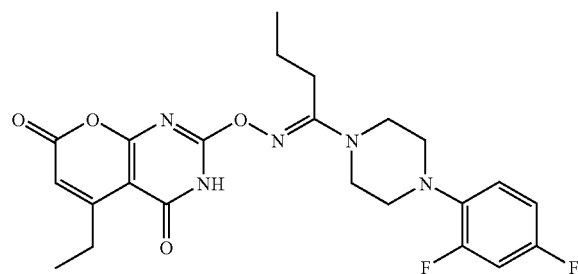

White powder (26% yield); $^1$H NMR (DMSO): δ 0.98 (t, 3 H, J=7.6 Hz), 1.15 (t, 3 H, J=7.3 Hz), 1.58-1.48 (m, 2 H), 2.62-2.55 (m, 2 H), 2.98-2.90 (m, 2 H), 3.07-2.98 (m, 4 H), 3.61-3.51 (m, 4 H), 5.95 (s, 1 H), 7.09-6.97 (m, 1 H), 7.17-7.08 (m, 1 H), 7.29-7.19 (m, 1H); Mass for $C_{23}H_{26}F_2N_5O_4$ (MH)$^+$: 474, Found: 474.

Compound 11:

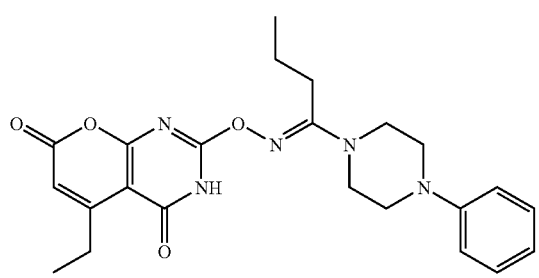

Off-white powder (18% yield); $^1$H NMR (DMSO): δ 0.98 (t, 3 H, J=7.6 Hz), 1.15 (t, 3 H, J=7.6 Hz), 1.57-1.49 (m, 2 H), 2.62-2.55 (m, 2 H), 2.97-2.91 (m, 2 H), 3.23-3.16 (m, 4 H), 3.59-3.52 (m, 4 H), 5.94 (s, 1 H), 6.83 (t, 1 H, J=7.5 Hz), 7.02-6.96 (m, 2 H), 7.28-7.23 (m, 2H); Mass for $C_{23}H_{28}N_5O_4$ (MH)$^+$: 438, Found: 438.

Compound 12:

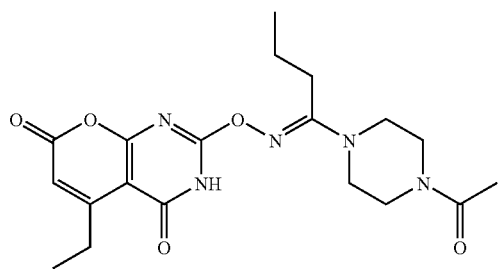

White powder (33% yield); $^1$H NMR (CD$_3$OD): δ 1.04 (t, 3 H, J=6.9 Hz), 1.22 (t, 3 H, J=7.3 Hz), 1.67-1.55 (m, 2 H), 2.14 (s, 2 H), 2.67 (t, 2 H, J=8.5 Hz), 3.08-2.98 (m, 2 H), 3.57-3.43 (m, 4 H), 3.70-3.59 (m, 4 H), 5.96 (s, 1 H); Mass for $C_{19}H_{26}N_5O_5$ (MH)$^+$: 404, Found: 404.

Compound 13:

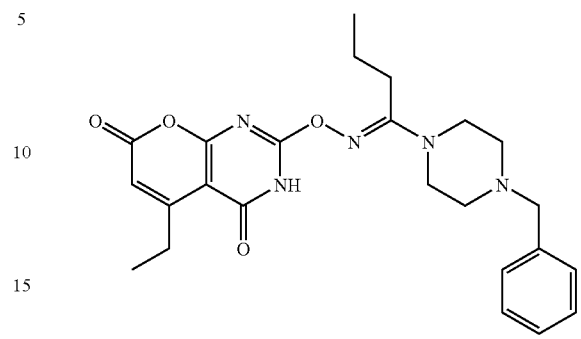

Brown powder (19% yield); $^1$H NMR (DMSO): δ 0.91 (t, 3 H, J=7.3 Hz), 1.11 (t, 3 H, J=6.6 Hz), 1.52-1.38 (m, 2 H), 2.42-2.34 (m, 4 H), 2.53-2.45 (m, 2 H), 2.97-2.86 (m, 2 H), 3.39-3.33 (m, 4 H), 3.52-3.47 (s, 2 H), 5.90 (s, 1 H), 7.36-7.20 (m, 5 H); Mass for $C_{24}H_{30}N_5O_4$ (MH)$^+$: 452, Found: 452.

Compound 14:

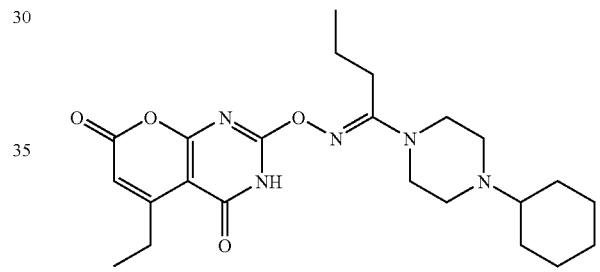

White powder (25% yield); $^1$H NMR (DMSO): δ 1.89-0.81 (m, 19 H), 2.40-2.24 (m, 2 H), 2.69-2.42 (m, 4 H), 3.07-2.87 (m, 4 H), 3.40-3.23 (m, 2 H), 5.89 (s, 1 H), 9.18 (s, 1 H); Mass for $C_{23}H_{34}N_5O_4$ (MH)$^+$: 444, Found: 444.

Compound 15:

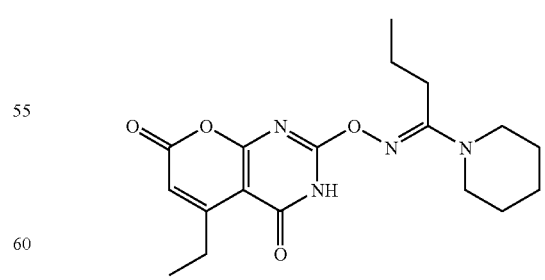

Off-white powder (21% yield); $^1$H NMR (DMSO): δ 0.96 (t, 3 H, J=7.2 Hz), 1.09 (t, 3 H, J=7.6 Hz), 1.70-1.50 (m, 8 H), 2.57-2.45 (m, 2 H), 2.87-2.79 (m, 2 H), 3.62-3.48 (m, 4 H), 5.28 (s, 1 H); Mass for $C_{18}H_{25}N_4O_4$ (MH)$^+$: 361, Found: 361.

Compound 16:

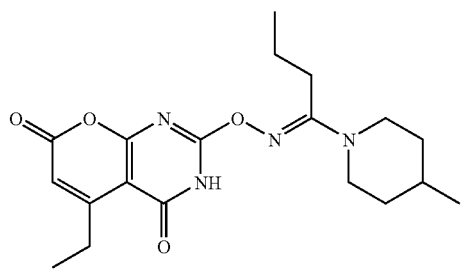

Brown oil (19% yield); $^1$H NMR (DMSO): δ 1.80-0.90 (m, 16 H), 2.69-2.61 (m, 2H), 2.92-2.82 (m, 2 H), 3.07-2.98 (m, 2 H), 4.10-4.01 (m, 2 H), 5.96 (s, 1 H); Mass for $C_{19}H_{27}N_4O_4$ $(MH)^+$: 375, Found: 375.

Compound 17:

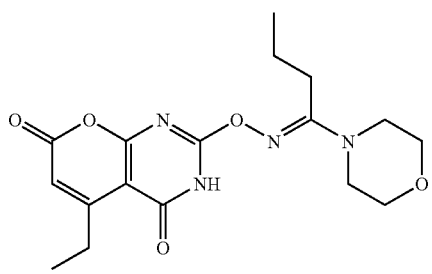

White powder (40% yield); $^1$H NMR (DMSO): δ 0.96 (t, 3 H, J=7.3 Hz), 1.14 (t, 3 H, J=7.3 Hz), 1.56-1.45 (m, 2 H), 2.57-2.50 (m, 2 H), 2.98-2.90 (m, 2 H), 3.42-3.36 (m, 4 H), 3.67-3.61 (m, 4 H), 5.94 (s, 1 H), 12.70-12.39 (br s, 1 H); Mass for $C_{17}H_{23}N_4O_5$ $(MH)^+$: 363, Found: 363.

Compound 18:

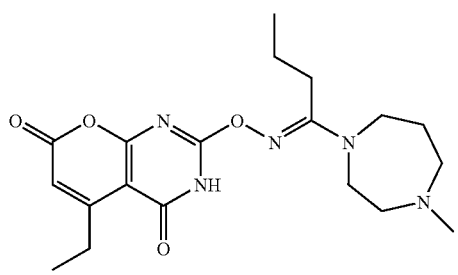

White powder (29% yield); $^1$H NMR (DMSO): δ 0.96 (t, 3 H, J=6.9 Hz), 1.14 (t, 3 H, J=7.2 Hz), 1.57-1.44 (m, 2 H), 1.93-1.83 (m, 2 H), 2.58-2.33 (m, 5 H), 2.80-2.62 (m, 4 H), 3.00-2.88 (m, 2 H), 3.66-3.42 (m, 4 H), 5.87 (s, 1 H); Mass for $C_{19}H_{28}N_5O_4$ $(MH)^+$: 390, Found: 390.

Compound 19:

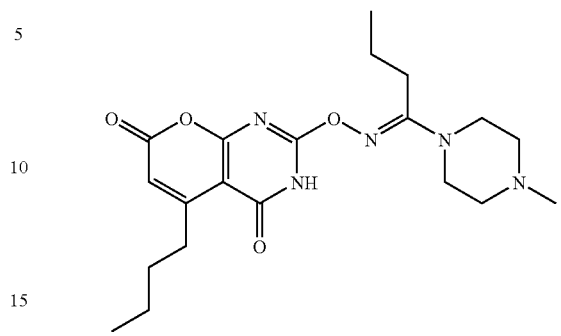

White powder (34% yield); $^1$H NMR (CD$_3$OD): δ 0.99 (t, 3 H, J=7.3 Hz), 1.05 (t, 3 H, J=7.2 Hz), 1.53-1.41 (m, 2 H), 1.68-1.55 (m, 4 H), 2.43 (s, 3 H), 2.70-2.59 (m, 6 H), 3.04-2.98 (m, 2 H), 3.57-3.49 (m, 4 H), 5.92 (s, 1 H); Mass for $C_{20}H_{30}N_5O_4$ $(MH)^+$: 404, Found: 404.

Compound 20:

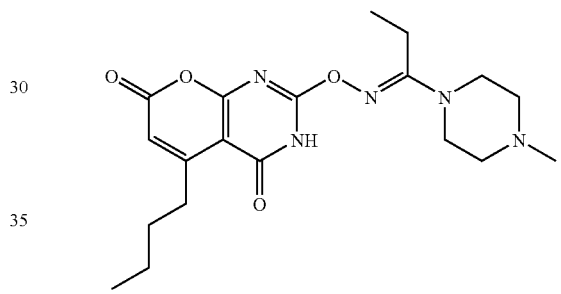

White powder (33% yield); $^1$H NMR (DMSO): δ 0.91 (t, 3 H, J=7.3 Hz), 1.07 (t, 3 H, J=7.6 Hz), 1.42-1.31 (m, 2 H), 1.58-1.44 (m, 2 H), 2.26 (s, 3 H), 2.60-2.38 (m, 6H), 2.95-2.85 (m, 2 H), 3.45-3.32 (m, 4 H), 5.91 (s, 1 H); Mass for $C_{19}H_{28}N_5O_4$ $(MH)^+$: 390, Found: 390.

Compound 21:

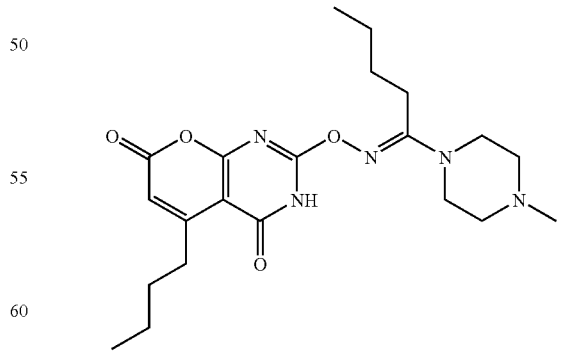

White powder (33% yield); $^1$H NMR (CD$_3$OD): δ 1.02-0.96 (m, 6 H), 1.68-1.40 (m, 8 H), 2.43 (s, 3 H), 2.73-2.58 (m, 6 H), 3.06-2.96 (m, 2 H), 3.58-3.48 (m, 4 H), 5.94 (s, 1 H); Mass for $C_{21}H_{32}N_5O_4$ $(MH)^+$: 418, Found: 418.

Compound 22:

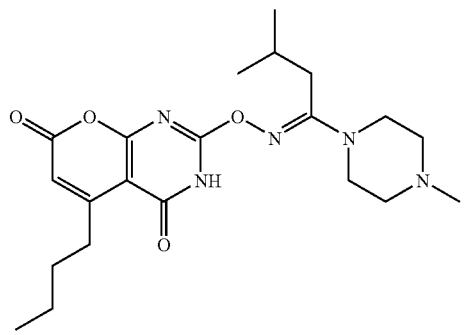

White powder (23% yield); $^1$H NMR (DMSO): δ 1.01-0.85 (m, 9 H), 1.43-1.30 (m, 2 H), 1.56-1.44 (m, 2 H), 1.91-1.77 (m, 1 H), 2.26 (s, 3 H), 2.59-2.34 (m, 6 H), 2.95-2.84 (m, 2 H), 3.47-3.37 (m, 4 H), 5.91 (s, 1 H); Mass for $C_{21}H_{32}N_5O_4$ (MH)$^+$: 418, Found: 418.

Compound 23:

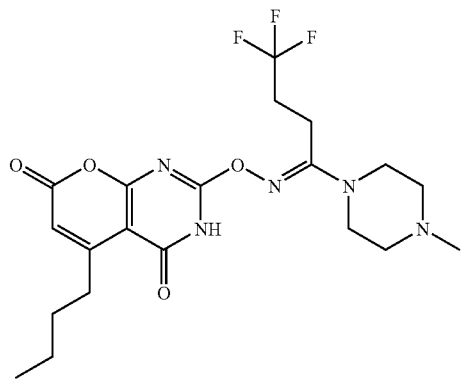

White powder (28% yield); $^1$H NMR (DMSO): δ 0.91 (t, 3 H, J=7.3 Hz), 1.43-1.29 (m, 2 H), 1.56-1.43 (m, 2 H), 2.27 (s, 3 H), 2.61-2.38 (m, 6 H), 2.81 (t, 2 H, J=8.5 Hz), 2.91 (t, 2H, J=7.6 Hz), 3.49-3.36 (m, 4 H), 5.91 (s, 1 H); Mass for $C_{20}H_{27}F_3N_5O_4$ (MH)$^+$: 458, Found: 458.

Compound 24:

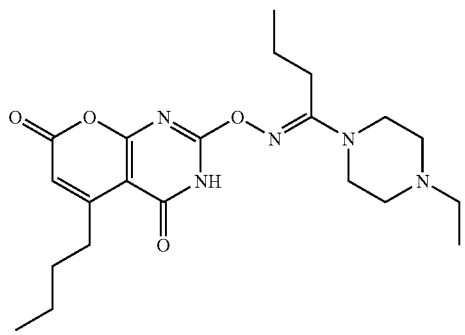

White powder (31% yield); $^1$H NMR (DMSO): δ 0.99 (t, 3 H, J=7.1 Hz), 1.05 (t, 3 H, J=7.3 Hz), 1.21 (t, 3 H, J=7.2 Hz), 1.53-1.42 (m, 2 H), 1.69-1.55 (m, 4 H), 2.77-2.60 (m, 8 H), 3.05-2.97 (m, 2 H), 3.62-3.49 (m, 4 H), 5.91 (s, 1 H); Mass for $C_{21}H_{32}N_5O_4$ (MH)$^+$: 418, Found: 418.

Compound 25:

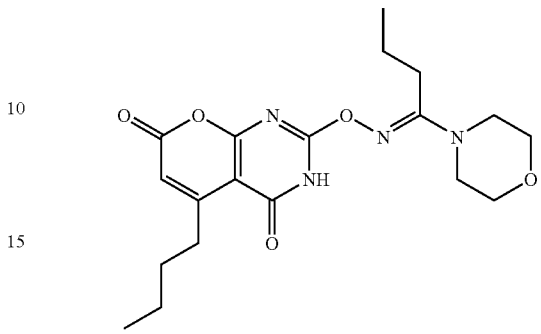

White powder (28% yield); $^1$H NMR (DMSO): δ 1.03-0.81 (m, 6 H), 1.42-1.30 (m, 2 H), 1.57-1.43 (m, 4 H), 2.60-2.42 (m, 2 H), 2.97-2.84 (m, 2 H), 3.45-3.35 (m, 4H), 3.70-3.58 (m, 4 H), 5.92 (s, 1 H); Mass for $C_{19}H_{27}N_4O_5$ (MH)$^+$: 391, Found: 391.

Compound 26:

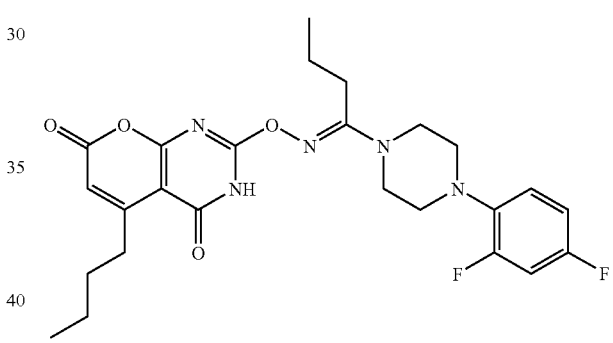

White powder (26% yield); $^1$H NMR (DMSO): δ 0.91 (t, 3 H, J=7.3 Hz), 0.98 (t, 3 H, J=6.9 Hz), 1.43-1.29 (m, 2 H), 1.60-1.43 (m, 4 H), 2.58 (t, 2 H, J=8.2 Hz), 2.91 (t, 2 H, J=7.9 Hz), 3.06-2.98 (m, 4 H), 3.60-3.51 (m, 4 H), 5.92 (s, 1 H), 7.30-6.95 (m, 3 H); Mass for $C_{25}H_{30}F_2N_5O_4$ (MH)$^+$: 502, Found: 502.

Compound 27:

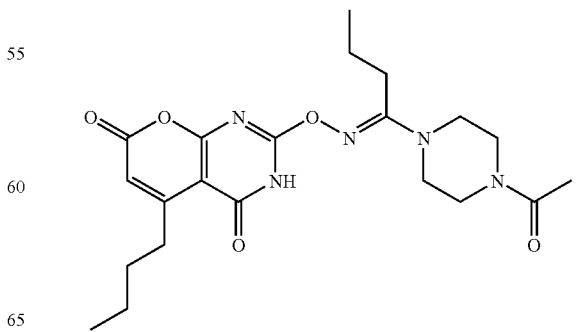

White powder (31% yield); ¹H NMR (CD₃OD): δ 0.99 (t, 3 H, J=7.6 Hz), 1.07 (t, 3 H, J=7.9 Hz), 1.54-1.40 (m, 2 H), 1.72-1.54 (m, 4 H), 2.17 (s, 3 H), 2.69 (t, 2 H, J=8.2 Hz), 3.06 (t, 2 H, J=8.2 Hz), 3.74-3.44 (m, 8 H), 5.95 (s, 1 H); Mass for $C_{21}H_{30}N_5O_5$ (MH)⁺: 432, Found: 432.

Compound 28:

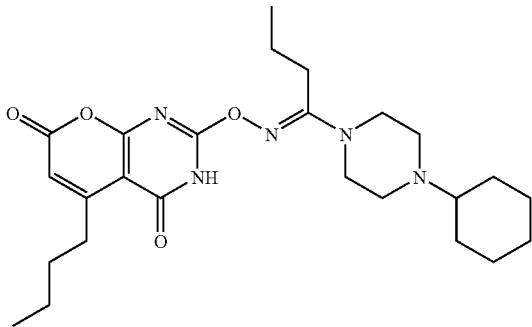

White powder (22% yield); ¹H NMR (CDCl₃): δ 1.00 (t, 3 H, J=7.3 Hz), 1.07 (t, 3 H, J=7.9 Hz), 2.06-1.12 (m, 17 H), 2.86-2.57 (m, 6 H), 3.01 (t, 2 H, J=7.9 Hz), 3.65-3.29 (m, 4 H), 5.98 (s, 1 H), 10.01-9.63 (br s, 1 H); Mass for $C_{25}H_{38}N_5O_4$ (MH)⁺: 472, Found: 472.

Compound 29:

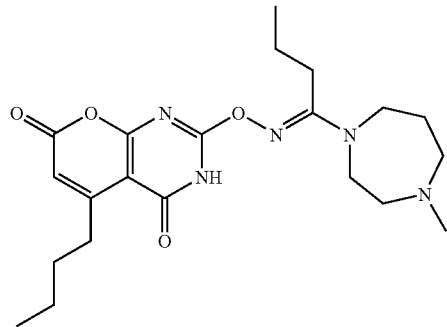

White powder (29% yield); ¹H NMR (DMSO): δ 1.02-0.76 (m, 6 H), 1.60-1.20 (m, 8 H), 1.91-1.79 (m, 2 H), 2.39 (s, 3 H), 2.81-2.58 (m, 4 H), 2.95-2.85 (m, 2 H), 3.66-3.42 (m, 4 H), 5.85 (s, 1 H); Mass for $C_{21}H_{32}N_5O_4$ (MH)⁺: 418, Found: 418.

Compound 30:

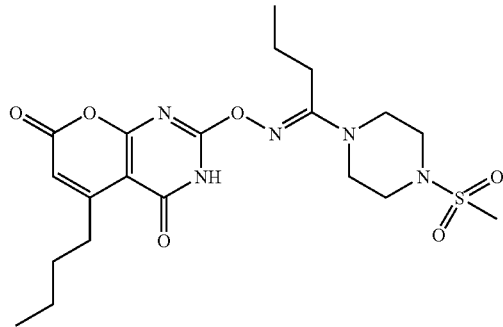

White powder (42% yield); ¹H NMR (DMSO): δ 0.91 (t, 3 H, J=7.3 Hz), 0.96 (t, 3 H, J=7.4 Hz), 1.40-1.30 (m, 2 H), 1.58-1.44 (m, 4 H), 2.58-2.50 (m, 2 H), 2.97-2.84 (m, 5 H), 3.22-3.12 (m, 4 H), 3.59-3.48 (m, 4 H), 5.93 (s, 1 H); Mass for $C_{20}H_{30}N_5O_6S$ (MH)⁺: 468, Found: 468.

Compound 31:

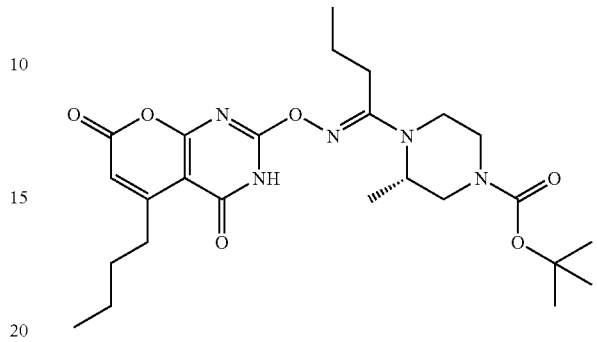

White powder (20% yield); ¹H NMR (DMSO): δ 0.91 (t, 3 H, J=7.5 Hz), 0.96 (t, 3 H, J=7.6 Hz), 1.10 (d, 3 H, J=6.9 Hz), 1.56-1.32 (m, 15 H), 2.67-2.41 (m, 2 H), 3.21-2.74 (m, 5 H), 3.99-3.65 (m, 3 H), 4.37-4.21 (m, 1 H), 5.93 (s, 1 H); Mass for $C_{24}H_{36}N_5O_6$ (MH)⁺: 490, Found: 490.

Compound 32:

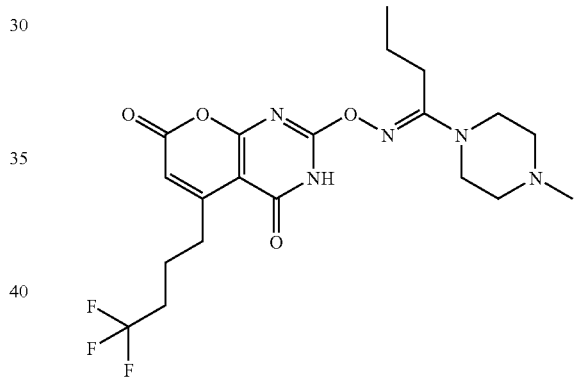

White powder (44% yield); ¹H NMR (CD₃OD): δ 1.05 (t, 3 H, J=7.5 Hz), 1.70-1.53 (m, 2 H), 1.93-1.81 (m, 2 H), 2.37-2.22 (m, 2 H), 2.46 (s, 3 H), 2.75-2.57 (m, 6 H), 3.12-3.01 (m, 2 H), 3.61-3.48 (m, 4 H), 5.93 (s, 1 H); Mass for $C_{20}H_{27}F_3N_5O_4$ (MH)⁺: 458, Found: 458.

Compound 33:

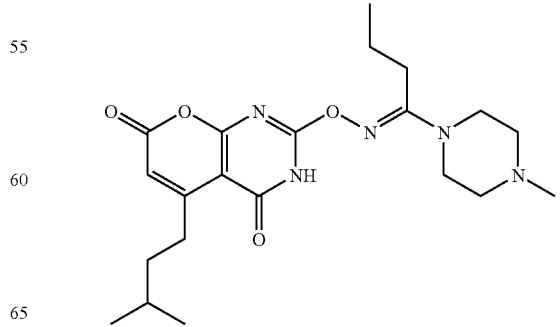

Off-white powder (42% yield); $^1$H NMR (DMSO): δ 0.97-0.90 (m, 9 H), 1.43-1.37 (m, 2 H), 1.53-1.44 (m, 2 H), 1.67-1.57 (m, 1 H), 2.25 (s, 3 H), 2.41 (t, 4 H, J=5.1 Hz), 2.55-2.51 (m, 2 H), 2.93-2.88 (m, 2 H), 3.39 (t, 4 H, J=4.8 Hz), 5.90 (s, 1 H); Mass for $C_{21}H_{32}N_5O_4$ (MH)$^+$: 418, Found: 418.

Compound 34:

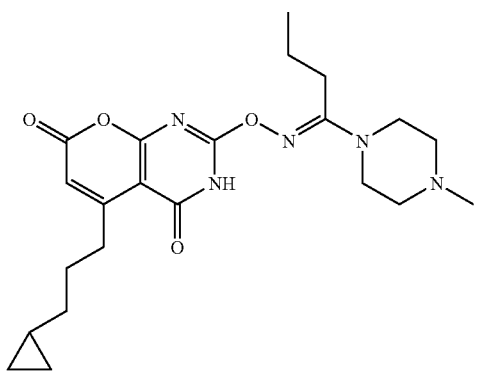

Pale yellow powder (37% yield); $^1$H NMR (DMSO): δ 0.01 (m, 2 H), 0.39 (m, 2H), 0.70 (m, 1 H), 0.95 (t, J=7.0 Hz, 3 H), 1.26 (q, J=7.0 Hz, 2 H), 1.49 (m, 2 H), 1.61 (m, 2 H), 2.26 (s, 3 H), 2.42 (m, 4 H), 2.53 (q, J=7.5 Hz, 2 H), 2.92 (t, J=7.5 Hz, 2 H), 3.40 (m, 4 H), 5.90 (1 H), δ 12.91 (s, 1 H); Mass for $C_{22}H_{32}N_5O_4$ (MH)$^+$: 430, Found: 430.

Compound 35:

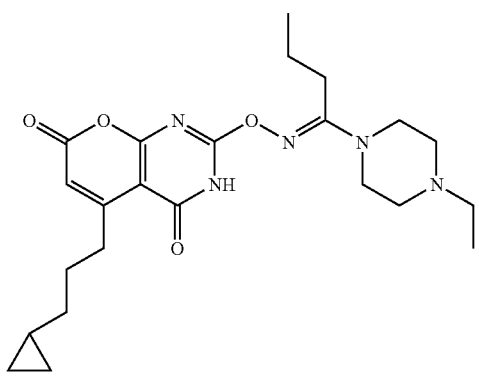

Pale yellow powder (27% yield); $^1$H NMR (DMSO): δ 0.01 (m, 2 H), 0.39 (m, 2H), 0.70 (m, 1H), 0.95 (t, J=7.0 Hz, 3 H), 1.0 (t, J=7.0 Hz, 3 H), 1.26 (q, J=7.0 Hz, 2 H), 1.49 (m, 2 H), 1.62 (m, 2 H), 2.43 (q, J=7.5 Hz, 2 H), 2.48 (m, 4 H), 2.92 (t, J=7.5 Hz, 2 H), 3.40 (m, 4 H), 5.90 (1H), 12.91 (s, 1 H); Mass for $C_{23}H_{34}N_5O_4$ (MH)$^+$: 444, Found: 444.

Example 2

General Procedure for Preparation of Thiophene Oxime Compounds 36 and 37

Step A:

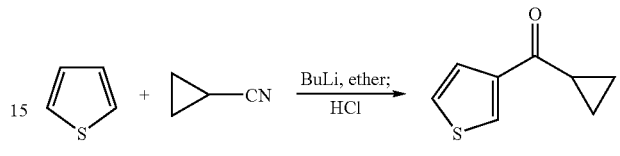

To a solution of thiophene (1.1 eq) in ether (ca. 0.5M concentration) was added n-BuLi/hexane (1 eq) at −78° C. under $N_2$ and stirred for 30 min. Then nitrile (1 eq) was added and the resulting mixture was stirred overnight and allowed to warm up to room temperature. It was then quenched with 0.5 N HCl, extracted with EtOAc, dried over $Na_2SO_4$, concentrated and purified by silica gel chromatography (EtOAc: hexane) to afford product 36a.

Step B:

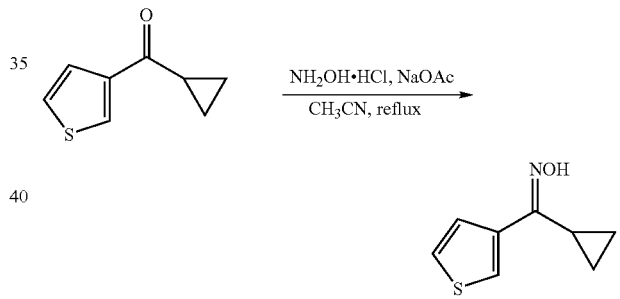

To a solution of thiophene ketone 36a (1 eq) in $CH_3CN$ (ca. 1 M concentration) was added $NH_2OH\cdot HCl$ (1.2 eq) and NaOAc (1.2 eq) and the resulting mixture was heated at reflux overnight. It was then cooled down to room temperature and filtered. The filtrate was concentrated to give crude product 36b as a mixture of E and Z isomers, which were separated by silica gel chromatography ($CH_2Cl_2$:MeOH) to provide pure E and Z isomers.

Step C:

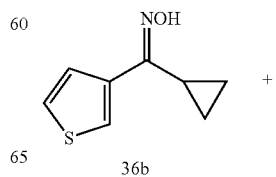

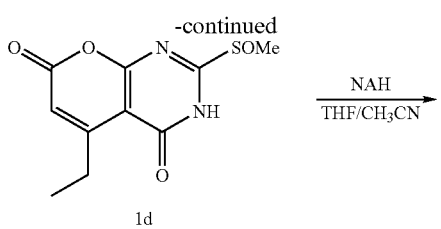

To a mixture of sulfoxide 1d (1 eq) and thiophene oxime 36b (1.5 eq) in THF/CH₃CH (1:1, ca. 0.1 M concentration) was added NaH (2.2 eq) and the resulting mixture was stirred at room temperature overnight. Then it was quenched with sat. aqueous NH₄Cl, extracted with CH₂Cl₂, dried over Na₂SO₄, concentrated and purified by silica gel chromatography (CH₂Cl₂:MeOH) to afford Compound 36.

The following compounds were prepared using the general procedure described above in Example 2, steps A-C using the appropriate starting materials (e.g., the appropriate nitrile and/or heterocycloalkyl reagent):

Compound 36:

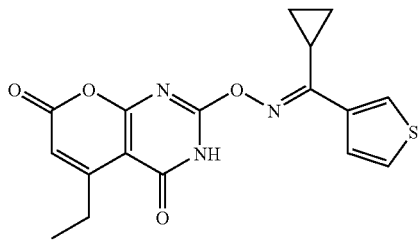

White powder (18% yield); ¹H NMR (CDCl₃): δ 1.20-1.13 (m, 4 H), 1.29 (t, 3 H, J=7.6 Hz), 2.14-2.03 (m, 1 H), 3.15-3.03 (m, 2 H), 6.06 (s, 1 H), 7.50-7.46 (m, 1 H), 7.74-7.67 (m, 1 H), 8.29-8.22 (m, 1 H); Mass for C₁₇H₁₆N₃O₄S (MH)⁺: 358, Found: 358.

Compound 37:

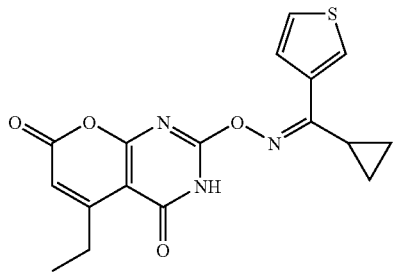

White powder (34% yield); ¹H NMR (DMSO): δ 0.98-0.91 (m, 2 H), 1.20-1.08 (m, 5 H), 2.40-2.31 (m, 1 H), 3.00-2.90 (m, 2 H), 6.00 (s, 1 H), 7.49-7.44 (m, 1 H), 7.70-7.65 (m, 1 H), 8.06-8.02 (m, 1 H); Mass for C₁₇H₁₆N₃O₄S (MH)⁺: 358, Found: 358.

Example 3

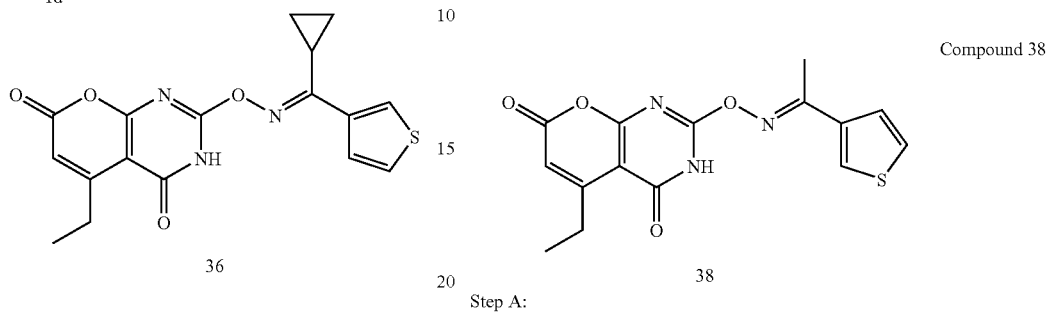

Step A:

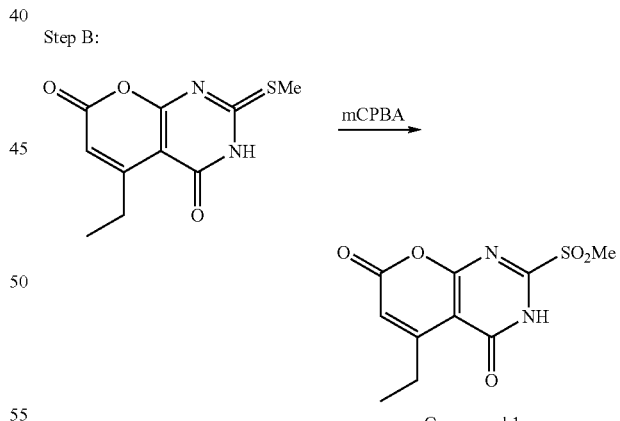

Pyridine (0.72 mL, 8.90 mmol) was added to the suspension of 3-acetylthiophene (1.05 g, 8.33 mmol), hydroxylamine hydrochloride salt (612 mg, 8.81 mmol) in EtOH (80 mL). The resulting mixture was stirred at room temperature overnight. The volatiles were removed from the reaction mixture and the crude mixture was purified by column chromatography (eluted with EtOAc/hexanes, 1:10) to give 38a (0.85 g, 72%).

Step B:

To a suspension of 5-ethyl-2-methylsulfanyl-3H-pyrano[2,3-d]pyrimidine-4,7-dione (5.0 g, 21.0 mmol) in DCM (250 mL), mCPBA (10.1 g, 77%, 45.2 mmol) was added. The resulting mixture was stirred at room temperature overnight. Me₂S (3.5 mL, 48 mmol) was added and stirred at room temperature for 1.5 h. Solvent was removed, and taken up with mixture of EtOAc/hexanes (1:3). Filtered, and the solid was washed with EtOAc/hexanes (1:3), extensively. The white solid was collected to give Compound 1e (2.6 g, 39%).

Step C:

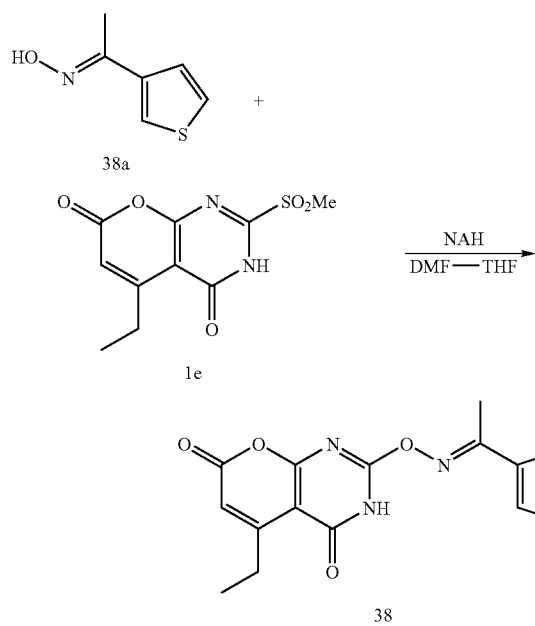

38a (0.26 g, 1.84 mmol) was taken up with THF (6 mL) under nitrogen. NaH (46 mg, 95% oil dispersion, 1.82 mmol) was added. The resulting slurry was stirred at room temperature for 1 h. A solution of 1e (246 mg, 0.91 mmol) in DMF (2 mL) was added dropwise. The resulting mixture was stirred at room temperature for 2 h. The reaction mixture was then poured into 10 mL of water, 3.5 mL of 1 N HCl and EtOAc. The solid that precipitated out was collected and dried to give Compound 38 (0.31 g, 54%). Electrospray MS [M+1]$^+$ 332.1

Example 4

Compound 39

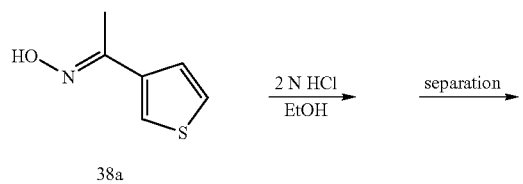

Step A:

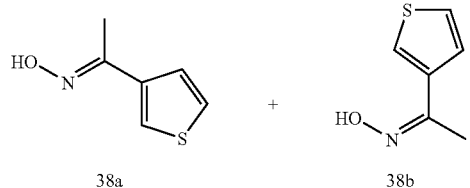

-continued

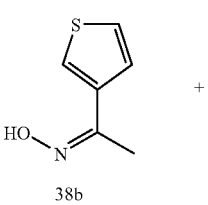

38a (1.8 g) was dissolved in EtOH (35 mL), and 2 N HCl in ether (20 mL) was added. The resulting solution was stirred at room temperature overnight. Solvent was removed, the residue was taken up with DCM and washed with satd. Na$_2$CO$_3$ (aqueous). The organic layer was separated, dried (MgSO$_4$), filtered and concentrated in vacuo. The residue was purified by silica gel chromatography (eluted with EtOAc/hexanes, 1:10), to give 38a (1.68 g, 93%) and 38b (0.13 g, 7%).

Step B:

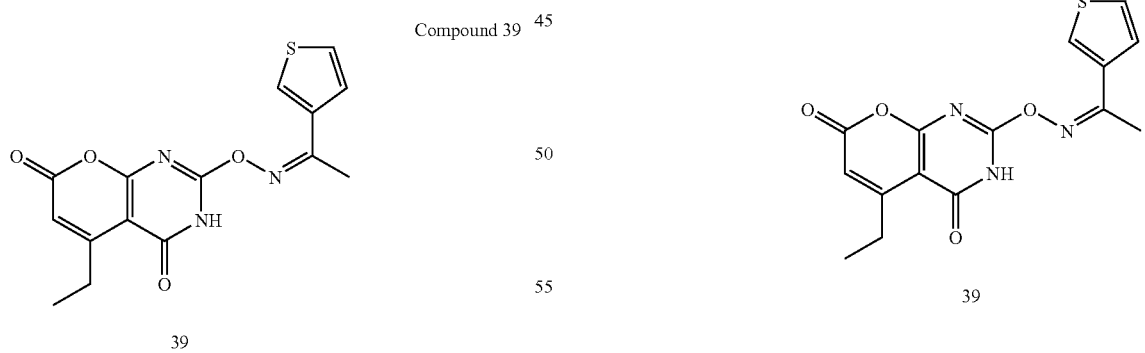

38b (0.13 g, 0.93 mmol) was taken up with THF (2 mL) under nitrogen. NaH (26 mg, 95% oil dispersion, 1.03 mmol) was added. The resulting slurry was stirred at room temperature for 1 h. A solution of 1e (126 mg, 0.47 mmol) in DMF (1 mL) was added dropwise. The resulting mixture was stirred at room temperature for 2 h. The reaction mixture was then poured into 10 mL of water, 3.5 mL of 1 N HCl and EtOAc. The organic layer was separated, washed with brine, dried (MgSO$_4$), filtered and concentrated to give a solid. The solid was taken up with EtOAc and filtered to give Compound 39 as a white solid (58 mg, 38%). Electrospray MS [M+1]+ 332.1

Example 5

Compound 40

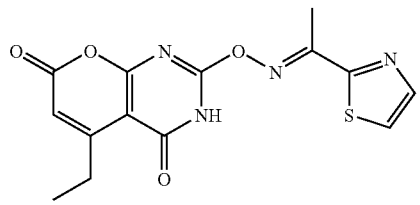

40, Isomers A and B

Step A:

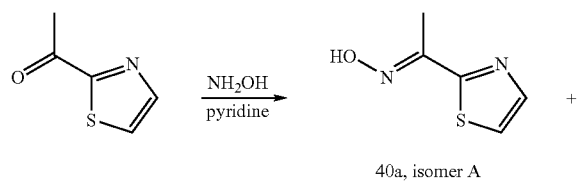

40a, isomer A

40b, isomer B

Pyridine (0.59 mL, 7.29 mmol) was added to the suspension of 2-acetylthiazole (1.05 g, 3.93 mmol), hydroxylamine hydrochloride salt (301 mg, 4.32 mmol) in THF (2 mL). The resulting mixture was stirred at room temperature overnight. The volatile was removed and the crude mixture was purified by column chromatography (eluted with 5% EtOAc in hexanes), to give 40a, isomer A (0.2 g, 36%) and 40b, isomer B (0.21 g, 37%).

Step B:

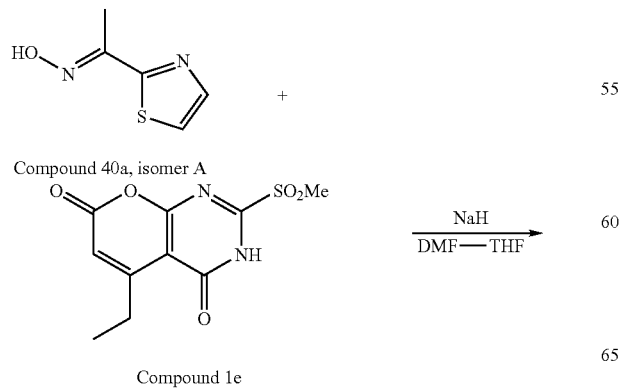

Compound 1e

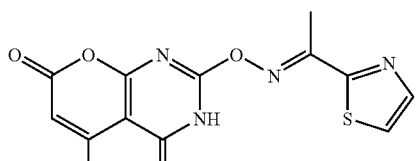

Compound 41, isomer A

The preparation of 40, isomer A and isomer B proceeded as described in the procedure for preparing Compound 38 using 40a isomer A and 40b isomer B, respectively. MS for both: Electrospray MS [M+Na]+: 355.2

Compounds 41-44 were prepared using procedures of example 2, steps A-C, appropriate nitrile starting material. Compounds 45-55 were prepared using the general procedures of Example 5, steps A and B, above, from the appropriate ketone:

Compound 41:

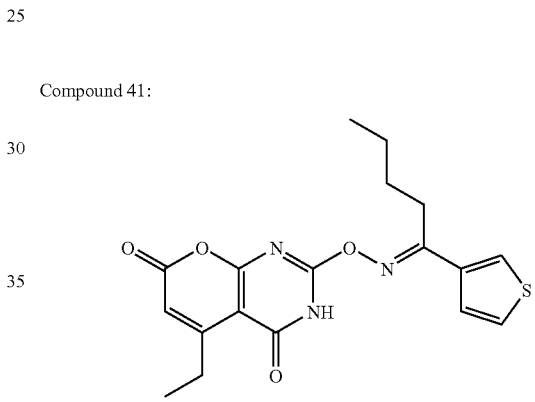

White powder (21%); $^1$H NMR (DMSO): δ 0.91 (t, 3 H, J=6.9 Hz), 1.16 (t, 3 H, J=7.2 Hz), 1.47-1.32 (m, 2 H), 1.60-1.46 (m, 2 H), 3.00-2.85 (m, 4 H), 6.01 (s, 1 H), 7.73-7.66 (m, 1 H), 7.82-7.73 (m, 1 H), 8.37-8.29 (m, 1 H); Mass for $C_{18}H_{20}N_3O_4S$ (MH)+: 374, Found: 374.

Compound 42:

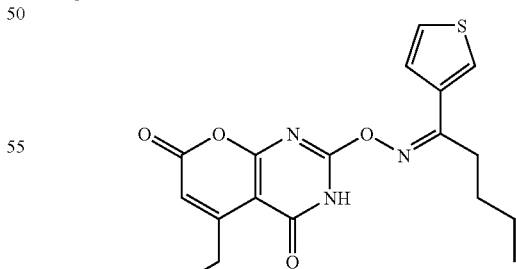

White powder (23%); $^1$H NMR (DMSO): δ 0.90 (t, 3 H, J=7.3 Hz), 1.15 (t, 3 H, J=7.6 Hz), 1.45-1.30 (m, 2 H), 1.60-1.46 (m, 2 H), 2.88-2.79 (m, 2 H), 3.01-2.88 (m, 2 H), 6.04 (s, 1 H), 7.67-7.62 (m, 1 H), 7.76-7.69 (m, 1 H), 8.48-8.41 (m, 1 H); Mass for $C_{18}H_{20}N_3O_4S$ (MH)+: 374, Found: 374.

Compound 43:

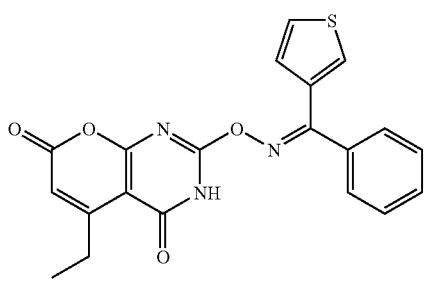

Off-white powder (15% yield, mixture of E and Z isomers); $^1$H NMR (DMSO): δ 1.18-1.13 (m, 3 H), 3.02-2.89 (m, 2 H), 6.05-5.89 (m, 1 H), 8.10-7.30 (m, 5 H); Mass for $C_{20}H_{16}N_3O_4S$ (MH)$^+$: 394, Found: 394.

Compound 44:

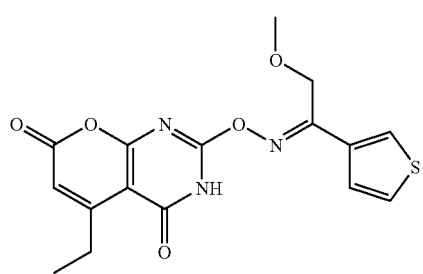

Off-white powder (23% yield); $^1$H NMR (DMSO): δ 1.16 (t, 3 H, J=7.3 Hz), 3.03-2.87 (m, 2 H), 3.33 (s, 3 H), 4.55 (s, 2 H), 6.03 (s, 1 H), 7.76-7.68 (m, 2 H), 8.62-8.53 (m, 1 H), 13.58-13.08 (br s, 1 H); Mass for $C_{16}H_{16}N_3O_5S$ (MH)$^+$: 362, Found: 362.

Compound 45:

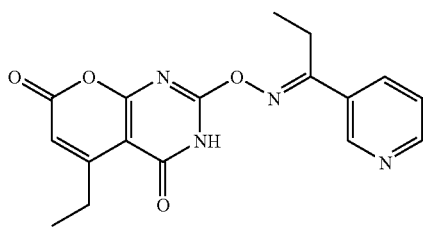

Yellow powder (13%); $^1$H NMR (DMSO): δ 1.14-1.02 (m, 6 H), 2.96-2.83 (m, 4 H), 5.83 (s, 1 H), 7.50-7.40 (m, 1 H), 8.27-8.18 (m, 1 H), 8.66-8.60 (m, 1 H), 9.00-8.96 (m, 1 H); Mass for $C_{17}H_{17}N_4O_4$ (MH)$^+$: 341, Found: 341.

Compound 46:

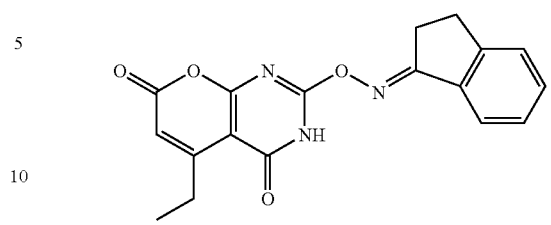

White powder (24% yield); $^1$H NMR (CDCl$_3$): δ 1.04 (t, 3 H, J=7.3 Hz), 3.09-2.83 (m, 6 H), 5.50 (s, 1 H), 7.35-7.24 (m, 1 H), 7.50-7.36 (m, 2 H), 7.69 (d, 1 H, J=8.8 Hz); Mass for $C_{18}H_{16}N_3O_4$ (MH)$^+$: 338, Found: 338.

Compound 47:

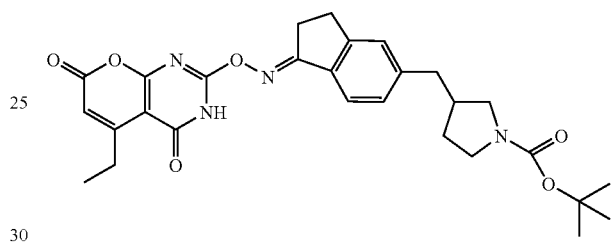

White powder (9% yield); $^1$H NMR (CDCl$_3$): δ 1.75-1.04 (m, 15 H), 2.68-2.50 (m, 4 H), 3.23-2.93 (m, 6 H), 4.05 (d, J=13.2 Hz, 2 H), 5.96 (s, 1 H), 7.19-7.10 (m, 2 H), 7.66 (d, J=8.9 Hz, 1 H), 10.19-9.72 (br s, 1H); Mass for $C_{28}H_{33}N_4O_6$ (MH)$^+$: 521, Found: 521.

Compound 48:

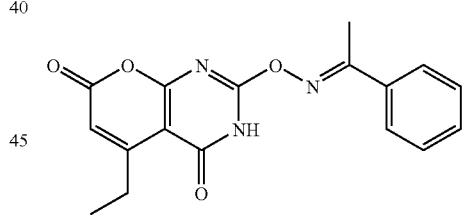

Mass for $C_{17}H_{16}N_3O_4$ (MH)$^+$: 326, Found: 326.

Compound 49:

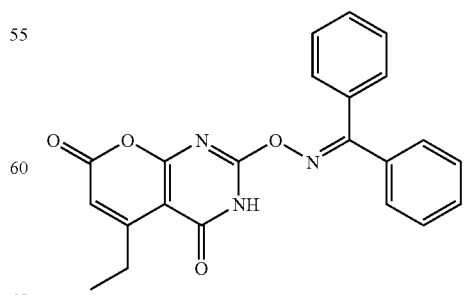

Mass for $C_{22}H_{18}N_3O_4$ (MH)$^+$: 388, Found: 388.

Compound 50:

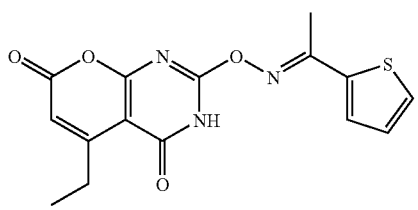

Mass for $C_{15}H_{14}N_3O_4S$ (MH)$^+$: 332, Found: 332.

Compound 51:

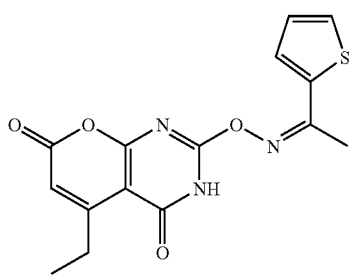

Mass for $C_{15}H_{14}N_3O_4S$ (MH)$^+$: 332, Found: 332.

Compound 52:

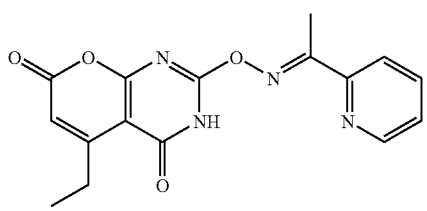

Mass for $C_{16}H_{15}N_4O_4$ (MH)$^+$: 327, Found: 327.

Compound 53:

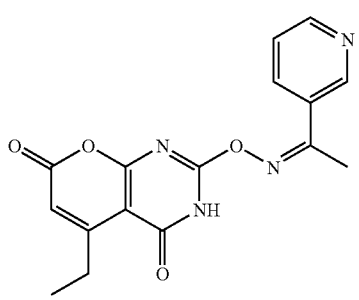

Mass for $C_{16}H_{15}N_4O_4$ (MH)$^+$: 327, Found: 327.

Compound 54:

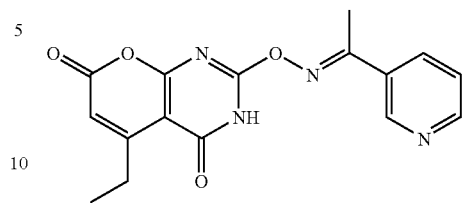

Mass for $C_{16}H_{15}N_4O_4$ (MH)$^+$: 327, Found: 327.

Compound 55:

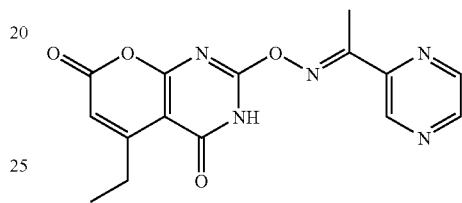

Mass for $C_{15}H_{14}N_5O_4$ (MH)$^+$: 328, Found: 328.

Example 6

Compound 56

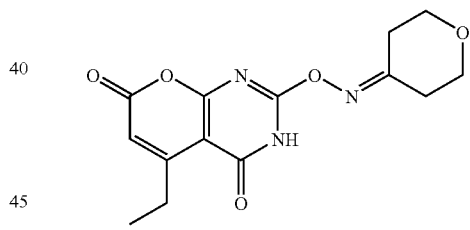

56

Step A:

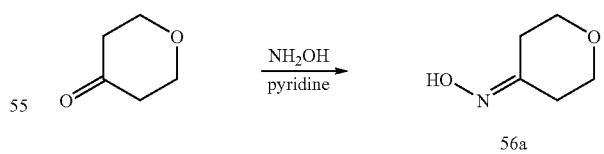

56a

Pyridine (0.75 mL, 9.27 mmol) was added to a suspension of tetrahydropyranone (0.50 g, 5.00 mmol) and hydroxylamine hydrochloride salt (282 mg, 5.49 mmol) in EtOH (5 mL). The resulting mixture was stirred at room temperature overnight. The volatiles were removed and the crude mixture was purified by silica gel column chromatography, eluted first with 10% EtOAc/DCM then 30% EtOAc/DCM, to give 56a (0.45 g, 78%) as a white solid.

Step B:

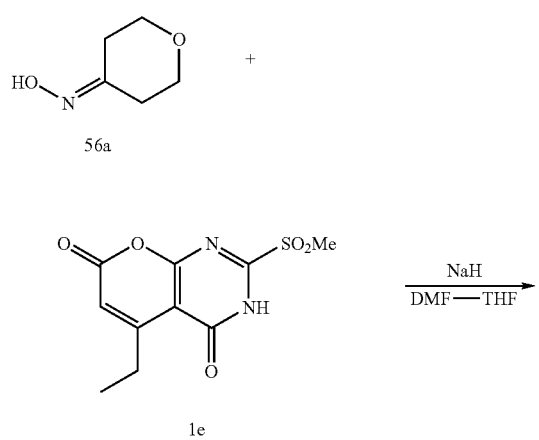

Compound 56 was prepared from 56a and 1e using the procedure for preparing Compound 38. Electrospray MS [M+1]⁺ 306.2

Compounds 57-60 were prepared using 1d and the appropriate oxime starting material, as described above in step B.

Compound 57:

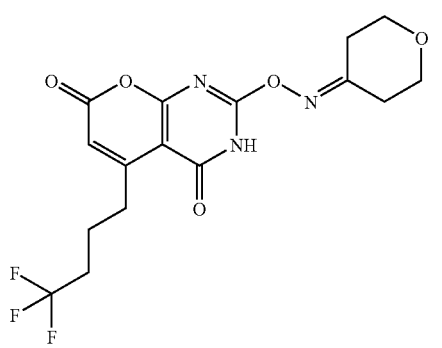

White powder (13% yield); ¹H NMR (DMSO): δ 1.86-1.70 (m, 2 H), 2.41-2.21 (m, 2H), 2.63-2.45 (m, 2 H), 2.79-2.68 (m, 2 H), 3.03-2.90 (m, 2H), 3.88-3.65 (m, 4H), 6.03 (s, 1 H), 13.10-12.78 (br s, 1 H); Mass for $C_{16}H_{17}F_3N_3O_5$ (MH)⁺: 388, Found: 388.

Compound 58:

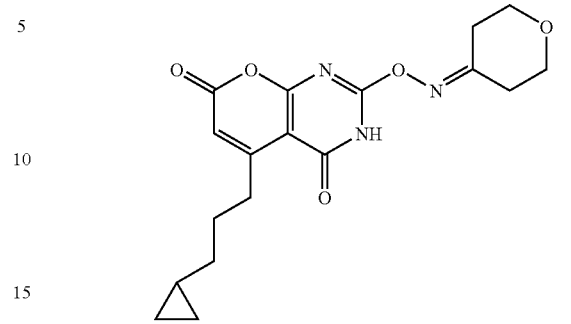

White powder (51% yield); ¹H NMR (DMSO): δ 0.01 (m, 2 H), 0.39 (m, 2 H), 0.70 (m, 1 H), 1.26 (q, J=7.0 Hz, 2 H), 1.62 (m, 2 H), 2.73 (t, J=5.5 Hz, 2 H), 2.93 (t, J=7.5 Hz, 2 H), 3.33 (m, 2 H), 3.74 (t, J=5.5 Hz, 2 H), 3.82 (t, J=6.0 Hz, 2 H), 5.98 (1 H), 12.91 (s, 1 H); Mass for $C_{18}H_{22}N_3O_5$ (MH)⁺: 360, Found: 360.

Compound 59:

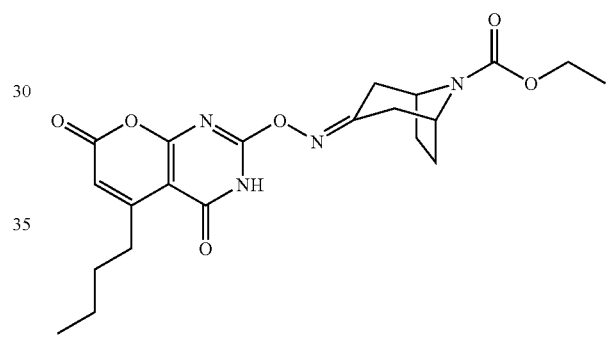

White powder (33% yield); ¹H NMR (DMSO): δ 0.91 (t, 3 H, J=6.4 Hz), 1.22 (t, 3 H, J=6.9 Hz), 1.42-1.31 (m, 2 H), 1.57-1.45 (m, 3 H), 1.73-1.62 (m, 1 H), 2.05-1.88 (m, 2 H), 2.70-2.29 (m, 3 H), 2.91 (t, 2 H, J=8.2 Hz), 3.08 (d, 1 H, J=13.9 Hz), 4.16-4.07 (m, 2 H), 4.46-4.31 (m, 2 H), 5.98 (s, 1 H); Mass for $C_{21}H_{27}N_4O_6$ (MH)⁺: 431, Found: 431.

The starting materials for 59 and 60 were prepared using the general procedure described in Example 7 (steps A-C).

Compound 60:

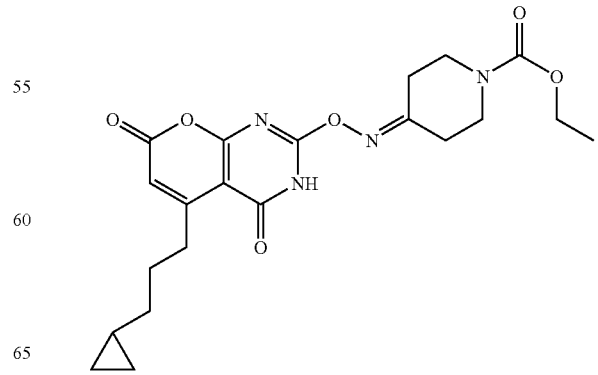

White powder (51% yield); ¹H NMR (DMSO): δ 0.01 (m, 2 H), 0.39 (m, 2 H), 0.70 (m, 1 H), 1.22 (t, J=7.5 Hz, 3 H), 1.24 (t, J=7.0 Hz, 2 H), 1.62 (m, 2 H), 2.52 (t, J=5.5 Hz, 2 H), 2.73 (t, J=6.0 Hz, 2 H), 2.92 (t, J=7.5 Hz, 2 H), 3.56 (t, J=6.0 Hz, 2 H), 3.61 (t, J=6.0 Hz, 2 H), 4.08 (q, J=7.5 Hz, 2 H), 5.98 (1 H), 12.91 (s, 1 H); Mass for $C_{21}H_{27}N_4O_6$ $(MH)^+$: 431, Found: 431.

Compounds 61-79

Compounds 61-64 were prepared in one step from commercially available oximes, and compounds 65-79 were prepared using a similar two-step procedure from the corresponding ketones, as described in the preparation of Compound 38.

| Compound | Electrospray LCMS $[M + 1]^+$ |
|---|---|
| 61 | 304.2 |
| 62 | 290.1 |
| 63 | 319.2 |
| 64 | 292.1 |
| 65 | 358.2 |

-continued
| Compound | Electrospray LCMS [M + 1]+ |
|---|---|
| 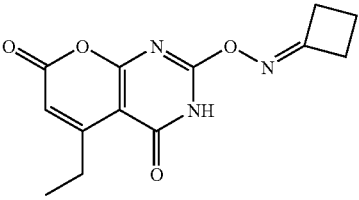<br>66 | 276.2 |
| 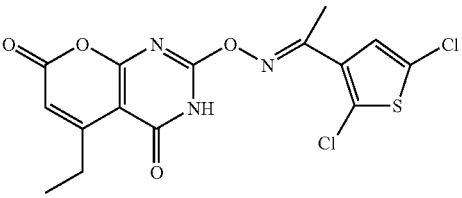<br>67 | 400.2 |
| 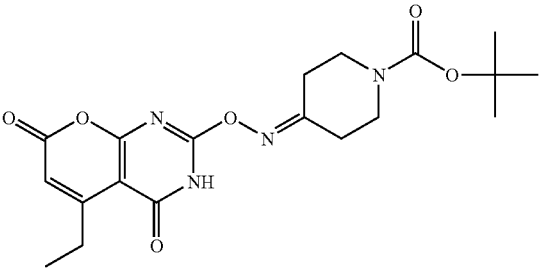<br>68 | 405.0 |
| 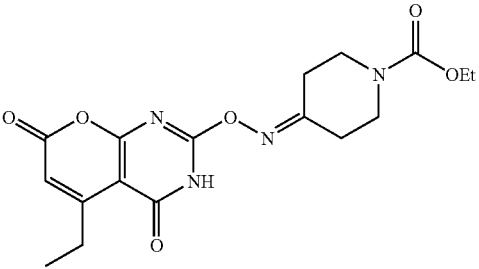<br>69 | 377.2 |
| 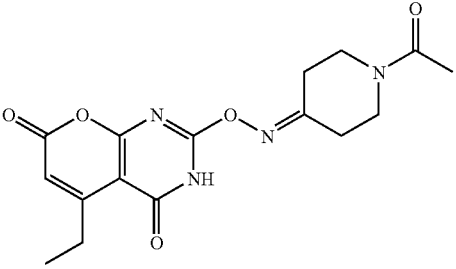<br>70 | 347.2 |

-continued
| Compound | Electrospray LCMS [M + 1]+ |
|---|---|
| 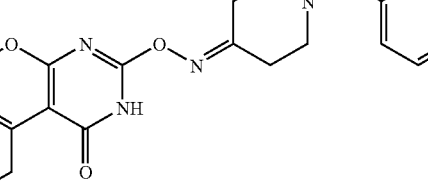<br>71 | 409.0 |
| 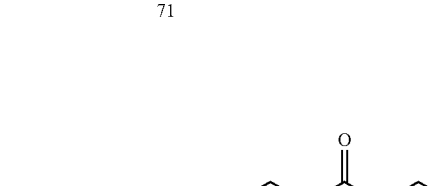<br>72 | 427.2 |
| 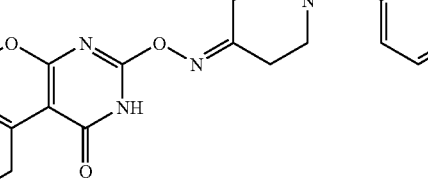<br>73 | 383.2 |
| 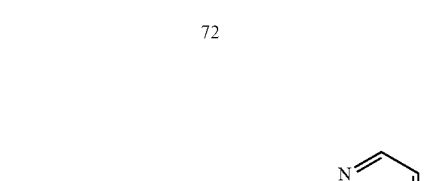<br>74 | 399.2 |

-continued
| Compound | Electrospray LCMS [M + 1]⁺ |
|---|---|
| 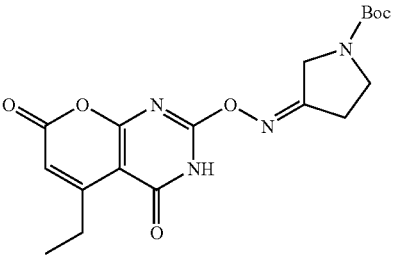<br>75, isomer A | 391.2 |
| 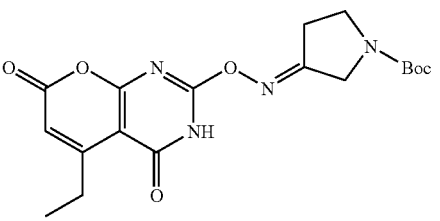<br>75, isomer B | 391.2 |
| 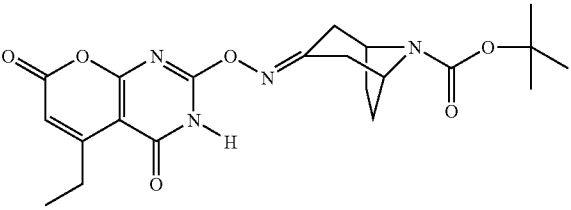<br>76 | 431.2 |
| 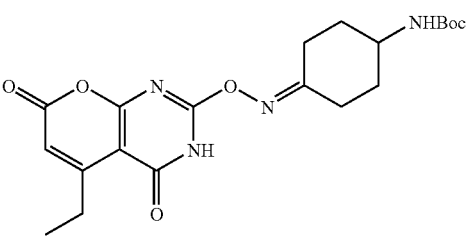<br>77 | 419.2 |
| 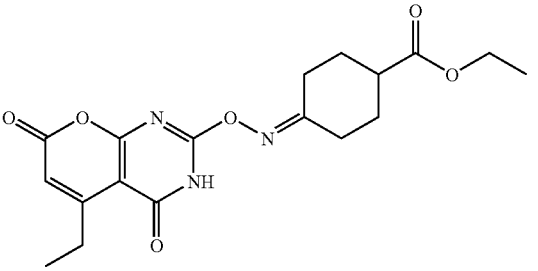<br>78 | 376.2 |

| Compound | Electrospray LCMS [M + 1]+ |
|---|---|
| 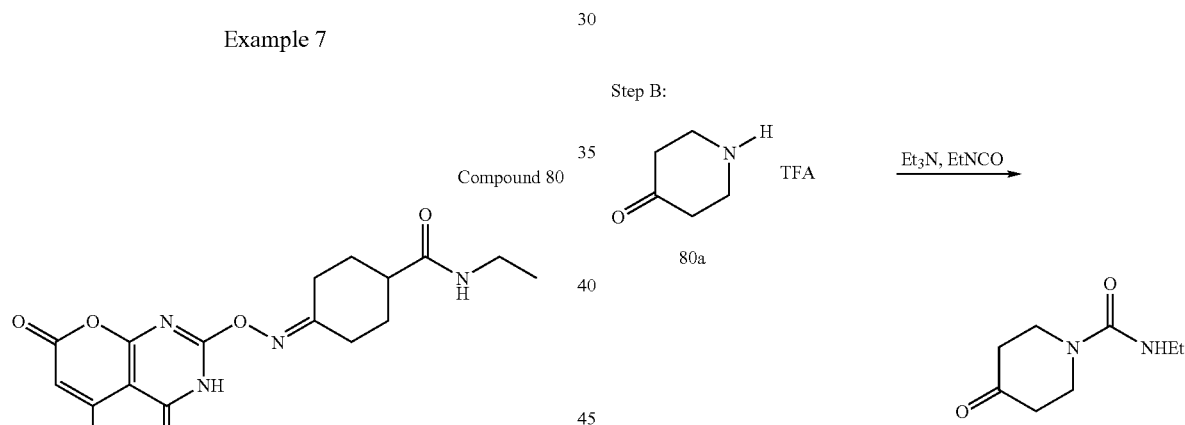
79, isomer A | 363.0 |
| 79, isomer B | 363.0 |

Example 7

Compound 80

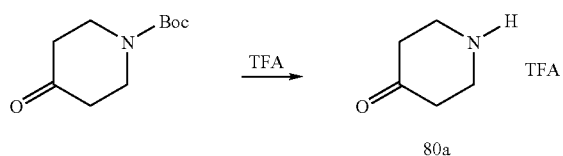

80

Step A:

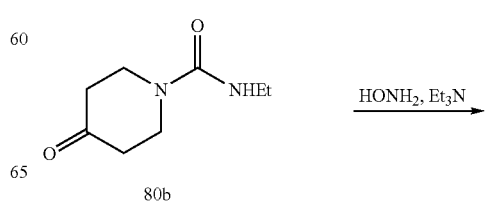

4-Boc-piperidone (0.50 g, 2.51 mmol) and TFA (1.49 mL, 20.08 mmol) were dissolved in DCM (6 mL). The resulting mixture was stirred at room temperature for 1 h. The solvent was removed by rotary evaporation to give 0.56 g (105%) of Compound 80a as a colorless oil.

Step B:

Compound 80a (440 mg, 1.13 mmol), triethylamine (0.87 mL, 6.25 mmol), ethyl isocyanate (0.27 mL, 3.39 mmol) were mixed in DCM (6 mL). The resulting solution was stirred at room temperature overnight. The volatiles were removed and the residue was purified by silica gel column chromatography (eluted with 3% $NH_3$-MeOH (4%) in DCM), to give 0.20 g (104%) of Compound 80b.

Step C:

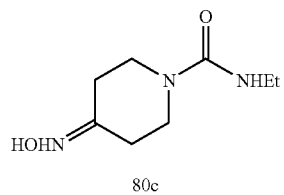

80c

Pyridine (0.18 mL, 1.3 mmol) was added to the suspension of Compound 80b (0.20 g, 1.2 mmol) and hydroxylamine hydrochloride salt (0.10 g, 1.3 mmol) in EtOH (5 mL). The resulting mixture was stirred at room temperature overnight. The volatiles were removed and the crude mixture was purified by silica gel column chromatography (eluted with 50% EtOAc in hexanes), to give Compound 80c (0.13 g, 59%).

Step D:

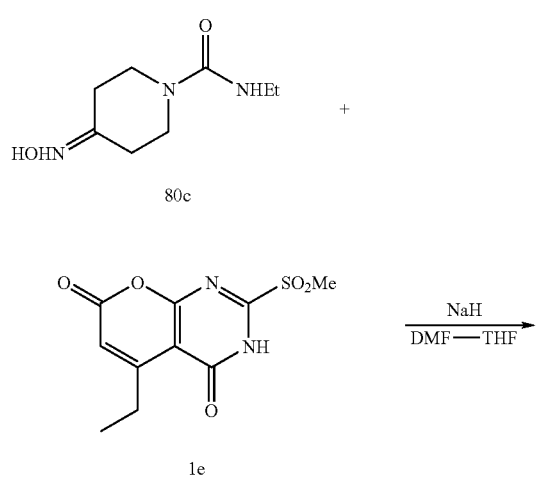

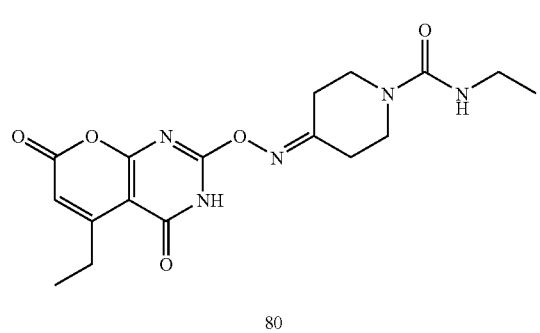

80

Compound 80c (0.13 g, 0.70 mmol) was taken up with THF (2 mL) under nitrogen. NaH (21 mg, 95% oil dispersion, 0.84 mmol) was added. The resulting slurry was stirred at room temperature for 1 h. A solution of Compound 1e (95 mg, 0.35 mmol) in DMF (1 mL) was added dropwise. The resulting mixture was stirred at room temperature for 2 h. The reaction mixture was then poured into 5 mL of water, 0.83 mL of 1 N HCl, and allowed to stand at room temperature, until solid started to precipitate out. The solid was collected by filtration and washed with water, EtOAc, and $CH_3CN$ to give 80 mg (61%) of Compound 80 as a white solid. Electrospray MS $[M+1]^+$ 376.2

Compounds 81-94

Compound 81-94 were prepared in a four-step procedure from the corresponding 4-Boc piperidone as described above in Example 7 for Compound 80, using the appropriate isocyanate, acyl chloride, chloroformate, and sulfonyl chloride.

| Compound | Electrospray LCMS $[M + 1]^+$ |
|---|---|
| 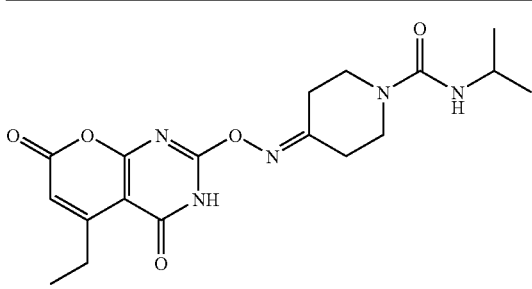 81 | 390.2 |

-continued
| Compound | Electrospray LCMS [M + 1]+ |
|---|---|
| 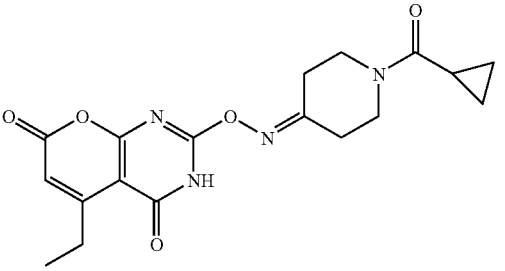 82 | 373.2 |
| 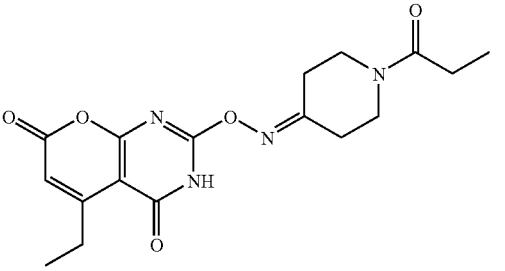 83 | 361.2 |
| 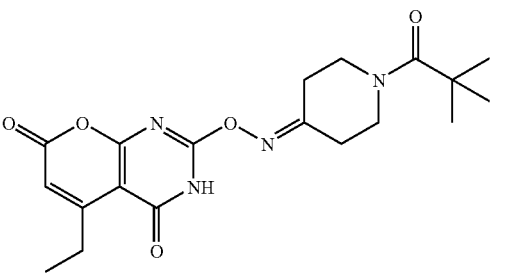 84 | 389.2 |
| 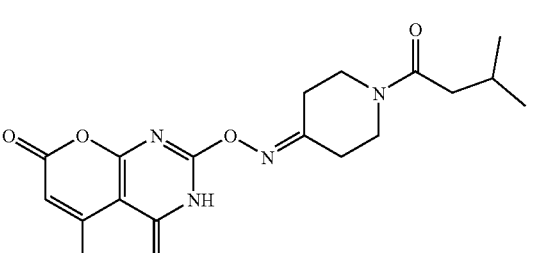 85 | 389.2 |
| 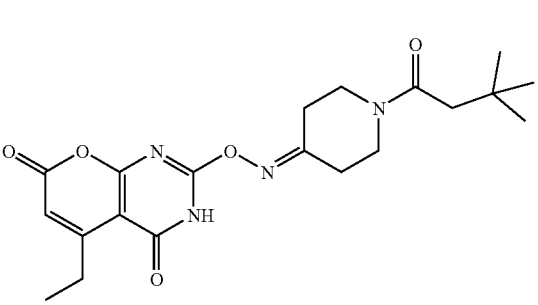 86 | 403.2 |

| Compound | Electrospray LCMS [M + 1]+ |
|---|---|
| 87 | 387.2 |
| 88 | 401.2 |
| 89 | 405.2 |
| 90 | 417.2 |
| 91 | 383.2 |

| Compound | Electrospray LCMS [M + 1]+ |
|---|---|
| 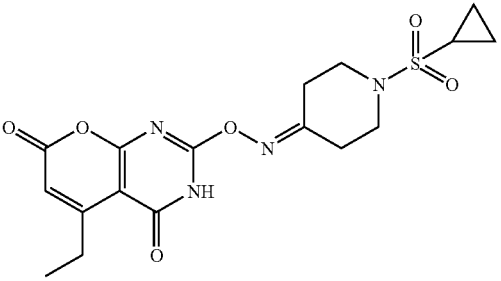 92 | 409.2 |
| 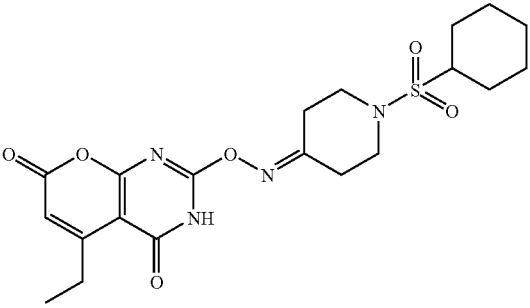 93 | 465.3 |
| 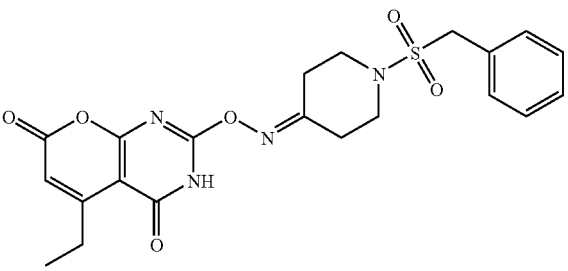 94 | 477.3 |
Compounds 95-100
Compounds 95-100 were prepared using a four-step procedure similar to that used to prepare Compound 80 from the appropriate N-Boc-ketones and chloroformates.
| Compound | Electrospray LCMS [M + 1]+ |
|---|---|
| 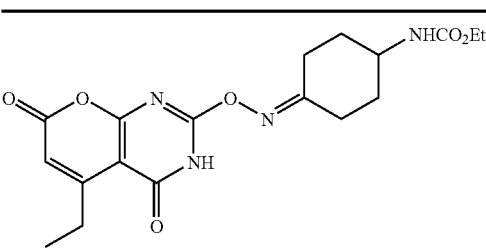 95 | 391.2 |

-continued
| Compound | Electrospray LCMS [M + 1]+ |
|---|---|
| 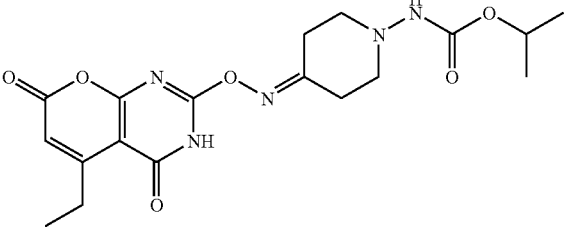
96 | 405.0 |
| 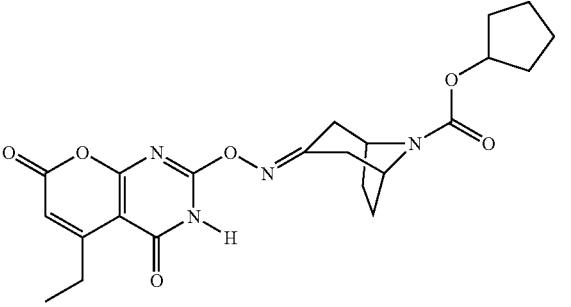
97 | 443.0 |
| 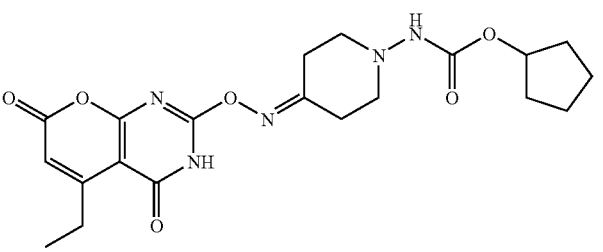
98 | 431.2 |
| 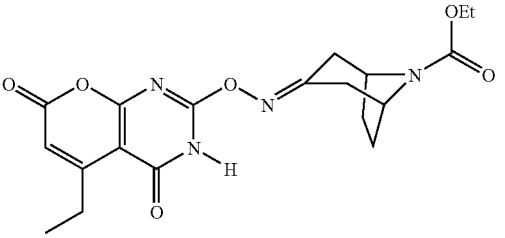
99 | 403.0 |

| Compound | Electrospray LCMS [M + 1]+ |
|---|---|
| 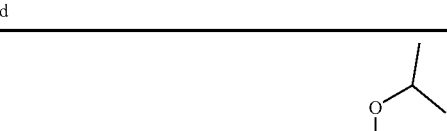

100 | 417.0 |

Exaple 8

Compounds 101-111

Step A:

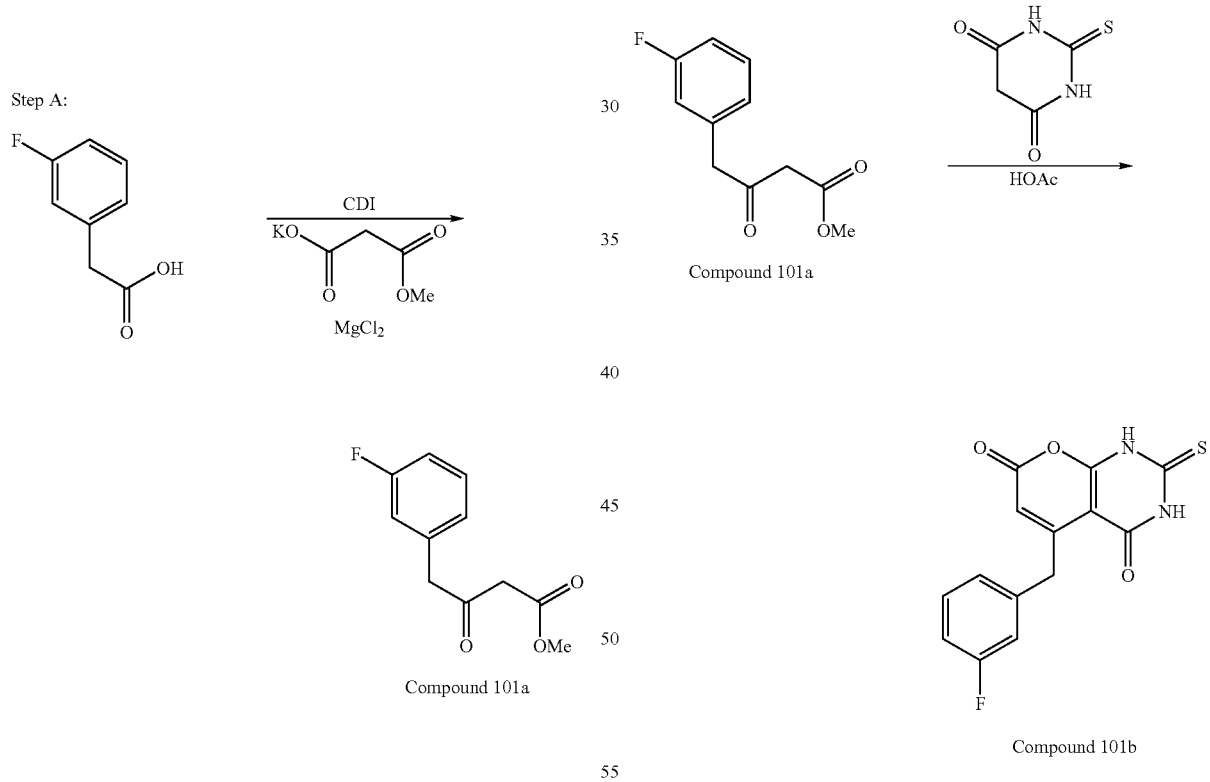

3-Fluorophenylacetic acid (10.2 g, 66.0 mmol) was dissolved in THF (200 mL) and to it CDI (12.8 g, 79.2 mmol) was added. The resulting solution was stirred at room temperature for 1 h. MgCl$_2$ (6.2 g, 65.4 mmol) and monomethyl monopotassium malonate (15.4 g, 98.3 mmol) was added. The resulting mixture was stirred at room temperature overnight. Water was added and extracted with DCM, dried (MgSO$_4$), filtered and concentrated. The residue was purified by silica gel chromatography (eluted with 5% EtOAc in hexanes) to give Compound 101a (7.0 g, 51%) as a yellow oil.

Step B:

Compound 101a (7.0 g, 33 mmol) and thiobarbituric acid (3.2 g, 22 mmol) was suspended in HOAc (33 mL), and heated in an oil bath at 120° C. overnight. The mixture was cooled to room temperature, and most of the acetic acid was removed by rotary evaporation. The residue was taken up with water and EtOAc, and heated at 85° C. for 0.5 h, filtered, and the yellow solid was collected to give Compound 101b (3.0 g, 45%).

Step C:

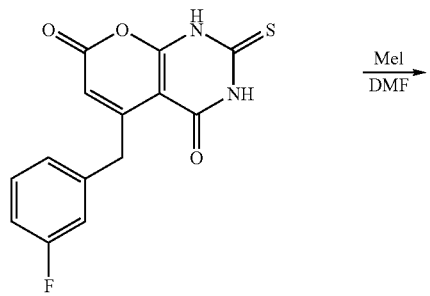

Compound 101b

Step D:

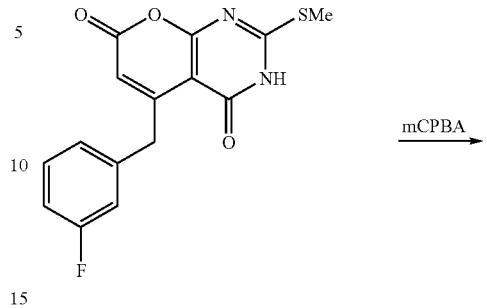

Compound 101c

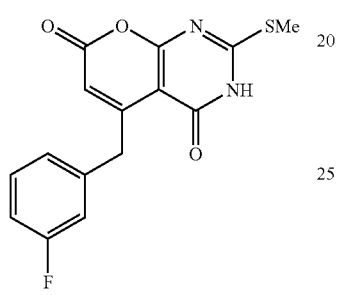

Compound 101c

Compound 101b (3.0 g, 10 mmol) was suspended in DMF (40 mL) and MeI (1.32 mL, 21 mmol) was added. The resulting mixture was stirred at room temperature overnight. The volume of solvent was reduced to ca. 5 mL by rotary evaporation. Water and EtOAc was added and yellow solid precipitated out. The solid was collected and washed with EtOAc to give pure Compound 101c (3.2 g, 100%).

To a suspension of Compound 101c (3.2 g, 10 mmol) in DCM (85 mL), mCPBA (4.8 g, 77%, 21.3 mmol) was added. The resulting mixture was stirred at room temperature overnight. Me$_2$S (2.0 mL, 27 mmol) was added and the mixture was stirred at room temperature for 1.5 h. The volume of solvent was reduced to an extent that solid started to precipitate out. Filtered, and the solid was washed with EtOAc/hexanes (1:3), extensively. The white solid was collected to give Compound 101d (1.0 g, 29%).

Examples 101-112 were prepared using a procedure similar to that used to prepare Compound 61, except that Compound 101d was used instead of Compound 1e.

| Compound | Electrospray LCMS [M + 1]$^+$ |
|---|---|
| (structure shown) | 384.2 |

-continued

| Compound | Electrospray LCMS [M + 1]+ |
|---|---|
| 102 | 457.3 |
| 103 | 427.2 |
| 104 | 511.3 |
| 105 | 483.0 |

-continued
| Compound | Electrospray LCMS [M + 1]+ |
|---|---|
| 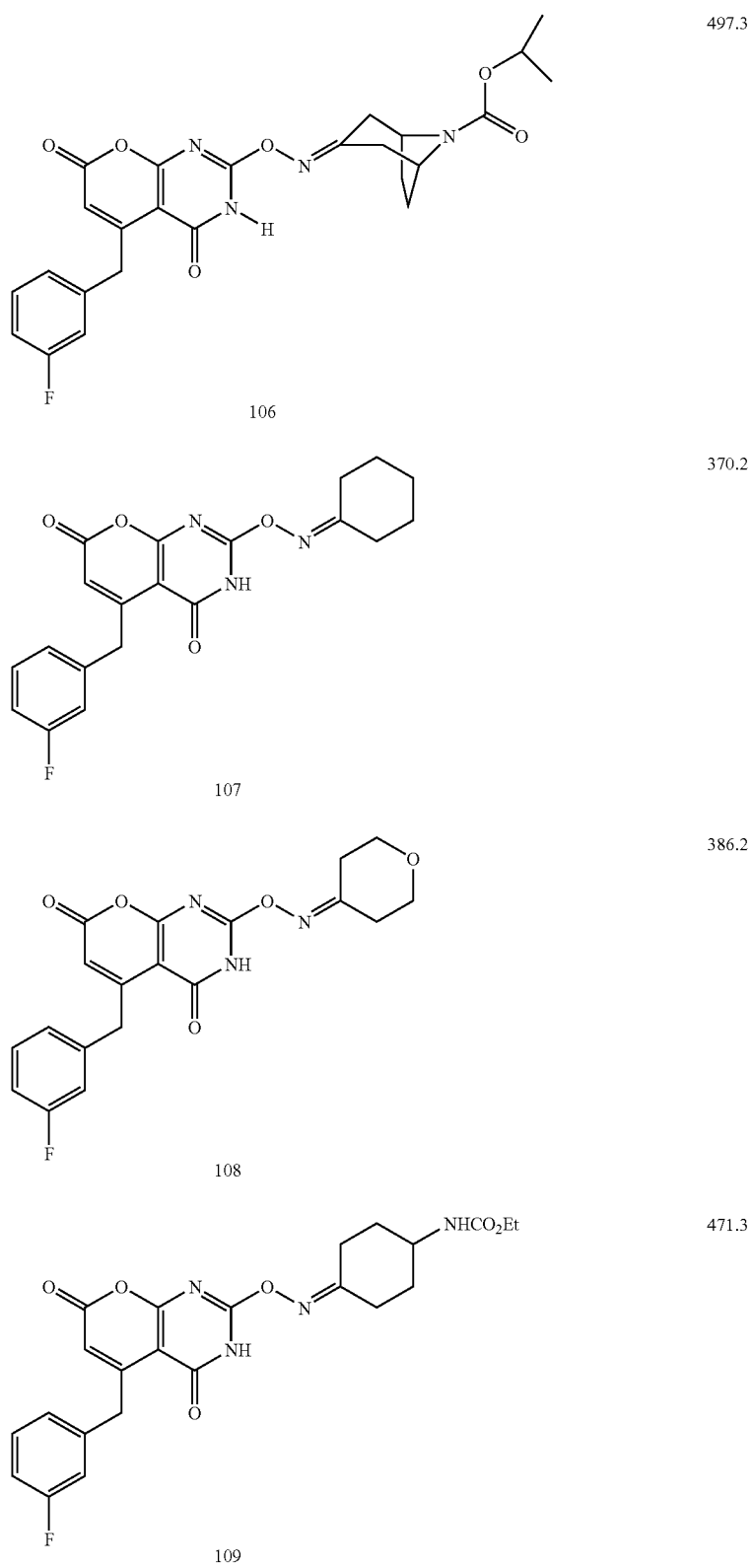 106 | 497.3 |
| 107 | 370.2 |
| 108 | 386.2 |
| 109 | 471.3 |

| Compound | Electrospray LCMS [M + 1]+ |
|---|---|
| 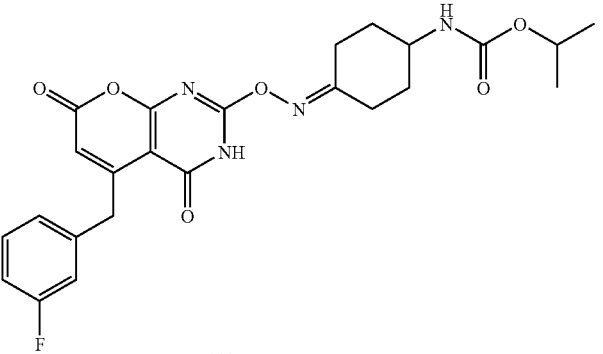 110 | 485.0 |
| 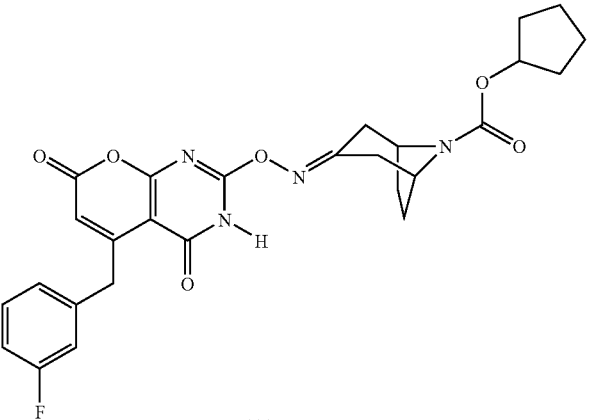 111 | 523.3 |
| 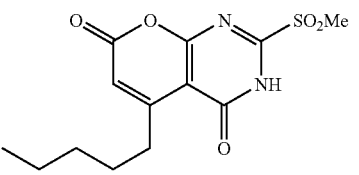 Compound 112a | |

Compound 112a was prepared using a 4-step method similar to that described for the preparation of Compound 101d, except that hexanoic acid was used instead of 3-fluorophenylacetic acid.

Compounds 112-124

Examples 112-124 were prepared using a procedure similar to that described for the preparation of Example 61, using Compound 112a instead of Compound 1e.

| Compound | Electrospray LCMS [M + 1]+ |
|---|---|
| 112 | 348.2 |
| 113 | 419.0 |
| 114 | 459.0 |
| 115 | 346.2 |

| Compound | Electrospray LCMS [M + 1]+ |
|---|---|
| 116 | 332.2 |
| 117 | 445.2 |
| 118 | 485.0 |
| 119 | 433.2 |

-continued
| Compound | Electrospray LCMS [M + 1]+ |
|---|---|
| 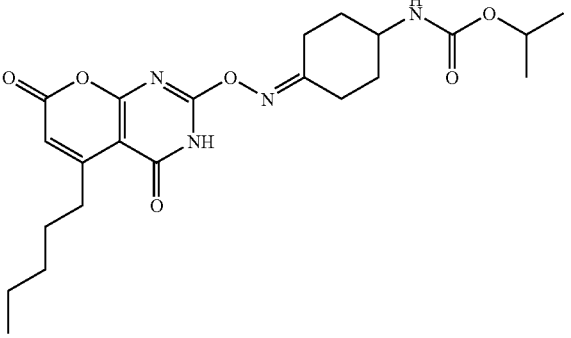<br>120 | 447.0 |
| 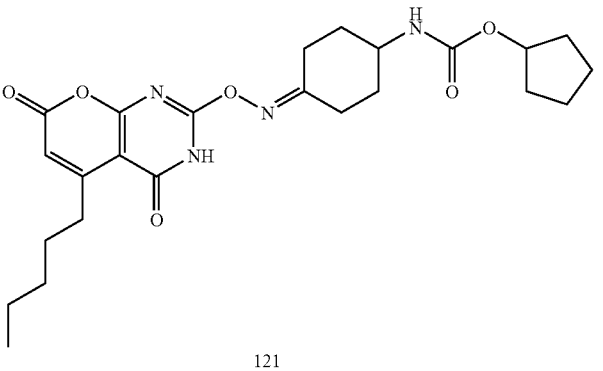<br>121 | 473.3 |
| 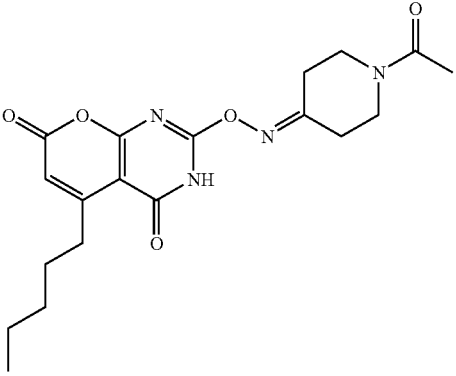<br>122 | 389.2 |
| 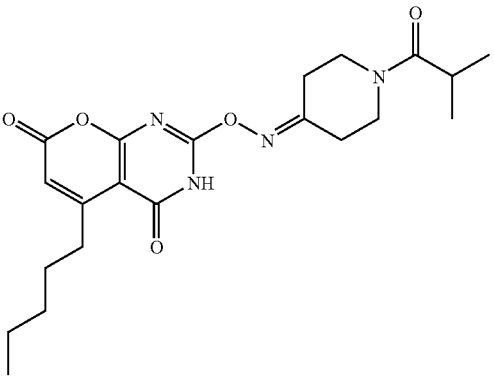<br>123 | 417.2 |

| Compound | Electrospray LCMS [M + 1]+ |
|---|---|
| 124 | 431.0 |
| Compound 125a | |

Compound 125a was prepared using 4-step method similar to that described for the preparation of Compound 101d, starting with 3-thiopheneacetic acid instead of 3-fluorophenylacetic acid.

Compounds 125-128

Compounds 125-128 were prepared using a procedure similar to that described for Example 61, except that Compound 125a was used instead of Compound 1e.

| Compound | Electrospray LCMS [M + 1]+ |
|---|---|
| 125 | 372.0 |
| 126 | 374.0 |
| 127 | 415.0 |

-continued

| Compound | Electrospray LCMS [M + 1]+ |
|---|---|
| 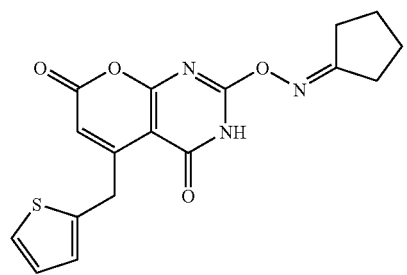 128 | 358.0 |

-continued

| Compound | Electrospray LCMS [M + 1]+ |
|---|---|
| 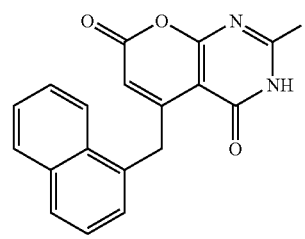 Compound 129a | |

Compound 129a was prepared using a 4-step procedure similar to that described for Compound 101d, except that 1-napthaleneacetic acid was used instead of 3-fluorophenylacetic acid.

Compounds 129-131

Compounds 129-131 were prepared using a procedure similar to that described for the preparation of Compound 80 in example 7, using Compound 129a instead of Compound 1e.

| Compound | Electrospray LCMS [M + 1]+ |
|---|---|
| 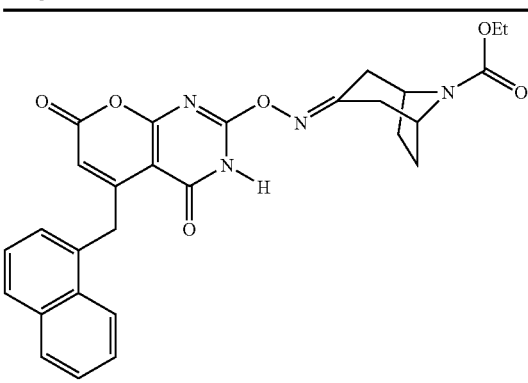 129 | 515.3 |
| 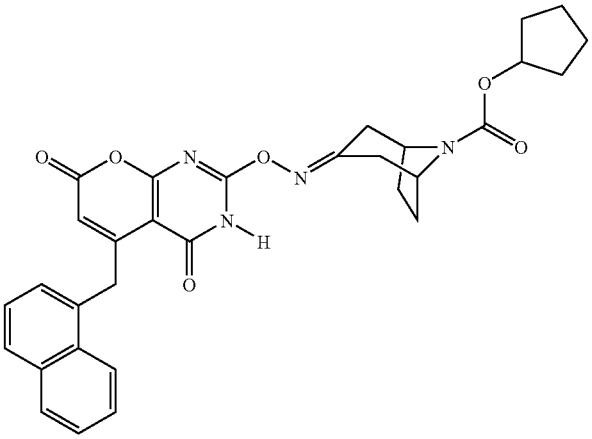 130 | 555.0 |

| Compound | Electrospray LCMS [M + 1]+ |
|---|---|
| 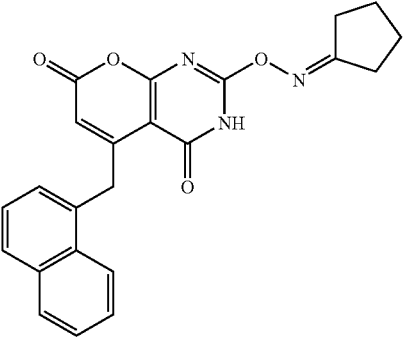 131 | 402.2 |

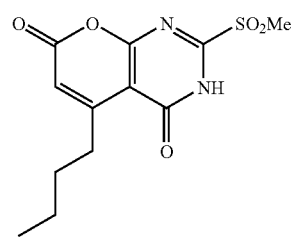

Compound 132a

Compound 132a was prepared using a 3-step method similar to that described for the preparation of Compound 101d, starting from commercially available methyl 3-oxoheptanoate instead of 3-fluorophenylacetic acid.

Compounds 132-142

Compounds 132-142 were prepared using a procedure similar to that described for the preparation of Compound 61, using Compound 132a instead of Compound 1e.

| Compound | Electrospray LCMS [M + 1]+ |
|---|---|
| 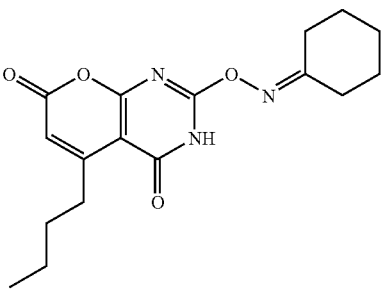 132 | 332.2 |

-continued
| Compound | Electrospray LCMS [M + 1]+ |
|---|---|
| 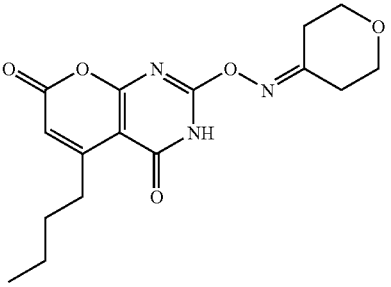<br>133 | 334.2 |
| 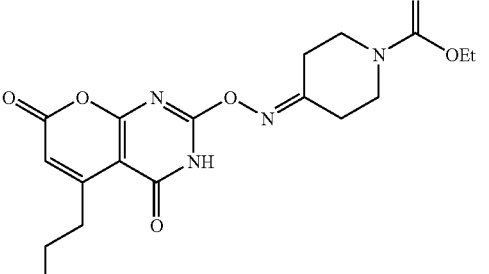<br>134 | 405.2 |
| 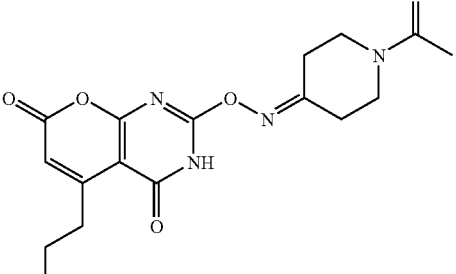<br>135 | 375.2 |
| 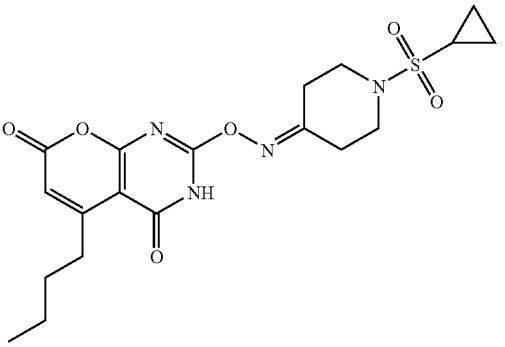<br>136 | 437.2 |

-continued
| Compound | Electrospray LCMS [M + 1]+ |
|---|---|
| 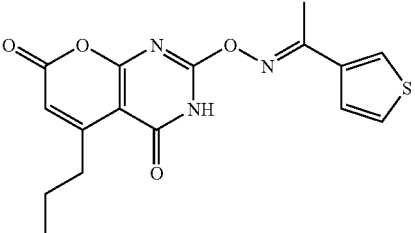<br>137 | 360.3 |
| 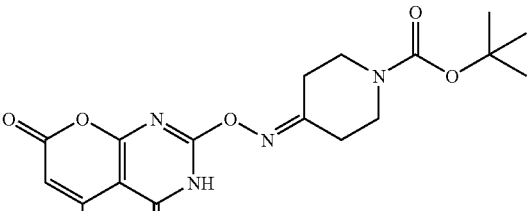<br>138 | 433.2 |
| 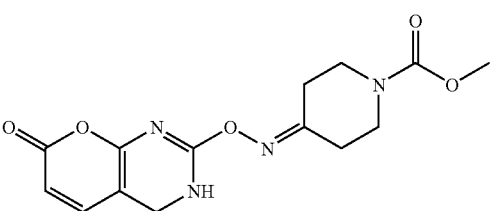<br>139 | 491.2 |
| 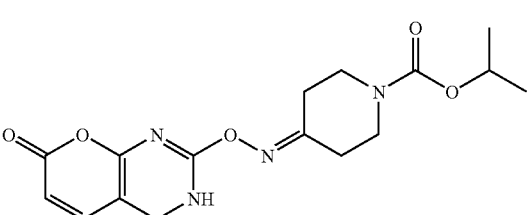<br>140 | 419.2 |

-continued

| Compound | Electrospray LCMS [M + 1]⁺ |
|---|---|
| 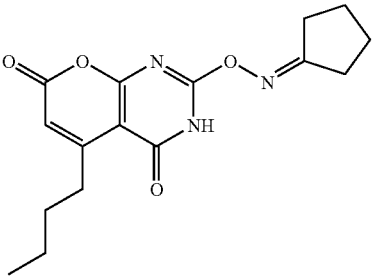<br>141 | 318.2 |
| 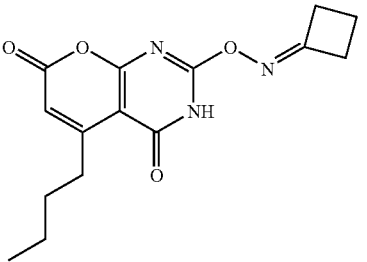<br>142 | 304.2 |
| 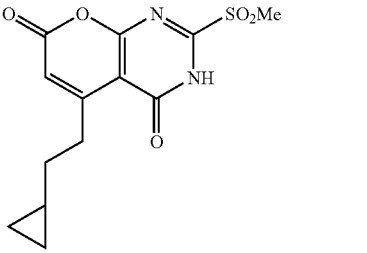<br>Compound 143a | |

Compound 143a was prepared using a 4-step sequence similar to that described for the preparation of Compound 101d, starting with 3-cyclopropylpropionic acid instead of 3-fluorophenylacetic acid.

Compounds 143-145

Compounds 143-145 were prepared using a procedure similar to that described for the preparation of Compound 80 in Example 7, using Compound 143a instead of Compound 1e.

| Compound | Electrospray LCMS [M + 1]⁺ |
|---|---|
| 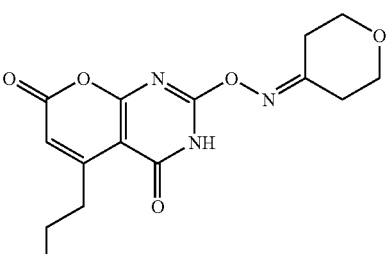<br>143 | 346.2 |

| Compound | Electrospray LCMS [M + 1]+ |
|---|---|
| 144 | 417.2 |
| 145 | 445.2 |
| Compound 146 | |

Compound 146 was prepared using the procedures described in Example 5, except that 1-pyridin-4-yl-ethanone oxime was used instead of 1-thiazol-2-yl-ethanone oxime.

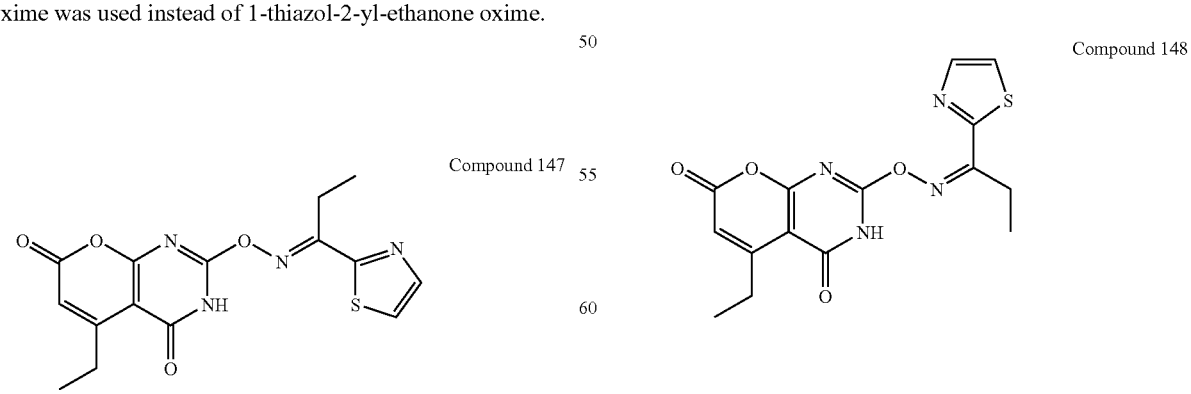

Compound 147

Compound 148

Compounds 147 and 148 were prepared using the procedures described in Example 5, except that 1-thiazol-2-yl-propan-1-one oxime was used instead of 1-thiazol-2-yl-ethanone oxime.

Compound 149

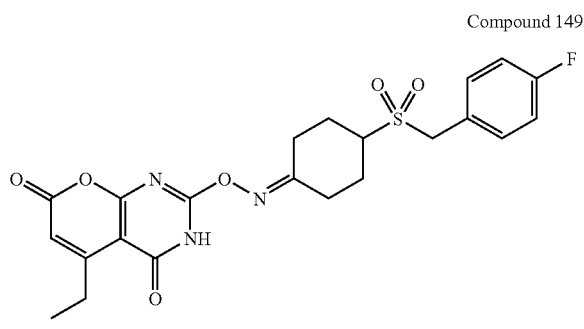

Compound 149 was prepared using the procedures described in Example 7, except that 4-(4-fluoro-phenyl-methanesulfonyl)-cyclohexanone oxime was used instead of 4-hydroxyimino-piperidine-1-carboxylic acid ethylamide.

Compound 150

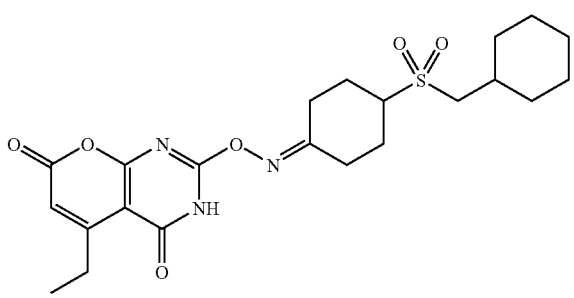

Compound 150 was prepared using the procedures described in Example 7, except that 4-cyclohexylmethane-sulfonyl-cyclohexanone oxime was used instead of 4-hydroxyimino-piperidine-1-carboxylic acid ethylamide.

Compound 151

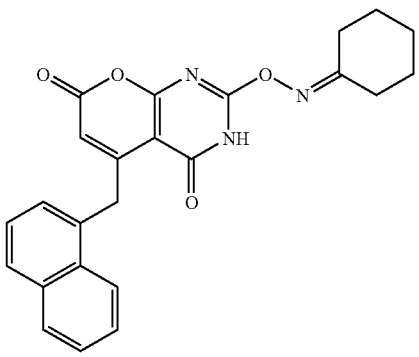

Compound 151 was prepared using the procedures described in Example 7, except that cyclohexanone oxime was used instead of 4-hydroxyimino-piperidine-1-carboxylic acid ethylamide and Compound 129a was used instead of 1e.

Compound 152

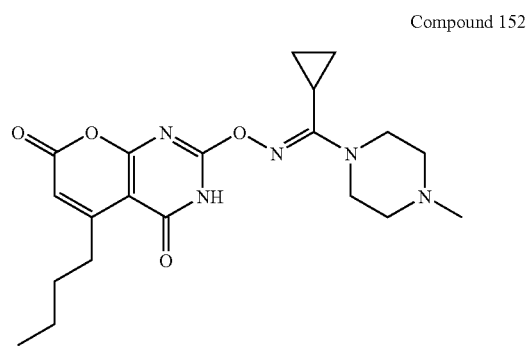

Compound 152 was prepared using the procedures described in Example 1, except that cyclopropyl-(4-methyl-piperazin-1-yl)-methanone oxime was used instead of 1-(4-methyl-piperazin-1-yl)-butan-1-one oxime and 5-butyl-2-methanesulfinyl-3H-pyrano[2,3-d]pyrimidine-4,7-dione was used instead of 1d.

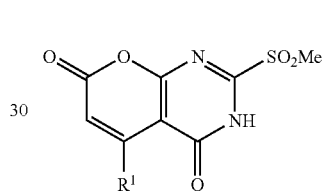
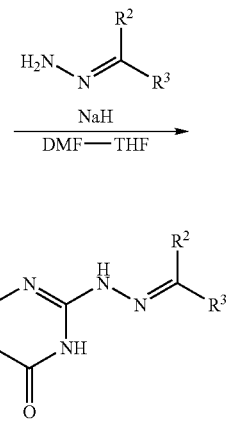
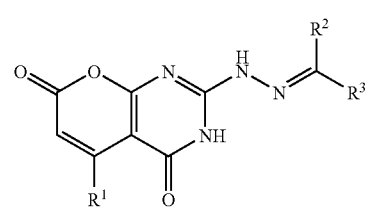

Compounds of Formula (I) wherein, for example, X is —NH— can be prepared by the method shown above.

One of skill in the art will recognize that compounds of Formula (I) wherein $R^2$ and $R^3$ form a

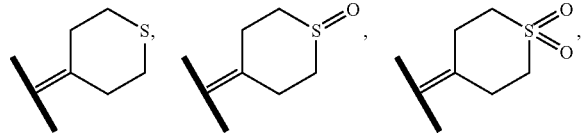

group (wherein the ring shown may be unsubstituted or substituted) can be prepared analogously to the procedure used to prepare, e.g, Compound 133, except that tetrahydro-thiopyran-4-one oxime was used instead of tetrahydro-pyran-4-one oxime. The tetrahydro-thiopyran substituted product can then be oxidized to the cyclic sulfoxide or sulfone derivative.

Compounds 153-285 were prepared using the various methods set forth above in the Examples section and substituting appropriate starting materials, reagents and reactants. Mass spectrometry data for these compounds is presented below:

| Compound No. | Structure | Electrospray LCMS [M + 1]+ |
|---|---|---|
| 153 | 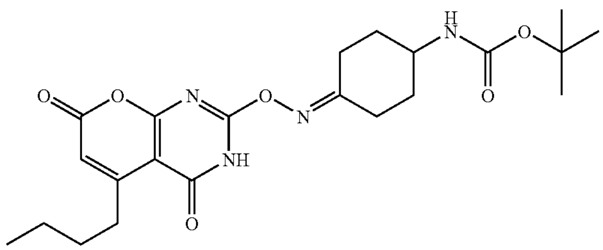 | 447.2 |
| 154 | 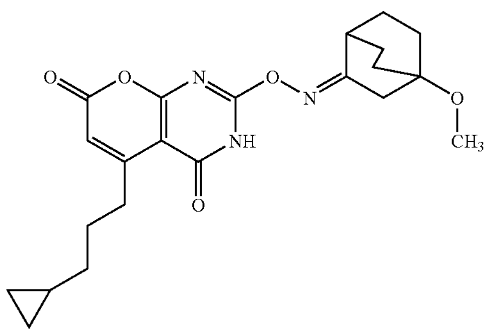 | 414.2 |
| 155 | 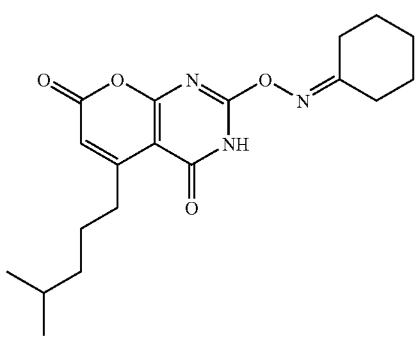 | 360.2 |
| 156 | 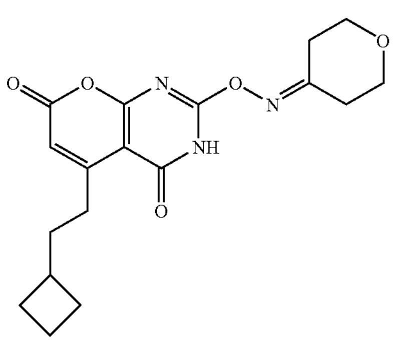 | 360.2 |

-continued

| Compound No. | Structure | Electrospray LCMS [M + 1]+ |
|---|---|---|
| 157 | 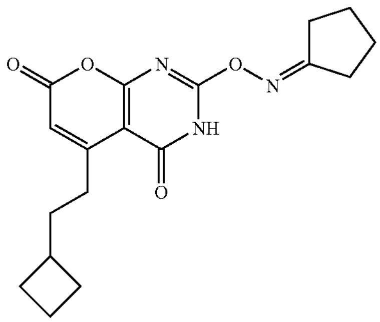 | 344.2 |
| 158 | 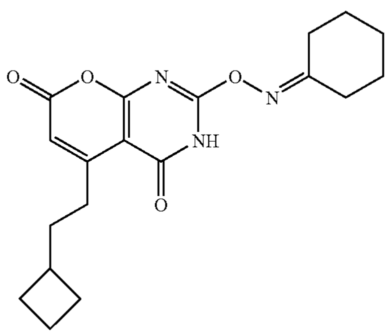 | 358.2 |
| 159 | 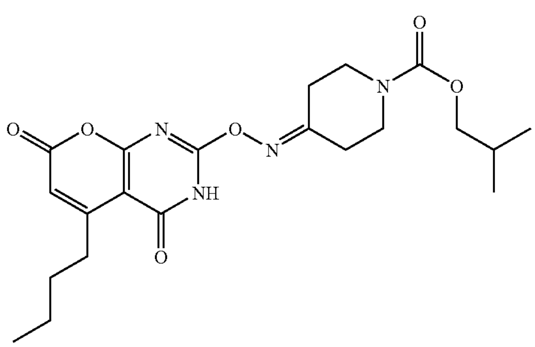 | 433.2 |
| 160 | 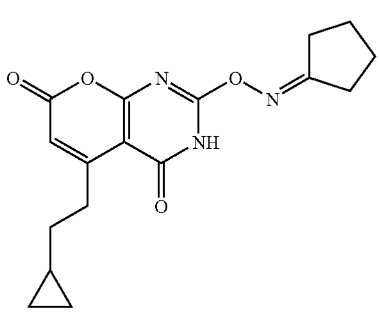 | 330.2 |

-continued

| Compound No. | Structure | Electrospray LCMS [M + 1]+ |
|---|---|---|
| 161 | 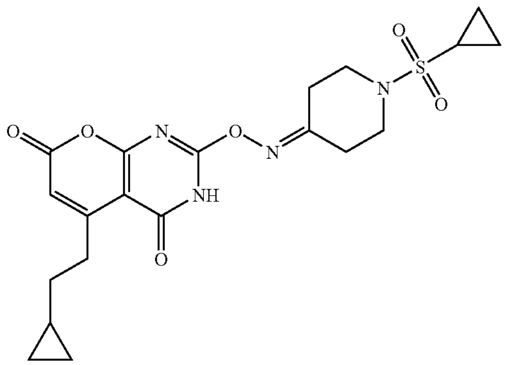 | 449.2 |
| 162 | 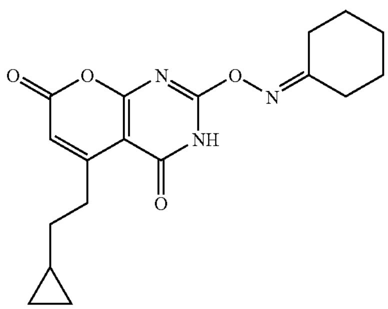 | 344.2 |
| 163 | 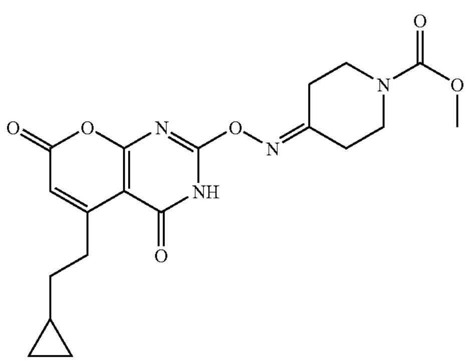 | 403.2 |
| 164 | 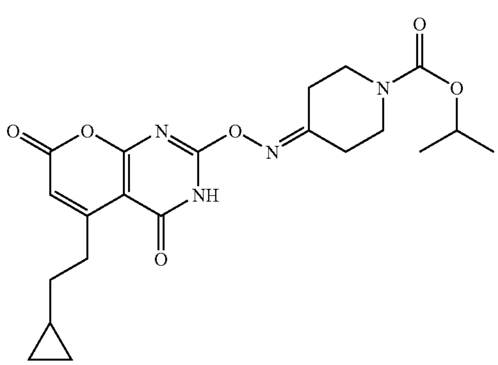 | 431.2 |

-continued

| Compound No. | Structure | Electrospray LCMS [M + 1]+ |
|---|---|---|
| 165 | 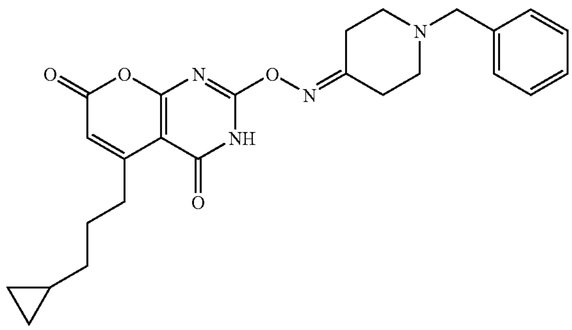 | 449.3 |
| 166 | 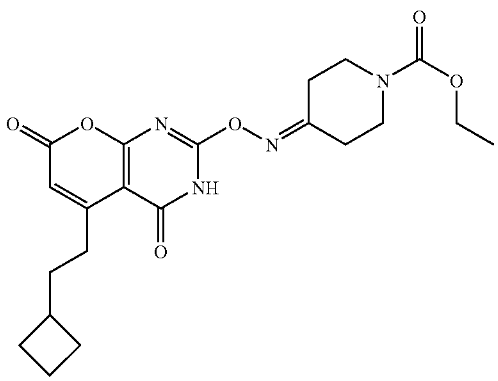 | 431.2 |
| 167 | 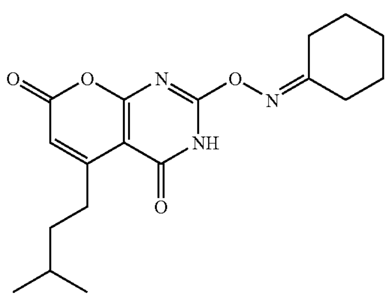 | 346.2 |
| 168 | 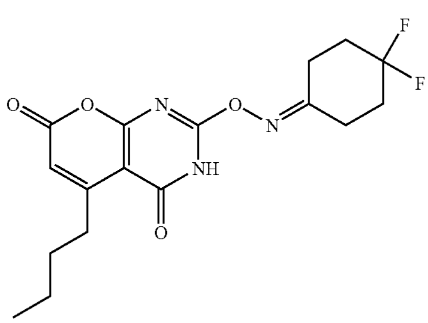 | 368.2 |

-continued

| Compound No. | Structure | Electrospray LCMS [M + 1]+ |
|---|---|---|
| 169 | 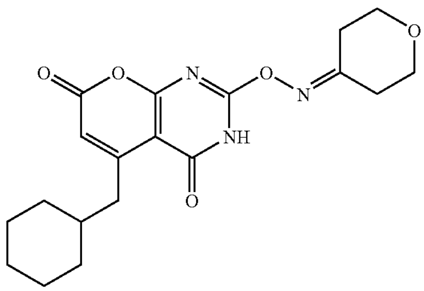 | 374.2 |
| 170 | 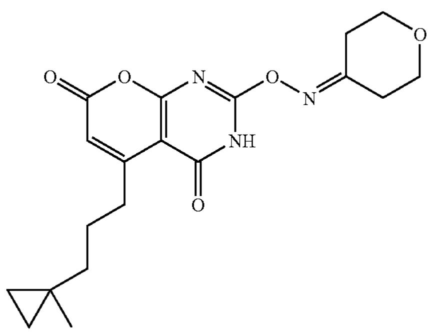 | 374.2 |
| 171 | 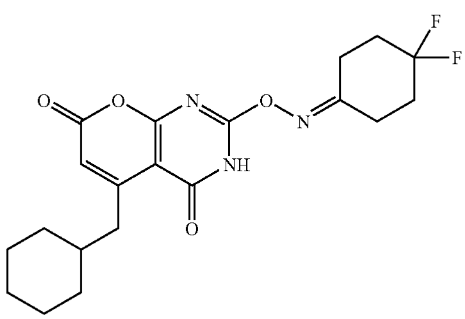 | 408.2 |
| 172 | 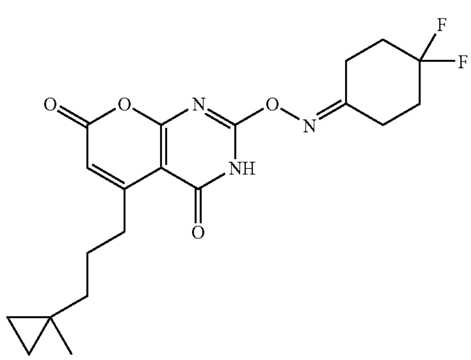 | 408.2 |

-continued

| Compound No. | Structure | Electrospray LCMS [M + 1]+ |
|---|---|---|
| 173 | 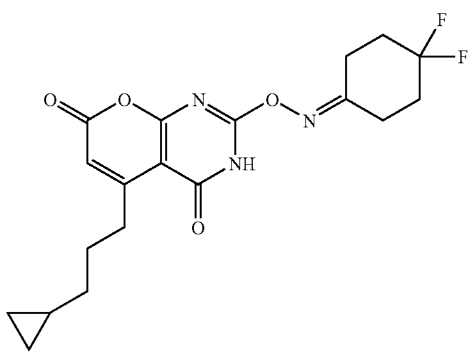 | 394.2 |
| 174 | 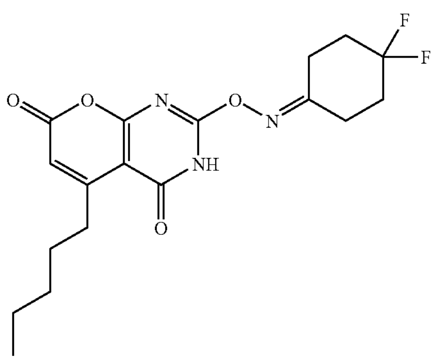 | 382.2 |
| 175 | 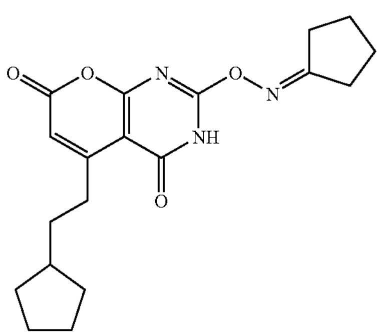 | 358.2 |
| 176 | 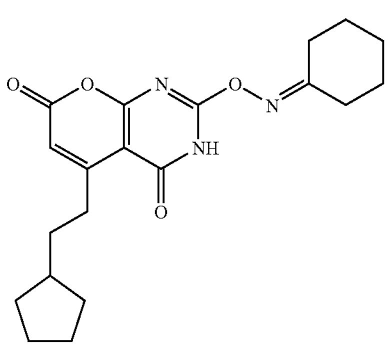 | 372.2 |

-continued
| Compound No. | Structure | Electrospray LCMS [M + 1]+ |
|---|---|---|
| 177 | 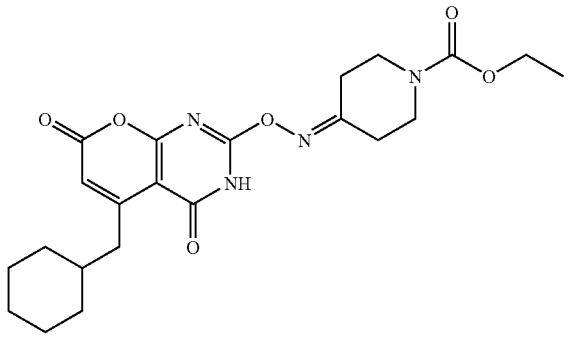 | 445.2 |
| 178 | 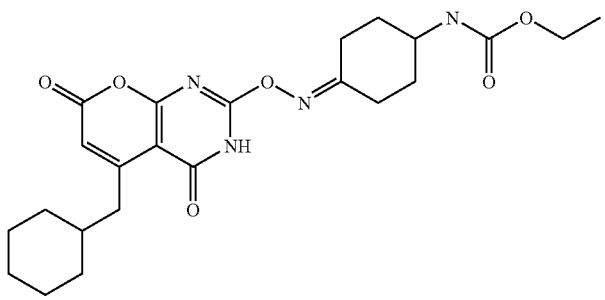 | 459.2 |
| 179 | 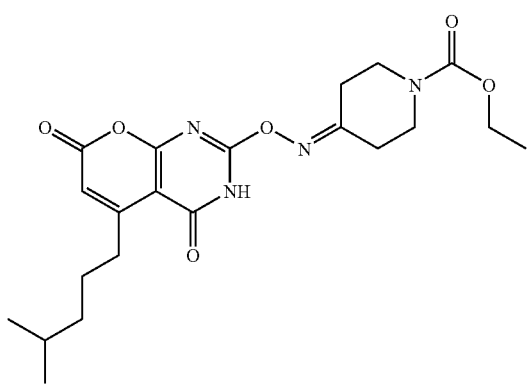 | 433.2 |
| 180 | 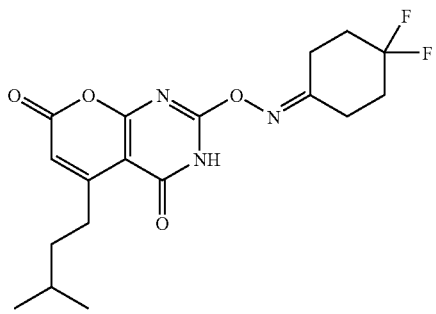 | 382.2 |

-continued
| Compound No. | Structure | Electrospray LCMS [M + 1]+ |
|---|---|---|
| 181 | 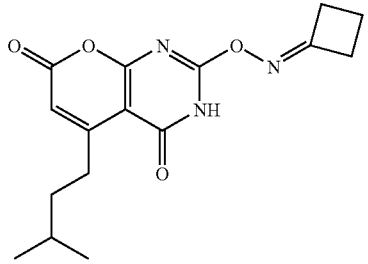 | 318.2 |
| 182 | 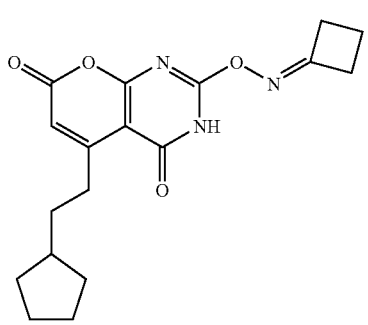 | 344.2 |
| 183 | 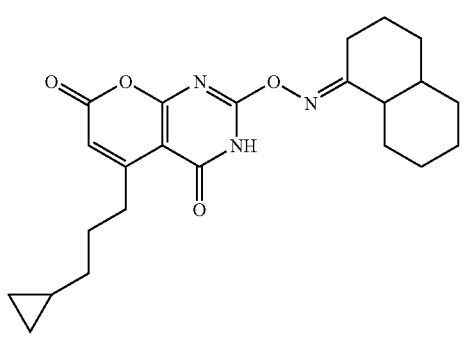 | 412.2 |
| 184 | 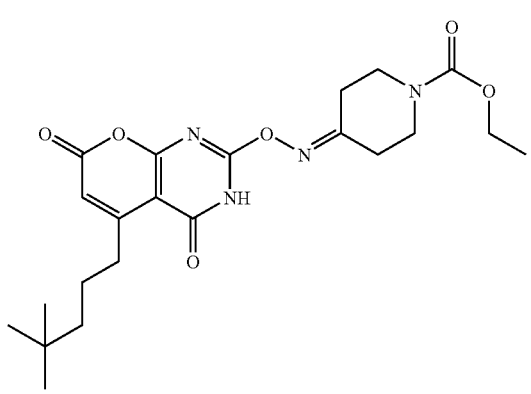 | 447.2 |

-continued

| Compound No. | Structure | Electrospray LCMS [M + 1]+ |
|---|---|---|
| 185 | 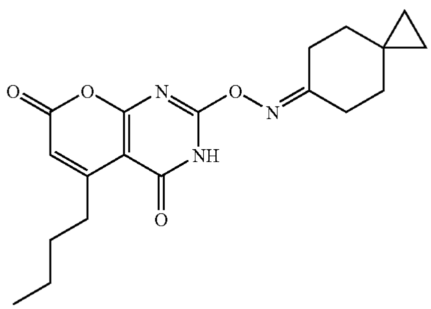 | 358.2 |
| 186 | 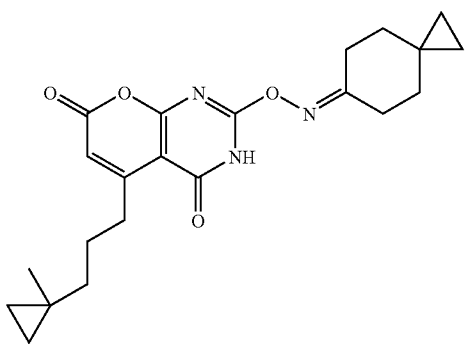 | 398.2 |
| 187 | 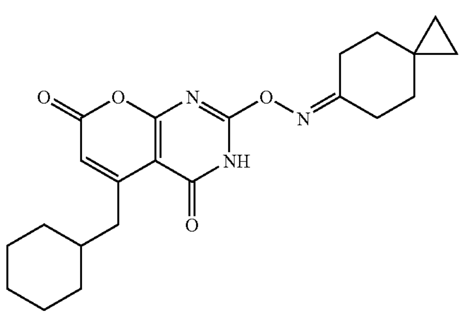 | 398.2 |
| 188 | 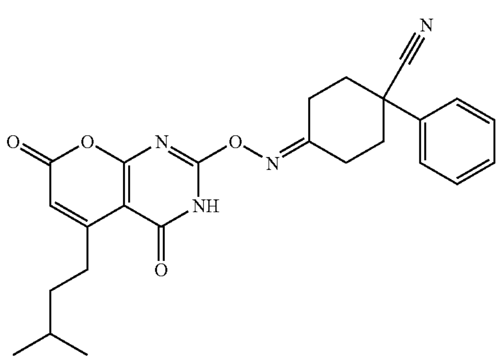 | 447.2 |

-continued

| Compound No. | Structure | Electrospray LCMS [M + 1]+ |
|---|---|---|
| 189 | 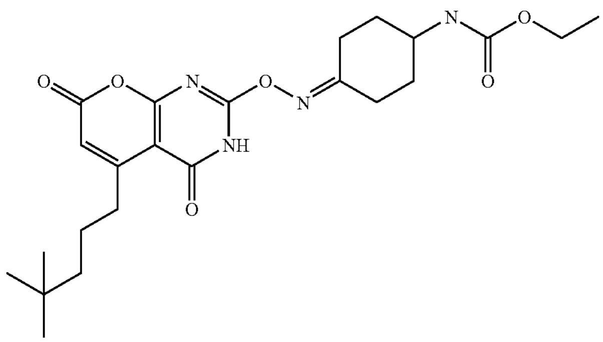 | 461.3 |
| 190 | 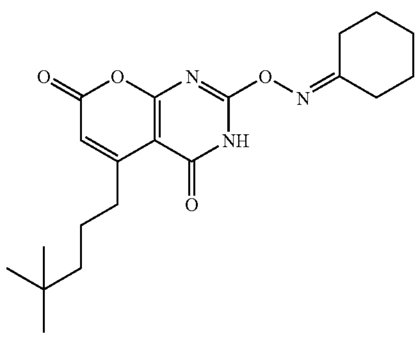 | 3.2 |
| 191 | 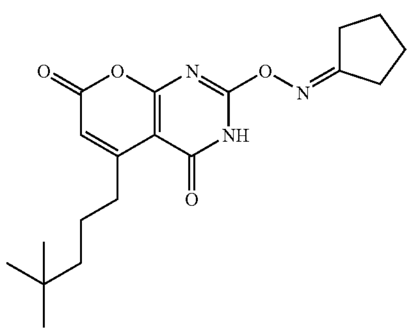 | 360.2 |
| 192 | 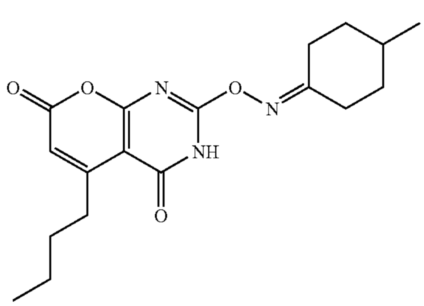 | 346.2 |

-continued

| Compound No. | Structure | Electrospray LCMS [M + 1]+ |
|---|---|---|
| 193 | 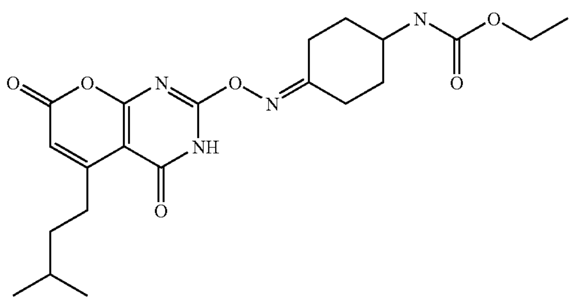 | 433.2 |
| 194 | 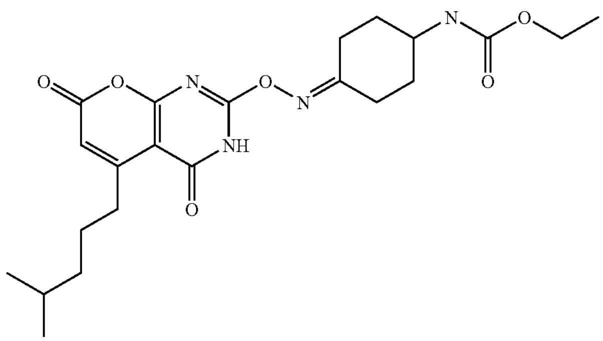 | 447.2 |
| 195 | 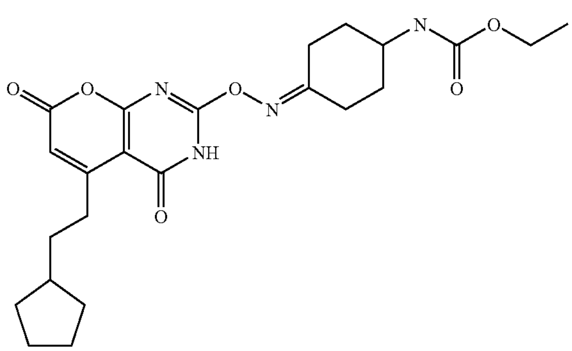 | 459.3 |
| 196 | 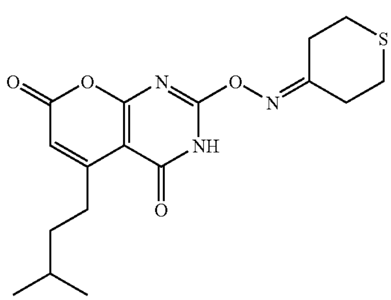 | 364.2 |
| 197 | 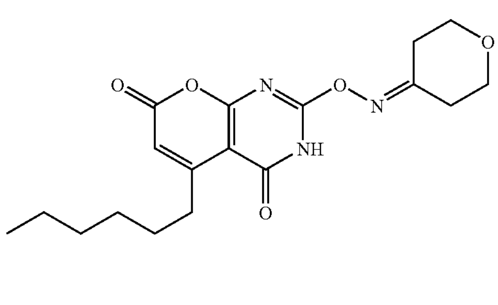 | 362.2 |

-continued

| Compound No. | Structure | Electrospray LCMS [M + 1]+ |
|---|---|---|
| 198 | 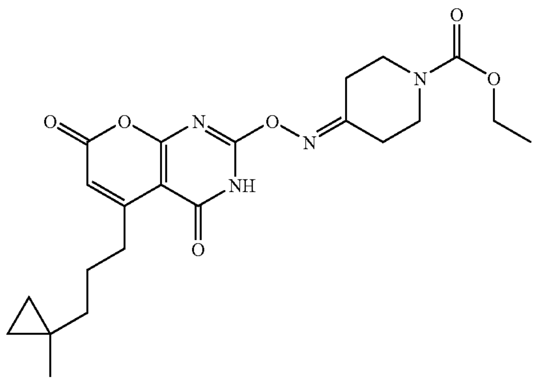 | 445.2 |
| 199 | 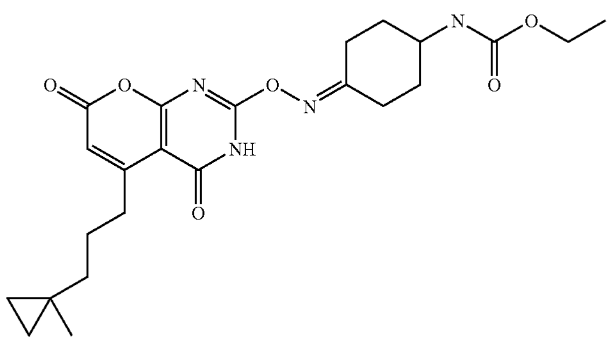 | 459.3 |
| 200 | 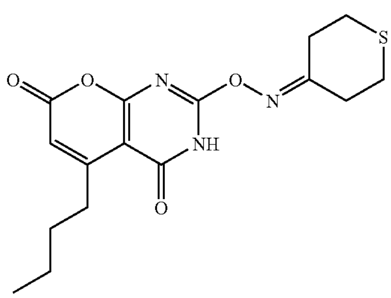 | 350.2 |
| 201 | 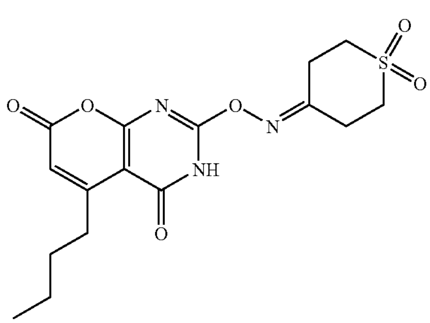 | 382.2 |

-continued

| Compound No. | Structure | Electrospray LCMS [M + 1]+ |
|---|---|---|
| 202 | 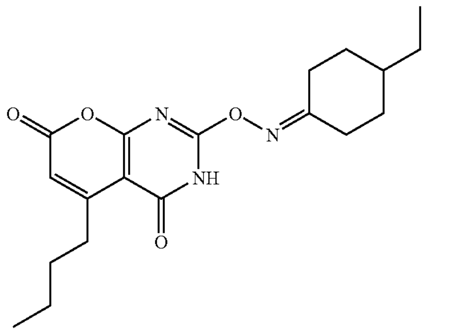 | 360.2 |
| 203 | 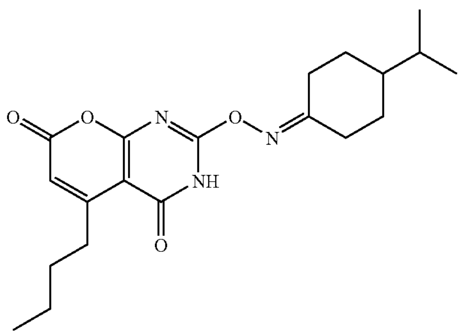 | 374.2 |
| 204 | 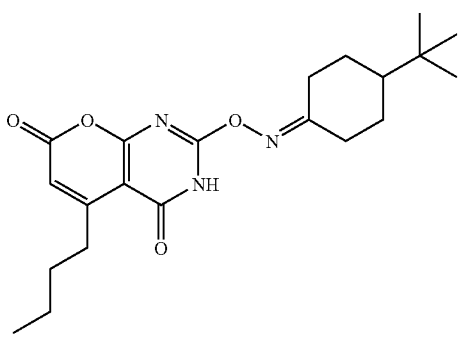 | 388.2 |
| 205 | 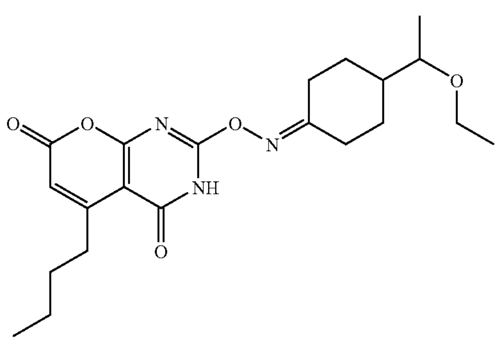 | 404.2 |

-continued

| Compound No. | Structure | Electrospray LCMS [M + 1]+ |
|---|---|---|
| 206 | 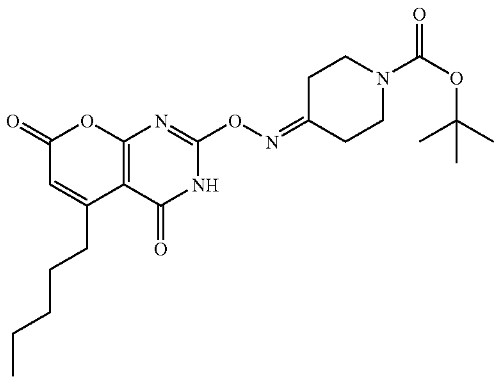 | 447.2 |
| 207 | 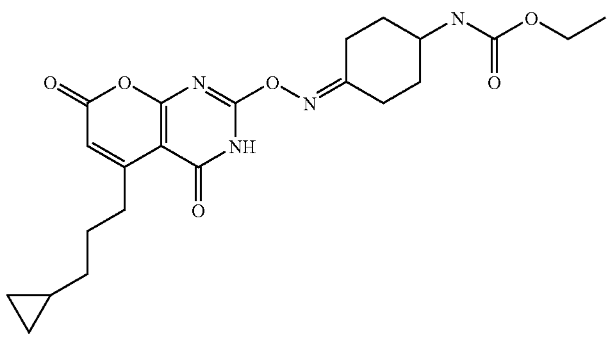 | 445.2 |
| 208 | 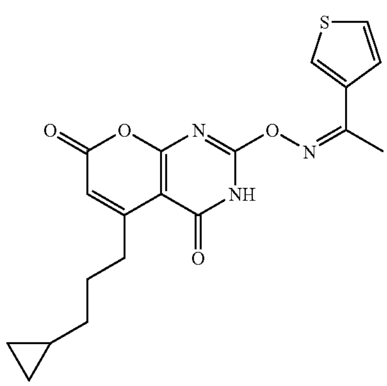 | 386.2 |
| 209 | 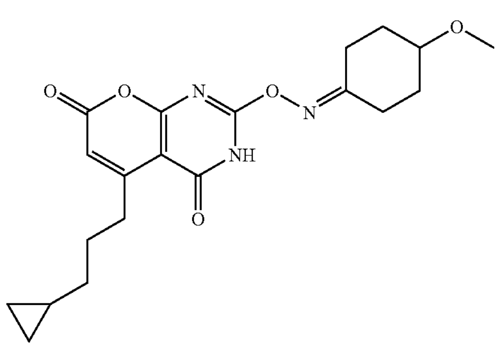 | 388.2 |

-continued

| Compound No. | Structure | Electrospray LCMS [M + 1]+ |
|---|---|---|
| 210 | 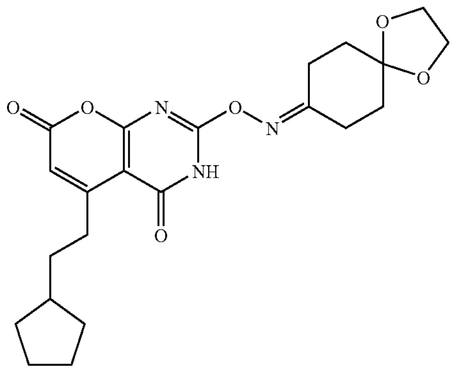 | 430.2 |
| 211 | 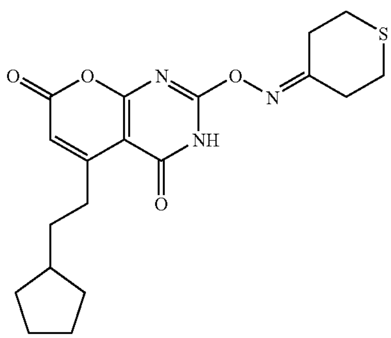 | 390.2 |
| 212 | 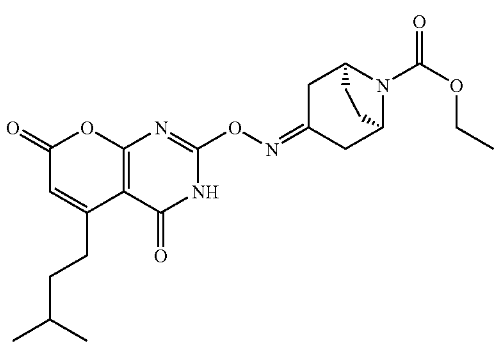 | 445.2 |
| 213 | 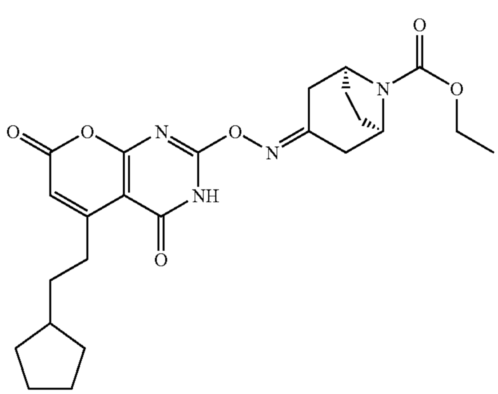 | 471.3 |

-continued
| Compound No. | Structure | Electrospray LCMS [M + 1]+ |
|---|---|---|
| 214 | 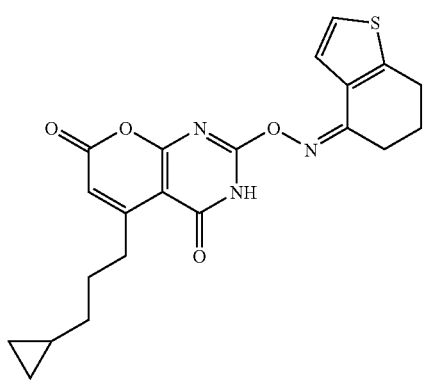 | 412.2 |
| 215 | 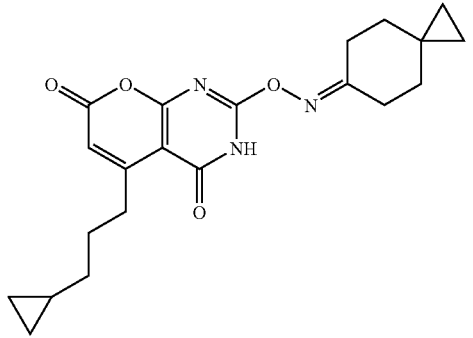 | 384.2 |
| 216 | 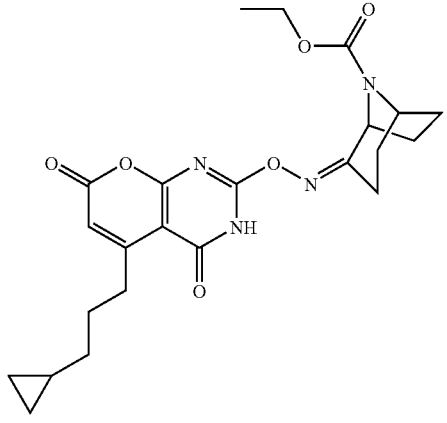 | 457.2 |
| 217 | 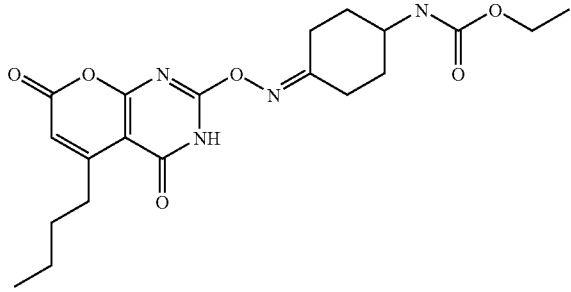 | 419.2 |

-continued

| Compound No. | Structure | Electrospray LCMS [M + 1]+ |
|---|---|---|
| 218 | 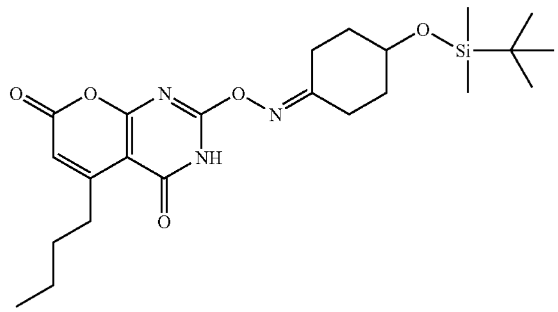 | 462.3 |
| 219 | 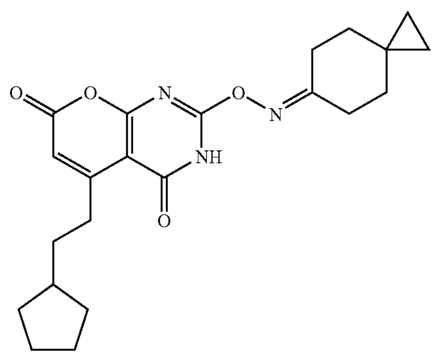 | 398.2 |
| 220 | 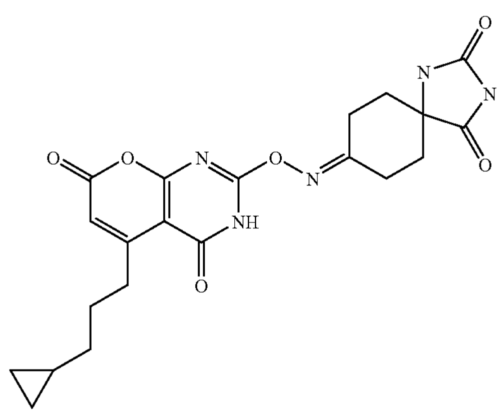 | 442.2 |
| 221 | 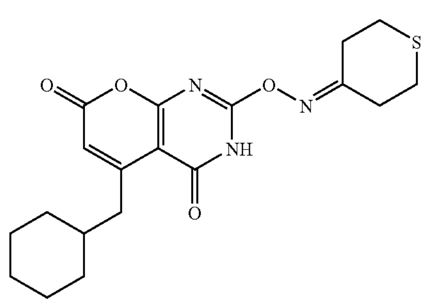 | 390.2 |

| Compound No. | Structure | Electrospray LCMS [M + 1]+ |
|---|---|---|
| 222 | 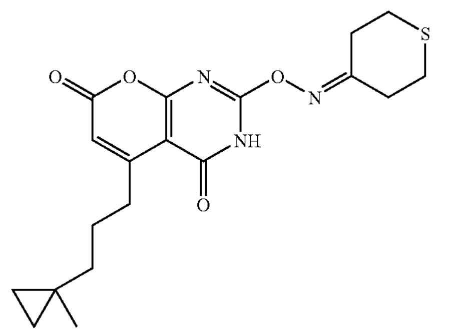 | 390.2 |
| 223 | 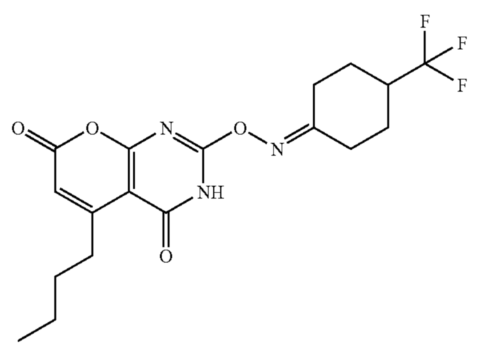 | 400.2 |
| 224 | 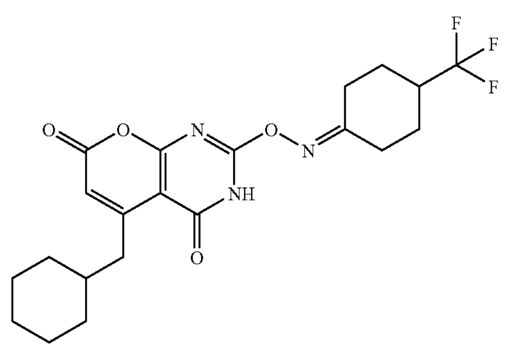 | 440.2 |
| 225 | 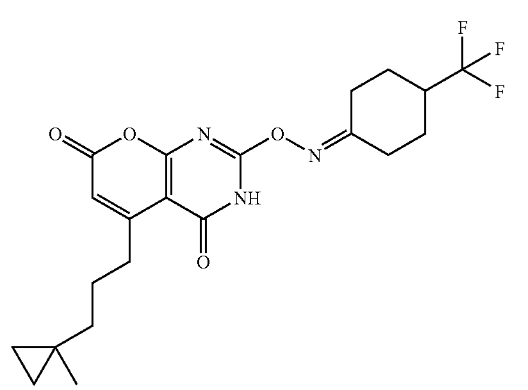 | 440.2 |

-continued

| Compound No. | Structure | Electrospray LCMS [M + 1]+ |
|---|---|---|
| 226 | 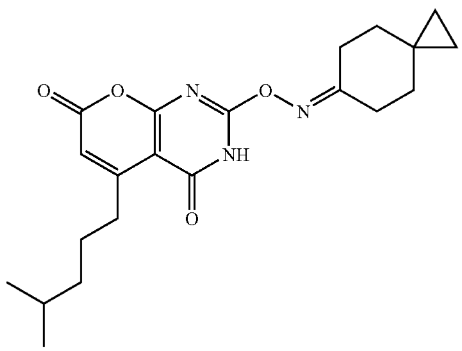 | 386.2 |
| 227 | 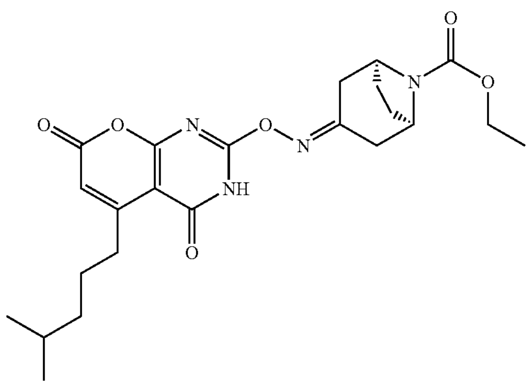 | 459.3 |
| 228 | 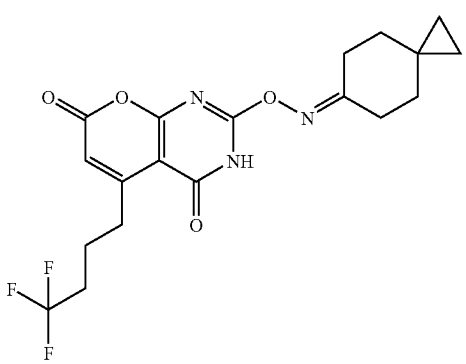 | 412.2 |
| 229 | 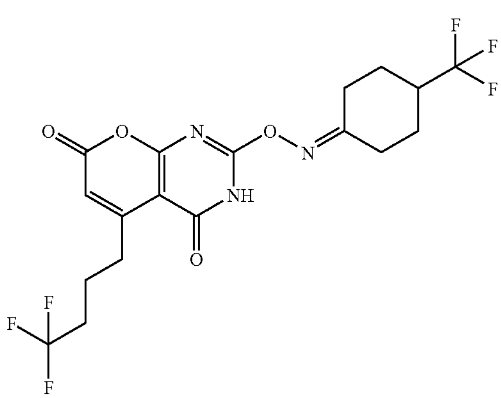 | 454.2 |

| Compound No. | Structure | Electrospray LCMS [M + 1]+ |
|---|---|---|
| 230 | 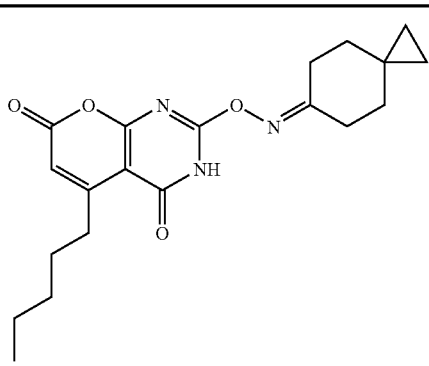 | 372.2 |
| 231 | 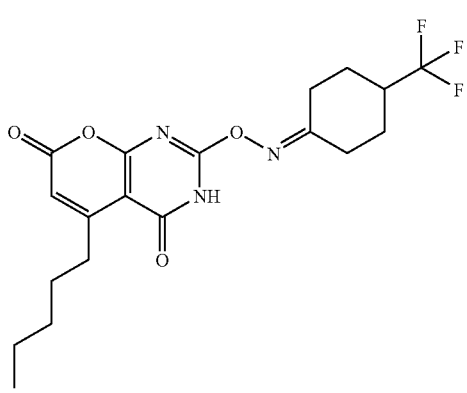 | 414.2 |
| 232 | 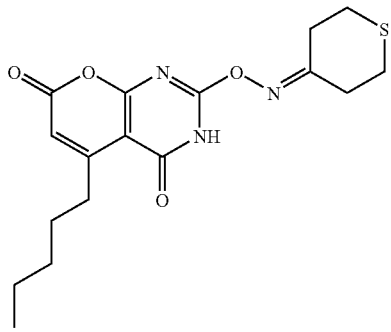 | 364.2 |
| 233 | 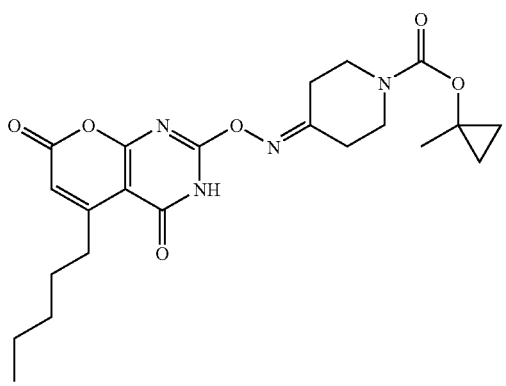 | 445.2 |

-continued

| Compound No. | Structure | Electrospray LCMS [M + 1]+ |
|---|---|---|
| 234 | 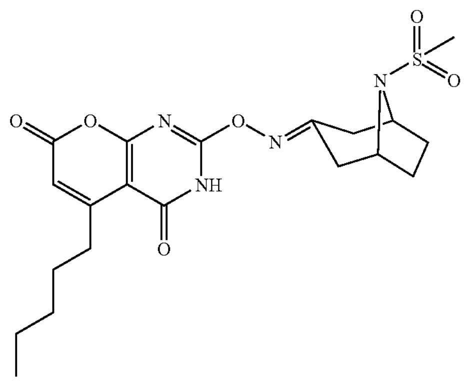 | 451.2 |
| 235 | 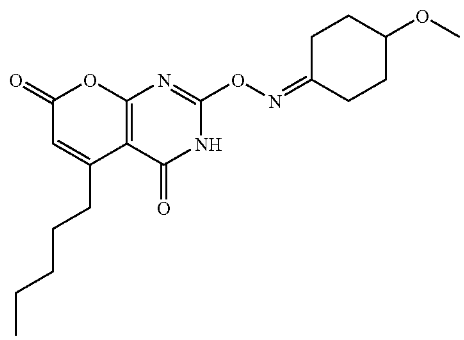 | 376.2 |
| 236 | 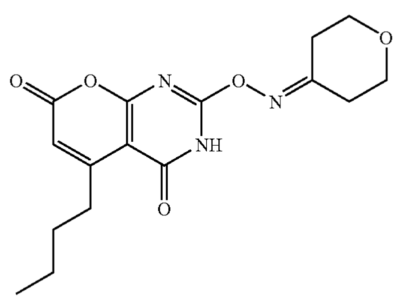 | 348.2 |
| 237 | 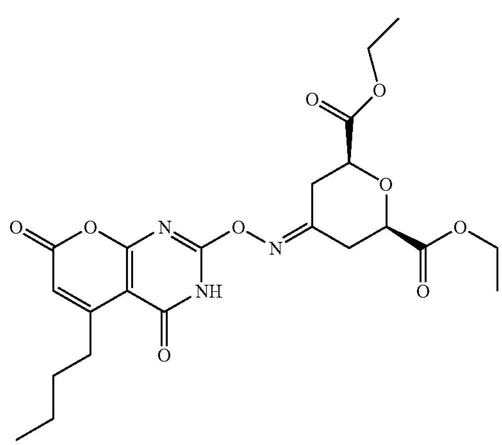 | 478.3 |

| Compound No. | Structure | Electrospray LCMS [M + 1]+ |
|---|---|---|
| 238 | 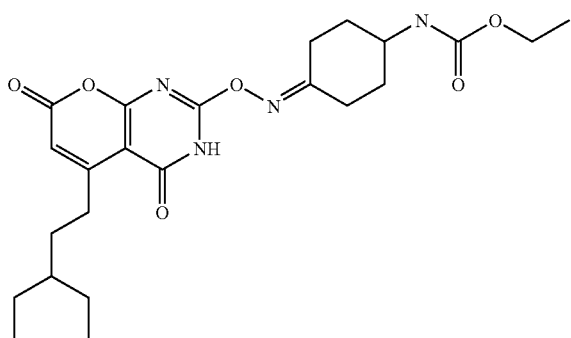 | 473.3 |
| 239 | 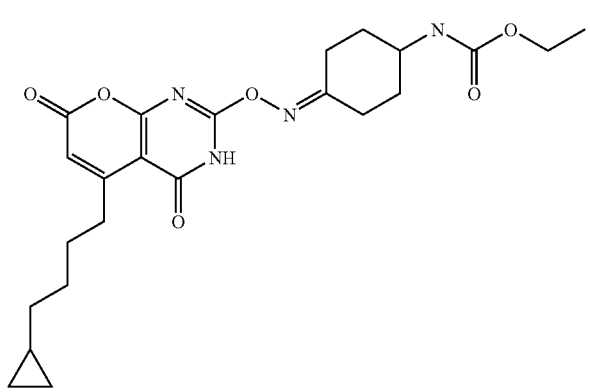 | 459.3 |
| 240 | 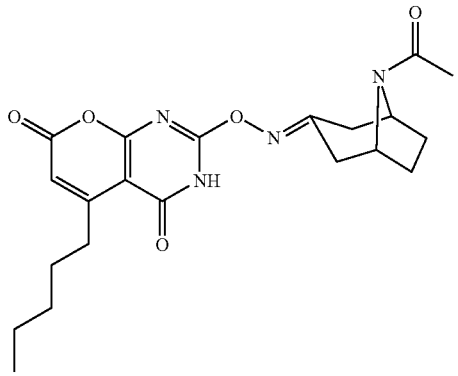 | 415.2 |
| 241 | 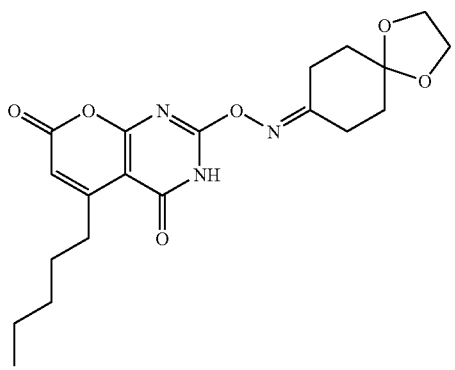 | 404.2 |

-continued

| Compound No. | Structure | Electrospray LCMS [M + 1]+ |
|---|---|---|
| 242 | 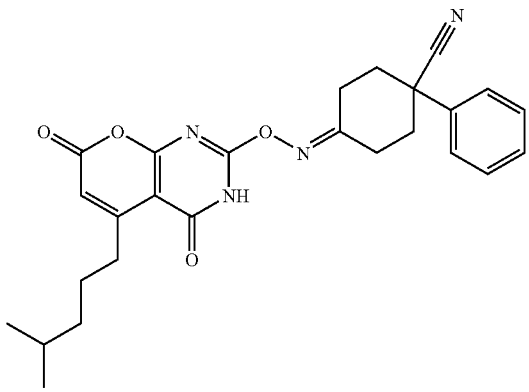 | 461.3 |
| 243 | 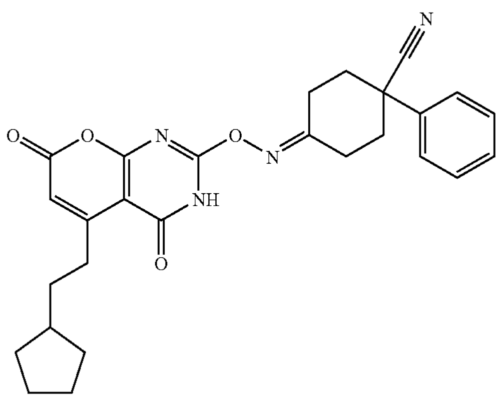 | 473.3 |
| 244 | 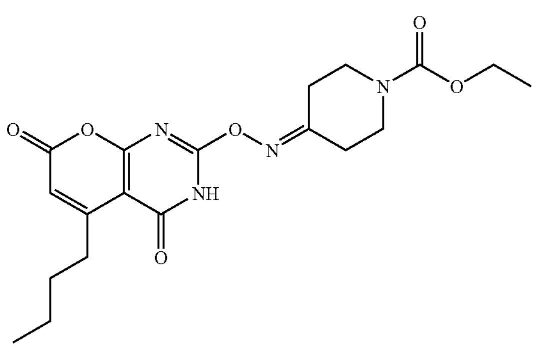 | 419.2 |
| 245 | 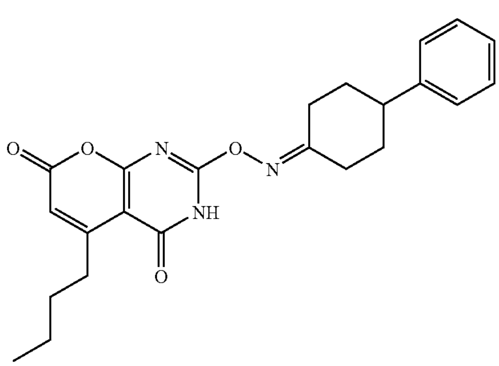 | 408.2 |

-continued

| Compound No. | Structure | Electrospray LCMS [M + 1]+ |
|---|---|---|
| 246 | 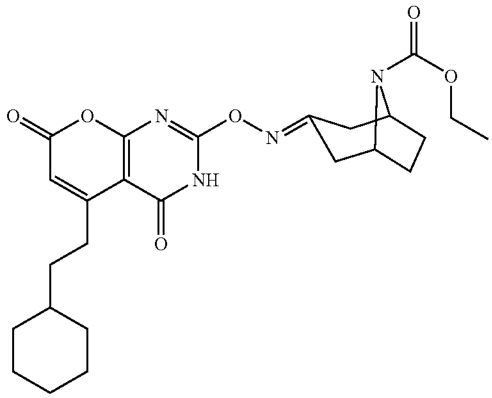 | 485.3 |
| 247 | 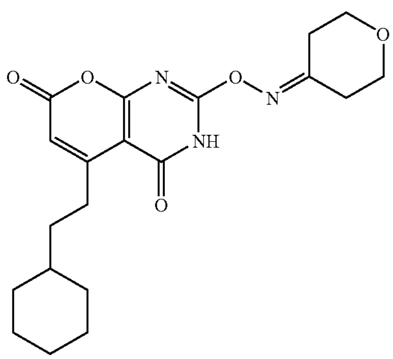 | 388.2 |
| 248 | 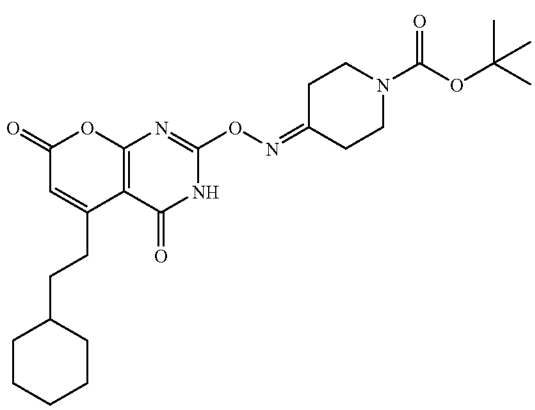 | 487.3 |
| 249 | 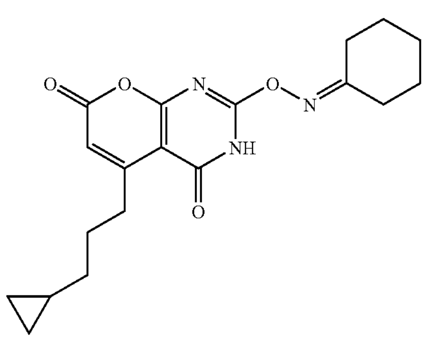 | 358.2 |

-continued
| Compound No. | Structure | Electrospray LCMS [M + 1]+ |
|---|---|---|
| 250 | 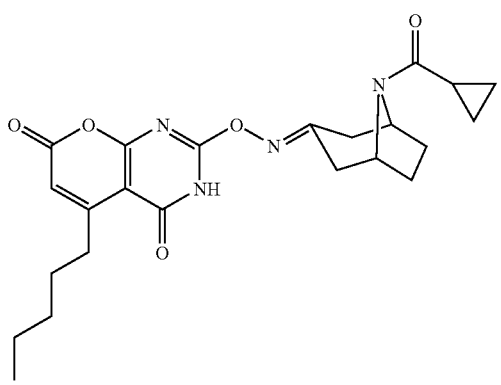 | 441.2 |
| 251 | 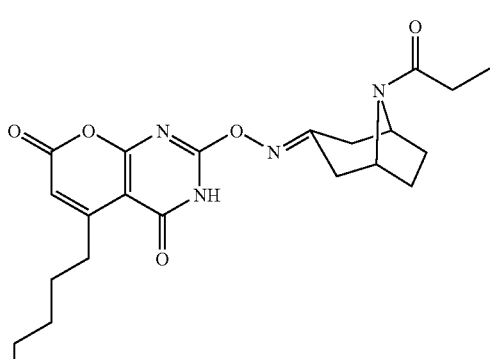 | 429.2 |
| 252 | 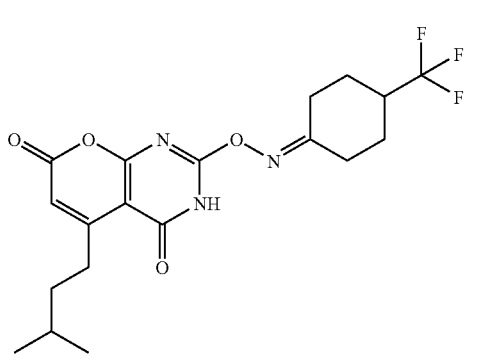 | 414.2 |
| 253 | 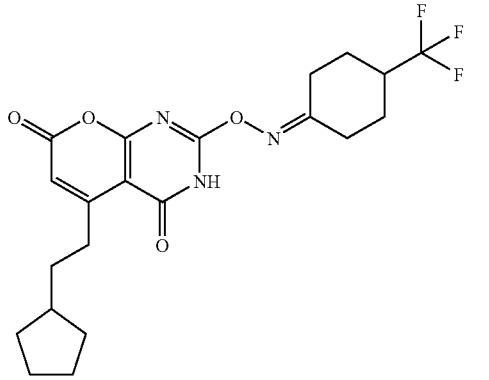 | 440.2 |

-continued
| Compound No. | Structure | Electrospray LCMS [M + 1]+ |
|---|---|---|
| 254 | 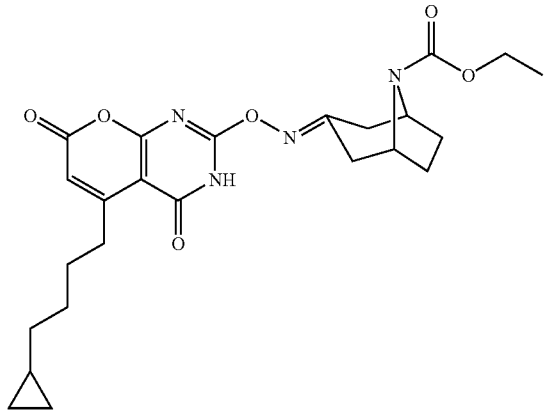 | 471.3 |
| 255 | 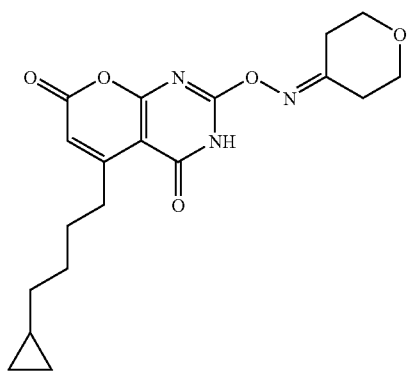 | 374.2 |
| 256 | 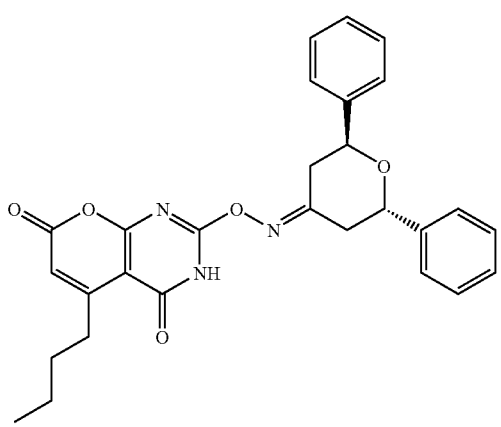 | 486.3 |

-continued

| Compound No. | Structure | Electrospray LCMS [M + 1]+ |
|---|---|---|
| 257 | 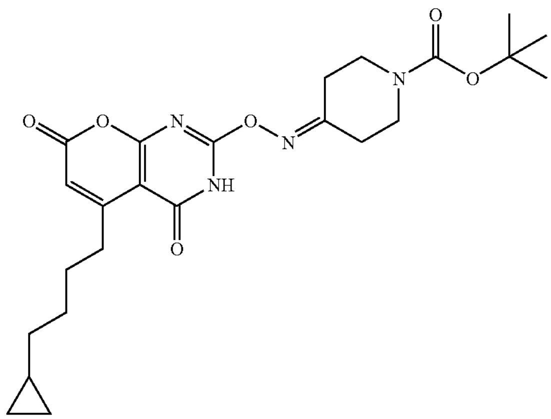 | 473.3 |
| 258 | 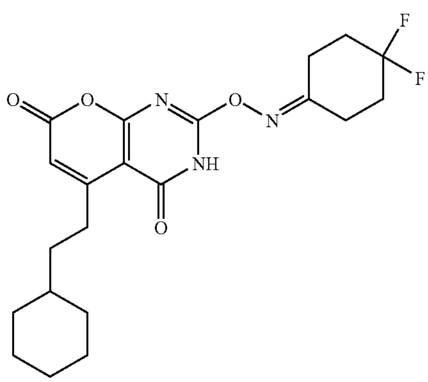 | 42.2 |
| 259 | 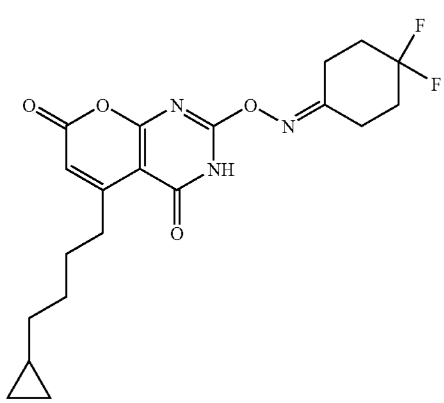 | 408.2 |

-continued
| Compound No. | Structure | Electrospray LCMS [M + 1]+ |
|---|---|---|
| 260 | 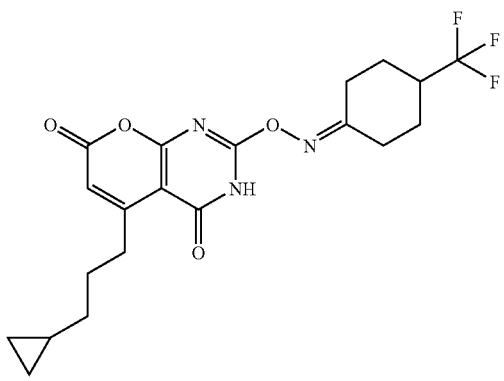 | 426.2 |
| 261 | 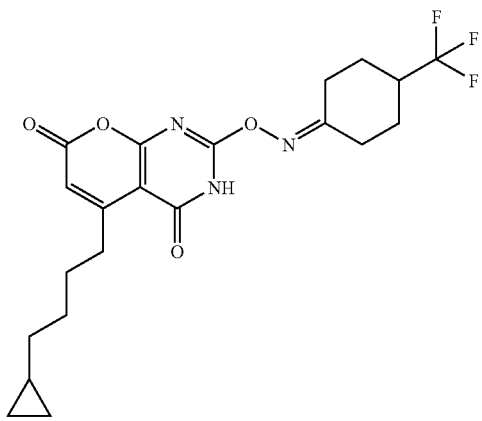 | 440.2 |
| 262 | 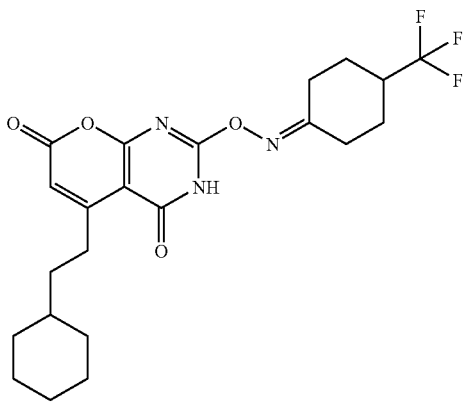 | 454.2 |

-continued

| Compound No. | Structure | Electrospray LCMS [M + 1]+ |
|---|---|---|
| 263 | 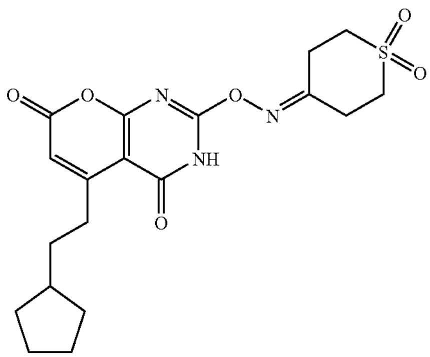 | 422.2 |
| 264 | 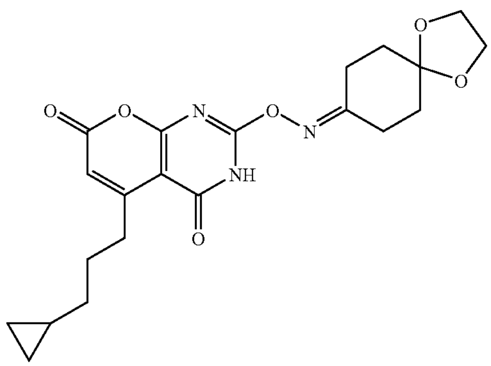 | 416.2 |
| 265 | 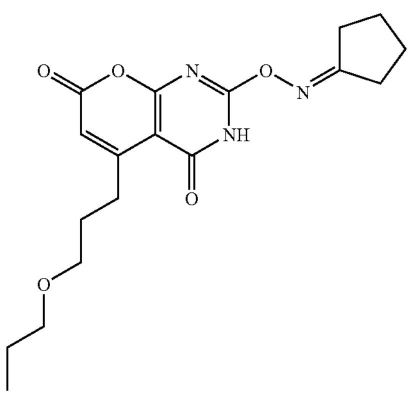 | 362.2 |
| 266 | 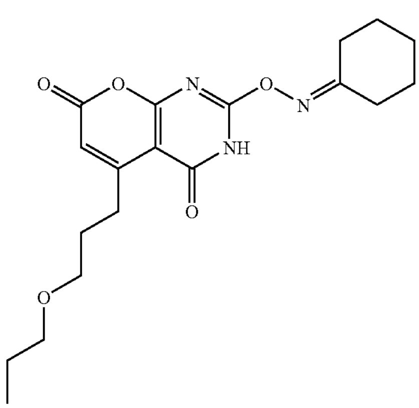 | 376.2 |

-continued

| Compound No. | Structure | Electrospray LCMS [M + 1]+ |
|---|---|---|
| 267 | 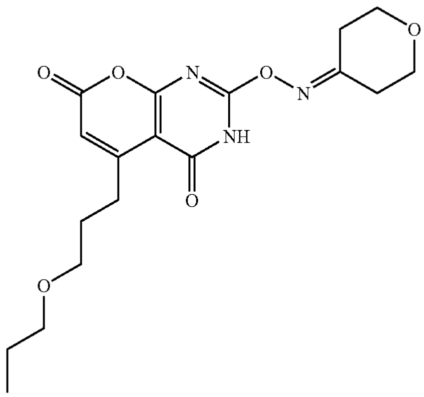 | 378.2 |
| 268 | 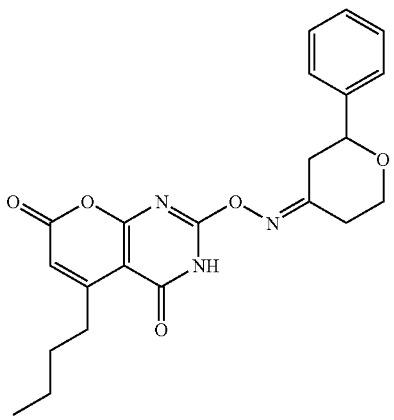 | 410.2 |
| 269 | 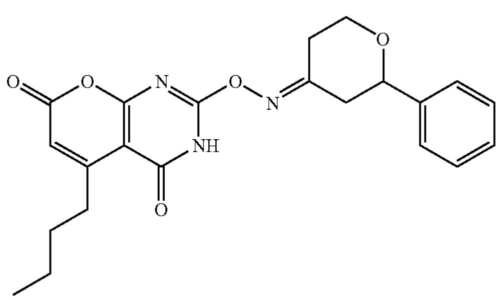 | 410.2 |
| 270 | 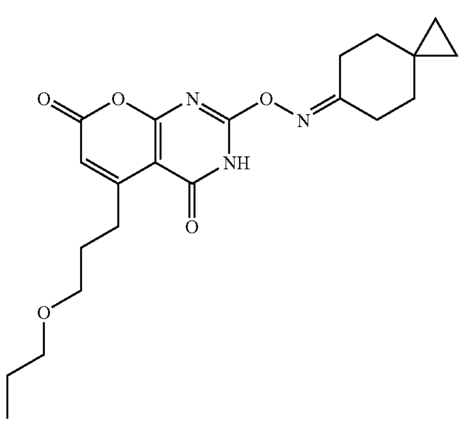 | 402.2 |

-continued
| Compound No. | Structure | Electrospray LCMS [M + 1]+ |
|---|---|---|
| 271 | 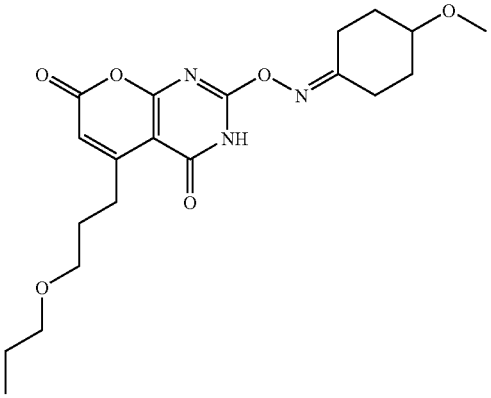 | 406.2 |
| 272 | 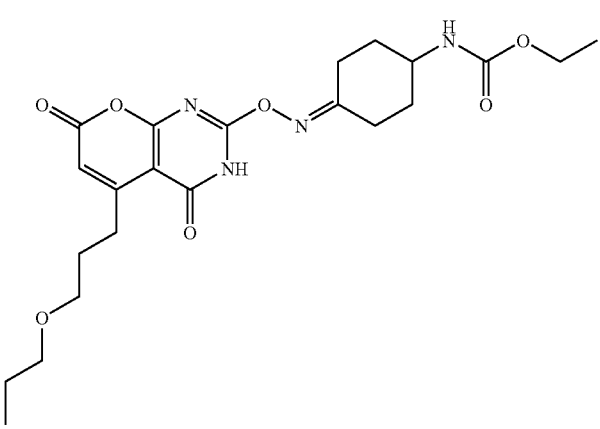 | 463.3 |
| 273 | 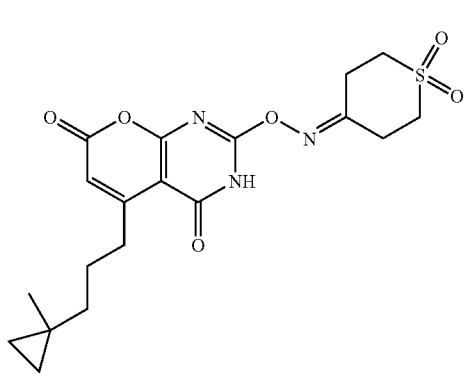 | 422.2 |

-continued
| Compound No. | Structure | Electrospray LCMS [M + 1]+ |
|---|---|---|
| 274 | 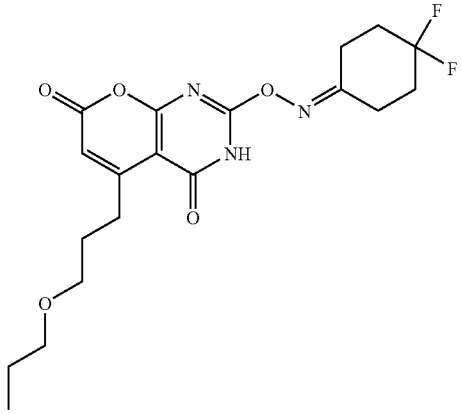 | 412.2 |
| 275 | 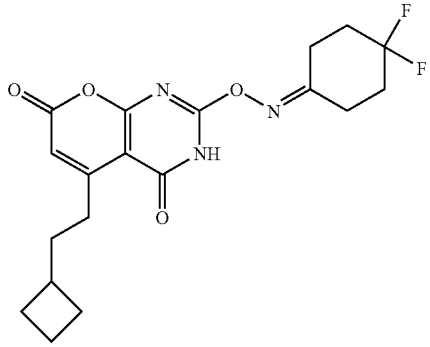 | 394.2 |
| 276 | 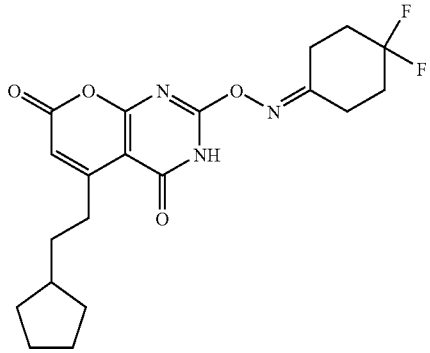 | 408.2 |
| 277 | 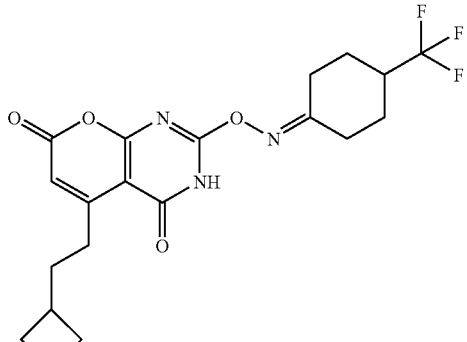 | 426.2 |

-continued

| Compound No. | Structure | Electrospray LCMS [M + 1]+ |
| --- | --- | --- |
| 278 | 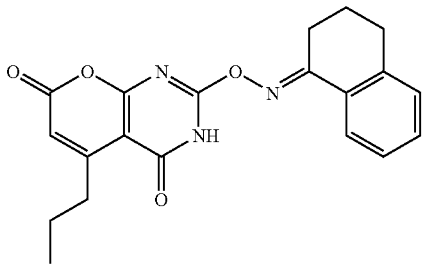 | 366.2 |
| 279 | 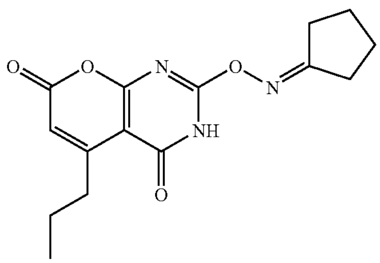 | 304.2 |
| 280 | 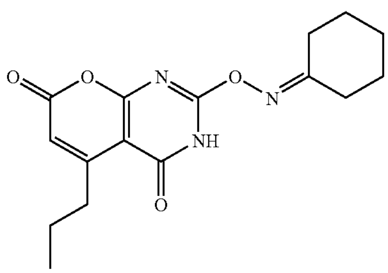 | 318.2 |
| 281 | 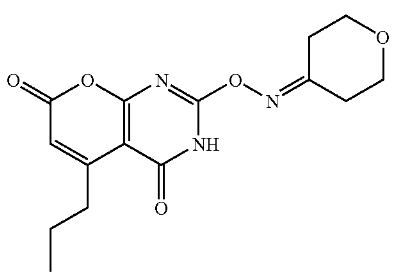 | 320.2 |
| 282 | 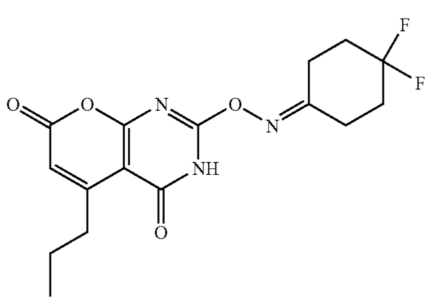 | 354.2 |

| Compound No. | Structure | Electrospray LCMS [M + 1]+ |
|---|---|---|
| 283 | 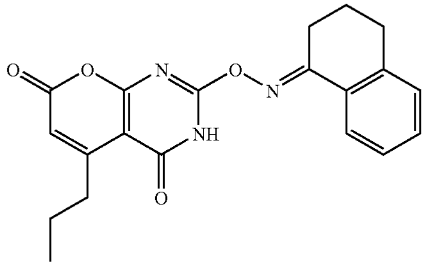 | 420.2 |
| 284 | 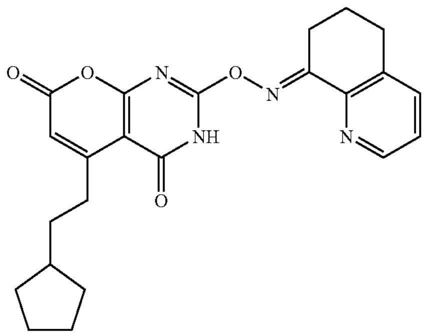 | 421.2 |
| 285 | 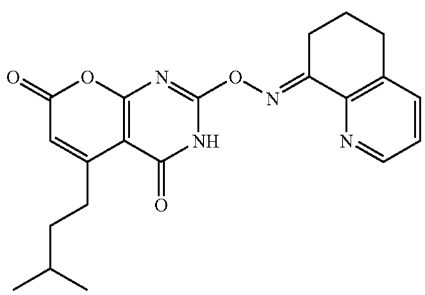 | 395.2 |

Determination of the Nicotinic Acid Receptor Agonist Activity of the Compounds of Formula (I)

The nicotinic acid receptor agonist activity of compounds 1-285 was determined by following the inhibition of forskolin-stimulated cAMP accumulation in cells using the MesoScale Discovery cAMP detection kit following the manufacturer's protocol. Briefly, Chinese Hamster Ovary (CHO) cells expressing recombinant human nicotinic acid receptor (NAR) were harvested enzymatically, washed 1× in phosphate buffered saline (PBS) and resuspended in PBS containing 0.5 mM IBMX at $3 \times 10^6$ cells/mL. Ten µL of cell suspension was added to each well of a 384-well plate which contained 10 µL of test compounds. Test compounds were diluted with PBS containing 6 µM of forskolin. Plates were incubated for 30 minutes at room temperature after the addition of cells. Lysis buffer containing cAMP-Tag was added to each well (10 µL/well) as per the manufacturer's protocol. Plates were then incubated from 45 minutes to overnight. Prior to reading, 10 µL of read buffer was added to each well, and the plate was read in a Sector 6000 plate imager. The signal was converted to cAMP concentration using a standard curve run on each plate. Compound $EC_{50}$ values were determined from concentration gradients of test compounds.

Compounds of Formula (I) of the present invention, and salts, solvates, or esters thereof, have cAMP $EC_{50}$ values of less than about 10,000 nM, preferably about 1000 nM or less, more preferably about 500 nM or less, even more preferably about 100 nM or less.

Using this assay, it was determined that compounds 1-285 all have cAMP $EC_{50}$ values of 1000 nM or less, except for Compounds 40, 55, 65, 129, 130, 131, 238, 246-248, 258, 262 and 278-282 which have cAMP $EC_{50}$ values greater than 1000 nM. Accordingly, the compounds of formula (I) can act as agonists of the nicotinic acid receptor.

What is claimed is:

1. A compound of Formula (I):

(I)

or a pharmaceutically acceptable salt, ester, or tautomer thereof, wherein:

$R^1$ is selected from the group consisting of H, alkyl, $R^4$, haloalkyl, -alkylene-$R^4$, -alkylene-$R^5$, -alkylene-$R^6$, alkenyl, alkynyl, and -alkylene-O-alkyl;

$R^2$ and $R^3$ together with the carbon atom to which they are both attached, combine to form a monocyclic cycloalkyl, bicyclic cycloalkyl or monocyclic heterocycloalkyl ring, wherein said monocyclic cycloalkyl, bicyclic cycloalkyl or monocyclic heterocycloalkyl ring is unsubstituted or optionally and independently substituted with one or more $X^5$ groups, and wherein said monocyclic cycloalkyl ring may be fused to a benzene ring, an aromatic heterocycle or a non-aromatic heterocycle, and wherein the monocyclic cycloalkyl ring can form a spirocyclic compound with a second cycloalkyl ring or with a heterocycloalkyl ring, wherein the second cycloalkyl ring or the heterocycloalkyl ring is unsubstituted or independently substituted with one or more $X^5$ groups;

$R^4$ is unsubstituted cycloalkyl or cycloalkyl substituted with one or more Xgroups;

$R^5$ is unsubstituted aryl and aryl substituted with one or more $X^2$ groups;

$R^6$ is selected from the group consisting of unsubstituted heteroaryl and heteroaryl substituted with one or more $X^3$ groups;

$R^7$ is unsubstituted heterocycloalkyl and heterocycloalkyl substituted with one or more $X^4$ groups;

$R^8$ is selected from the group consisting of H, alkyl, $R^4$, $R^5$, $R^6$, $R^7$, —C(O)-alkyl, —C(O)—$R^5$;

each $R^9$ is independently selected from the group consisting of H, alkyl, $R^4$, $R^5$, $R^6$, and $R^7$;

$R^{10}$ is selected from the group consisting of $R^9$, —C(O)-alkyl, and —C(O)—$R^5$;

Y is —O— or —N($R^{10}$)—;

each $X^1$ is independently selected from the group consisting of halogen, alkyl, —O-alkyl, —OH, haloalkyl, aryl, and alkynyl;

each $X^2$ is independently selected from the group consisting of halogen, alkyl, —O-alkyl, —OH, haloalkyl, aryl, and alkynyl;

each $X^3$ is independently selected from the group consisting of halogen, alkyl, and N-oxide;

each $X^4$ is independently selected form the group consisting of alkyl, $R^5$, —C(O)-alkyl, —C(O)—$R^5$, —C(O)—O-alkyl, -alkylene-$R^5$, $R^4$, and —S($O_2$)-alkyl; and each $X^5$ is independently selected from the group consisting of alkyl, aryl, —C(O)-alkyl, heteroaryl, —C(O)—O-alkyl, —C(O)—$R^5$, —S($O_2$)-alkyl, —C(O)—N($R^9$)$_2$, $R^5$, $R^6$, —C(O)—$R^4$, —C(O)—O—$R^4$, —S($O_2$)—$R^4$, —S($O_2$)-alkylene-$R^4$, —S($O_2$)-alkylene-$R^5$, —N($R^9$)—C(O)—O-alkyl, —N($R^9$)—C(O)—O—$R^4$, —N($R^9$)—C(O)—N($R^9$)$_2$ and —N($R^9$)$_2$, wherein said aryl is unsubstituted or independently substituted with one or more substituent selected from -alkylene-$R^7$ or $X^2$, and said heteroaryl is unsubstituted or substituted with one or more $X^3$ groups.

2. The compound of claim 1, or a pharmaceutically acceptable salt, ester, or tautomer thereof, wherein $R^1$ is alkyl.

3. The compound of claim 1, or a pharmaceutically acceptable salt, ester, or tautomer thereof, wherein $R^1$ is -alkylene-$R^4$.

4. The compound of claim 1, or a pharmaceutically acceptable salt, ester, or tautomer thereof, wherein $R^1$ is -alkylene-$R^5$.

5. The compound of claim 1, or a pharmaceutically acceptable salt, ester, or tautomer thereof, wherein $R^1$ is -alkylene-$R^6$.

6. The compound of claim 1, or a pharmaceutically acceptable salt, ester, or tautomer thereof, wherein:

$R^1$ is alkyl; and $R^2$ and $R^3$ together with the carbon atom to which they are both attached form a cycloalkyl ring, wherein said cycloalkyl ring is unsubstituted or substituted with one or more $X^1$ groups.

7. The compound of claim 1, or a pharmaceutically acceptable salt, ester, or tautomer thereof, wherein:

$R^1$ is alkyl; and $R^2$ and $R^3$ together with the carbon atom to which they are both attached form a heterocycloalkyl ring, wherein said heterocycloalkyl ring is unsubstituted or substituted with one or more $X^4$ groups.

8. The compound of claim 7, or a pharmaceutically acceptable salt, ester, or tautomer thereof, wherein:

$R^1$ is —$CH_2CH_3$, —$CH_2CH_2CH_3$, —$CH_2CH_2CH_2CH_3$, or —$CH_2CH_2CH(CH_3)_2$; and $R^2$ and $R^3$ together with the carbon atom to which they are both attached form a cycloalkyl or heterocycloalkyl group selected from:

wherein each of said cycloalkyl or heterocycloalkyl rings is unsubstituted or substituted with one or more $X^4$ groups.

9. The compound of claim 7, or a pharmaceutically acceptable salt, ester, or tautomer thereof, selected from the group consisting of:

191
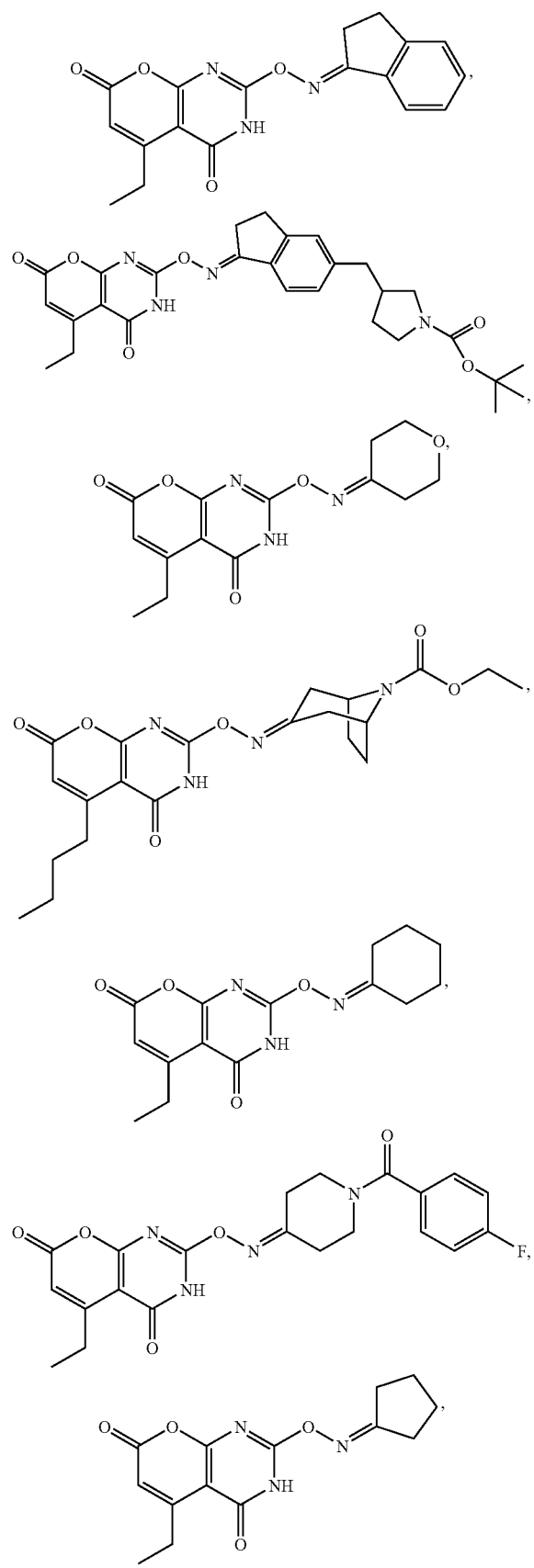
192
-continued
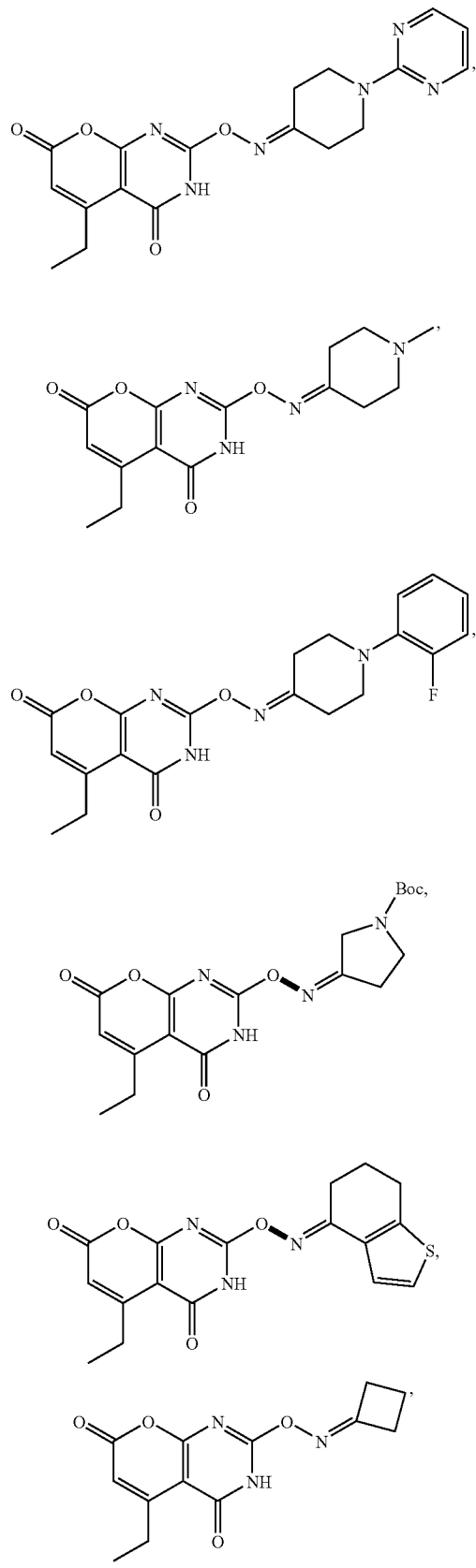

193
-continued
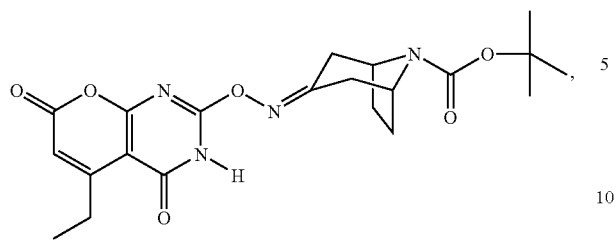
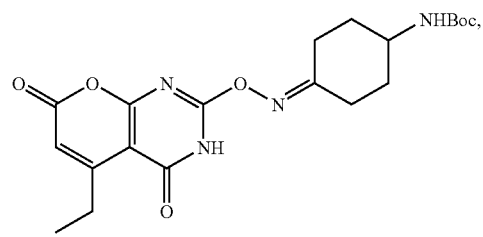
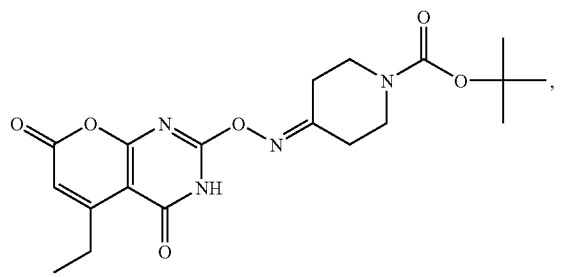
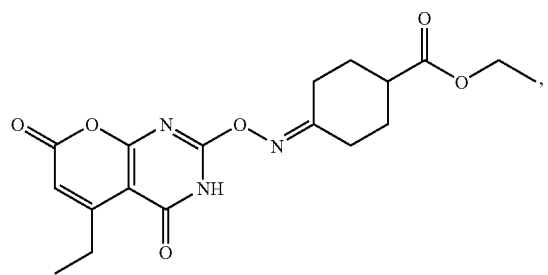
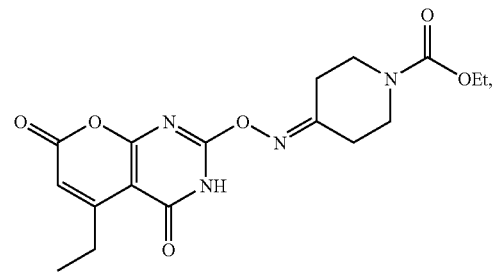
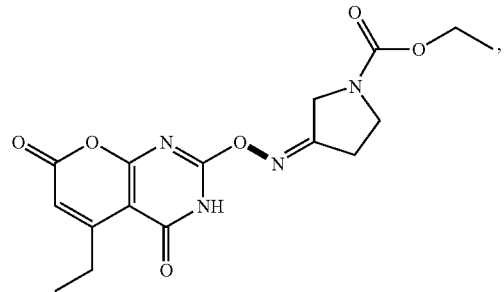
194
-continued
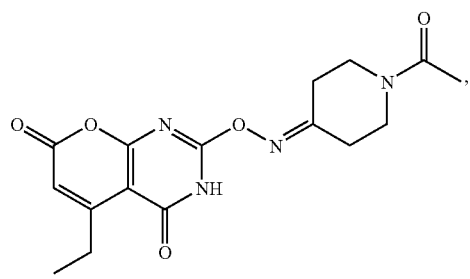
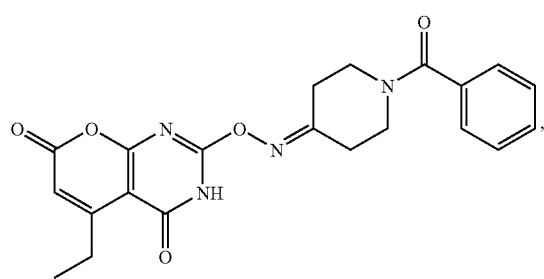
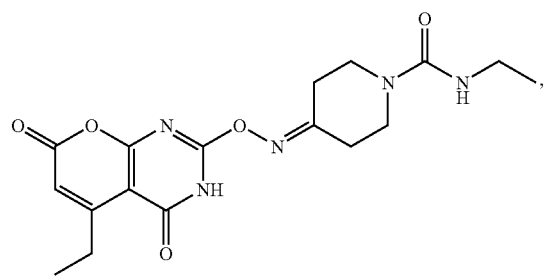
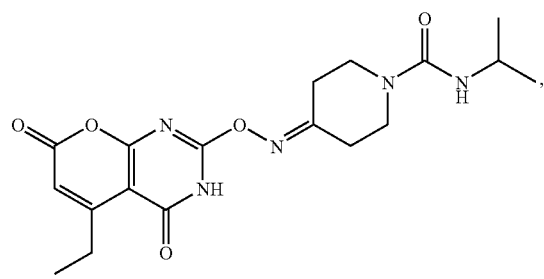
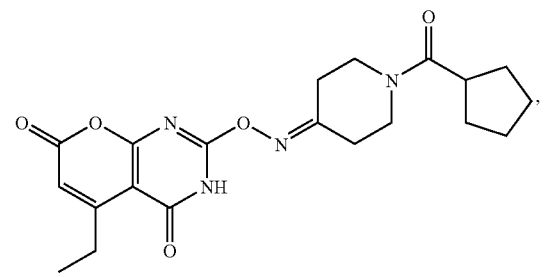
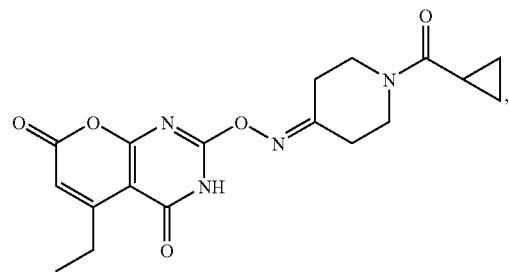

195
-continued
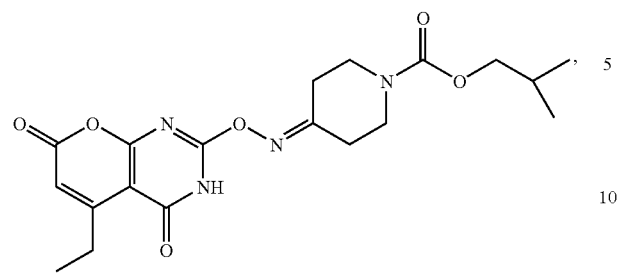
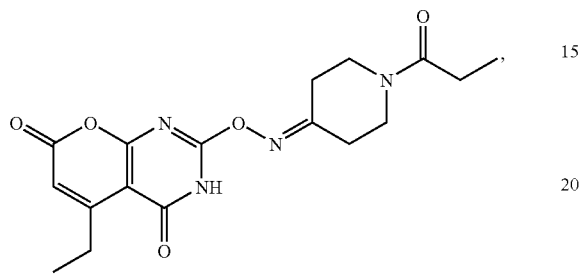
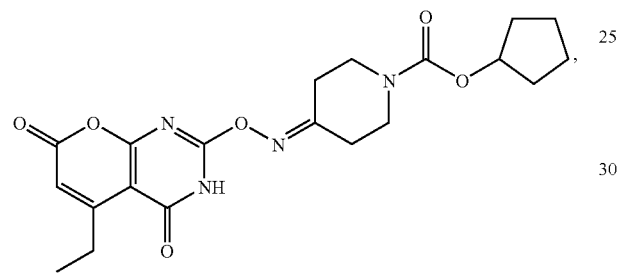
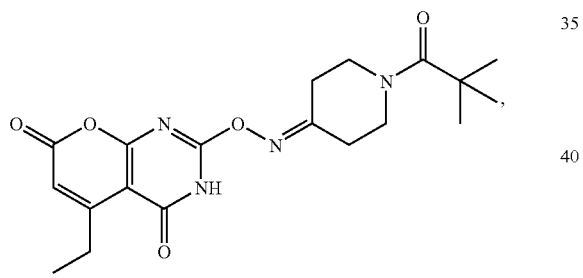
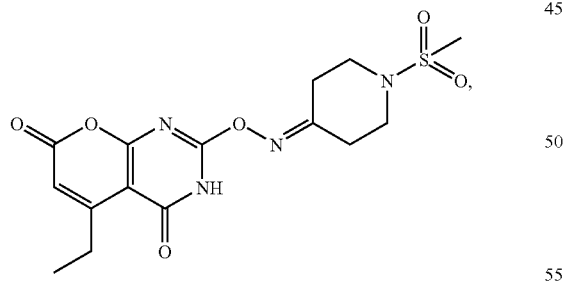
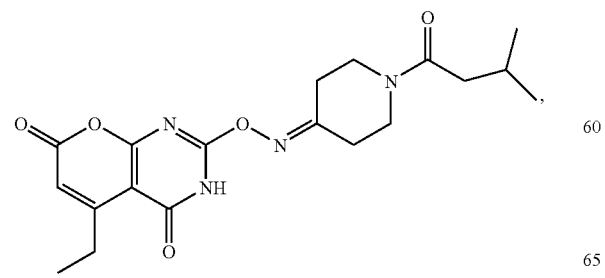
196
-continued
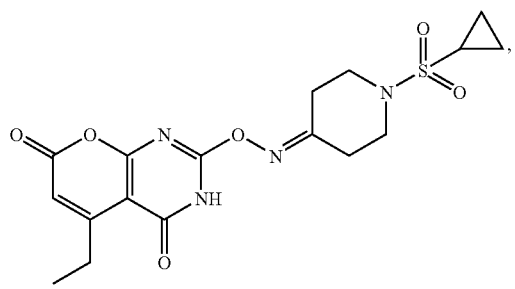
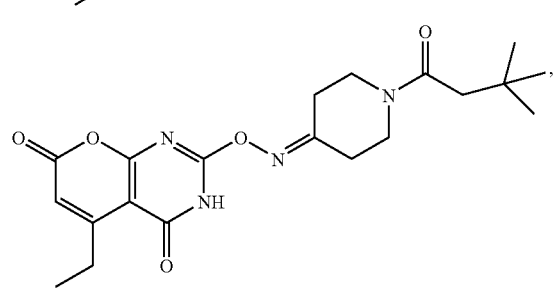
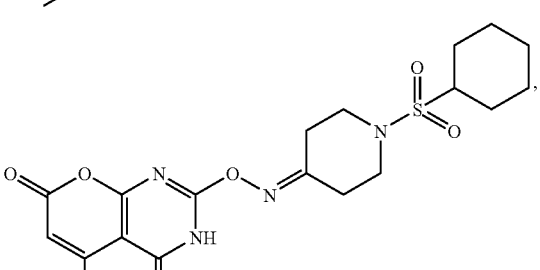
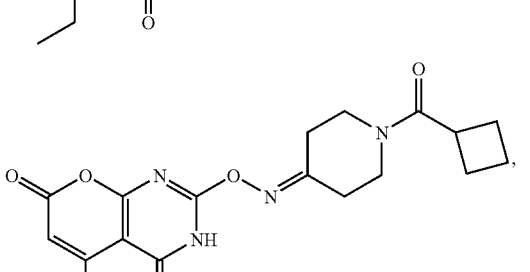
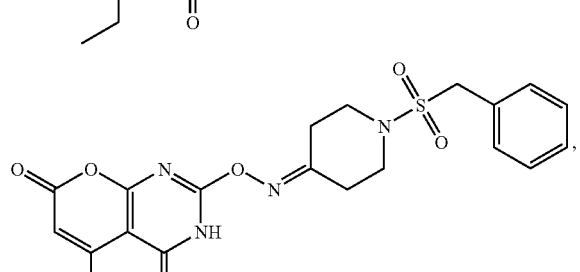
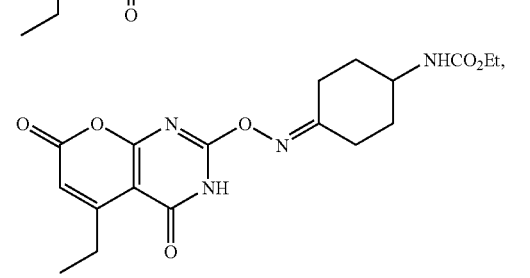

197
-continued
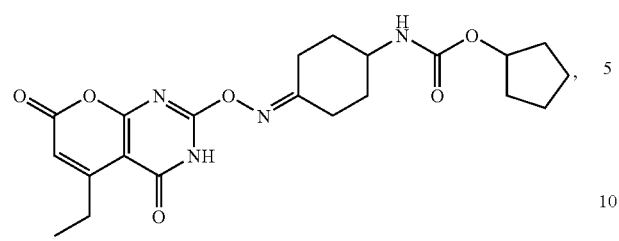
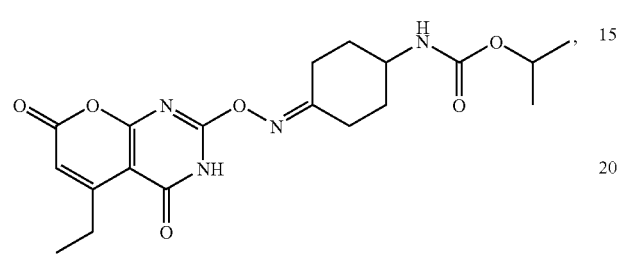
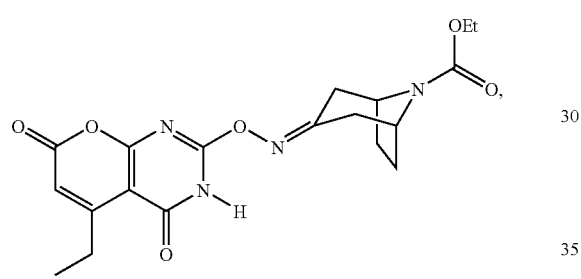
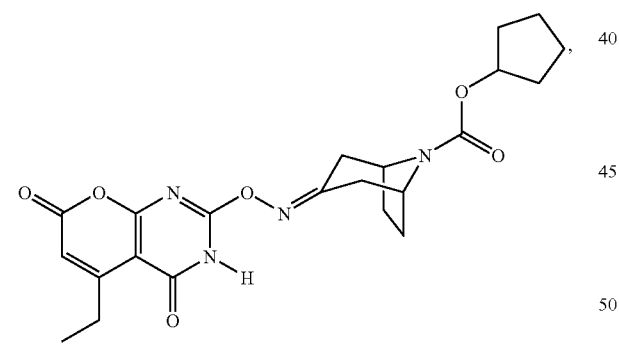
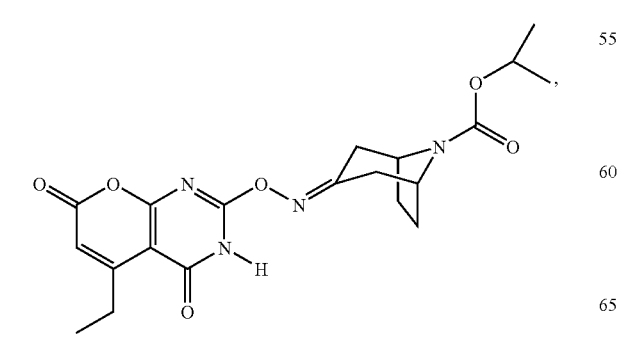
198
-continued
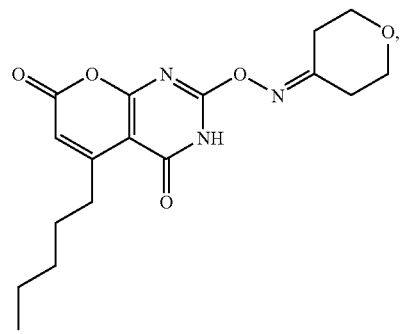
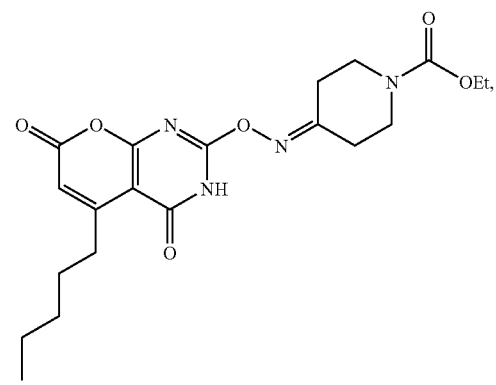
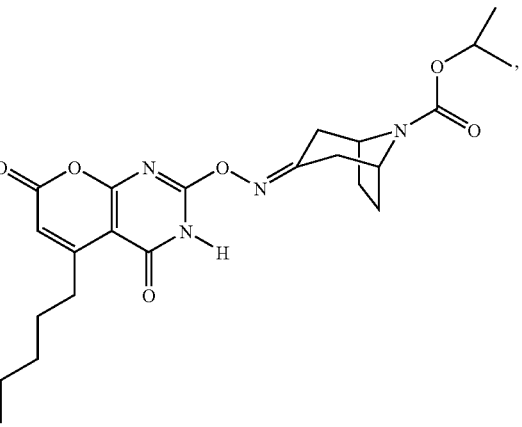
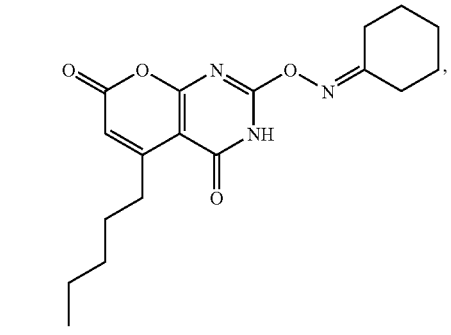

-continued
| 199 | 200 |
|---|---|
| 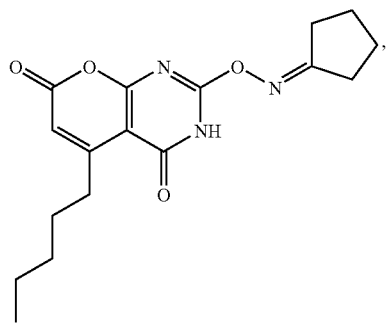 | 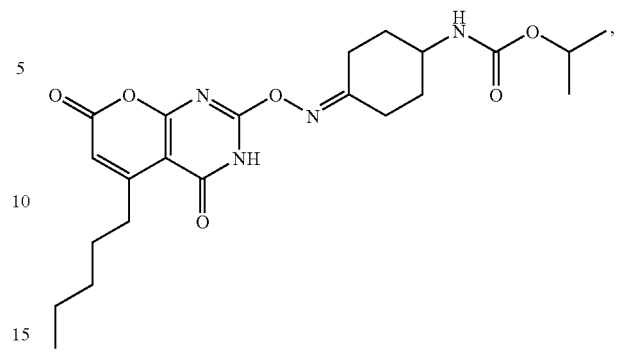 |
| 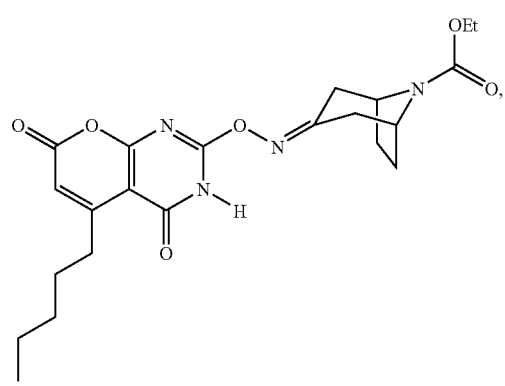 | 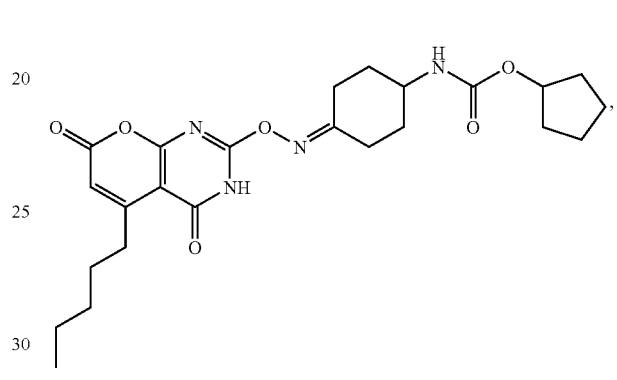 |
| 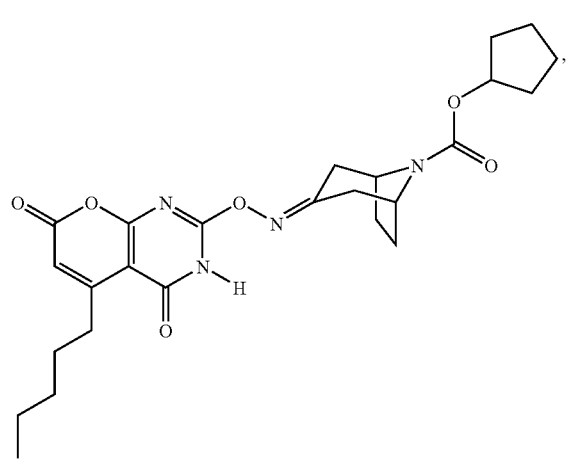 | 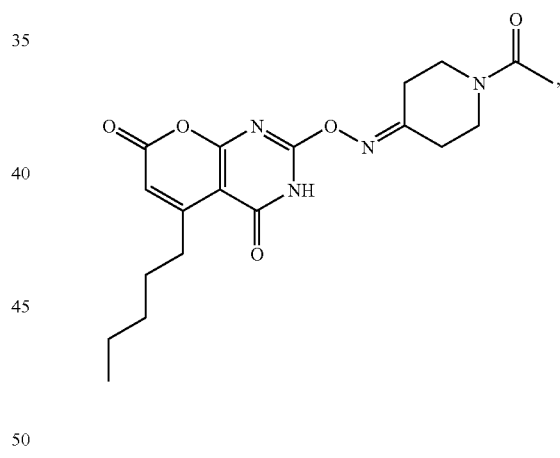 |
| 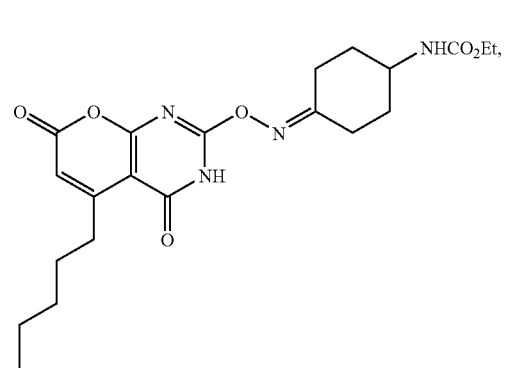 | 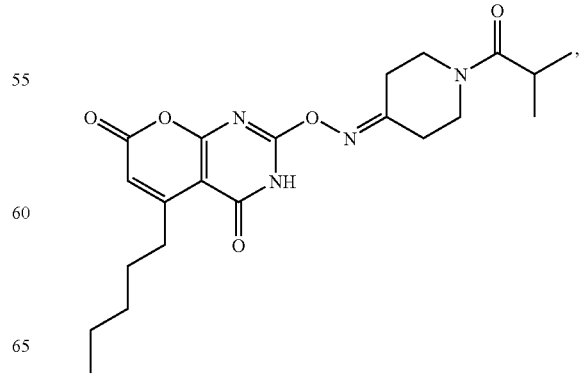 |

-continued
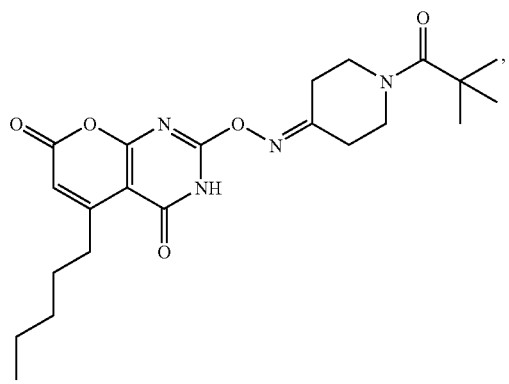
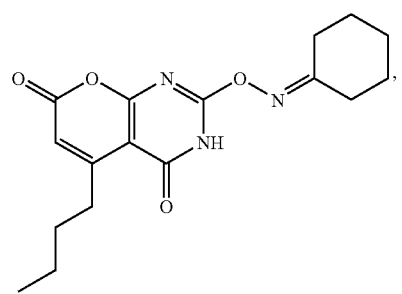
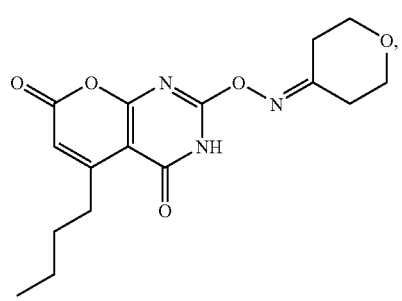
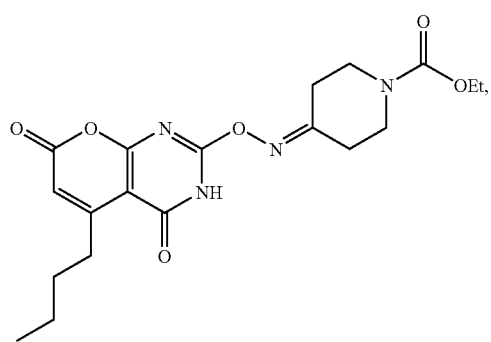
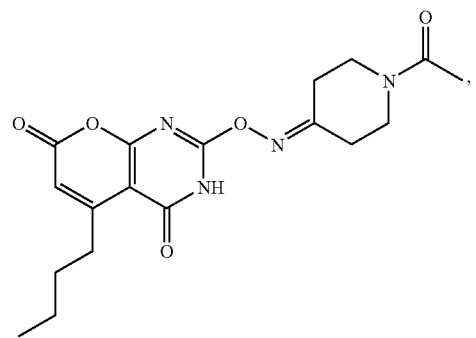
-continued
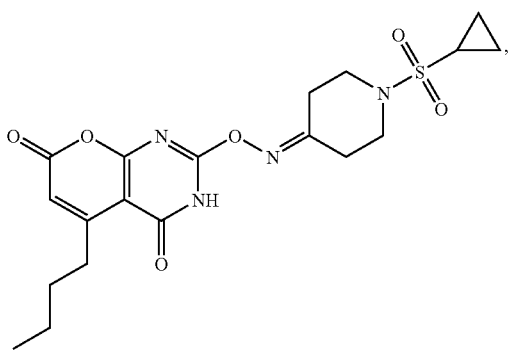
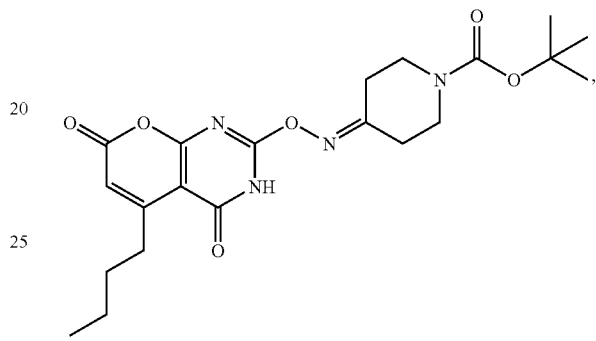
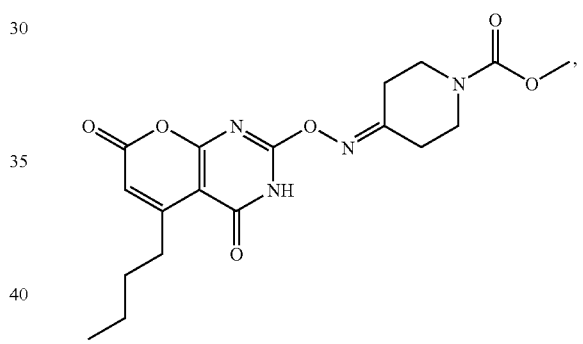
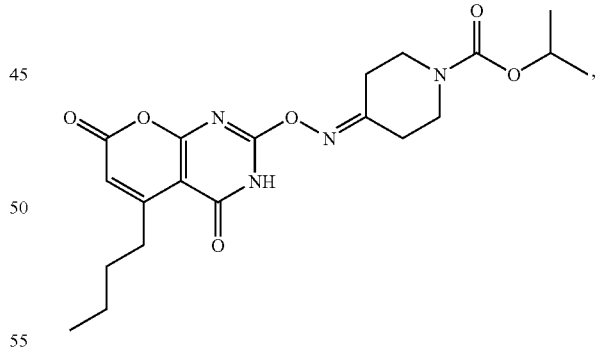
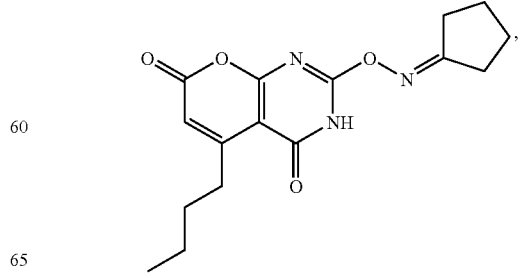

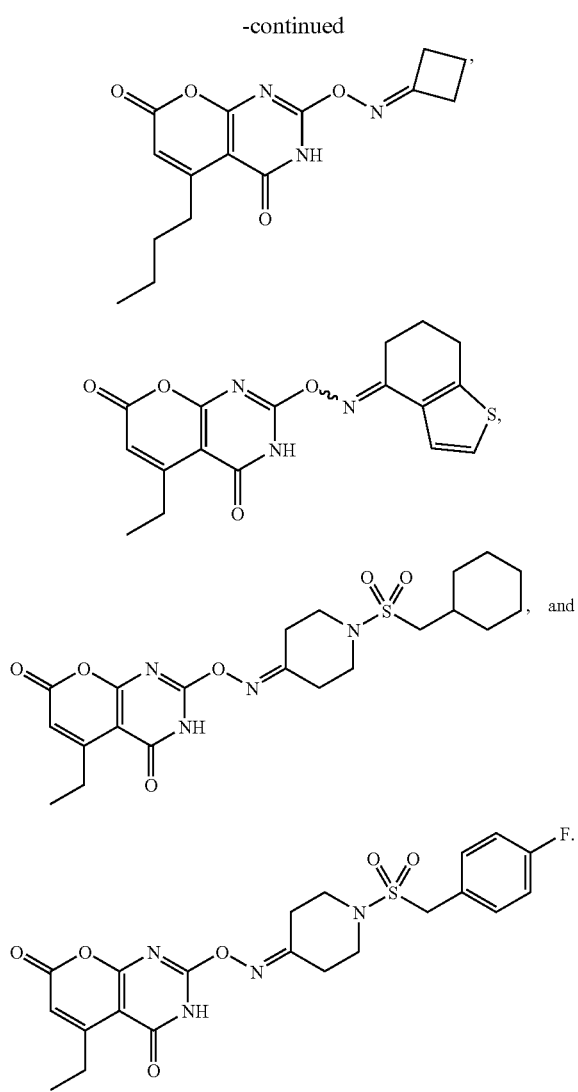

10. The compound of claim 1, or a pharmaceutically acceptable salt, ester, or tautomer thereof, wherein R is —CH$_2$CH$_2$CF$_3$, —CH$_2$CH$_2$—R$^4$, —CH$_2$CH$_2$CH$_2$—R$^4$, —CH$_2$—R$^5$, or —CH$_2$—R$^6$.

11. The compound of claim 10, or a pharmaceutically acceptable salt, ester, or tautomer thereof, wherein:

R$^2$ and R$^3$ together with the carbon atom to which they are both attached form a cycloalkyl or heterocycloalkyl group selected from:

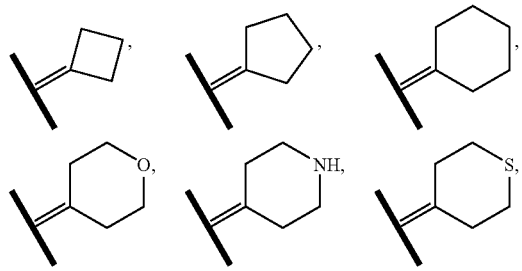

wherein each of said cycloalkyl or heterocycloalkyl rings is unsubstituted or substituted with one or more X$^4$ groups.

12. The compound of claim 11, or a pharmaceutically acceptable salt, ester, or tautomer thereof, selected from the group consisting of:

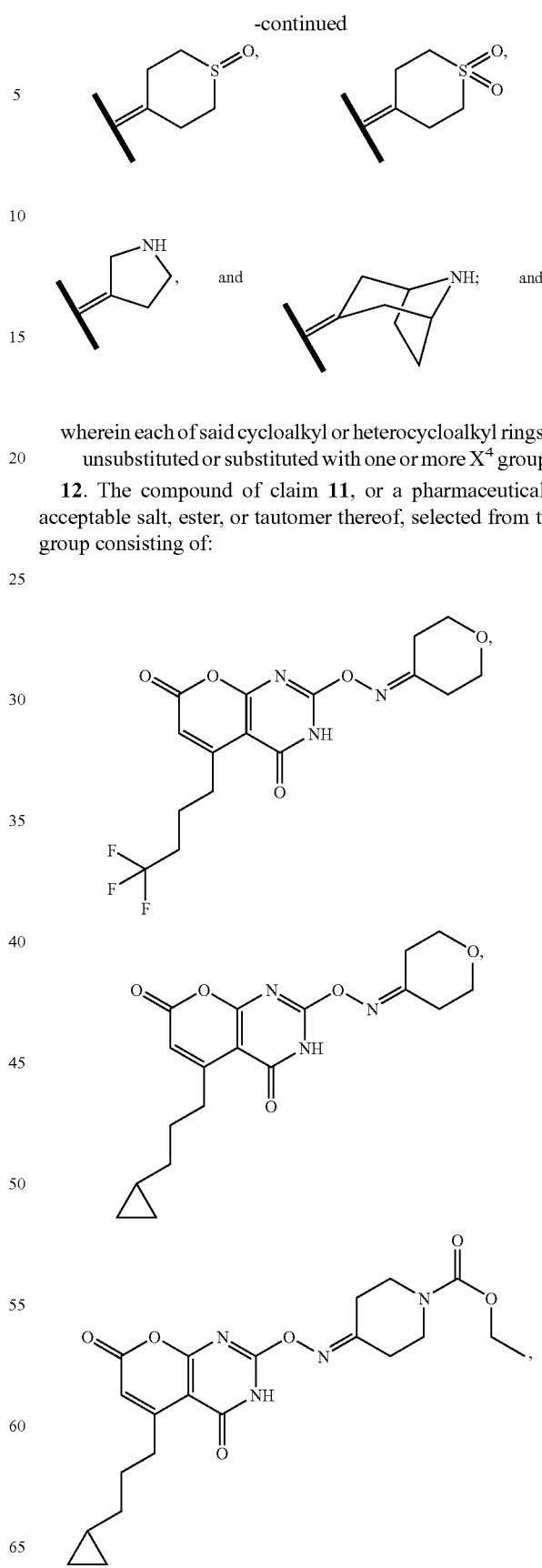

205
-continued
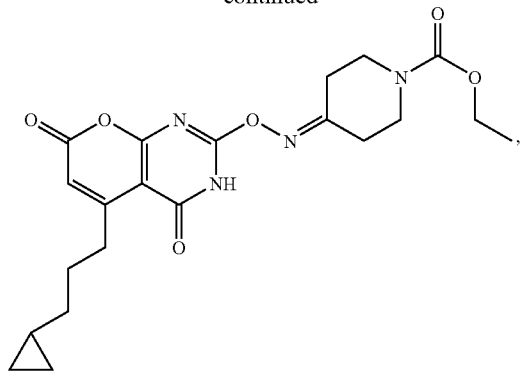
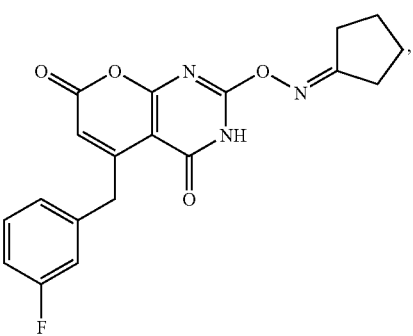
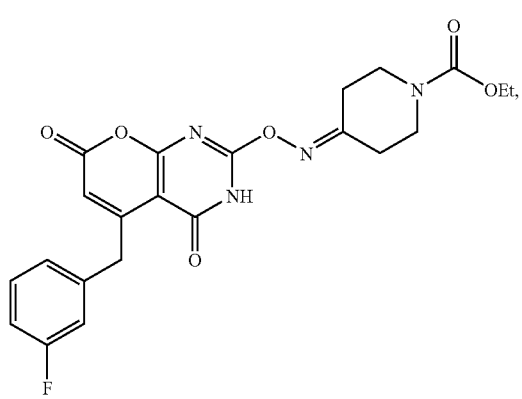
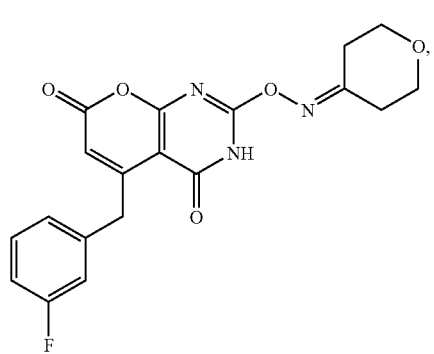
206
-continued
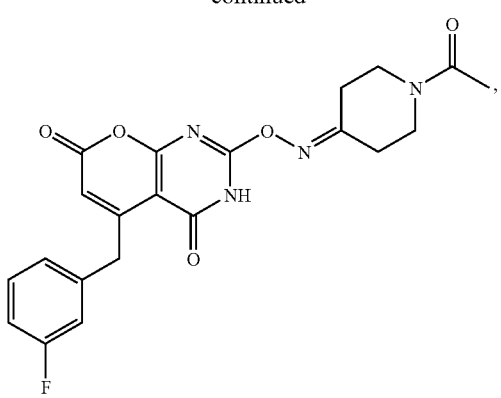
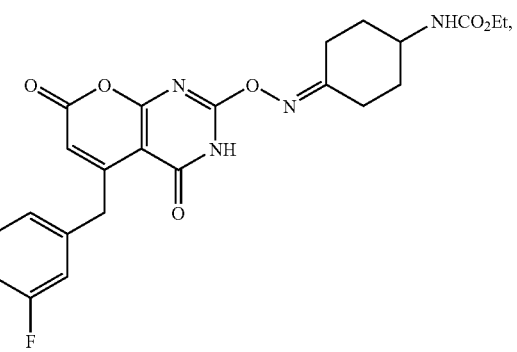
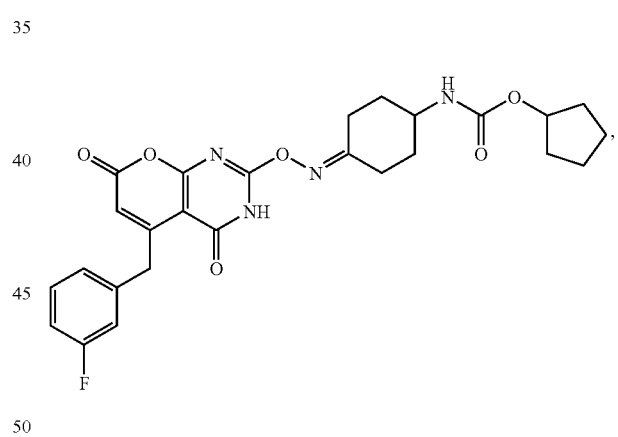

207
-continued
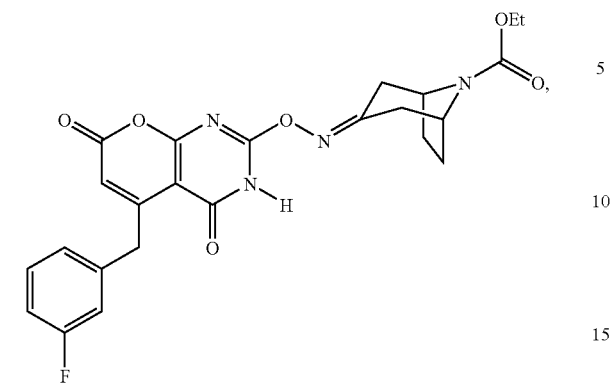
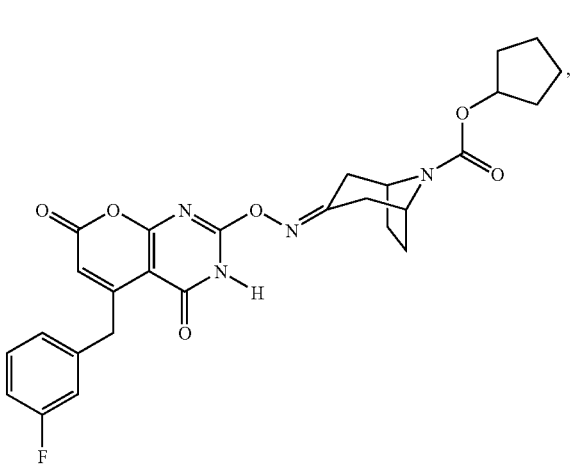
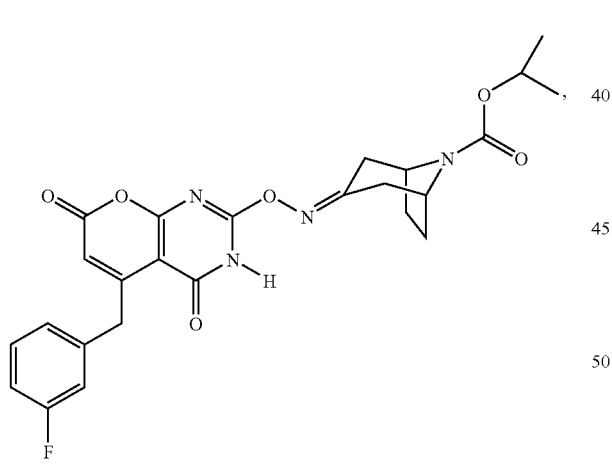
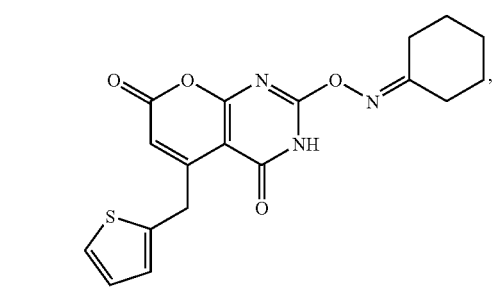
208
-continued
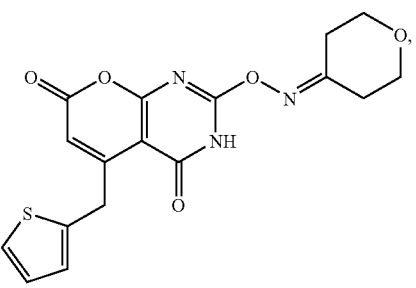
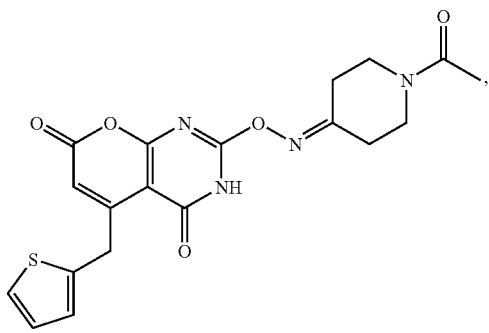
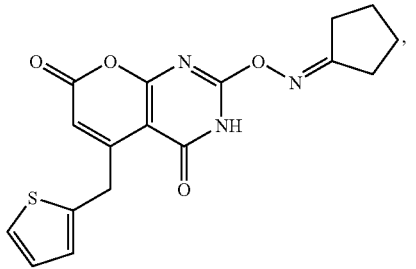
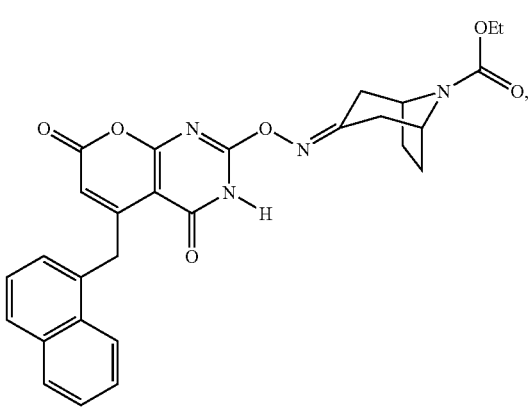

-continued

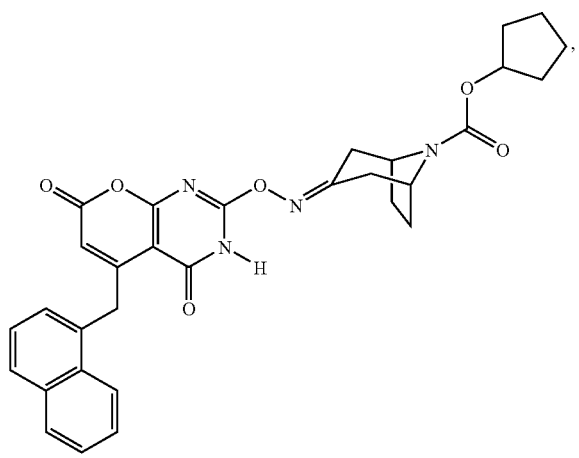

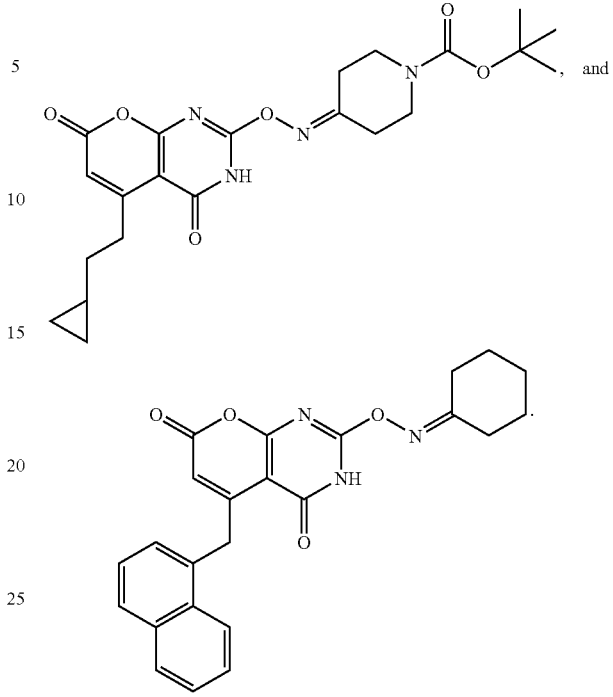

13. A composition comprising: a compound of claim 1, or a pharmaceutically acceptable salt, ester, or tautomer thereof; and at least one pharmaceutically acceptable carrier.

14. The composition of claim 13, further comprising at least one additional therapeutic agent selected from the group consisting of a β-lactam, HMG CoA reductase inhibitor compounds, HMG CoA synthetase inhibitors, squalene synthesis inhibitors, squalene epoxidase inhibitors, sterol biosynthesis inhibitors, nicotinic acid, a nicotinic acid receptor agonist, bile acid sequestrants, aspirin, NSAID agents, a combination of ezetimibe and simvastatin, ezetimibe, inorganic cholesterol sequestrants, AcylCoA:Cholesterol O-acyltransferaseinhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, opioid antagonists, orexin receptor antagonists, BRS3 agonists, CCK-A agonists, CNTF, CNTF agonists/modulators, 5HT2c agonists, Mc4r agonists, monoamine reuptake inhibitors, serotonin reuptake inhibitors, GLP-1 agonists, phentermine, topiramate, phytopharm compound 57, ghrelin antibodies, Mc3r agonists, ACC inhibitors, β3 agonists, DGAT1 inhibitors, DGAT2 inhibitors, FAS inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanin concentrating hormone antagonists, leptons, galanin receptor antagonists, bombesin agonists, neuropeptide-Y antagonists, thyromimetic agents, dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, α-glucosidase inhibitors, apo A1 milano reverse cholesterol transport inhibitors, fatty acid binding protein inhibitors (FABP), and fatty acid transporter protein inhibitors (FATP).

15. The composition of claim 14, wherein said at least one additional therapeutic agent is a HMG CoA reductase inhibitor selected from the group consisting of lovastatin, simvastatin, pravastatin, atorvastatin, fluvastatin, cerivastatin, rivastatin, rosuvastatin calcium, and pitavastatin.

16. The composition of claim 15, wherein said HMG CoA reductase inhibitor is simvastatin.

17. The composition of claim 14, wherein said at least one additional therapeutic agent is a cholesteryl ester transfer protein inhibitor.

18. The compound of claim 1 having the formula:

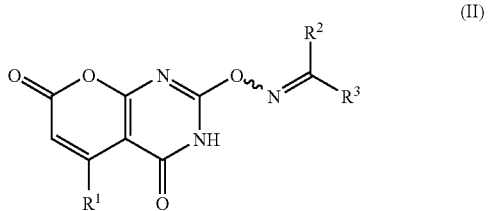

(II)

or a pharmaceutically acceptable salt, ester, or tautomer thereof, wherein:

$R^1$ is alkyl, -alkylene-cycloalkyl, haloalkyl or -alkylene-O-alkyl;

$R^2$ and $R^3$ together with the carbon atom to which they are both attached, combine to form a monocyclic cycloalkyl, bicyclic cycloalkyl or monocyclic heterocycloalkyl, wherein a monocyclic cycloalkyl, bicyclic cycloalkyl or monocyclic heterocycloalkyl group is unsubstituted or optionally and independently substituted with one or more $X^5$ groups, and wherein a monocyclic cycloalkyl group may be fused to a benzene ring, an aromatic heterocycle or a non-aromatic heterocycle, and wherein the monocyclic cycloalkyl ring can form a spirocyclic compound with a second cycloalkyl ring or with a heterocycloalkyl ring, wherein the second cycloalkyl ring or the heterocycloalkyl ring is unsubstituted or independently substituted with one or more $X^5$ groups;

each occurrence of $X^5$ is independently alkyl, —O-alkyl, -alkylene-aryl, halo, —O—Si$(R^{11})_3$, haloalkyl, —CN, —C(O)—$R^4$, —C(O)—O—$R^4$, —NHC(O)—O—$R^4$, —S$(O_2)$—$R^4$, or phenyl;

$R^4$ is alkyl or cycloalkyl, wherein the cycloalkyl group can be optionally and independently substituted with one or more $X^1$ groups, and wherein the alkyl group can be optionally substituted with a cycloalkyl group;

each $R^{11}$ is independently alkyl or phenyl; and each occurrence of $X^1$ is independently halogen, alkyl, —O-alkyl, —OH, haloalkyl, aryl or alkynyl.

19. The compound of claim 18, wherein $R^1$ is alkyl.

20. The compound of claim 18, wherein $R^1$ is -alkylene-cycloalkyl.

21. The compound of claim 18, wherein $R^1$ is alkylene-O-alkyl.

22. The compound of claim 18, wherein $R^2$ and $R^3$ together with the carbon atom to which they are both attached, combine to form a monocyclic cycloalkyl.

23. The compound of claim 18, wherein $R^2$ and $R^3$ together with the carbon atom to which they are both attached, combine to form: (i) a bicyclic cycloalkyl; or (ii) a monocyclic cycloalkyl which forms a spirocycle with a second cycloalkyl group or with a heterocycloalkyl group.

24. The compound of claim 18, wherein $R^2$ and $R^3$ together with the carbon atom to which they are both attached, combine to form a monocyclic heterocycloalkyl.

25. The compound of claim 19, wherein $R^2$ and $R^3$ together with the carbon atom to which they are both attached, combine to form a monocyclic cycloalkyl.

26. The compound of claim 19, wherein $R^2$ and $R^3$ together with the carbon atom to which they are both attached, combine to form: (i) a bicyclic cycloalkyl; or (ii) a monocyclic cycloalkyl which forms a spirocycle with a second cycloalkyl group or with a heterocycloalkyl group.

27. The compound of claim 19, wherein $R^2$ and $R^3$ together with the carbon atom to which they are both attached, combine to form a monocyclic heterocycloalkyl.

28. The compound of claim 20, wherein $R^2$ and $R^3$ together with the carbon atom to which they are both attached, combine to form a monocyclic cycloalkyl.

29. The compound of claim 20, wherein $R^2$ and $R^3$ together with the carbon atom to which they are both attached, combine to form: (i) a bicyclic cycloalkyl; or (ii) a monocyclic cycloalkyl which forms a spirocycle with a second cycloalkyl group or with a heterocycloalkyl group.

30. The compound of claim 20, wherein $R^2$ and $R^3$ together with the carbon atom to which they are both attached, combine to form a monocyclic heterocycloalkyl.

31. The compound of claim 21, wherein $R^2$ and $R^3$ together with the carbon atom to which they are both attached, combine to form a monocyclic cycloalkyl.

32. The compound of claim 21, wherein $R^2$ and $R^3$ together with the carbon atom to which they are both attached, combine to form: (i) a bicyclic cycloalkyl; or (ii) a monocyclic cycloalkyl which forms a spirocycle with a second cycloalkyl group or with a heterocycloalkyl group.

33. The compound of claim 21, wherein $R^2$ and $R^3$ together with the carbon atom to which they are both attached, combine to form a monocyclic heterocycloalkyl.

34. The compound of claim 18 having the structure:
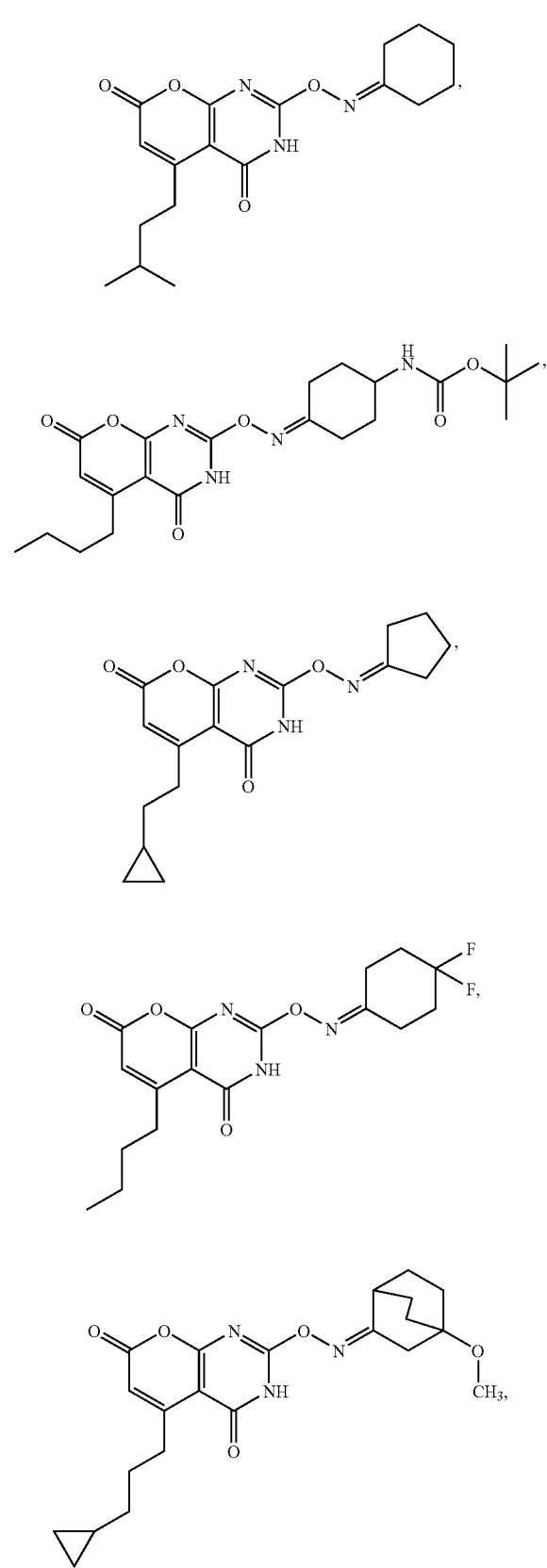
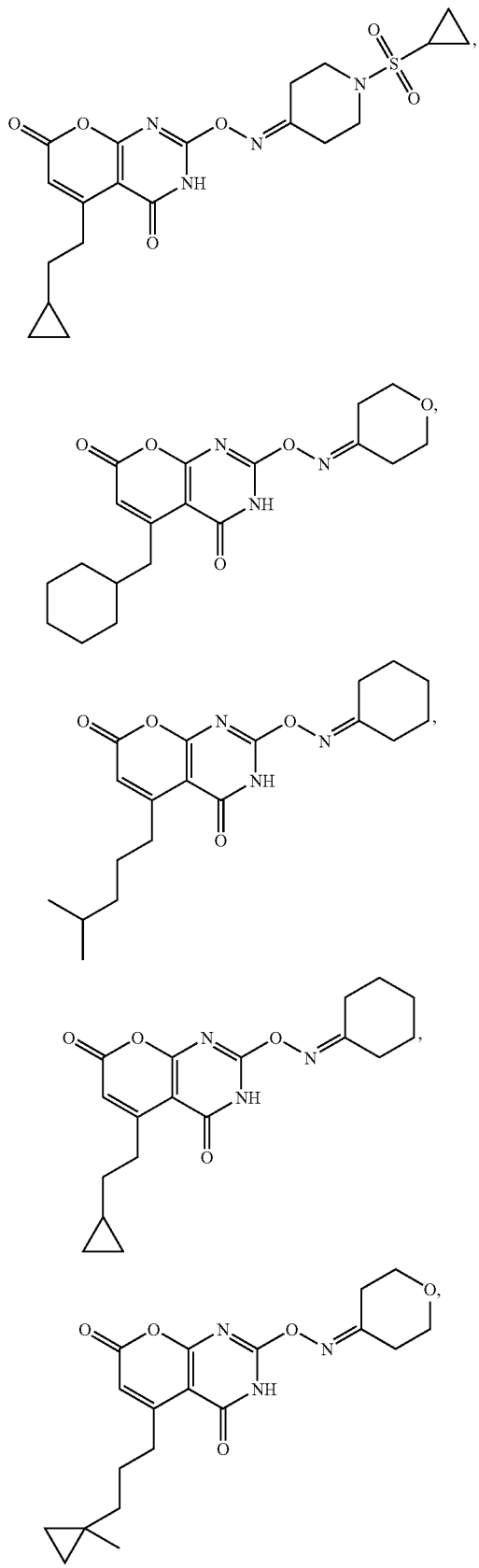

215
-continued
216
-continued
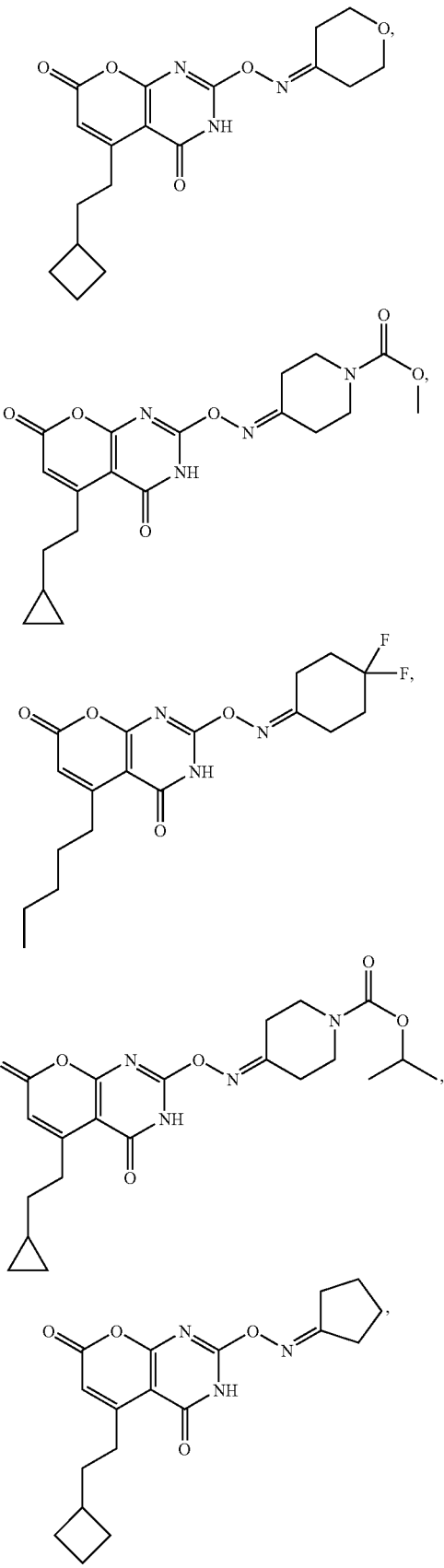
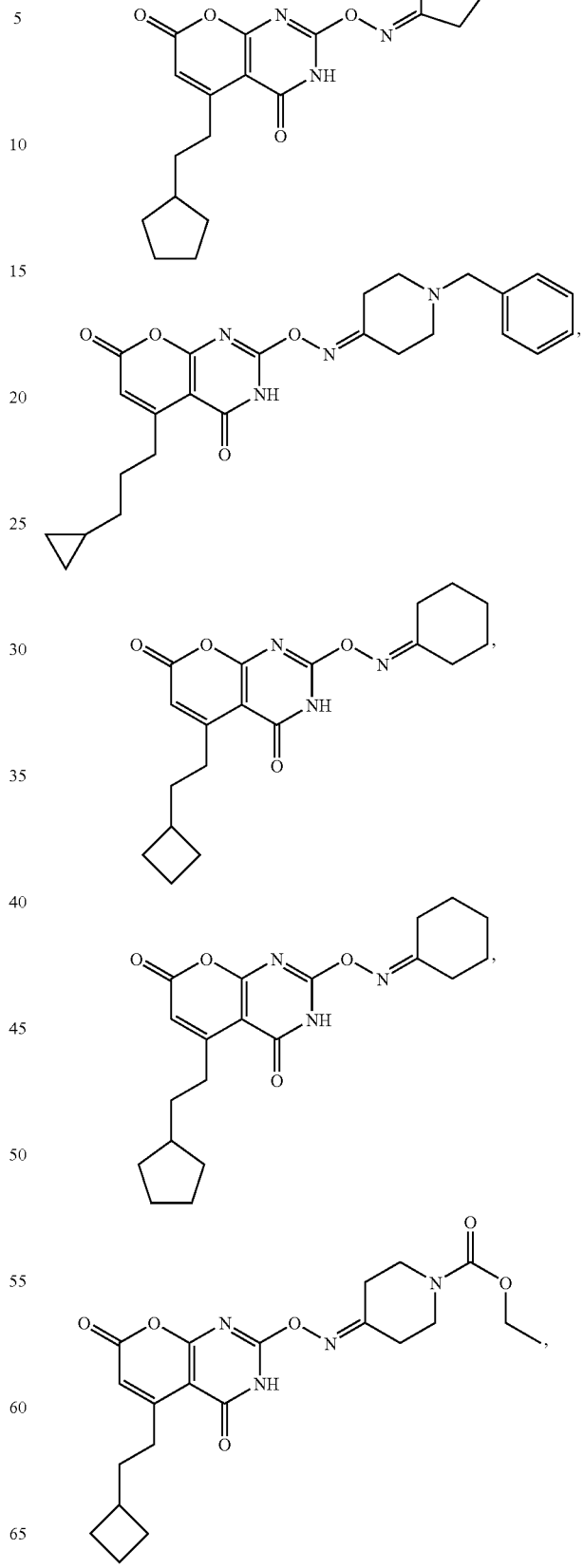

-continued
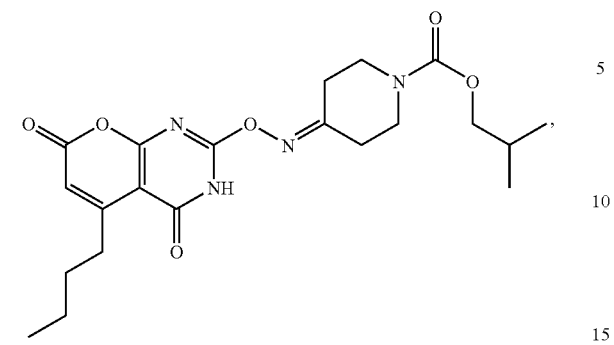
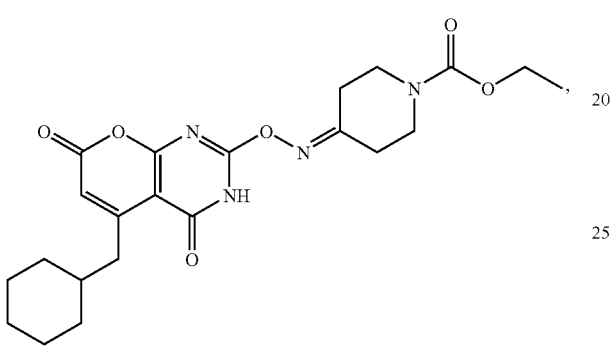
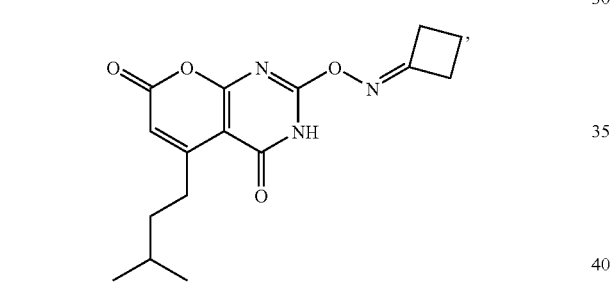
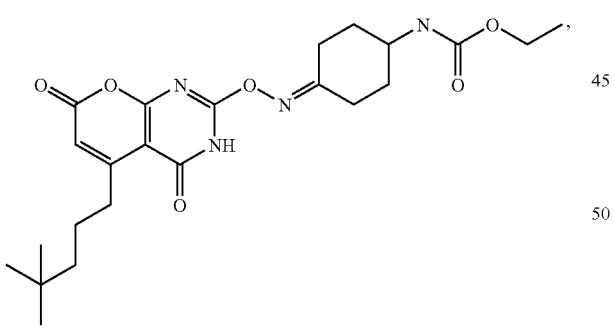
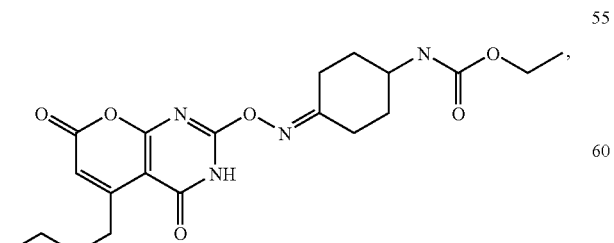
-continued
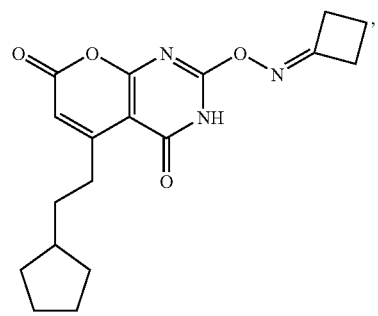
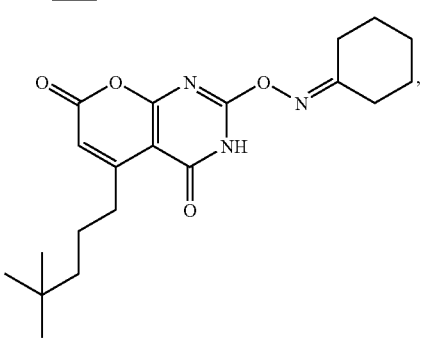
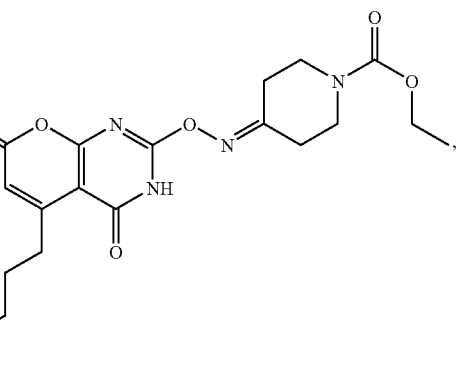
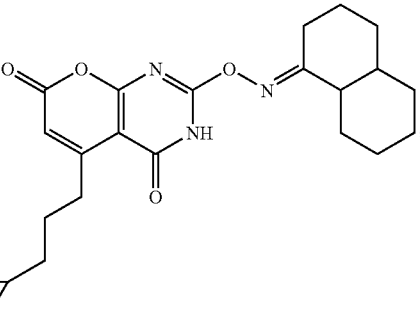
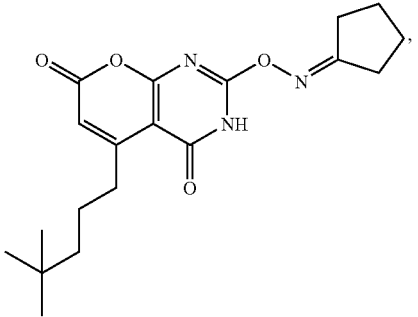

219
-continued
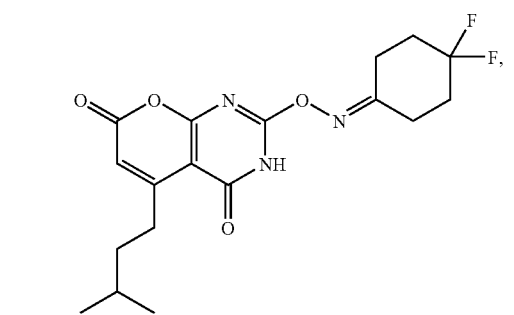
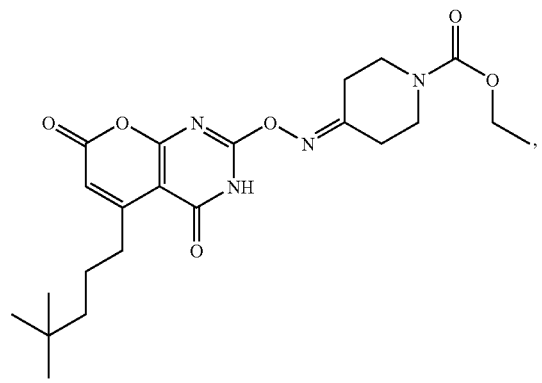
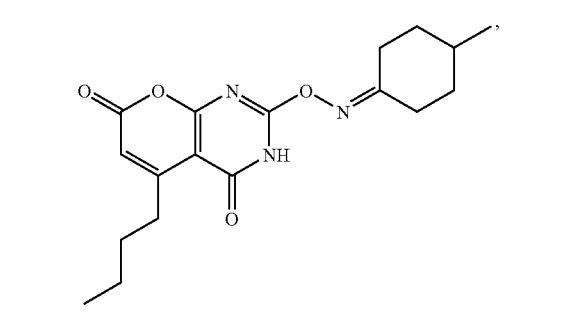
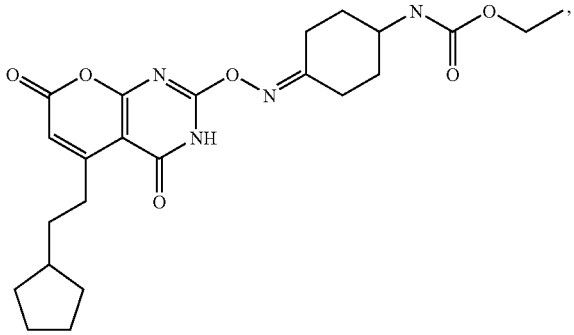
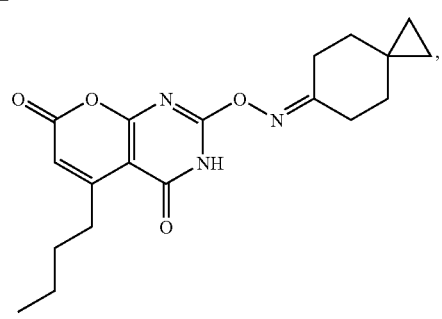
220
-continued
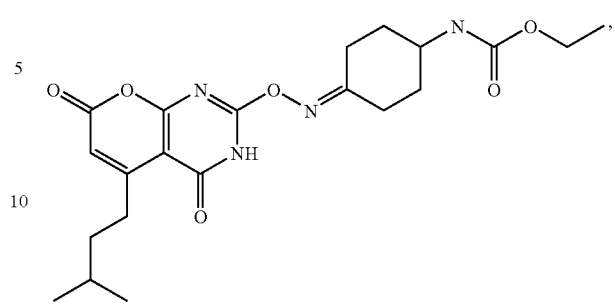
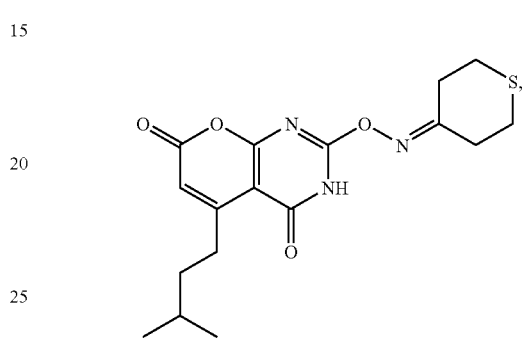
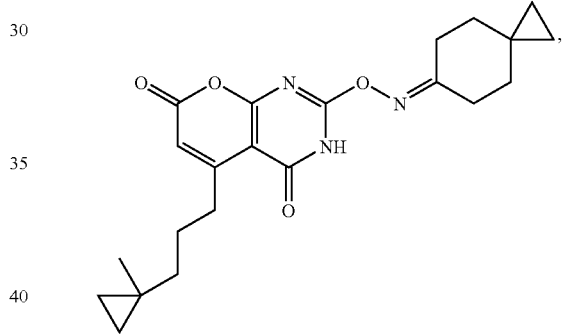
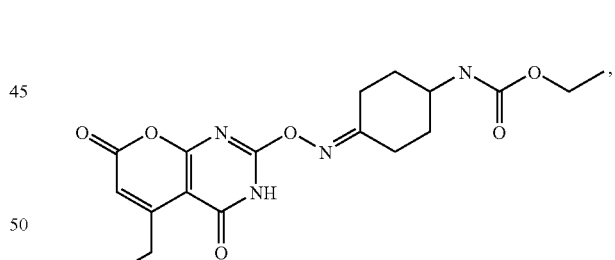
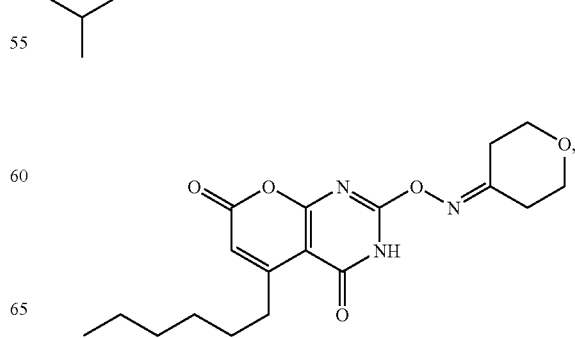

221
-continued
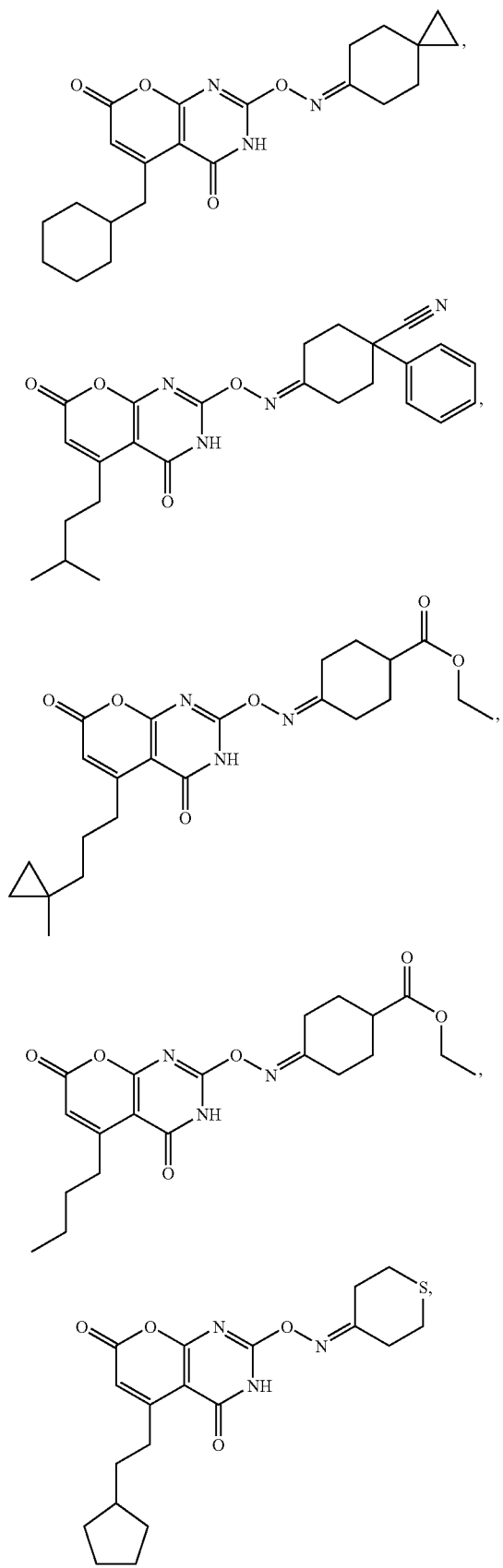
222
-continued
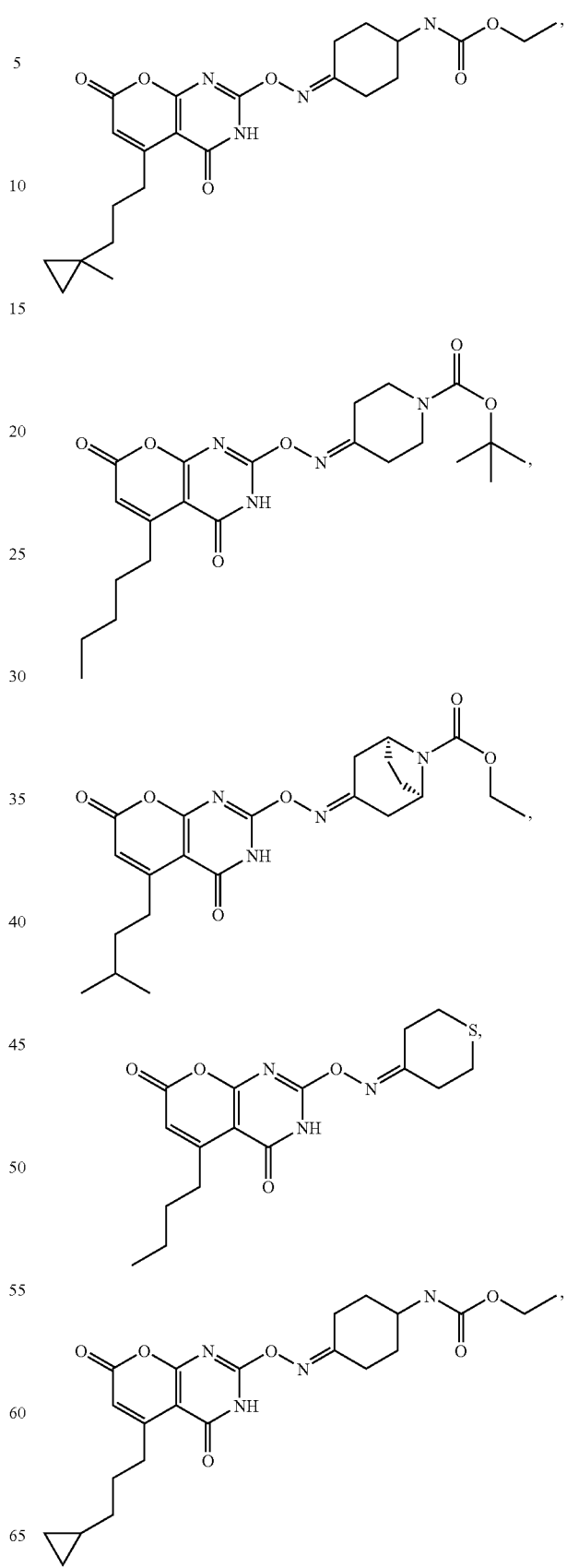

223
-continued
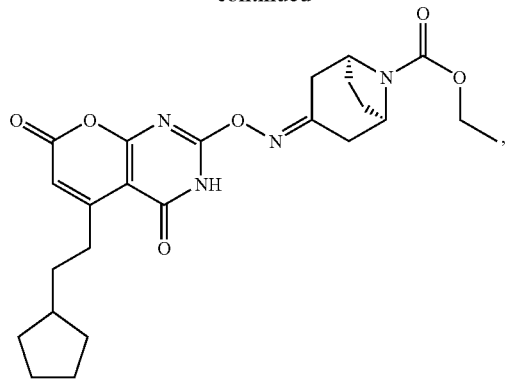
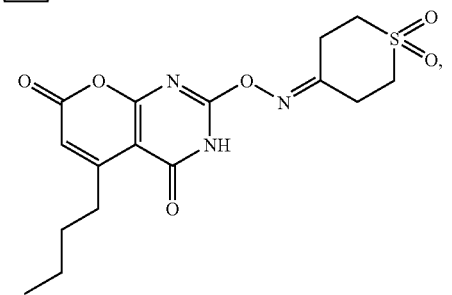
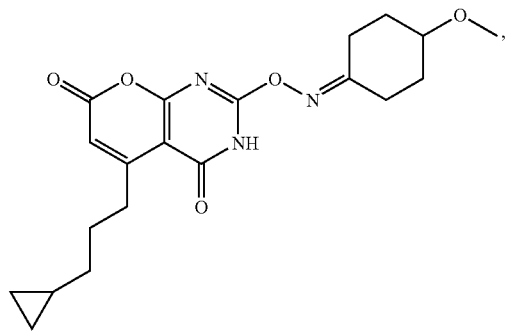
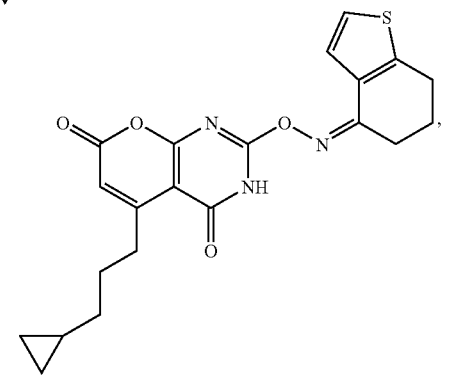
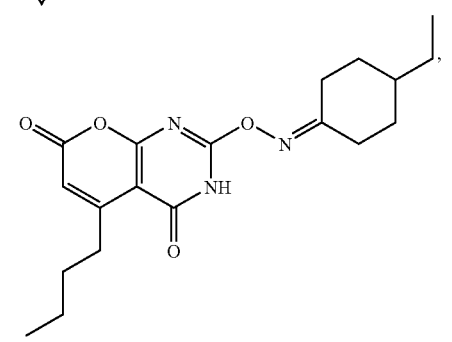
224
-continued
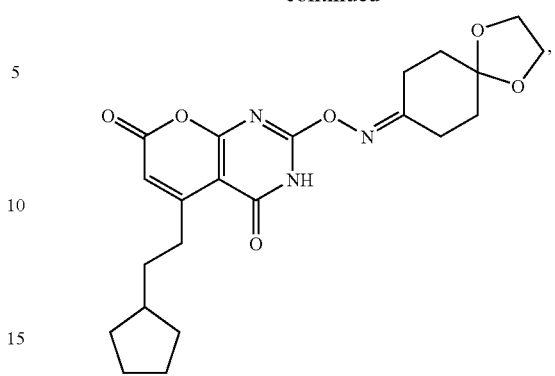
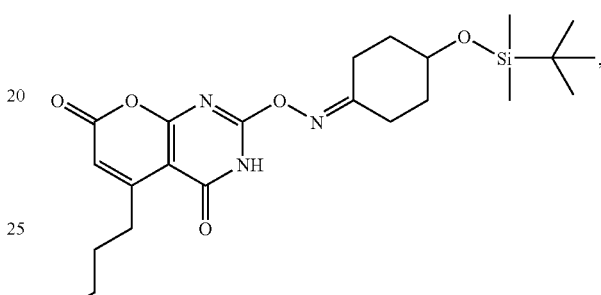
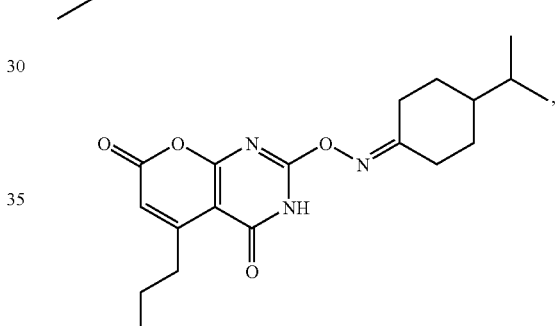
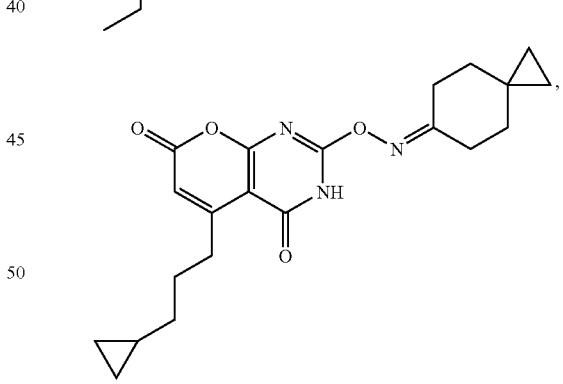
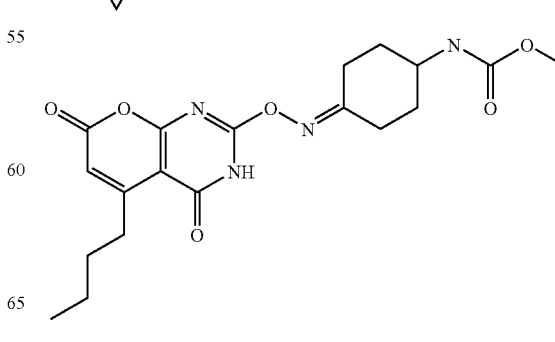

225
-continued
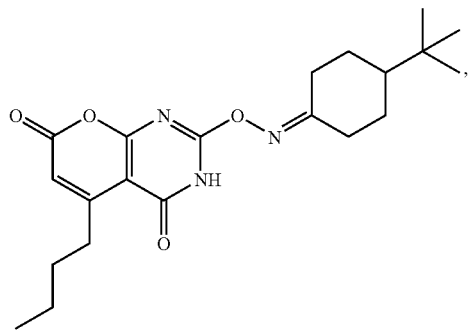
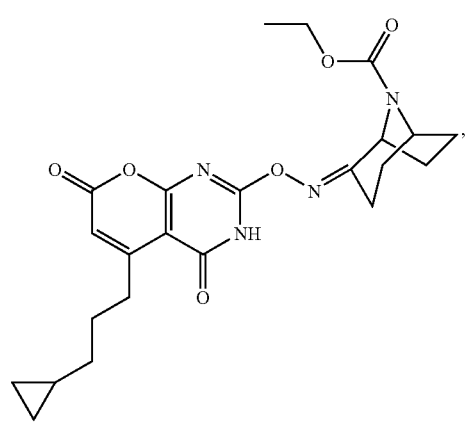
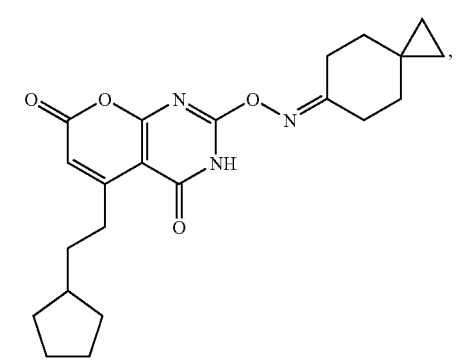
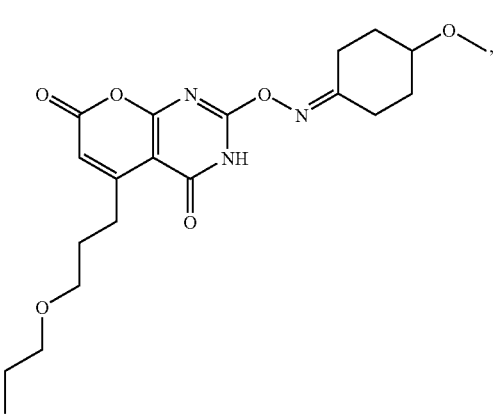
226
-continued
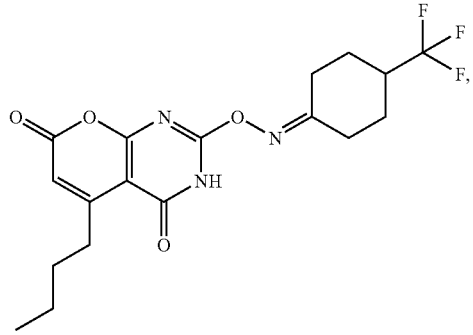
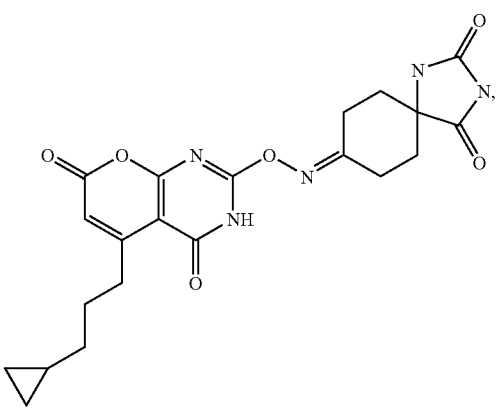
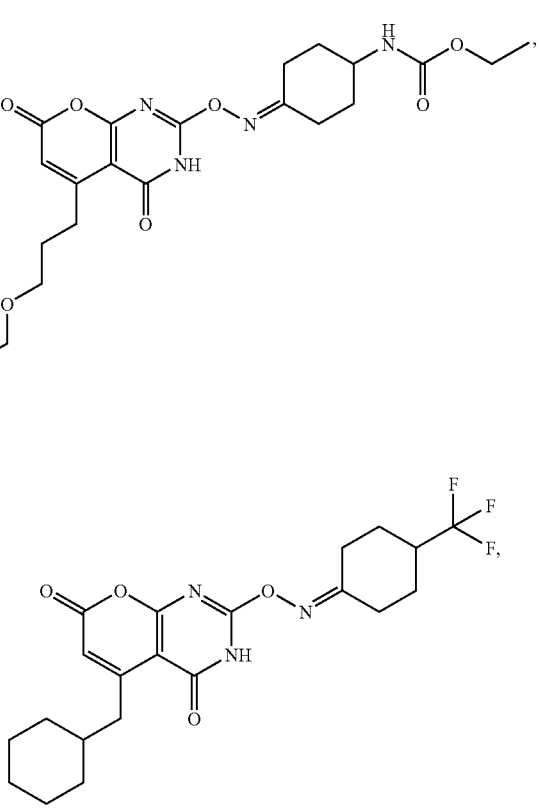

227
-continued
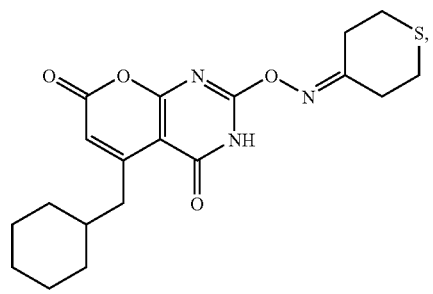
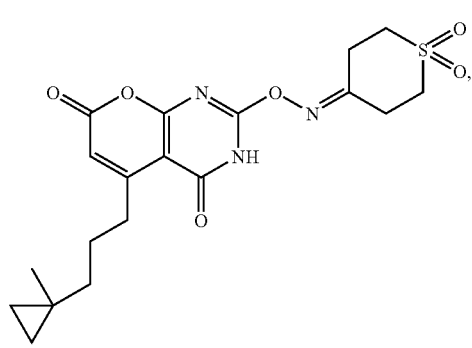
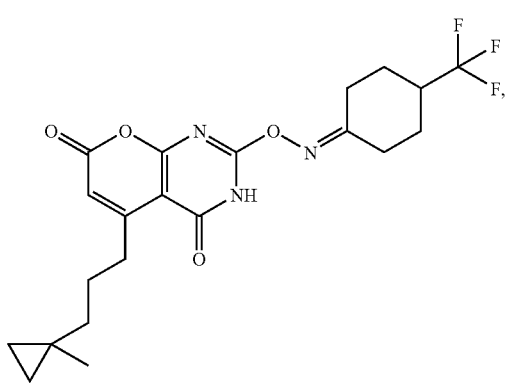
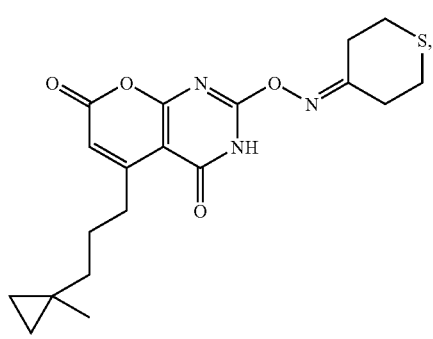
228
-continued
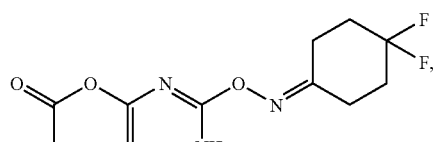
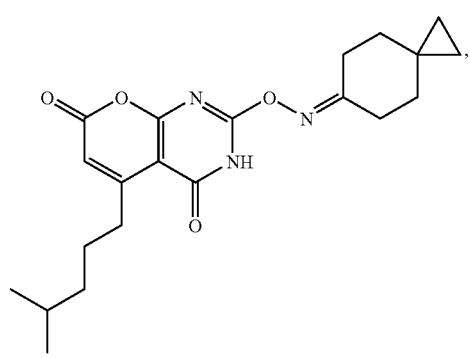
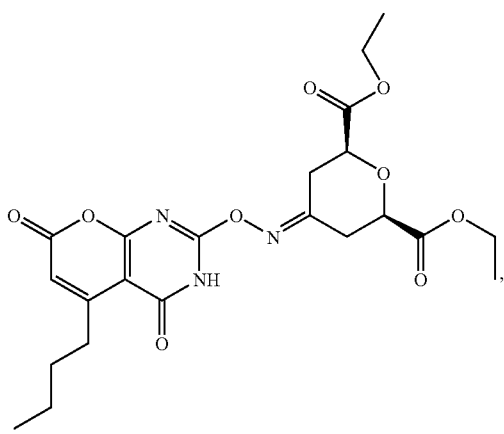
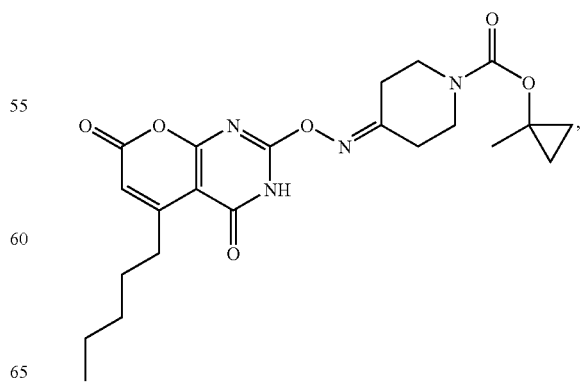

229
-continued
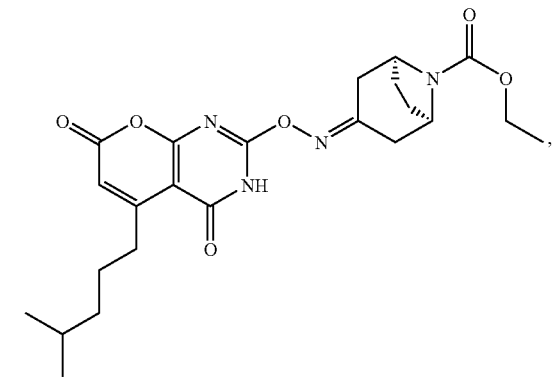
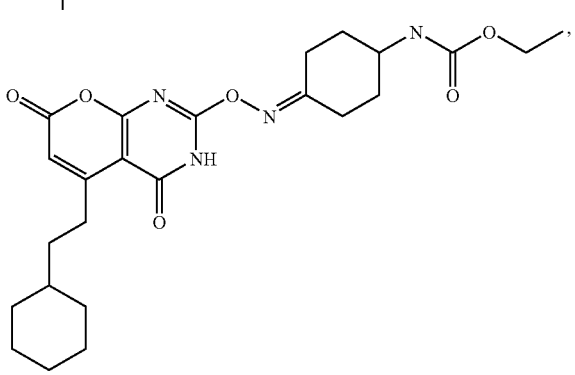
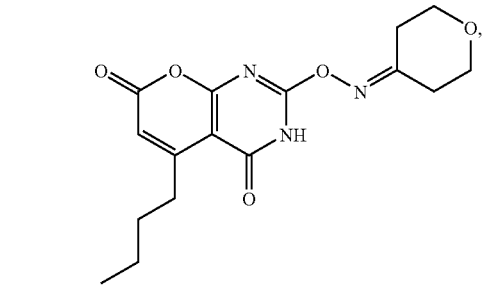
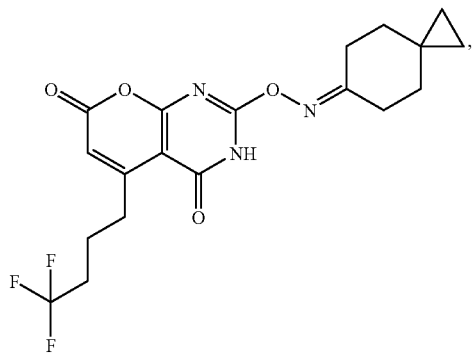
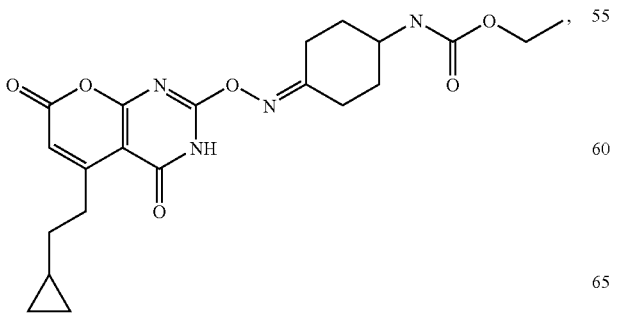
230
-continued
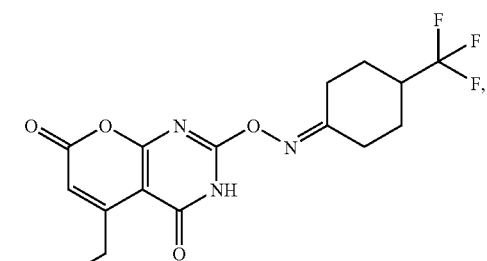
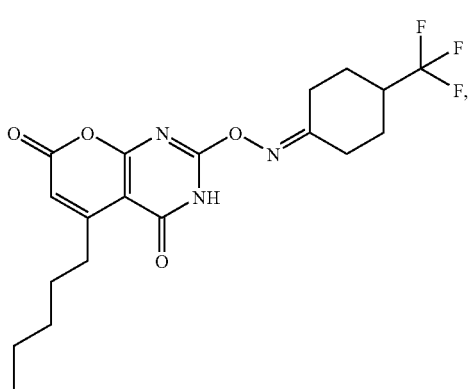
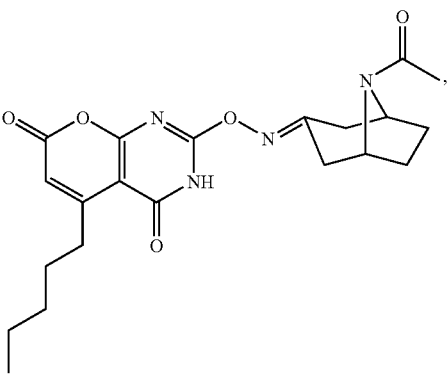
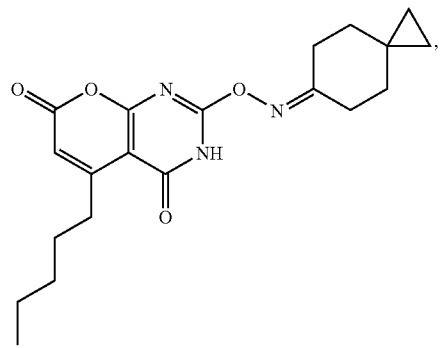

231
-continued
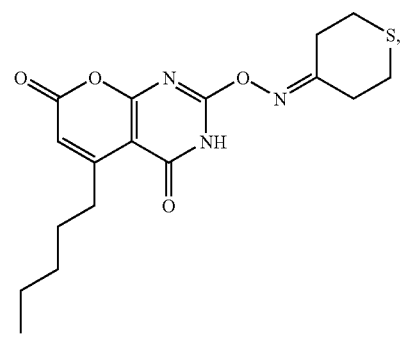
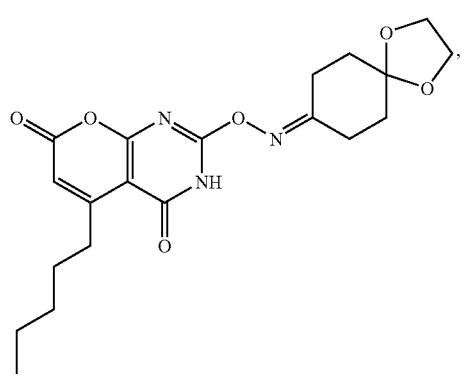
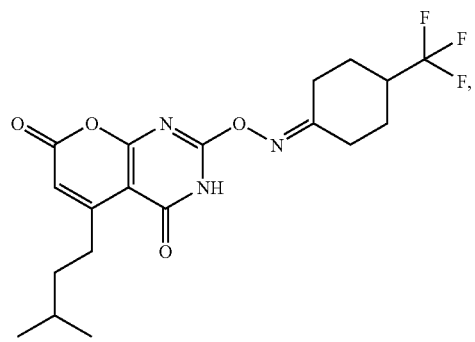
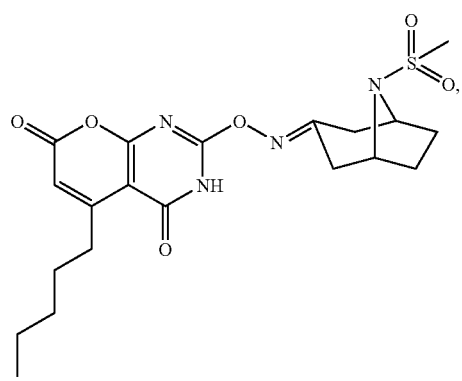
232
-continued
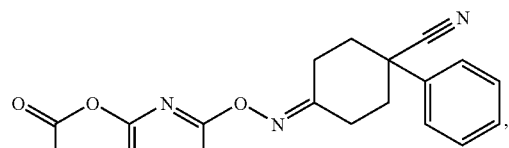
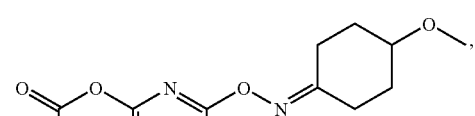
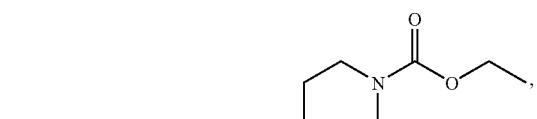
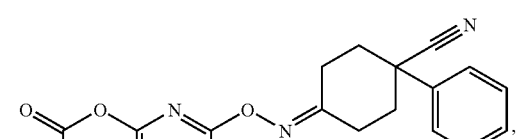
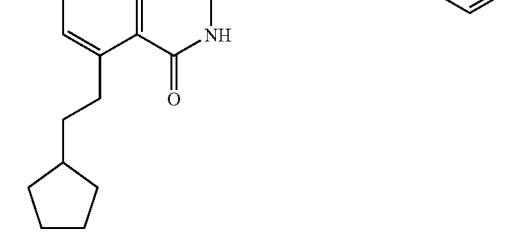

-continued
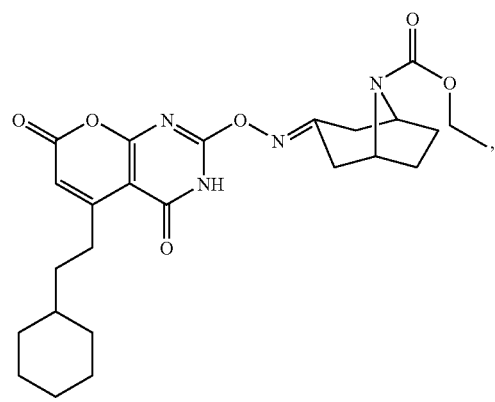
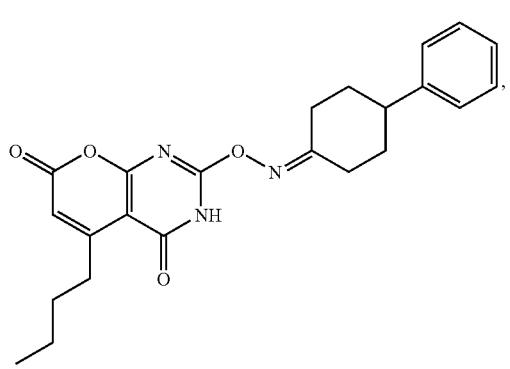
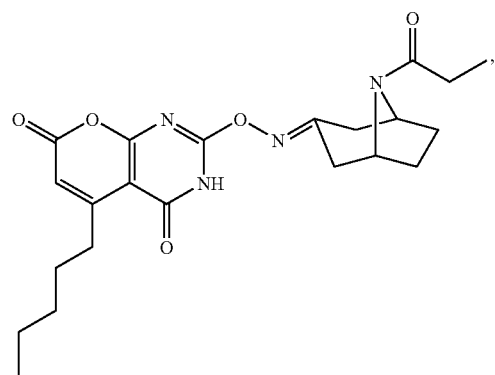
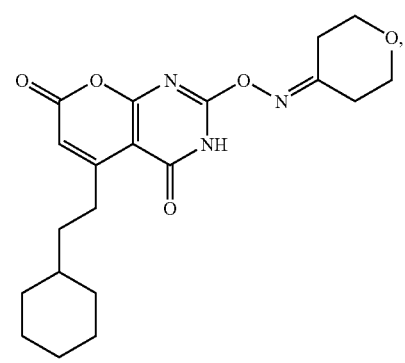
-continued
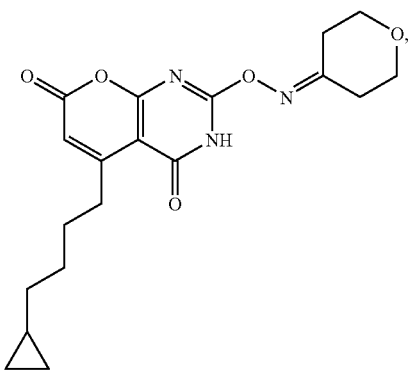
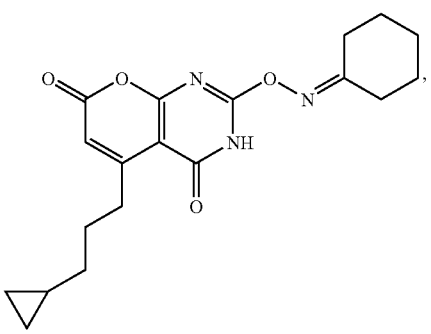
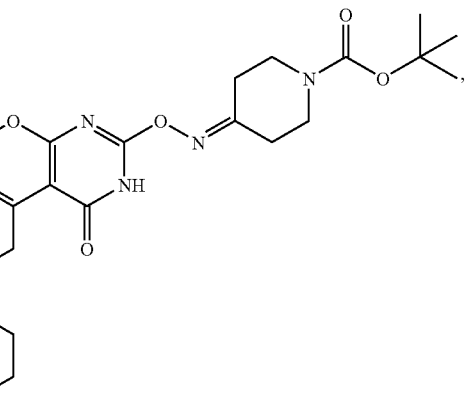
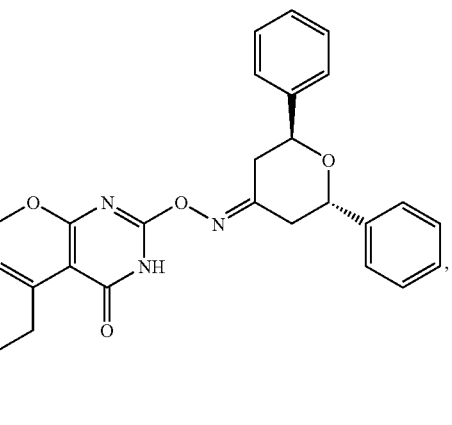

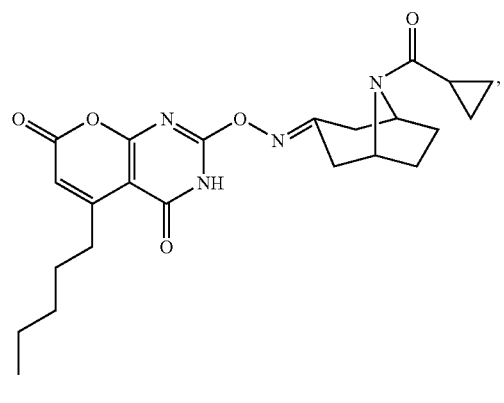
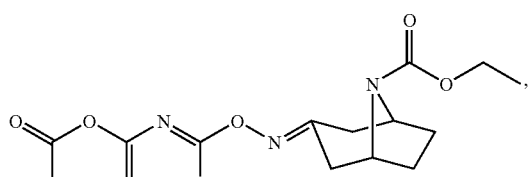
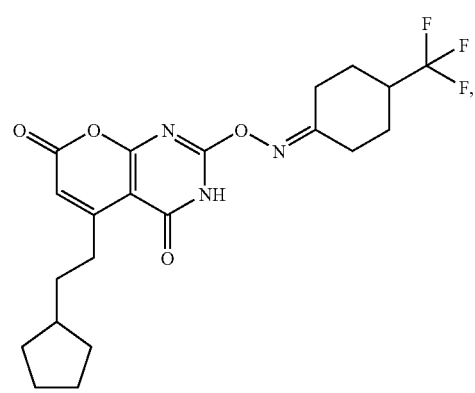
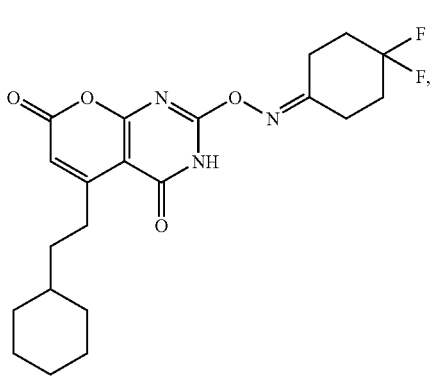
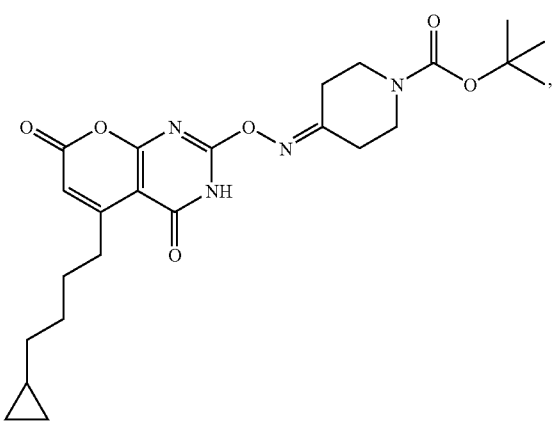
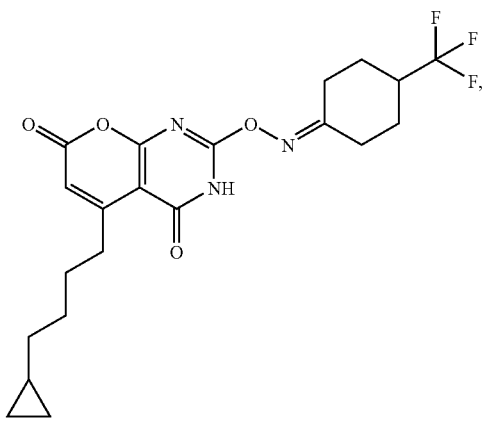
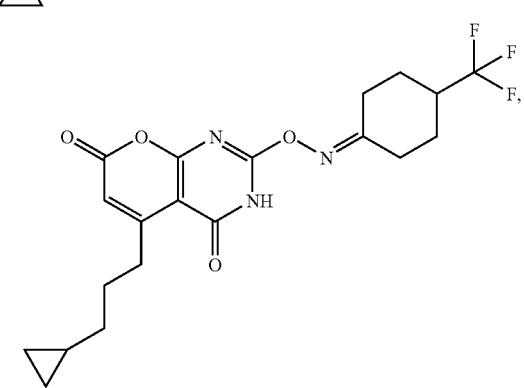
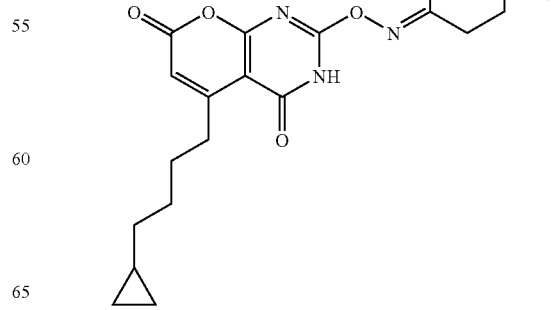

-continued
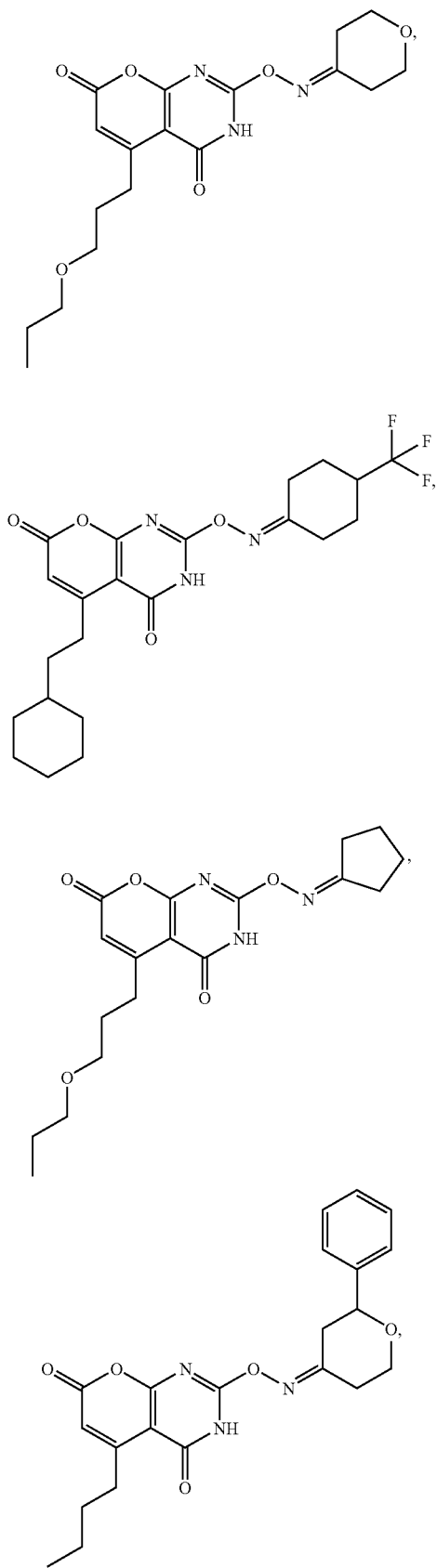
-continued
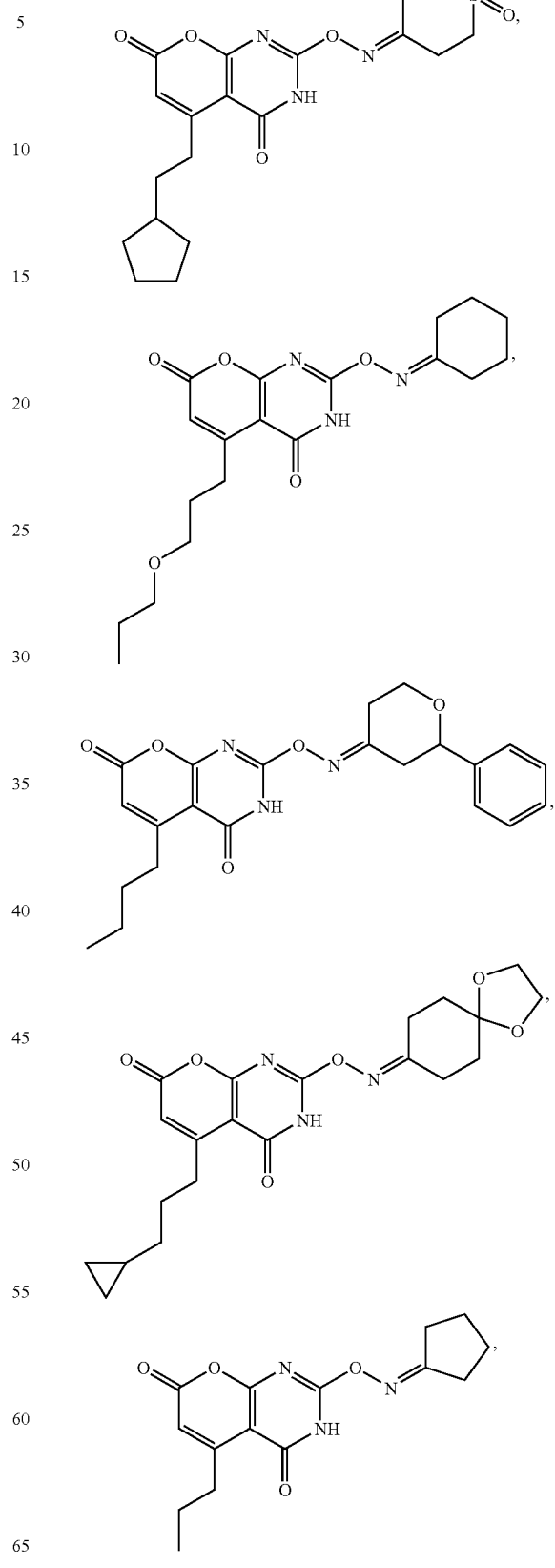

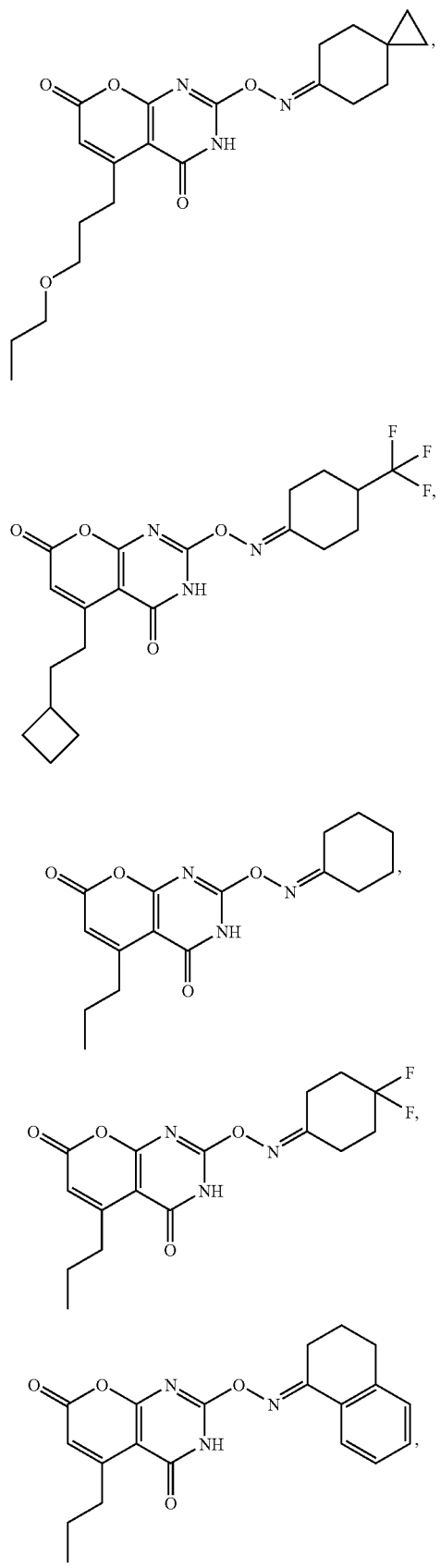
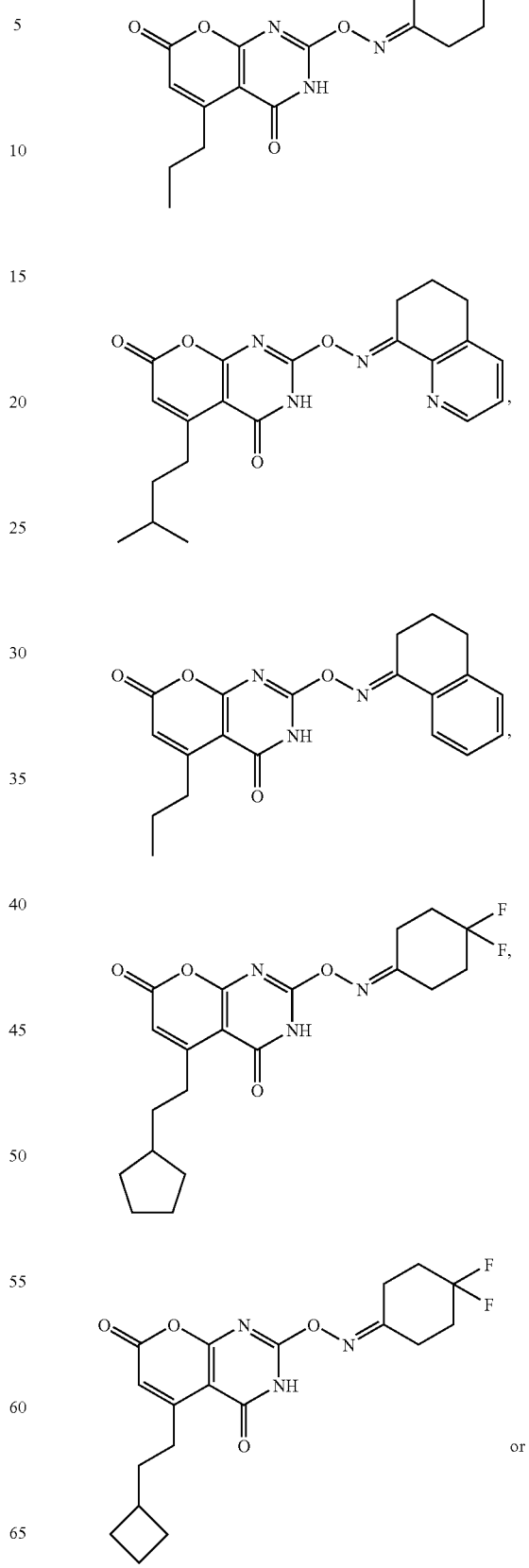

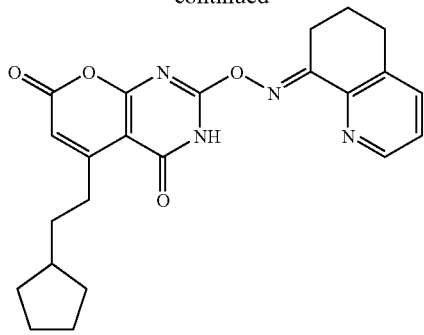

or a pharmaceutically acceptable salt, ester, or tautomer thereof.

35. A composition comprising: a compound of claim 18, or a pharmaceutically acceptable salt, ester, or tautomer thereof; and at least one pharmaceutically acceptable carrier.

36. The composition of claim 35, further comprising at least one additional therapeutic agent selected from the group consisting of a β-lactam, HMG CoA reductase inhibitor compounds, HMG CoA synthetase inhibitors, squalene synthesis inhibitors, squalene epoxidase inhibitors, sterol biosynthesis inhibitors, nicotinic acid, a nicotinic acid receptor agonist, bile acid sequestrants, aspirin, NSAID agents, a combination of ezetimibe and simvastatin, ezetimibe, inorganic cholesterol sequestrants, AcylCoA:Cholesterol O-acyltransferase inhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, opioid antagonists, orexin receptor antagonists, BRS3 agonists, CCK-A agonists, CNTF, CNTF agonists/modulators, 5HT2c agonists, Mc4r agonists, monoamine reuptake inhibitors, serotonin reuptake inhibitors, GLP-1 agonists, phentermine, topiramate, phytopharm compound 57, ghrelin antibodies, Mc3r agonists, ACC inhibitors, β agonists, DGAT1 inhibitors, DGAT2 inhibitors, FAS inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanin concentrating hormone antagonists, leptons, galanin receptor antagonists, bombesin agonists, neuropeptide-Y antagonists, thyromimetic agents, dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, a-glucosidase inhibitors, apo A1 milano reverse cholesterol transport inhibitors, fatty acid binding protein inhibitors (FABP), and fatty acid transporter protein inhibitors (FATP).

37. The composition of claim 36, wherein said at least one additional therapeutic agent is a HMG CoA reductase inhibitor selected from the group consisting of lovastatin, simvastatin, pravastatin, atorvastatin, fluvastatin, cerivastatin, rivastatin, rosuvastatin calcium, and pitavastatin.

38. The composition of claim 37, wherein said HMG CoA reductase inhibitor is simvastatin.

39. The composition of claim 36, wherein said at least one additional therapeutic agent is a cholesteryl ester transfer protein inhibitor.

* * * * *